(12) United States Patent
Vodnala et al.

(10) Patent No.: US 12,365,871 B2
(45) Date of Patent: Jul. 22, 2025

(54) METHODS FOR CULTURING CELLS

(71) Applicant: LYELL IMMUNOPHARMA, INC., South San Francisco, CA (US)

(72) Inventors: Suman Kumar Vodnala, San Mateo, CA (US); Nicholas P. Restifo, San Francisco, CA (US); Robert Langland Eil, New York, NY (US)

(73) Assignee: LYELL IMMUNOPHARMA, INC.

( * ) Notice: Subject to any disclaimer, the term of this patent is extended or adjusted under 35 U.S.C. 154(b) by 148 days.

(21) Appl. No.: 17/243,566

(22) Filed: Apr. 28, 2021

(65) Prior Publication Data

US 2021/0332326 A1 Oct. 28, 2021

Related U.S. Application Data

(60) Provisional application No. 63/016,907, filed on Apr. 28, 2020.

(51) Int. Cl.
| | | |
|---|---|---|
| *C12N 5/074* | (2010.01) | |
| *A61K 40/11* | (2025.01) | |
| *A61K 40/31* | (2025.01) | |
| *A61K 40/42* | (2025.01) | |
| *C07K 14/725* | (2006.01) | |
| *C12N 5/0783* | (2010.01) | |

(52) U.S. Cl.
CPC ............ *C12N 5/0607* (2013.01); *A61K 40/11* (2025.01); *A61K 40/31* (2025.01); *A61K 40/421* (2025.01); *C07K 14/7051* (2013.01); *C12N 5/0636* (2013.01); *A61K 2239/55* (2023.05); *C12N 2500/05* (2013.01); *C12N 2500/34* (2013.01); *C12N 2501/2302* (2013.01); *C12N 2501/2307* (2013.01); *C12N 2501/2315* (2013.01); *C12N 2501/2321* (2013.01); *C12N 2501/999* (2013.01)

(58) Field of Classification Search
CPC ............... C12N 5/0636; C12N 5/0607; C12N 2500/05; C12N 2500/34; C12N 2501/2302; C12N 2501/2307; C12N 2501/2315; C12N 2501/2321; C12N 2501/999; A61K 35/17; C07K 14/7051
See application file for complete search history.

(56) References Cited

U.S. PATENT DOCUMENTS

| | | | |
|---|---|---|---|
| 5,968,755 A | 10/1999 | Roederer et al. | |
| 6,399,054 B1 | 6/2002 | Casorati et al. | |
| 7,381,405 B2 | 6/2008 | Liu et al. | |
| 7,731,953 B2 | 6/2010 | Leonard et al. | |
| 8,383,099 B2 | 2/2013 | Dudley et al. | |
| 8,883,500 B2 | 11/2014 | Sitkovsky et al. | |
| 8,951,747 B2 | 2/2015 | Demotte et al. | |
| 9,074,185 B2 | 7/2015 | Dudley et al. | |
| 9,334,522 B2 | 5/2016 | Gu et al. | |
| 9,345,691 B2 | 5/2016 | Cohen et al. | |
| 9,512,401 B2 | 12/2016 | Radvanyi et al. | |
| 9,528,088 B2 | 12/2016 | Berenson et al. | |
| 9,951,310 B2 | 4/2018 | Yee | |
| 9,987,308 B2 | 6/2018 | Riddell et al. | |
| 10,016,421 B2 | 7/2018 | Sotomayor et al. | |
| 10,098,939 B2 | 10/2018 | Schneck et al. | |
| 10,166,257 B2 | 1/2019 | Wardell et al. | |
| 10,233,425 B2 | 3/2019 | Powell, Jr. | |
| 10,316,289 B2 | 6/2019 | Gattinoni et al. | |
| 10,400,215 B2 | 9/2019 | Riddell et al. | |
| 10,406,177 B2 | 9/2019 | Moriarity et al. | |
| 10,415,015 B2 | 9/2019 | Veerapathran et al. | |
| 10,415,016 B2 | 9/2019 | Ostertag et al. | |
| 10,420,799 B2 | 9/2019 | Wardell et al. | |
| 10,513,686 B2 | 12/2019 | Ostertag et al. | |
| 10,517,894 B2 | 12/2019 | Frank et al. | |
| 10,639,330 B2 | 5/2020 | Wardell et al. | |
| 10,731,129 B2 | 8/2020 | Sanchez-Schmitz et al. | |
| 10,857,182 B2 | 12/2020 | O'Reilly et al. | |
| 10,858,626 B2 | 12/2020 | Doucey et al. | |
| 10,900,019 B2 | 1/2021 | Powell, Jr. | |
| 10,912,797 B2 | 2/2021 | Moriarity et al. | |

(Continued)

FOREIGN PATENT DOCUMENTS

| | | |
|---|---|---|
| CN | 111440773 A | 7/2020 |
| EP | 0460065 B1 | 8/1994 |

(Continued)

OTHER PUBLICATIONS

Shirakawa, F., et al., "Calcium dependency in the growth of adult T-cell leukemia cells in vitro," Cancer Research 46(2): 658-661 (1986) (Year: 1986).*

Dwyer et al., "Ex vivo blockade of PI3K gamma or delta signaling enhances the antitumor potency of adoptively transferred CD8+ T cells," European Journal of Immunology 50(9): 1386-1399. doi: 10.1002/eji.201948455. Epub May 28, 2020. (Year: 2020).*

Baixauli, F., et al., "Potassium shapes antitumor immunity," Science 363(6434): 1395-1396. doi: 10.1126/science.aaw8800. Mar. 29, 2019. (Year: 2019).*

(Continued)

*Primary Examiner* — Tracy Vivlemore
*Assistant Examiner* — Eric J Rogers
(74) *Attorney, Agent, or Firm* — Sterne, Kessler, Goldstein & Fox P.L.L.C.

(57) ABSTRACT

The preset disclosure provides methods of culturing cells, e.g., pluripotent cells, multipotent cells, and/or immune cells (e.g., T cells, NK cells, and/or TILs) in a medium comprising at least about 5 mM potassium ion, wherein the medium is not hypertonic. In some aspects, the medium is hypotonic. In some aspects, the methods disclosed herein increases the number of less-differentiated cells in the population of cells. In some aspects, the cultured cells are engineered, e.g., to comprise a chimeric antigen receptor or an engineered T cell receptor. In some aspects, the cells are administered to a subject in need thereof.

32 Claims, 27 Drawing Sheets

(56) References Cited

U.S. PATENT DOCUMENTS

| | | |
|---|---|---|
| 10,918,638 B2 | 2/2021 | Sotomayor et al. |
| 11,007,222 B2 | 5/2021 | Oelke et al. |
| 11,026,974 B2 | 6/2021 | Frank et al. |
| 11,045,496 B2 | 6/2021 | Wan et al. |
| 11,058,728 B1 | 7/2021 | Frank et al. |
| 2002/0081635 A1 | 6/2002 | Thomas et al. |
| 2004/0058445 A1 | 3/2004 | Ledbetter et al. |
| 2009/0246212 A1 | 10/2009 | Koshiba et al. |
| 2010/0068192 A1 | 3/2010 | Enoki et al. |
| 2010/0310533 A1 | 12/2010 | Yee |
| 2012/0244133 A1 | 9/2012 | Rosenberg et al. |
| 2013/0102075 A1 | 4/2013 | Vera et al. |
| 2015/0017120 A1 | 1/2015 | Wittrup et al. |
| 2016/0175358 A1 | 6/2016 | Jakobovits et al. |
| 2017/0065690 A1 | 3/2017 | Debenedette et al. |
| 2017/0067021 A1 | 3/2017 | Moriarity et al. |
| 2017/0081635 A1 | 3/2017 | Sarnaik et al. |
| 2017/0107490 A1 | 4/2017 | Maeurer |
| 2017/0224734 A1 | 8/2017 | Chapman et al. |
| 2017/0246277 A1 | 8/2017 | Schneck et al. |
| 2017/0260507 A1 | 9/2017 | Kalinski et al. |
| 2017/0349880 A1 | 12/2017 | Doucey et al. |
| 2017/0360801 A1 | 12/2017 | Sotomayor et al. |
| 2018/0018750 A1 | 1/2018 | Jones et al. |
| 2018/0064793 A1 | 3/2018 | McGranahan et al. |
| 2018/0133296 A1 | 5/2018 | Barrett et al. |
| 2018/0185525 A1 | 7/2018 | Markel |
| 2018/0197150 A1 | 7/2018 | Bender et al. |
| 2018/0228841 A1 | 8/2018 | Frank et al. |
| 2018/0250338 A1 | 9/2018 | He et al. |
| 2018/0296602 A1 | 10/2018 | Riddell et al. |
| 2019/0000880 A1 | 1/2019 | Motz et al. |
| 2019/0008899 A1 | 1/2019 | Moriarity et al. |
| 2019/0038670 A1 | 2/2019 | Camilio et al. |
| 2019/0070177 A1 | 3/2019 | Sotomayor et al. |
| 2019/0076385 A1 | 3/2019 | Erti et al. |
| 2019/0106678 A1 | 4/2019 | Regev et al. |
| 2019/0106679 A1 | 4/2019 | Regev et al. |
| 2019/0119639 A1 | 4/2019 | Oelke et al. |
| 2019/0125795 A1 | 5/2019 | Rosen et al. |
| 2019/0127694 A1 | 5/2019 | Khleif et al. |
| 2019/0175648 A1 | 6/2019 | Brown et al. |
| 2019/0177693 A1 | 6/2019 | Sarnaik et al. |
| 2019/0231820 A1 | 8/2019 | Fardis |
| 2019/0255107 A1 | 8/2019 | Kuchroo et al. |
| 2019/0262399 A1 | 8/2019 | Wang et al. |
| 2019/0262400 A1 | 8/2019 | Davila |
| 2019/0264175 A1 | 8/2019 | Gattinoni et al. |
| 2019/0276802 A1 | 9/2019 | Simpson-Abelson et al. |
| 2019/0292520 A1 | 9/2019 | Alpert |
| 2019/0298715 A1 | 10/2019 | Motz et al. |
| 2019/0298770 A1 | 10/2019 | Rabinovich et al. |
| 2019/0307796 A1 | 10/2019 | Delgoffe |
| 2019/0316085 A1 | 10/2019 | Johnson et al. |
| 2019/0316088 A1 | 10/2019 | Yee |
| 2019/0321400 A1 | 10/2019 | Wan et al. |
| 2019/0345444 A1 | 11/2019 | Rosenberg et al. |
| 2019/0345445 A1 | 11/2019 | Veerapathran et al. |
| 2019/0352608 A1 | 11/2019 | Powell, Jr. |
| 2019/0359938 A1 | 11/2019 | Riddell et al. |
| 2019/0374576 A1 | 12/2019 | Henley et al. |
| 2019/0374577 A1 | 12/2019 | Ritthipichai et al. |
| 2019/0374662 A1 | 12/2019 | Markel |
| 2020/0032208 A1 | 1/2020 | Brunk et al. |
| 2020/0032209 A1 | 1/2020 | Sarnaik et al. |
| 2020/0063103 A1 | 2/2020 | Xu et al. |
| 2020/0087625 A1 | 3/2020 | Carson et al. |
| 2020/0095547 A1 | 3/2020 | Alizadeh et al. |
| 2020/0101108 A1 | 4/2020 | Lynn et al. |
| 2020/0115680 A1 | 4/2020 | Bronevetsky et al. |
| 2020/0121719 A1 | 4/2020 | Lotze et al. |
| 2020/0140814 A1 | 5/2020 | Ostertag et al. |
| 2020/0147210 A1 | 5/2020 | Sade-Feldman et al. |
| 2020/0149009 A1 | 5/2020 | Regev et al. |
| 2020/0165567 A1 | 5/2020 | Van Buuren et al. |
| 2020/0179451 A1 | 6/2020 | Rosen et al. |
| 2020/0181573 A1 | 6/2020 | Rosen et al. |
| 2020/0206265 A1 | 7/2020 | Perez et al. |
| 2020/0216551 A1 | 7/2020 | Li et al. |
| 2020/0224161 A1 | 7/2020 | Karyampudi et al. |
| 2020/0239910 A1 | 7/2020 | Bonyhadi |
| 2020/0277573 A1 | 9/2020 | Simpson-Abelson et al. |
| 2020/0289571 A1 | 9/2020 | Moriarity et al. |
| 2020/0299644 A1 | 9/2020 | Frank et al. |
| 2020/0339944 A1 | 10/2020 | Vargas-Inchaus-Tegui et al. |
| 2020/0377849 A1 | 12/2020 | Wang et al. |
| 2020/0377855 A1 | 12/2020 | Kelley et al. |
| 2021/0000872 A1 | 1/2021 | Price et al. |
| 2021/0033595 A1 | 2/2021 | Wherry et al. |
| 2021/0062150 A1 | 3/2021 | Ni et al. |
| 2021/0071141 A1 | 3/2021 | Vodnala et al. |
| 2021/0079348 A1 | 3/2021 | Wardell et al. |
| 2021/0087529 A1 | 3/2021 | Gosling et al. |
| 2021/0102168 A1 | 4/2021 | Singer et al. |
| 2021/0130779 A1 | 5/2021 | Chartier-Courtaud et al. |
| 2021/0137930 A1 | 5/2021 | Fardis |
| 2021/0169937 A1 | 6/2021 | Dodoo et al. |
| 2021/0214686 A1 | 7/2021 | Dodoo et al. |
| 2021/0230543 A1 | 7/2021 | Davila |
| 2021/0236547 A1 | 8/2021 | Davila |
| 2022/0175834 A1 | 6/2022 | Vodnala et al. |

FOREIGN PATENT DOCUMENTS

| | | |
|---|---|---|
| EP | 0611263 A2 | 8/1994 |
| EP | 0340793 B1 | 8/1995 |
| EP | 2102241 A2 | 9/2009 |
| EP | 1814580 B1 | 8/2016 |
| EP | 3154567 A1 | 4/2017 |
| EP | 3288581 A1 | 3/2018 |
| EP | 3317400 A1 | 5/2018 |
| EP | 2099902 B1 | 8/2018 |
| EP | 3324984 A4 | 3/2019 |
| EP | 3500298 A2 | 6/2019 |
| EP | 3519561 A1 | 8/2019 |
| EP | 3119477 B1 | 1/2020 |
| EP | 3107996 B1 | 2/2020 |
| EP | 3622055 A1 | 3/2020 |
| EP | 3697434 A1 | 8/2020 |
| EP | 3702447 A1 | 9/2020 |
| EP | 3707245 A1 | 9/2020 |
| EP | 3724885 A2 | 10/2020 |
| EP | 3154567 B1 | 11/2020 |
| EP | 3737695 A1 | 11/2020 |
| EP | 3737743 A1 | 11/2020 |
| EP | 3775165 A1 | 2/2021 |
| EP | 3841196 A1 | 6/2021 |
| EP | 3844266 A1 | 7/2021 |
| EP | 3856208 A1 | 8/2021 |
| WO | WO-1990014097 A1 | 11/1990 |
| WO | WO-03028630 A2 | 4/2003 |
| WO | WO-2004034789 A1 | 4/2004 |
| WO | WO-2007071390 A1 | 6/2007 |
| WO | WO-2007071409 A1 | 6/2007 |
| WO | WO-2008066609 A1 | 6/2008 |
| WO | WO-2008099088 A2 | 8/2008 |
| WO | WO-2010056144 A2 | 5/2010 |
| WO | WO-2012129201 A1 | 9/2012 |
| WO | WO-2012129514 A1 | 9/2012 |
| WO | WO-2013014535 A1 | 1/2013 |
| WO | WO-2013057500 A1 | 4/2013 |
| WO | WO-2013088147 A1 | 6/2013 |
| WO | WO-2013167136 A1 | 11/2013 |
| WO | WO-2014031687 A1 | 2/2014 |
| WO | WO-2015112626 A1 | 7/2015 |
| WO | WO-2015188839 A2 | 12/2015 |
| WO | WO-2015189301 A1 | 12/2015 |
| WO | WO-2016044853 A1 | 3/2016 |
| WO | WO-2016053338 A1 | 4/2016 |
| WO | WO-2016081518 A2 | 5/2016 |
| WO | WO-2017070042 A1 | 4/2017 |
| WO | WO-2017070608 A1 | 4/2017 |
| WO | WO-2017194924 A1 | 11/2017 |
| WO | WO-2018072105 A1 | 4/2018 |

(56) References Cited

FOREIGN PATENT DOCUMENTS

| | | |
|---|---|---|
| WO | WO-2018200582 A1 | 11/2018 |
| WO | WO-2018200583 A1 | 11/2018 |
| WO | WO-2018200585 A1 | 11/2018 |
| WO | WO-2018204761 A1 | 11/2018 |
| WO | WO-2019014684 A1 | 1/2019 |
| WO | WO-2019036815 A1 | 2/2019 |
| WO | WO-2019040590 A1 | 2/2019 |
| WO | WO-2019068099 A1 | 4/2019 |
| WO | WO2019100023 A1 | 5/2019 |
| WO | WO-2019118873 A2 | 6/2019 |
| WO | WO-2019136456 A1 | 7/2019 |
| WO | WO-2019136459 A1 | 7/2019 |
| WO | WO-2019140137 A1 | 7/2019 |
| WO | WO-2019160829 A1 | 8/2019 |
| WO | WO-2019201970 A1 | 10/2019 |
| WO | WO-2019209715 A1 * 10/2019 ............ A61K 31/194 |
| WO | WO-2019210131 A1 | 10/2019 |
| WO | WO-2019217753 A1 | 11/2019 |
| WO | WO-2019222763 A1 | 11/2019 |
| WO | WO-2019227176 A1 | 12/2019 |
| WO | WO-2019236681 A1 | 12/2019 |
| WO | WO-2019241536 A1 | 12/2019 |
| WO | WO-2019191501 A9 | 2/2020 |
| WO | WO-2020025706 A1 | 2/2020 |
| WO | WO-2020028400 A1 | 2/2020 |
| WO | WO-2020047452 A2 | 3/2020 |
| WO | WO-2020061429 A1 | 3/2020 |
| WO | WO-2020068816 A1 | 4/2020 |
| WO | WO-2020081987 A1 | 4/2020 |
| WO | WO-2020086742 A1 | 4/2020 |
| WO | WO-2020092440 A1 | 5/2020 |
| WO | WO-2020092475 A1 | 5/2020 |
| WO | WO-2020096682 A2 | 5/2020 |
| WO | WO-2020096927 A1 | 5/2020 |
| WO | WO-2020096986 A2 | 5/2020 |
| WO | WO-2020096988 A2 | 5/2020 |
| WO | WO-2020096989 A1 | 5/2020 |
| WO | WO-2020116606 A1 | 6/2020 |
| WO | WO-2020131547 A1 | 6/2020 |
| WO | WO-2020146740 A1 | 7/2020 |
| WO | WO-2020163569 A1 | 8/2020 |
| WO | WO-2020177071 A1 | 9/2020 |
| WO | WO-2020180733 A1 | 9/2020 |
| WO | WO-2020187340 A2 | 9/2020 |
| WO | WO-2020206061 A1 | 10/2020 |
| WO | WO-2020224042 A1 | 11/2020 |
| WO | WO-2020227546 A1 | 11/2020 |
| WO | WO-2020231059 A1 | 11/2020 |
| WO | WO-2020232029 A1 | 11/2020 |
| WO | WO-2020263919 A1 | 12/2020 |
| WO | WO-2020264019 A1 | 12/2020 |
| WO | WO-2020153800 A9 | 1/2021 |
| WO | WO-2021011882 A1 | 1/2021 |
| WO | WO-2021014174 A1 | 1/2021 |
| WO | WO-2021021804 A1 | 2/2021 |
| WO | WO-2021026290 A1 | 2/2021 |
| WO | WO-2021034774 A1 | 2/2021 |
| WO | WO-2021081378 A1 | 4/2021 |
| WO | WO-2021108455 A1 | 6/2021 |
| WO | WO-2021108727 A1 | 6/2021 |
| WO | WO-2021118990 A1 | 6/2021 |
| WO | WO-2021123255 A1 | 6/2021 |
| WO | WO-2021123832 A1 | 6/2021 |
| WO | WO-2021142081 A1 | 7/2021 |
| WO | WO-2021167908 A1 | 8/2021 |
| WO | WO-2021173964 A1 | 9/2021 |
| WO | WO-2021222479 A1 | 11/2021 |
| WO | WO-2022109501 A2 | 5/2022 |
| WO | WO-2022182915 A1 | 9/2022 |

OTHER PUBLICATIONS

Lien, E. C., et al., "Putting the K+ in K+aloric Restriction," *Immunity* 50(5): 1129-1131. doi: 10.1016/j.immuni.2019.04.016. May 21, 2019. (Year: 2019).*

Arora, M., "Cell Culture Media: A Review," *Mater. Methods.* 2013;3:175. doi.org/10.13070/mm.en.3.175. (Year: 2013).*

Ataie, N., et al., "Structure of a TCR-Mimic Antibody with Target Predicts Pharmacogenetics," *Journal of Molecular Biology* 428(1):194-205, Elsevier, Netherlands (published online Dec. 2015, published in print Jan. 2016).

Chang, A. Y., et al., "A therapeutic T cell receptor mimic antibody targets tumor-associated PRAME peptide/HLA-I antigens," *The Journal of Clinical Investigation* 127(7):2705-2718, American Society for Clinical Investigation, United States (Jun. 2017).

Dubrovsky, L., et al., "T cell receptor mimic antibodies for cancer therapy," *Oncoimmunology* 5(1):e1049803, Taylor & Francis, United States (Jun. 2015).

Dudley, M. E., et al., "CD8+ enriched "young" tumor infiltrating lymphocytes can mediate regression of metastatic melanoma," *Clinical Cancer Research* 16(24):6122-6131, (published online Jul. 2010, published in print Dec. 2010).

Eil, R., et al., "Ionic immune suppression within the tumour microenvironment limits T cell effector function," *Nature* 537(7621):539-543, Nature Publishing Group, United Kingdom (Sep. 2016).

Gattinoni, L., et al., "Acquisition of full effector function in vitro paradoxically impairs the in vivo antitumor efficacy of adoptively transferred CD8+ T cells," *Journal of Clinical Investigation* 115(6):1616-1626, American Society for Clinical Investigation, United States (Jun. 2005).

Gattinoni, L., et al., "Wnt signaling arrests effector T cell differentiation and generates CD8+ memory stem cells," *Nature Medicine* 15(7):808-813, Nature Publishing Company, United States (published online Jun. 2009, published in print Jul. 2009).

Gattinoni, L., et al., "A human memory T cell subset with stem cell-like properties," *Nature Medicine* 17(10):1290-1297, Nature Publishing Company, United States (Sep. 2011).

Gattinoni, L., et al., "Paths to stemness: building the ultimate antitumour T cell," *Nature Reviews Cancer* 12(10):671-684, Nature Publishing Group, United Kingdom (published online Sep. 2012, published in print Oct. 2012).

Hinrichs, C. S., et al., "IL-2 and IL-21 confer opposing differentiation programs to CD8+ T cells for adoptive immunotherapy," *Blood* 111(11):5326-5333, Elsevier, United States (published online Feb. 2008, published in print Jun. 2008).

Kurosawa, N., et al., "High throughput development of TCR-mimic antibody that targets survivin-2B 80-88/HLA-A*A24 and its application in a bispecific T-cell engager," *Scientific Reports* 9(1):9827, Nature Publishing Group, United Kingdom (Jul. 2019).

Lynn, R. C., et al., "c-Jun overexpression in Car T cells induces exhaustion resistance," *Nature* 576(7786):293-300, Nature Publishing Group, United Kingdom (Dec. 2019).

Moore, G. E., et al., "Culture of normal human leukocytes," *Journal of the American Medical Association* 199(8):519-524, American Medical Association, United States (Feb. 1967).

Peterson, C. T., et al., "Improving T-cell expansion and function for adoptive T-cell therapy using ex vivo treatment with PI3K8 inhibitors and VIP antagonists," *Blood Advances* 2(3):210-223, American Society of Hematology, United States (Feb. 2018).

Rosenberg, S. A., et al., "Durable complete responses in heavily pretreated patients with metastatic melanoma using T-cell transfer immunotherapy," *Clinical Cancer Research* 17(13):4550-4557, American Association for Cancer Research, United States (published online Apr. 2011, published in print Jul. 2011).

Trebak, M., and Kinet, J-P., "Calcium signalling in T cells," *Nature Reviews Immunology* 19(3):154-169, Nature Publishing Group, United Kingdom (Mar. 2019).

Trenevska, I., et al., "Therapeutic Antibodies against Intracellular Tumor Antigens," *Frontiers in Immunology* 8:1001, Frontiers Research Foundation, Switzerland (Aug. 2017).

UniProtKB, "P13232 (IL7_HUMAN)," Accession No. P13232, accessed at https://www.uniprot.org/uniprot/P13232, accessed on Jul. 1, 2021, 9 pages.

(56) References Cited

OTHER PUBLICATIONS

UniProtKB, "P40933 (IL15_HUMAN)," Accession No. P40933, accessed at https://www.uniprot.org/uniprot/P40933, accessed on Jul. 1, 2021, 9 pages.
UniProtKB"P60568 (IL2_HUMAN)," Accession No. P60568, accessed at https://www.uniprot.org/uniprot/P60568, accessed on Jul. 1, 2021, 10 pages.
UniProtKB, "Q9HBE4 (IL21_HUMAN)," Accession No. Q9HBE4, accessed at https://www.uniprot.org/uniprot/Q9HBE4, accessed on Jul. 1, 2021, 9 pages.
Verkhratsky et al, "Crosslink between calcium and sodium signaling," *Experimental Physiology* 103:157-69, Wiley-Blackwell on behalf of The Physiological Society, United Kingdom (published online Jan. 2018, published in print Feb. 2018).
Vodnala, S. K., et al., "T cell stemness and dysfunction in tumors are triggered by a common mechanism," *Science* 363(6434):eaau0135, American Association for the Advancement of Science, United States (Mar. 2019).
Waldmann, T. A., "The biology of interleukin-2 and interleukin-15: implications for cancer therapy and vaccine design," *Nature Reviews Immunology* 6(8):595-601, Nature Publishing Group, United Kingdom (Aug. 2006).
Wang, Y., et al., "Phosphorylated α-synuclein in Parkinson's disease," *Science Translational Medicine* 4(121):121ra20, American Association for the Advancement of Science, United States (Feb. 2012).
Xu, Y., et al., "A novel antibody-TCR (AbTCR) platform combines Fab-based antigen recognition with gamma/delta-TCR signaling to facilitate T-cell cytotoxicity with low cytokine release," *Cell Discovery* 4:62, Nature Publishing Group, United Kingdom (Nov. 2018).
Eil, R., et al., "Extracellular ion gradients limit intratumoral T cell differentiation through functional caloric restriction," Poster, Keystone Symposia, National Cancer Institute, United States (Oct. 2018).
Alves, N. L., et al., "IL-21 sustains CD28 expression on IL-15-activated human naive CD8+ T cells," *J Immunology* 175(2):755-762, Lippincott Williams and Wilkins Ltd. on behalf of The American Association of Immunologists, Inc., United States (Jul. 2005).
Battaglia, A., "Interleukin-21 (IL-21) synergizes with IL-2 to enhance T-cell receptor-induced human T-cell proliferation and counteracts IL-2/transforming growth factor-β-induced regulatory T-cell development," *Immunology* 139(1):109-120, Blackwell Publishing Ltd., on behalf of the British Society for Immunology, United Kingdom (May 2013).
Bedognetti, D., et al., "CXCR3/CCR5 pathways in metastatic melanoma patients treated with adoptive therapy and interleukin-2," *British Journal of Cancer* 109(9):2412-2423, Nature Publishing Group, United Kingdom (Oct. 2013).
Berman, D., et al., "The development of immunomodulatory monoclonal antibodies as a new therapeutic modality for cancer: the Bristol-Myers Squibb experience," *Pharmacology & Therapeutics* 148:132-153, Elsevier Inc., Netherlands (published online Dec. 2014, published in print Apr. 2015).
Besser, M. J., et al., "Clinical responses in a phase II study using adoptive transfer of short-term cultured tumor infiltration lymphocytes in metastatic melanoma patients," *Clinical Cancer Research* 16(9):2646-2655, American Association for Cancer Research, United States (published online Apr. 2010, published in print May 2010).
Crompton, J. G., et al., "Akt inhibition enhances expansion of potent tumor-specific lymphocytes with memory cell characteristics," *Cancer Research* 75(2):296-305, American Association for Cancer Research, United States (Nov. 2014).
Deniger, D. C., "T-Cell Treatments For Solid And Hematological Tumors," The University of Texas MD Anderson Cancer Center UTHealth Graduate School of Biomedical Sciences Dissertations and Theses (Open Access), #377, accessed at URL:[https://digitalcommons.library.tmc.edu/utgsbs_dissertations/377] on Aug. 26, 2021, 310 pages (Aug. 2013).

Dudley, M. E., et al., "Generation of tumor-infiltrating lymphocyte cultures for use in adoptive transfer therapy for melanoma patients," *Journal of Immunotherapy* 26(4):332-342, Lippincott Williams and Wilkins Ltd. on behalf of The American Association of Immunologists, Inc., United States (Jul.-Aug. 2003).
Dudley, M. E., and Rosenberg, S. A., "Adoptive cell transfer therapy," *Seminars in Oncology* 34(6):524-531, W.B. Saunders Ltd., United Kingdom (Dec. 2007).
Feucht, J., et al., "Adoptive T-cell therapy with hexon-specific Th1 cells as a treatment of refractory adenovirus infection after HSCT," *Blood* 125(12):1986-1994, The American Society of Hematology, United States (Mar. 2015).
Forget, M-A., et al., "The beneficial effects of a gas-permeable flask for expansion of Tumor-Infiltrating lymphocytes as reflected in their mitochondrial function and respiration capacity," *Oncoimmunology* 5(2):e1057386, Landes Bioscience, United States (Jun. 2015).
Forget, M-A., et al., "A novel method to generate and expand clinical-grade, genetically modified, tumor-infiltrating lymphocytes," *Frontiers in Immunology* 8:908, 8 pages, Frontiers Media S.A., Switzerland (Aug. 2017).
Frumento, G., et al., "CD117 (c-Kit) Is Expressed During CD8 + T Cell Priming and Stratifies Sensitivity to Apoptosis According to Strength of TCR Engagement," *Frontiers in Immunology* 10:468, 13 pages, Frontiers Media S.A., Switzerland (Mar. 2019).
Fujisaki, H., et al., "Expansion of highly cytotoxic human natural killer cells for cancer cell therapy," *Cancer Res* 69(9):4010-4017, American Association for Cancer Research, United States (published online Apr. 2009, published in print May 2009).
Heemskerk, B., et al., "Adoptive cell therapy for patients with melanoma, using tumor-infiltrating lymphocytes genetically engineered to secrete interleukin-2," *Hum Gene Ther* 19(5):496-510, Mary Ann Liebert, Inc., United States (May 2008).
Hernandez-Chacon, J. A., et al., "Co-stimulation through the CD137/4-1BB pathway protects human melanoma tumor-infiltrating lymphocytes from activation-induced cell death and enhances antitumor effector function," *J Immunother* 34(3):236-250, Lippincott Williams and Wilkins Ltd. on behalf of The American Association of Immunologists, Inc., United States (Apr. 2011).
Hoepner, S., et al., "Synergy between CD8 T cells and Th1 or Th2 polarised CD4 T cells for adoptive immunotherapy of brain tumours," *PLoS One* 8(5):363933, 9 pages, Public Library of Science, United States (May 2013).
Houot, R., et al., "T-cell-based Immunotherapy: Adoptive Cell Transfer and Checkpoint Inhibition," *Cancer Immunology Research* 3(10):1115-1122, American Association for Cancer Research, United States (Oct. 2015).
Huarte, E., et al., "Ex vivo expansion of tumor specific lymphocytes with IL-15 and IL-21 for adoptive immunotherapy in melanoma," *Cancer Letters* 285(1):80-88, Elsevier Ireland Ltd., Ireland (published online Jun. 2009, published in print Nov. 2009).
Ikarashi, H., et al., "Solid-phase anti-CD3 antibody activation and cryopreservation of human tumor-infiltrating lymphocytes derived from epithelial ovarian cancer," *Japanese Journal of Cancer Research GANN* 83(12):1359-1365, Japanese Cancer Association, Japan (Dec. 1992).
Kim, C. H., et al., "Rules of chemokine receptor association with T cell polarization in vivo," *The Journal of Clinical Investigation* 108(9):1331-1339, The American Society for Clinical Investigation, United States (Nov. 2001).
Klebanoff, C. A., et al., "Sorting through subsets: which T-cell populations mediate highly effective adoptive immunotherapy?" *J Immunother* 35(9):651-660, Lippincott Williams and Wilkins Ltd. on behalf of The American Association of Immunologists, Inc., United States (Nov.-Dec. 2012).
Krishna, S., et al., "Stem-like CD8 T cells mediate response of adoptive cell immunotherapy against human cancer," *Science* 370(6522):1328-1334, 7 pages, American Association for the Advancement of Science, United States (Dec. 2020).
Li, Y., et al., "IL-21 influences the frequency, phenotype, and affinity of the antigen-specific CD8 T cell response," *J Immunol* 175(4):2261-2269, Lippincott Williams and Wilkins Ltd. on behalf of The American Association of Immunologists, Inc., United States (Aug. 2005).

(56) References Cited

OTHER PUBLICATIONS

Li, X., et al., "Efficient Treg depletion induces T-cell infiltration and rejection of large tumors," *European Journal of Immunology* 40(12):3325-3335, Wiley-VCH Verlag, Germany (Dec. 2010).

Li, Y., et al., "MART-1-specific melanoma tumor-infiltrating lymphocytes maintaining CD28 expression have improved survival and expansion capability following antigenic restimulation in vitro," *J Immunol* 184(1):452-465, Lippincott Williams and Wilkins Ltd. on behalf of The American Association of Immunologists, Inc., United States (published online Nov. 2009, published in print Jan. 2010).

Lim, D-P., et al., "Effect of exposure to interleukin-21 at various time points on human natural killer cell culture," *Cytotherapy* 16(10):1419-1430, Elsevier, Netherlands (published online Jun. 2014, published in print Oct. 2014).

Liu, S., et al., "Comparison of common gamma-chain cytokines, interleukin-2, interleukin-7, and interleukin-15 for the in vitro generation of human tumor-reactive T lymphocytes for adoptive cell transfer therapy," *J Immunother* 29(3):284-293, Lippincott Williams and Wilkins Ltd. on behalf of The American Association of Immunologists, Inc., United States (May/Jun. 2006).

Markel, G., et al., "Preclinical evaluation of adoptive cell therapy for patients with metastatic renal cell carcinoma," *Anticancer Research* 29(1):145-154, International Institute of Anticancer Research, Greece (Jan. 2009).

Markley, J. C., and Sadelain, M., "IL-7 and IL-21 are superior to IL-2 and IL-15 in promoting human T cell-mediated rejection of systemic lymphoma in immunodeficient mice," *Blood* 115(17):3508-3519, American Society of Hematology, United States (Apr. 2010).

Meng, Q., et al., "Generation of tumor-infiltrating lymphocytes from pancreatic cancer lesions for cellular therapy," *Journal for ImmunoTherapy of Cancer* 2(Suppl 3):P26, BioMed Central Ltd., United Kingdom (Nov. 2014).

Meraviglia, S., et al., "Vγ9Vδ2 T cells as a promising innovative tool for immunotherapy of hematologic malignancies," *Oncology Reviews* 4:211-218, Springer Nature AG, Switzerland (Jun. 2010).

Moon, E. K., et al., "Blockade of Programmed Death 1 Augments the Ability of Human T Cells Engineered to Target NY-ESO-1 to Control Tumor Growth after Adoptive Transfer," *Clinical Cancer Research* 22(2):436-447, American Association for Cancer Research, United States (published online Aug. 2015, published in print Jan. 2016).

Moroz, A., et al., "IL-21 enhances and sustains CD8+ T cell responses to achieve durable tumor immunity: comparative evaluation of IL-2, IL-15, and IL-21," *J Immunol* 173(2):900-909, Lippincott Williams and Wilkins Ltd. on behalf of The American Association of Immunologists, Inc., United States (Jul. 2004).

Nguyen, L. T., et al., "Expansion and characterization of human melanoma tumor-infiltrating lymphocytes (TILs)," *PLoS One* 5(11):e13940, Public Library of Science, United States (Nov. 2010).

Nicol, A. J., et al., "Clinical evaluation of autologous gamma delta T cell-based immunotherapy for metastatic solid tumours," *British Journal of Cancer* 105(6):778-786, Nature Publishing Group, United Kingdom (published online Aug. 2011, published in print Sep. 2011).

Park, Y-K., et al., "Interleukin-21 increases direct cytotoxicity and IFN-γ production of ex vivo expanded NK cells towards breast cancer cells," *Anticancer Research* 32(3):839-846, International Institute of Anticancer Research, Greece (Mar. 2012).

Parrish-Novak, J., et al., "Interleukin 21 and its receptor are involved in NK cell expansion and regulation of lymphocyte function," *Nature* 408(6808):57-63, Nature Publishing Group, United Kingdom (Nov. 2000).

Priority Document of PCT/EP2015/063107, DE201410211167, filed Jun. 11, 2014, 23 pages.

Rosenberg, S. A., et al., "Use of tumor-infiltrating lymphocytes and interleukin-2 in the immunotherapy of patients with metastatic melanoma," *The New England Journal of Medicine* 319(25):1676-1680, Massachusetts Medical Society, United States (Dec. 1988).

Rosenberg, S. A., et al., "Treatment of patients with metastatic melanoma with autologous tumor-infiltrating lymphocytes and interleukin 2," *J Natl Cancer Inst* 86(15):1159-1166, Oxford University Press, United Kingdom (Aug. 1994).

Rosenberg, S. A., and Dudley, M. E., "Cancer regression in patients with metastatic melanoma after the transfer of autologous antitumor lymphocytes," *Proc Natl Acad Sci US-A* 101(Suppl 2):14639-14645, National Academy of Science, United States (published online Sep. 2004, published in print Oct. 2004).

Sade-Feldman, M., et al., "Defining T cell states associated with response to checkpoint immunotherapy in melanoma," *Cell* 175:998-1013, Cell Press, United States (Nov. 2018).

Sadeghi, A., et al., "Rapid expansion of T cells: Effects of culture and cryopreservation and importance of short-term cell recovery," *Acta Oncologica* 52(5):978-986, Informa Healthcare, United Kingdom (published online Nov. 2012, published in print Jun. 2013).

Santegoets, S. J. A. M., et al., "IL-21 promotes the expansion of CD27+ CD28+ tumor infiltrating lymphocytes with high cytotoxic potential and low collateral expansion of regulatory T cells," *Journal of Translational Medicine* 11(1):37, BioMed Central Ltd., United Kingdom (Feb. 2013).

Turcotte, S., et al., "Tumor-reactive CD8+ T cells in Metastatic Gastrointestinal Cancer Refractory to Chemotherapy," *Clinical Cancer Research* 20(2):331-343, American Association for Cancer Research, United States (Nov. 2013).

Turcotte, S., et al., "Phenotype and function of T cells infiltrating visceral metastases from gastrointestinal cancers and melanoma: implications for adoptive cell transfer therapy," *The Journal of Immunology* 191(5):2217-2225, Lippincott Williams and Wilkins Ltd., on behalf of The American Association of Immunologists, Inc., United States (published online Jul. 2013, published in print Sep. 2013).

Veatch, J. R., et al., "Tumor-infiltrating BRAFV600E-specific CD4+ T cells correlated with complete clinical response in melanoma," *Journal of Clinical Investigation* 128(4):1563-1568, The American Society for Clinical Investigation, United States (Apr. 2018).

Wei, C., et al., "The CIK cells stimulated with combination of IL-2 and IL-15 provide an improved cytotoxic capacity against human lung adenocarcinoma," *Tumor Biol* 35(3):1997-2007, International Society of Oncology and Biomarkers, SAGE Publications, United States (published online Oct. 2013, published in print Mar. 2014).

Wilson Wolf Manufacturing Corporation, "G-Rex Instructions for Use," WilsonWolf.com, accessed at URL:[https://www.wilsonwolf.com/wp-content/uploads/2016/11/G-Rex-Instructions-Guide.pdf] on Aug. 27, 2021, 19 pages (Nov. 2016).

Wilson Wolf Manufacturing Corporation, "G-Rex™ Brochure," WilsonWolf.com, accessed at URL:[https://www.wilsonwolf.com/wp-content/uploads/2016/11/G-Rex-Brochure.pdf] on Aug. 27, 2021, 2 pages (Oct. 31, 2016).

Wilson Wolf Manufacturing Corporation, "Quick Guide to G-Rex Optimization," WilsonWolf.com, accessed at URL:[https://www.wilsonwolf.com/wp-content/uploads/2016/11/Quick-Guide-to-G-Rex-Optimization.pdf] on Aug. 27, 2021, 4 pages (Oct. 31, 2016).

Zeng, R., et al., "Synergy of IL-21 and IL-15 in regulating CD8+ T cell expansion and function," *The Journal of Experimental Medicine* 201(1):139-148, Rockefeller University Press, United States (Jan. 2005).

Zhou, J., et al., "Characterization of T-cell memory phenotype after in vitro expansion of tumor-infiltrating lymphocytes from melanoma patients," *Anticancer Research* 31(12):4099-4109, International Institute of Anticancer Research, Greece (Dec. 2011).

Itzhaki, O., et al., "Establishment and large-scale expansion of minimally cultured 'young' tumor infiltrating lymphocytes for adoptive transfer therapy," *J. Immunother.* 34:212-20, Lippincott Williams and Wilkins Ltd., United States (Mar. 2011).

Chacon, J. A., "Activating the 4-1BB pathway for the expansion of tumor-infiltrating lymphocytes for adoptive T-cell therapy for metastatic melanoma patients," *The University of Texas MD Anderson Cancer Center UTHealth Graduate School of Biomedical Sciences and Theses (Open Access).* 442 (2014), available at URL:[https://digitalcommons.library.tmc.edu/utgsbs_dissertations/442], 262 pages.

Bajgain, P., et al., "Optimizing the production of suspension cells using the G-Rex 'M' series," *Mol. Therap.—Methods & Clinical Development* 1:14015, Cell Press, United States (May 2014).

(56) References Cited

OTHER PUBLICATIONS

Goff, S. L., et al., "Tumor infiltrating lymphocyte therapy for metastatic melanoma: analysis of tumors resected form TIL," *J. Immunother.* 33(8):840-47, Lippincott Williams and Wilkins Ltd., United States (2010).

Jin, J., et al., "Simplified method of the growth of human tumor infiltrating lymphocytes in Gas-permeable flasks to numbers needed for patient treatment," *J. Immunother.* 35:283-92, Lippincott Williams and Wilkins Ltd., United States (2012).

Lee, S., and Margolin, K., "Tumor-infiltrating lymphocytes in melanoma," *Curr. Oncol. Rep.* 14(5):468-74, Current Science, Inc., United States (2012).

Tran, K. Q., et al., "Minimally cultured tumor-infiltrating lymphocytes display optimal characteristics for adoptive cell therapy," *J. Immunother.* 31(8):742-51, Lippincott Williams and Wilkins Ltd., United States (2008).

Wu, R., et al., "Adoptive T-cell therapy using autologous tumor-infiltrating lymphocytes for metastatic melanoma: current status and future outlook," *Cancer J.* 18(2):160-75, Lippincott Williams and Wilkins Ltd., United States (2012).

Riddell, S. R., et al., "Restoration of viral immunity in immunodeficient humans by the adoptive transfer of T cell clones," *Science* 257:238-41, American Association for the Advancement of Science, United States (1992).

International Search Report and Written Opinion for International Application No. PCT/US2021/029762, mailed Jul. 12, 2021, European Patent Office, Netherlands, 10 pages.

Vodnala, S.K., et al., "T cell stemness and dysfunction in tumors are triggered by a common mechanism—Supplementary Materials," Science 363, accessed at https://science.sciencemag.org/content/sci/suppl/2019/03/27/363.6434.eaau0135.DC1/aau0135_vodnala_SM.pdf, 41 pages, published Mar. 29, 2019.

International Search Report and Written Opinion for International Application No. PCT/US2022/078827, mailed Apr. 13, 2023, European Patent Office, Netherlands, 20 pages.

Han, J., et al., "Memory CD8+ T cell responses to cancer," Seminars in Immunology 49:101435, Elsevier, Netherlands (Nov. 30, 2020).

Franco, F., et al., "Metabolic and epigenetic regulation of T-cell exhaustion," Nature Metabolism 2(10):1001-1012, Nature Publishing Group, United Kingdom (Oct. 2020).

Xu, Y., et al., "Closely related T-memory stem cells correlate with in vivo expansion of CAR.CD19-T cells and are preserved by IL-7 and IL-15," Blood 123(24):3750-3759, American Society of Hematology, United States (Apr. 2014).

Sommermeyer, D., et al., "Chimeric antigen receptor-modified T cells derived from defined CD8+ and CD4+ subsets confer superior antitumor reactivity in vivo," Leukemia 30:492-500, Nature Publishing Group, United Kingdom (2016).

Cartellieri, M., et al., "Chimeric Antigen Receptor-Engineered T Cells for Immunotherapy of Cancer," J. Biomedicine and Biotechnology 2010:1-13, Hindawi Publishers, United Arab Emirates (2010).

Bleakley, M., et al., "Exploiting T cells specific for human minor histocompatibility antigens for therapy of leukemia," Immunology and Cell Biology 89:396-407, Wiley, United States (2011).

June, C.H., "Principles of adoptive T cell cancer therapy," J. Clin. Invest. 117(5):1204-1212, American Society of Clinical Investigation, United States (2007).

Berger, C., et al., "Adoptive transfer of effector CD8+ T cells derived from central memory cells establishes persistent T cell memory in primates," J. Clin. Invest. 118:294-305, American Society of Clinical Investigation, United States (2008).

Levite, M., et al., "Extracellular K + and Opening of Voltage-gated Potassium Channels Activate T Cell Integrin Function: Physical and Functional Association between Kv1.3 Channels and b1 Integrins," J. Exp. Med. 191(7):1167-1176, Rockefeller University Press, United States (2000).

Sadeghi, A., et al., "Large-Scale Bioreactor Expansion of Tumor-Infiltrating Lymphocytes," J Immunol Methods. 364(1-2):94-100, Elsevier, The Netherlands (Feb. 2011).

RPMI-1640 Medium Data Sheet, Sigma-Aldrich, 2 pages (2024).

Final Office Action mailed Jul. 25, 2024, in U.S. Appl. No. 17/456,374, Vodnala, S., et al., filed Nov. 23, 2021, 11 pages.

Donia, M., et al., "Characterization and comparison of 'standard' and 'young' tumour-infiltrating lymphocytes for adoptive cell therapy at a Danish translational research institution," Scand. J. Immunol. 75(2):157-167, Wiley, United Kingdom (Feb. 2012).

Dudley, M.E., et al., "Cancer regression and autoimmunity in patients after clonal repopulation with antitumor lymphocytes," Science. 298(5594):850-854, NIH, United States (Oct. 2002).

Dudley, M.E., et al., "Adoptive cell therapy for patients with metastatic melanoma: evaluation of intensive myeloablative chemoradiation preparative regimens," J. Clin. Oncol. 26(32):5233-5239, American Society of Clinical Oncology, United States (Nov. 2008).

Dudley, M.E., et al., "Adoptive cell transfer therapy following non-myeloablative but lymphodepleting chemotherapy for the treatment of patients with refractory metastatic melanoma," J. Clin. Oncol. 23(10):2346-2357, NIH, United States (Apr. 2005).

Dudley, M.E., and Rosenberg, S.A., "Adoptive-cell-transfer therapy for the treatment of patients with cancer," Nat. Rev. Cancer 3(9):666-665, NIH, United States (Sep. 2003).

Emerson, R.O., et al., "High-throughput sequencing of T-cell receptors reveals a homogeneous repertoire of tumour-infiltrating lymphocytes in ovarian cancer," J. Pathol. 231(4):433-440, Wiley, United Kingdom (Dec. 2013).

Galletti, G., et al., "Two subsets of stem-like CD8+ memory T cell progenitors with distinct fate commitments in humans," Nat Immunol. 21(21):1552-1562, Nature Publishing Group, United Kingdom (Oct. 2020).

Gattinoni, L., et al., "Adoptive immunotherapy for cancer: building on success," Nature Publishing Group 6(5):383-393, United Kingdom (May 2006).

Geltink, R., et al., "Mitochondrial Priming by CD28," Cell. 171(2):385-397, Cell Press, United States (Oct. 2017).

Goda, C., et al., "Involvement of IL-32 in activation-induced cell death in T cells," Int. Immunol. 18(2):233-240, The Japanese Society for Immunology, Japan (Feb. 2006).

Gros, A., et al., "PD-1 identifies the patient-specific CD8+ tumor-reactive repertoire infiltrating human tumors," J. Clin. Investi. 124(5):2246059, American Society for Clinical Investigation, United States (May 2014).

Guidance for Industry, "Sterile Drug products Produced by Aseptic Processing—Current Good Manufacturing Practice," Pharmaceutical CGMPs (Sep. 2004).

Hinrichs. C.S., and Rosenberg, S., "Exploiting the curative potential of adoptive T-cell therapy for cancer," Immunol. Rev. 257(1):56-71, Wiley, United Kingdom (Jan. 2014).

Huang, J., et al., "Modulation by IL-2 of CD70 and CD27 expression on CD8+ T cells: importance for the therapeutic effectiveness of cell transfer immunotherapy," J. Immunol. 176(12):7726-7735, NIH, United States (Jun. 2006).

Im, S.J., et al., "Defining CD8+ T cells that provide the proliferative burst after PD-1 therapy," Nature. 537(7620):417-421, Nature Publishing Group, United Kingdom (Sep. 2016).

International Preliminary Report on Patentability for International Application No. PCT/US2021/060667, The International Bureau of WIPO, mailed on Nov. 23, 2021, 8 pages.

International Search Report and Written Opinion for International Application No. PCT/US2022/017774, European Patent Office, Netherlands, mailed on Jun. 9, 2022, 10 pages.

Johnnidis, J., et al., "Inhibitory signaling sustains a distinct early memory CD8+ T cell precursor that is resistant to DNA damage," Sci. Immunol. 6(55):eabe3702, American Association for the Advancement of Science, United States (Jan. 2021).

Kaech, S.M., et al., "Molecular and Functional Profiling of Memory CD8 T Cell Differentiation," Cell. 111:837-851, Cell Press, United States (Dec. 2002).

Kaiser, A.D., et al., "Towards a commercial process for the manufacture of genetically modified T cells for therapy," Cancer Gene Ther. 22(2):71-78, Nature Publishing Group, United Kingdom (Mar. 2015).

(56) References Cited

OTHER PUBLICATIONS

Lu, T.L., et al., "A Rapid Cell Expansion Process for Production of Engineered Autologous CAR-T Cell Therapies," Hum Gene Ther. Methods. 27(6):208-218, Mary Ann Liebert Inc., United States (Dec. 2016).

Malarkannan, S., "NKG7 makes a better killer," Nat. Immunol. 21(10):1139-1140, Nature Publishing Group, United Kingdom (Aug. 2020).

Klebanoff, C.A., et al., "Inhibition of AKT signaling uncouples T cell differentiation form expansion for receptor-engineered adoptive immunotherapy," JCI Insight 2(23):e95103 (Dec. 7, 2017).

Office Action mailed Dec. 8, 2023, in United States U.S. Appl. No. 17/456,374, Vodnala, F., et al., filed Nov. 23, 2021, 14 pages.

Poch, M., et al., "Expansion of tumor infiltrating lymphocytes (TIL) from bladder cancer," Oncoimmunology. 7(9):e1476816, Taylor & Francis Group, United States (Jul. 2018).

Poschke, I., et al., "Identification of a tumor-reactive T-cell repertoire in the immune infiltrate of patients with resectable pancreatic ductal adenocarcinoma," Oncoimmunology. 5(12):e1240859, Taylor & Francis Group, United States (Oct. 2016).

Poschke, I.C., et al., "The Outcome of Ex Vivo TIL Expansion Is Highly Influenced by Spatial Heterogeneity of the Tumor T-Cell Repertoire and Differences in Intrinsic In Vitro Growth Capacity between T-Cell Clones," Clin. Cancer Res. 26(16):4289-4301, American Association Cancer Research, United States (Aug. 2020).

Restifo, N.P., et al., "Adoptive immunotherapy for cancer: harnessing the T cell response," Nat. Rev. Immunol. 12(4):269-281, NIH, United States (Mar. 2012).

Rosenberg, S.A., et al.: "A New Approach to the Adoptive Immunotherapy of Cancer with Tumor-Infiltrating Lymphocytes," Science. 19(233):1318-1321 (Sep. 1986).

Rosenberg, S.A., and Dudley, M.E., "Adoptive cell therapy for the treatment of patients with metastatic melanoma," Curr. Opin. Immunol. 21(2):233-240, Elsevier, Netherlands (Apr. 2009).

Rosenberg, S.A., et al., "Adoptive cell transfer: a clinical path to effective cancer immunotherapy," Nat. Rev. Cancer. 8(4):299-308, Nature Publishing Group, United Kingdom (Apr. 2008).

Rosenberg, S.A., et al., "Adoptive cell transfer as personalized immunotherapy for human cancer," Science. 348(6230):62-68, American Association for the Advancement of Science, United States (Apr. 2015).

Sarnaik, A,A., et al., "Lifileucel, a Tumor-Infiltrating Lymphocyte Therapy, in Metastatic Melanoma," J. Clin. Oncol. 39(34):2656;2666, American Society of Clinical Oncology, United States (May 2021).

Shapiro, L., and Dinarello, C.A., "Osmotic regulation of cytokine synthesis in vitro," Proc. Natl. Acad. Sci. U.S.A. 92(26):12230-12234, National Academy of Science, United States (Dec. 1995).

Spiess, P. J., et al., "In Vivo Antitumor Activity of Tumor-Infiltrating Lymphocytes Expanded in Recombinant Interleukin-2," J. Natl. Cancer Inst. 79(5):1067-1075, NIH, United States (Nov. 1987).

Ye, Q., et al., "Engineered artificial antigen presenting cells facilitate direct and efficient expansion of tumor infiltrating lymphocytes" J. Transl. Med. 9:131, BioMed Central, United Kingdom (Aug. 2011).

Suhoski, M., et al., "Engineering artificial antigen-presenting cells to express a diverse array of co-stimulatory molecules," Mol. Ther. 15(5):981-988, Cell Press, United States (May 2007).

Sznol, M., "TIL in Melanoma-Similar Approaches, Different Results, Unanswered Questions," Clin. Cancer Res. 27(19):5156-5157, American Association Cancer Research, United States (Oct. 2021).

Tripathi, P., et al., "STAT5 Is Critical To Maintain Effector CD8+ T Cell Responses," J. Immunol. 185:2116-2142, American Association of Immunologists, United States (Aug. 2010).

Venturi, V., et al., "Methods for comparing the diversity of samples of the T cell receptor repertoire," J. Immunol. Methods. 321(1-2):182-195, Elsevier, Netherlands (Apr. 2007).

Wang, X., and Riviere, I., "Clinical manufacturing of CAR T cells: foundation of a promising therapy," Mol. Ther. Oncolytics. 3:16015, Cell Press, United States (Jun. 2016).

Wang, X., and Riviere, I., "Manufacture of tumor- and virus-specific T lymphocytes for adoptive cell therapies," Cancer Gene Therapy. 22:85-94, Nature, United States (Mar. 2015).

Wilson Wolf-Superior Cell Culture Devices, G-Rex, Oct. 31, 2016.

Woods, E.J., et al., "Off the shelf cellular therapeutics: Factors to consider during cryopreservation and storage of human cells for clinical use," Cytotherapy. 18(6);697-711, Elsevier, Netherlands (Jun. 2016).

\* cited by examiner

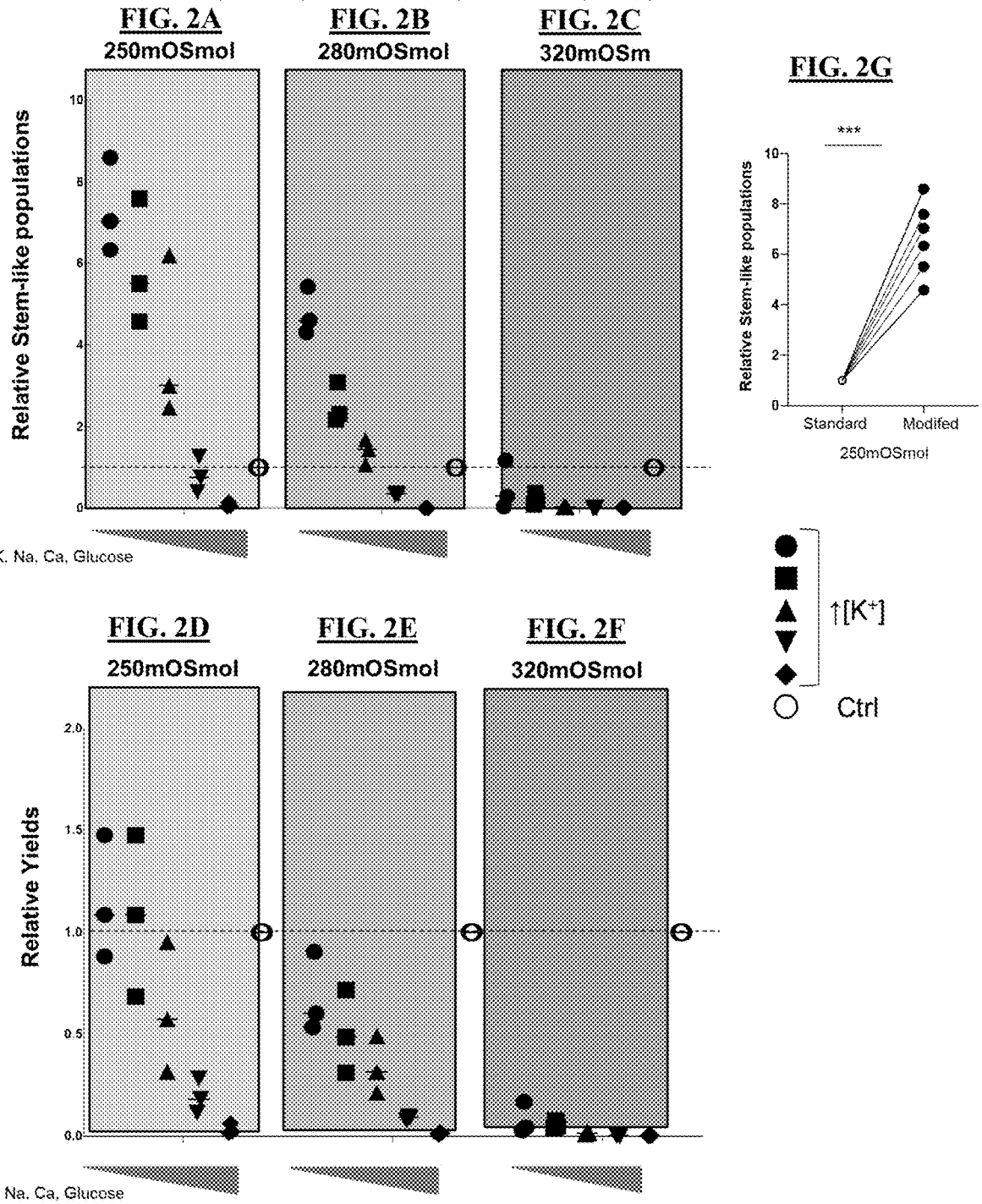

METHODS FOR CULTURING CELLS

CROSS-REFERENCE TO RELATED APPLICATIONS

This application claims priority to and benefit of U.S. Provisional Application No. 63/016,907, filed on Apr. 28, 2020, which is hereby incorporated by reference herein in its entirety.

FIELD

The present disclosure relates to methods of culturing cells, e.g., pluripotent, multipotent, and/or immune cells (e.g., T cells, NK cells, and/or TILs). In some aspects, the methods disclosed herein promote enrichment of less-differentiated cells and/or undifferentiated cells in culture. Cells cultured using the methods disclosed herein can be used for various cell therapies, including but not limited to chimeric antigen receptor (CAR) T cell therapy and TCR T cell therapy including neoantigen directed-T cell therapies.

BACKGROUND

Cancer immunotherapy relies on harnessing T cells—the immune system's primary killers of infected and diseased cells—to attack and kill tumor cells. However, there is an important stumbling block for immunotherapy: T cells' ability to kill can fade, a phenomenon often referred to as exhaustion or terminal differentiation of T cells. Immune checkpoint blockade, ex vivo-expanded Tumor-Infiltrating Lymphocytes (TILs) therapy, chimeric antigen receptor (CAR) T cell therapy, and T cell receptor-engineered (TCR) T cell therapy are treatments that make use of functionally active T cells isolated from patients and require highly functional T cells in order to be effective. These T cells are engineered and expanded ex vivo to recognize antigens on target cancer cells. T cell therapies have not been consistently effective at curing solid cancers, in part because the T cells lose their ability to proliferate or kill over time.

One means of overcoming T cell exhaustion is to selectively administer T cells having a less-differentiated state. For example, T memory stem cells ($T_{SCM}$) persist for a greater period in patients following administration than do more differentiated T central memory ($T_{CM}$) or T effector memory ($T_{EM}$) cells, and $T_{SCM}$ elicit a more pronounced and prolonged effect on tumor size than more differentiated cells. However, there remains a need in the art for methods of efficiently enriching for less differentiated and/or naïve T cells from a mixed population of isolated T cells.

BRIEF SUMMARY

Certain aspects of the present disclosure are directed to a method of culturing immune cells and/or stem cells ex vivo or in vitro comprising placing immune cells and/or stem cells in a medium comprising potassium ion at a concentration higher than 40 mM, wherein the medium is not hypertonic. Certain aspects of the present disclosure are directed to a method of preparing a population of immune cells and/or stem cells comprising placing immune cells and/or stem cells into a medium comprising potassium ion at a concentration higher than 40 mM, wherein the medium is not hypertonic.

In some aspects, the medium further comprises one or more cytokines. In some aspects, the one or more cytokines comprise Interleukin-2 (IL-2), Interleukin-21 (IL-21), Interleukin-15 (IL-15), Interleukin-7 (IL-7), or any combination thereof.

Certain aspects of the present disclosure are directed to a method of increasing a number or percentage of undifferentiated or less differentiated cells ex vivo or in vitro comprising culturing immune cells and/or stem cells in a medium comprising potassium ion at a concentration of higher than 40 mM, wherein the medium comprises IL-2, but does not comprise IL-7 and IL-15. In some aspects, the immune cells and/or stem cells after the culturing comprises a higher number and/or percentage of undifferentiated or less differentiated immune cells and/or stem cells compared to immune cells and/or stem cells that are cultured in a medium comprising IL-2, IL-7, and IL-15.

Certain aspects of the present disclosure are directed to a method of increasing a number and/or percentage of undifferentiated or less differentiated immune cells and/or stem cells ex vivo or in vitro comprising placing immune cells and/or stem cells in a medium comprising potassium ion at a concentration higher than 40 mM, wherein the medium comprises IL-7 and IL-21 or wherein the medium comprises IL-2, IL-7 and IL-15.

Certain aspects of the present disclosure are directed to a method of increasing a number or percentage of undifferentiated or less differentiated immune cells and/or stem cells ex vivo or in vitro comprising placing the immune cells and/or stem cells in a medium comprising potassium ion at a concentration higher than 40 mM, wherein the medium comprises IL-15 and IL-21.

In some aspects, the cells comprise immune cells. In some aspects, the immune cells comprise T cells, TILs, NK cells, TILs, Tregs, and any combination thereof. In some aspects, the cells comprise stem cells. In some aspects, the cells express chimeric antigen receptor (CAR). In some aspects, the cells express T cell receptor (TCR), which may be an engineered TCR. In some aspects, the medium is hypotonic. In some aspects, the medium further comprises sodium ion, e.g., NaCl, calcium ion, glucose, and/or any combination thereof.

In some aspects, the medium further comprises a cell expansion agent. In some aspects, the cell expansion agent comprises a GSK3B inhibitor, an ACLY inhibitor, a PI3K inhibitor, an AKT inhibitor, or any combination thereof. In some aspects, the PI3K inhibitor is selected from LY294002, pictilisib, CAL101, IC87114, and any combination thereof. In some aspects, the AKT inhibitor is selected from MK2206, A443654, AKTi-VIII, and any combination thereof. In some aspects, the medium is capable of: increasing the number and/or percentage of less differentiated and/or undifferentiated cells; increasing transduction efficiency; increasing stem-like immune cells; increasing in vivo viability; increasing cell potency; preventing cell exhaustion; or any combination thereof, e.g., in the final cell product as compared to the starting cell population.

In some aspects, the concentration of potassium ion is at least about 45 mM, at least about 50 mM, at least about 55 mM, at least about 60 mM, at least about 65 mM, at least about 70 mM, about 75 mM, about 80 mM, about 85 mM, about 90 mM, about 95 mM, or about 100 mM. In some aspects, the concentration of potassium ion is about 45 mM to about 110 mM, about 45 mM to about 100 mM, about 45 mM to about 90 mM, about 45 mM to about 80 mM, about 45 mM to about 70 mM, about 45 mM to about 60 mM, about 45 mM to about 50 mM, about 50 mM to about 110 mM, about 50 mM to about 100 mM, about 50 mM to about 90 mM, about 50 mM to about 80 mM, about 50 mM to about 70 mM, about 60 mM to about 110 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 110 mM, about 80 mM to about 100 mM, about 80 mM to about 90 mM, about 90 mM to about 110 mM, about 90 mM to about 100 mM, or about 100 mM to about 110 mM. In some aspects, the concentration of potassium ion is about 50 mM to about 90 mM. In some aspects, the concentration of potassium ion is about 50 mM to about 80 mM.

In some aspects, the medium has an osmolality lower than about 280 mOsm/L. In some aspects, the medium has an osmolality between about 100 mOsm/L to about 280 mOsm/L, about 125 mOsm/L to about 280 mOsm/L, about 150 mOsm/L to about 280 mOsm/L, about 175 mOsm/L to about 280 mOsm/L, about 200 mOsm/L to about 280 mOsm/L, about 210 mOsm/L to about 280 mOsm/L, about 220 mOsm/L to about 280 mOsm/L, about 225 mOsm/L to about 280 mOsm/L, about 230 mOsm/L to about 280 mOsm/L, about 235 mOsm/L to about 280 mOsm/L, about 240 mOsm/L to about 280 mOsm/L, about 245 mOsm/L to about 280 mOsm/L, about 250 mOsm/L to about 280 mOsm/L, about 255 mOsm/L to about 280 mOsm/L, about 260 mOsm/L to about 280 mOsm/L, about 265 mOsm/L to about 280 mOsm/L, about 270 mOsm/L to about 280 mOsm/L, or about 275 mOsm/L to about 280 mOsm/L. In some aspects, the medium has an osmolality of about 100 mOsm/L to about 280 mOsm/L, about 125 mOsm/L, about 150 mOsm/L, about 175 mOsm/L, about 200 mOsm/L, about 210 mOsm/L, about 220 mOsm/L, about 225 mOsm/L, about 230 mOsm/L, about 235 mOsm/L, about 240 mOsm/L, about 245 mOsm/L, about 250 mOsm/L, about 255 mOsm/L, about 260 mOsm/L, about 265 mOsm/L, about 270 mOsm/L, or about 275 mOsm/L.

In some aspects, the medium has an osmolality of about 250. In some aspects, the medium has an osmolality of about 255. In some aspects, the medium has an osmolality of about 260.

In some aspects, the medium is isotonic. In some aspects, the medium has an osmolality of about 280 mOsm/L to about 285 mOsm/L, about 280 mOsm/L to about 290 mOsm/L, about 280 mOsm/L to about 295 mOsm/L, about 280 mOsm/L to about 300 mOsm/L, about 280 mOsm/L to about 305 mOsm/L, about 280 mOsm/L to about 310 mOsm/L, about 280 mOsm/L to about 315 mOsm/L, or about 280 mOsm/L to less than 320 mOsm/L. In some aspects, the medium has an osmolality of about 285 mOsm/L, about 290 mOsm/L, about 295 mOsm/L, about 300 mOsm/L, about 305 mOsm/L, about 310 mOsm/L, or about 315 mOsm/L.

In some aspects, the medium further comprises sodium ion. In some aspects, the concentration of the sodium ion is from about 25 mM to about 100 mM. In some aspects, the concentration of the sodium ion is from about 30 mM to about 40 mM, about 30 mM to about 50 mM, about 30 mM to about 60 mM, about 30 mM to about 70 mM, about 30 mM to about 80 mM, about 40 mM to about 50 mM, about 40 mM to about 60 mM, about 40 mM to about 70 mM, about 40 mM to about 80 mM, about 50 mM to about 55 mM, about 50 mM to about 60 mM, about 50 mM to about 65 mM, about 50 mM to about 70 mM, about 50 mM to about 75 mM, about 50 mM to about 80 mM, about 55 mM to about 60 mM, about 55 mM to about 65 mM, about 55 mM to about 70 mM, about 55 mM to about 75 mM, about 55 mM to about 80 mM, about 60 mM to about 65 mM, about 60 mM to about 70 mM, about 60 mM to about 75 mM, about 60 mM to about 80 mM, about 70 mM to about 75 mM, about 70 mM to about 80 mM, or about 75 mM to about 80 mM. In some aspects, the concentration of the sodium ion is about 30 mM, about 35 mM, about 40 mM, about 45 mM, about 50 mM, about 55 mM, about 60 mM, about 65 mM, about 70 mM, about 75 mM, or about 80 mM.

In some aspects, the concentration of the sodium ion is about 55 mM. In some aspects, the concentration of the sodium ion is about 60 mM. In some aspects, the concentration of the sodium ion is about 65 mM. In some aspects, the concentration of the sodium ion is about 70 mM. In some aspects, the concentration of the sodium ion is about 75 mM. In some aspects, the concentration of the sodium ion is about 80 to about 85 mM. In some aspects, the concentration of the sodium ion is about 80 to about 90 mM.

In some aspects, the medium further comprises glucose. In some aspects, the concentration of glucose is more than about 10 mM. In some aspects, the concentration of glucose is from about 10 mM to about 25 mM, about 10 mM to about 20 mM, about 15 mM to about 25 mM, about 15 mM to about 20 mM, about 15 mM to about 19 mM, about 15 mM to about 18 mM, about 15 mM to about 17 mM, about 15 mM to about 16 mM, about 16 mM to about 20 mM, about 16 mM to about 19 mM, about 16 mM to about 18 mM, about 16 mM to about 17 mM, about 17 mM to about 20 mM, about 17 mM to about 19 mM, or about 17 mM to about 18 mM. In some aspects, the concentration of glucose is about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM. In some aspects, the concentration of glucose is about 15.4 mM, about 15.9 mM, about 16.3 mM, about 16.8 mM, about 17.2 mM, or about 17.7 mM.

In some aspects, the medium further comprises calcium ion. In some aspects, the concentration of calcium ion is more than about 0.4 mM. In some aspects, the concentration of calcium ion is from about 0.4 mM to about 2.5 mM, about 0.5 mM to about 2.0 mM, about 1.0 mM to about 2.0 mM, about 1.1 mM to about 2.0 mM, about 1.2 mM to about 2.0 mM, about 1.3 mM to about 2.0 mM, about 1.4 mM to about 2.0 mM, about 1.5 mM to about 2.0 mM, about 1.6 mM to about 2.0 mM, about 1.7 mM to about 2.0 mM, about 1.8 mM to about 2.0 mM, about 1.2 to about 1.3 mM, about 1.2 to about 1.4 mM, about 1.2 to about 1.5 mM, about 1.2 to about 1.6 mM, about 1.2 to about 1.7 mM, about 1.2 to about 1.8 mM, about 1.3 to about 1.4 mM, about 1.3 to about 1.5 mM, about 1.3 to about 1.6 mM, about 1.3 to about 1.7 mM, about 1.3 to about 1.8 mM, about 1.4 to about 1.5 mM, about 1.4 to about 1.6 mM, about 1.4 to about 1.7 mM, about 1.4 to about 1.8 mM, about 1.5 to about 1.6 mM, about 1.5 to about 1.7 mM, about 1.5 to about 1.8 mM, about 1.6 to about 1.7 mM, about 1.6 to about 1.8 mM, or about 1.7 to about 1.8 mM. In some aspects, the concentration of calcium ion is about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, or about 2.0 mM.

In some aspects, the medium comprises about 50 mM potassium ion and (i) about 80.5 mM sodium ion; (ii) about 17.7 mM glucose; (iii) about 1.8 mM calcium ion; or (iv) any combination of (i)-(iii). In some aspects, the medium has an osmolality of about 254.7 mOsmol.

In some aspects, the medium comprises about 55 mM potassium ion and (i) about 76 mM sodium ion; (ii) about 17.2 mM glucose; (iii) about 1.7 mM calcium ion; or (iv) any combination of (i)-(iii). In some aspects, the medium has an osmolality of about 255.2 mOsmol.

In some aspects, the medium comprises about 60 mM potassium ion and (i) about 72.2 mM sodium ion; (ii) about 16.8 mM glucose; (iii) about 1.6 mM calcium ion; or (iv) any combination of (i)-(iii). In some aspects, the medium has an osmolality of about 257.2 mOsmol.

In some aspects, the medium comprises about 65 mM potassium ion and (i) about 67.6 mM sodium ion; (ii) about 16.3 mM glucose; (iii) about 1.5 mM calcium ion; or (iv) any combination of (i)-(iii). In some aspects, the medium has an osmolality of about 257.5 mOsmol.

In some aspects, the medium comprises about 70 mM potassium ion and (i) about 63.9 mM sodium ion; (ii) about 15.9 mM glucose; (iii) about 1.4 mM calcium ion; or (iv) any combination of (i)-(iii). In some aspects, the medium has an osmolality of about 259.7 mOsmol.

In some aspects, the medium comprises about 75 mM potassium ion and (i) about 59.3 mM sodium ion; (ii) about 15.4 mM glucose; (iii) about 1.3 mM calcium ion; or (iv) any combination of (i)-(iii). In some aspects, the medium has an osmolality of about 260 mOsmol.

In some aspects, the medium comprises about 80 mM potassium ion and (i) about 55.6 mM sodium ion; (ii) about 15 mM glucose; (iii) about 1.2 mM calcium ion; or (iv) any combination of (i)-(iii). In some aspects, the medium has an osmolality of about 262.26 mOsmol.

In some aspects, the immune cells are CD3+, CD45RO−, CCR7+, CD45RA+, CD62L+CD27+, CD28+, or TCF7+, or any combination thereof, following culture.

In some aspects, the concentration of IL-2 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL.

In some aspects, the concentration of IL-2 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL. In some aspects, the concentration of IL-2 is about 1.0 ng/mL. In some aspects, the concentration of IL-2 is about 10 ng/mL.

In some aspects, the concentration of IL-21 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL. In some aspects, the concentration of IL-21 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL. In some aspects, the concentration of IL-21 is about 1.0 ng/mL. In some aspects, the concentration of IL-21 is about 10 ng/mL.

In some aspects, the concentration of IL-7 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL. In some aspects, the concentration of IL-7 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL. In some aspects, the concentration of IL-7 is about 1.0 ng/mL. In some aspects, the concentration of IL-7 is about 10 ng/mL.

In some aspects, the concentration of IL-15 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL. In some aspects, the concentration of IL-15 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL. In some aspects, the concentration of IL-15 is about 1.0 ng/mL. In some aspects, the concentration of IL-15 is about 10 ng/mL.

In some aspects, the immune cells and/or stem cells comprises a chimeric antigen receptor, an engineered T cell receptor, or any combination thereof.

In some aspects, the immune cells and/or stem cells are administered to a human subject following culture.

In some aspects, the cells are further transduced with a vector. In some aspects, the vector comprises a transgene encoding a chimeric antigen receptor (CAR), a T cell receptor (TCR), or a TCR mimic. In some aspects, the CAR targets CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof. In some aspects, the TCR targets AFP, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof. In some aspects, the vector is a retroviral vector, a lentiviral vector, an adeno-associated virus (AAV), an adenovirus, an AAV hybrid virus, a baculovirus, or any combination thereof. Certain aspects of the present disclosure are directed to a population of cells prepared by a method disclosed herein. Certain aspects of the present disclosure are directed to a population of cells comprising at least about 5%, at least about 10%, at least about 15%, at least about 20%, at least about 25%, at least about 30%, at least about 35%, at least about 40%, at least about 45%, at least about 50%, at least about 60%, or at least about 70% of the cells are CD3+, CD45RO−, CCR7+, CD45RA+, CD62L+, CD27+, CD28+, and TCF7+, wherein the cells are cultured according to a method disclosed herein. Certain aspects of the present disclosure are directed to a cell culture medium useful for a method disclosed herein. Certain aspects of the present disclosure are directed to a cell culture medium comprising (i) immune cells or stem cells as disclosed herein and (ii) a potassium ion at a concentration higher than 40 mM, wherein the culture medium is not hypertonic.

In some aspects, the concentration of the potassium ion is at least about 45 mM, at least about 50 mM, at least about 55 mM, at least about 60 mM, at least about 65 mM, at least about 70 mM, about 75 mM, about 80 mM, about 85 mM, about 90 mM, about 95 mM, or about 100 mM. In some aspects, the concentration of the potassium ion is about 50 mM, about 60 mM, about 70 mM, or about 80 mM. In some aspects, the culture medium further comprises one or more cytokines. In some aspects, the one or more cytokines are IL-2, IL-7, IL-15, IL-21, or any combination thereof. Certain aspects of the present disclosure are directed to a method of treating a disease or condition in a subject in need thereof comprising administering a population of cells disclosed herein to the subject. In some aspects, the disease or condition comprises a tumor derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, carcinoma, sarcoma, leukemia, lymphoma, myeloma, or a combination thereof.

Aspects

Aspect 1. A method of culturing immune cells and/or stem cells ex vivo or in vitro comprising placing immune cells and/or stem cells in a medium comprising potassium ion at a concentration higher than 40 mM, wherein the medium is not hypertonic.

Aspect 2. A method of preparing a population of immune cells and/or stem cells comprising placing immune cells and/or stem cells into a medium comprising potassium ion at a concentration higher than 40 mM, wherein the medium is not hypertonic.

Aspect 3. The method of aspect 1 or 2, wherein the medium further comprises one or more cytokines.

Aspect 4. The method of aspect 3, wherein the one or more cytokines comprise Interleukin-2 (IL-2), Interleukin-7, Interleukin 21, Interleukin-15 (IL-15), or any combination thereof.

Aspect 5. A method of increasing a number or percentage of undifferentiated or less differentiated cells ex vivo or in vitro comprising culturing immune cells and/or stem cells in a medium comprising potassium ion at a concentration of higher than 40 mM, wherein the medium comprises IL-2, but does not comprise IL-7 and IL-15.

Aspect 6. The method of aspect 5, wherein the immune cells and/or stem cells after the culturing comprises a higher number and/or percentage of undifferentiated or less differentiated immune cells and/or stem cells compared to immune cells and/or stem cells that are cultured in a medium comprising IL-2, IL-7, and IL-15.

Aspect 7. A method of increasing a number and/or percentage of undifferentiated or less differentiated immune cells and/or stem cells ex vivo or in vitro comprising placing immune cells and/or stem cells in a medium comprising potassium ion at a concentration higher than 40 mM, wherein the medium comprises IL-7 and IL-21.

Aspect 8. A method of increasing a number or percentage of undifferentiated or less differentiated immune cells and/or stem cells ex vivo or in vitro comprising placing the immune cells and/or stem cells in a medium comprising potassium ion at a concentration higher than 40 mM, wherein the medium comprises IL-15 and IL-21.

Aspect 9. The method of any one of aspects 1 to 8, wherein the cells comprise immune cells.

Aspect 10. The method of aspect 8, wherein the immune cells comprise T cells, TILs, NK cells, TILs, Tregs, and any combination thereof.

Aspect 11. The method of any one of aspects 1 to 8, wherein the cells comprise stem cells.

Aspect 12. The method of any one of aspects 1 to 11, wherein the cells express chimeric antigen receptor (CAR).

Aspect 13. The method of any one of aspects 1 to 11, wherein the cells express an engineered T cell receptor (TCR).

Aspect 14. The method of any one of aspects 1 to 13, wherein the medium is hypotonic.

Aspect 15. The method of any one of aspects 1 to 14, wherein the medium further comprises sodium ion, calcium ion, glucose, and/or any combination thereof.

Aspect 16. The method of any one of aspects 1 to 15, wherein the medium further comprises a cell expansion agent.

Aspect 17. The method of aspect 16, wherein the cell expansion agent comprises a GSK3B inhibitor, an ACLY inhibitor, a PI3K inhibitor, an AKT inhibitor, or any combination thereof.

Aspect 18. The method of aspect 17, wherein the PI3K inhibitor is selected from LY294002, pictilisib, CAL101, IC87114, and any combination thereof.

Aspect 19. The method of aspect 17, wherein the AKT inhibitor is selected from MK2206, A443654, AKTi-VIII, and any combination thereof.

Aspect 20. The method of any one of aspects 1 to 19, wherein the medium is capable of: a. increasing the number and/or percentage of less differentiated and/or undifferentiated cells; b. increasing transduction efficiency; c. increasing stem-like immune cells; d. increasing in vivo viability; e. increasing cell potency; f preventing cell exhaustion; or g. any combination thereof.

Aspect 21. The method of any one of aspects 1 to 20, wherein the concentration of potassium ion is at least about 45 mM, at least about 50 mM, at least about 55 mM, at least about 60 mM, at least about 65 mM, at least about 70 mM, about 75 mM, about 80 mM, about 85 mM, about 90 mM, about 95 mM, or about 100 mM.

Aspect 22. The method of any one of aspects 1 to 21, wherein the concentration of potassium ion is about 45 mM to about 110 mM, about 45 mM to about 100 mM, about 45 mM to about 90 mM, about 45 mM to about 80 mM, about 45 mM to about 70 mM, about 45 mM to about 60 mM, about 45 mM to about 50 mM, about 50 mM to about 110 mM, about 50 mM to about 100 mM, about 50 mM to about 90 mM, about 50 mM to about 80 mM, about 50 mM to about 70 mM, about 60 mM to about 110 mM, about 60 mM to about 100 mM, about 60 mM to about 90 mM, about 60 mM to about 80 mM, about 60 mM to about 70 mM, about 70 mM to about 100 mM, about 70 mM to about 90 mM, about 70 mM to about 80 mM, about 80 mM to about 110 mM, about 80 mM to about 100 mM, about 80 mM to about 90 mM, about 90 mM to about 110 mM, about 90 mM to about 100 mM, or about 100 mM to about 110 mM.

Aspect 23. The method of any one of aspects 1 to 22, wherein the concentration of potassium ion is about 50 mM to about 90 mM.

Aspect 24. The method of any one of aspects 1 to 23, wherein the concentration of potassium ion is about 50 mM to about 80 mM.

Aspect 25. The method of any one of aspects 1 to 24, wherein the medium has an osmolality lower than about 280 mOsm/L.

Aspect 26. The method of any one of aspects 1 to 25, wherein the medium has an osmolality between about 100 mOsm/L to about 280 mOsm/L, about 125 mOsm/L to about 280 mOsm/L, about 150 mOsm/L to about 280 mOsm/L, about 175 mOsm/L to about 280 mOsm/L, about 200 mOsm/L to about 280 mOsm/L, about 210 mOsm/L to about 280 mOsm/L, about 220 mOsm/L to about 280 mOsm/L, about 225 mOsm/L to about 280 mOsm/L, about 230 mOsm/L to about 280 mOsm/L, about 235 mOsm/L to about 280 mOsm/L, about 240 mOsm/L to about 280 mOsm/L, about 245 mOsm/L to about 280 mOsm/L, about 250 mOsm/L to about 280 mOsm/L, about 255 mOsm/L to about 280 mOsm/L, about 260 mOsm/L to about 280 mOsm/L, about 265 mOsm/L to about 280 mOsm/L, about 270 mOsm/L to about 280 mOsm/L, or about 275 mOsm/L to about 280 mOsm/L.

Aspect 27. The method of any one of aspects 1 to 26, wherein the medium has an osmolality of about 100 mOsm/L to about 280 mOsm/L, about 125 mOsm/L, about 150 mOsm/L, about 175 mOsm/L, about 200 mOsm/L, about 210 mOsm/L, about 220 mOsm/L, about 225 mOsm/L, about 230 mOsm/L, about 235 mOsm/L, about 240 mOsm/L, about 245 mOsm/L, about 250 mOsm/L, about 255 mOsm/L, about 260 mOsm/L, about 265 mOsm/L, about 270 mOsm/L, or about 275 mOsm/L.

Aspect 28. The method of any one of aspects 1 to 27, wherein the medium has an osmolality of about 250.

Aspect 29. The method of any one of aspects 1 to 28, wherein the medium has an osmolality of about 255.

Aspect 30. The method of any one of aspects 1 to 29, wherein the medium has an osmolality of about 260.

Aspect 31. The method of any one of aspects 1 to 24, wherein the medium is isotonic.

Aspect 32. The method of aspect 31, wherein the medium has an osmolality of about 280 mOsm/L to about 285 mOsm/L, about 280 mOsm/L to about 290 mOsm/L, about 280 mOsm/L to about 295 mOsm/L, about 280 mOsm/L to about 300 mOsm/L, about 280 mOsm/L to about 305 mOsm/L, about 280 mOsm/L to about 310 mOsm/L, about 280 mOsm/L to about 315 mOsm/L, or about 280 mOsm/L to less than 320 mOsm/L.

Aspect 33. The method of aspect 31 or 32, wherein the medium has an osmolality of about 285 mOsm/L, about 290 mOsm/L, about 295 mOsm/L, about 300 mOsm/L, about 305 mOsm/L, about 310 mOsm/L, or about 315 mOsm/L.

Aspect 34. The method of any one of aspects 1 to 33, wherein the medium further comprises sodium ion.

Aspect 35. The method of aspect 34, wherein the concentration of the sodium ion is from about 25 mM to about 100 mM.

Aspect 36. The method of aspect 34 or 35, wherein the concentration of the sodium ion is from about 30 mM to about 40 mM, about 30 mM to about 50 mM, about 30 mM to about 60 mM, about 30 mM to about 70 mM, about 30 mM to about 80 mM, about 40 mM to about 50 mM, about 40 mM to about 60 mM, about 40 mM to about 70 mM, about 40 mM to about 80 mM, about 50 mM to about 55 mM, about 50 mM to about 60 mM, about 50 mM to about 65 mM, about 50 mM to about 70 mM, about 50 mM to about 75 mM, about 50 mM to about 80 mM, about 55 mM to about 60 mM, about 55 mM to about 65 mM, about 55 mM to about 70 mM, about 55 mM to about 75 mM, about 55 mM to about 80 mM, about 60 mM to about 65 mM, about 60 mM to about 70 mM, about 60 mM to about 75 mM, about 60 mM to about 80 mM, about 70 mM to about 75 mM, about 70 mM to about 80 mM, or about 75 mM to about 80 mM.

Aspect 37. The method of any one of aspects 34 to 36, wherein the concentration of the sodium ion is about 30 mM, about 35 mM, about 40 mM, about 45 mM, about 50 mM, about 55 mM, about 60 mM, about 65 mM, about 70 mM, about 75 mM, or about 80 mM.

Aspect 38. The method of any one of aspects 34 to 37, wherein the concentration of the sodium ion is about 55 mM.

Aspect 39. The method of any one of aspects 34 to 38, wherein the concentration of the sodium ion is about 60 mM.

Aspect 40. The method of any one of aspects 34 to 39, wherein the concentration of the sodium ion is about 65 mM.

Aspect 41. The method of any one of aspects 1 to 40, wherein the medium further comprises glucose.

Aspect 42. The method of aspect 41, wherein the concentration of glucose is more than about 10 mM.

Aspect 43. The method of aspect 41 or 42, wherein the concentration of glucose is from about 10 mM to about 25 mM, about 10 mM to about 20 mM, about 15 mM to about 25 mM, about 15 mM to about 20 mM, about 15 mM to about 19 mM, about 15 mM to about 18 mM, about 15 mM to about 17 mM, about 15 mM to about 16 mM, about 16 mM to about 20 mM, about 16 mM to about 19 mM, about 16 mM to about 18 mM, about 16 mM to about 17 mM, about 17 mM to about 20 mM, about 17 mM to about 19 mM, or about 17 mM to about 18 mM.

Aspect 44. The method of any one of aspects 41 to 43, wherein the concentration of glucose is about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM.

Aspect 45. The method of any one of aspects 41 to 44, wherein the concentration of glucose is about 15.4 mM, about 15.9 mM, about 16.3 mM, about 16.8 mM, about 17.2 mM, or about 17.7 mM.

Aspect 46. The method of any one of aspects 1 to 45, wherein the medium further comprises calcium ion.

Aspect 47. The method of aspect 46, wherein the concentration of calcium ion is more than about 0.4 mM.

Aspect 48. The method of aspect 46 or 47, wherein the concentration of calcium ion is from about 0.4 mM to about 2.5 mM, about 0.5 mM to about 2.0 mM, about 1.0 mM to about 2.0 mM, about 1.1 mM to about 2.0 mM, about 1.2 mM to about 2.0 mM, about 1.3 mM to about 2.0 mM, about 1.4 mM to about 2.0 mM, about 1.5 mM to about 2.0 mM, about 1.6 mM to about 2.0 mM, about 1.7 mM to about 2.0 mM, about 1.8 mM to about 2.0 mM, about 1.2 to about 1.3 mM, about 1.2 to about 1.4 mM, about 1.2 to about 1.5 mM, about 1.2 to about 1.6 mM, about 1.2 to about 1.7 mM, about 1.2 to about 1.8 mM, about 1.3 to about 1.4 mM, about 1.3 to about 1.5 mM, about 1.3 to about 1.6 mM, about 1.3 to about 1.7 mM, about 1.3 to about 1.8 mM, about 1.4 to about 1.5 mM, about 1.4 to about 1.6 mM, about 1.4 to about 1.7 mM, about 1.4 to about 1.8 mM, about 1.5 to about 1.6 mM, about 1.5 to about 1.7 mM, about 1.5 to about 1.8 mM, about 1.6 to about 1.7 mM, about 1.6 to about 1.8 mM, or about 1.7 to about 1.8 mM.

Aspect 49. The method of any one of aspects 46 to 48, wherein the concentration of calcium ion is about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, or about 2.0 mM.

Aspect 50. The method of any one of aspects 1 to 49, wherein the medium comprises about 50 mM potassium ion and (i) about 80.5 mM sodium ion; (ii) about 17.7 mM glucose; (iii) about 1.8 mM calcium ion; or (iv) any combination of (i)-(iii).

Aspect 51. The method of aspect 50, wherein the medium has an osmolality of about 254.7 mOsmol.

Aspect 52. The method of any one of aspects 1 to 49, wherein the medium comprises about 55 mM potassium ion and (i) about 76 mM sodium ion; (ii) about 17.2 mM glucose; (iii) about 1.7 mM calcium ion; or (iv) any combination of (i)-(iii).

Aspect 53. The method of aspect 52, wherein the medium has an osmolality of about 255.2 mOsmol.

Aspect 54. The method of any one of aspects 1 to 49, wherein the medium comprises about 60 mM potassium ion and (i) about 72.2 mM sodium ion; (ii) about 16.8 mM glucose; (iii) about 1.6 mM calcium ion; or (iv) any combination of (i)-(iii).

Aspect 55. The method of aspect 54, wherein the medium has an osmolality of about 257.2 mOsmol.

Aspect 56. The method of any one of aspects 1 to 49, wherein the medium comprises about 65 mM potassium ion and (i) about 67.6 mM sodium ion; (ii) about 16.3 mM glucose; (iii) about 1.5 mM calcium ion; or (iv) any combination of (i)-(iii).

Aspect 57. The method of aspect 56, wherein the medium has an osmolality of about 257.5 mOsmol.

Aspect 58. The method of any one of aspects 1 to 49, wherein the medium comprises about 70 mM potassium ion and (i) about 63.9 mM sodium ion; (ii) about 15.9 mM glucose; (iii) about 1.4 mM calcium ion; or (iv) any combination of (i)-(iii).

Aspect 59. The method of aspect 58, wherein the medium has an osmolality of about 259.7 mOsmol.

Aspect 60. The method of any one of aspects 1 to 49, wherein the medium comprises about 75 mM potassium ion and (i) about 59.3 mM sodium ion; (ii) about 15.4 mM glucose; (iii) about 1.3 mM calcium ion; or (iv) any combination of (i)-(iii).

Aspect 61. The method of aspect 60, wherein the medium has an osmolality of about 260 mOsmol.

Aspect 62. The method of any one of aspects 1 to 49, wherein the medium comprises about 80 mM potassium ion and (i) about 55.6 mM sodium ion; (ii) about 15 mM glucose; (iii) about 1.2 mM calcium ion; or (iv) any combination of (i)-(iii).

Aspect 63. The method of aspect 62, wherein the medium has an osmolality of about 262.26 mOsmol.

Aspect 64. The method of any one of aspects 9 to 55, wherein the immune cells are CD3+, CD45RO−, CCR7+, CD45RA+, CD62L+CD27+, CD28+, or TCF7+, or any combination thereof, following culture.

Aspect 65. The method of any one of aspects 4 to 6 and 9 to 64, wherein the concentration of IL-2 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL.

Aspect 66. The method of aspect 65, wherein the concentration of IL-2 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL.

Aspect 67. The method of aspect 65 or 66, wherein the concentration of IL-2 is about 1.0 ng/mL.

Aspect 68. The method of aspect 65 or 66, wherein the concentration of IL-2 is about 10 ng/mL.

Aspect 69. The method of any one of aspects 4, 7, and 8 to 68, wherein the concentration of IL-21 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL.

Aspect 70. The method of aspect 69, wherein the concentration of IL-21 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL.

Aspect 71. The method of aspect 69 or 70, wherein the concentration of IL-21 is about 1.0 ng/mL.

Aspect 72. The method of aspect 69 or 70, wherein the concentration of IL-21 is about 10 ng/mL.

Aspect 73. The method of any one of aspects 5 to 7 and 9 to 72, wherein the concentration of IL-7 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL.

Aspect 74. The method of aspect 73, wherein the concentration of IL-7 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL.

Aspect 75. The method of aspect 73 or 74, wherein the concentration of IL-7 is about 1.0 ng/mL.

Aspect 76. The method of aspect 73 or 74, wherein the concentration of IL-7 is about 10 ng/mL.

Aspect 77. The method of any one of aspects 4-6 and 8 to 76, wherein the concentration of IL-15 is from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL.

Aspect 78. The method of aspect 77, wherein the concentration of IL-15 is about 0.1 ng/mL, about 0.5 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL.

Aspect 79. The method of aspect 77 or 78, wherein the concentration of IL-15 is about 1.0 ng/mL.

Aspect 80. The method of aspect 77 or 78, wherein the concentration of IL-15 is about 10 ng/mL.

Aspect 81. The method of any one of aspects 1 to 80, wherein the immune cells and/or stem cells comprises a chimeric antigen receptor, an engineered T cell receptor, or any combination thereof.

Aspect 82. The method of any one of aspects 1 to 81, wherein the immune cells and/or stem cells are administered to a human subject following culture.

Aspect 83. The method of any one of aspects 1 to 82, wherein the cells are further transduced with a vector.

Aspect 84. The method of aspect 83, wherein the vector comprises a transgene encoding a chimeric antigen receptor (CAR), a T cell receptor (TCR), or a TCR mimic.

Aspect 85. The method of aspect 84, wherein the CAR targets CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

Aspect 86. The method of aspect 84, wherein the TCR targets AFP, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

Aspect 87. The method of aspect 84, wherein the vector is a retroviral vector, a lentiviral vector, an adeno-associated virus (AAV), an adenovirus, an AAV hybrid virus, a baculovirus, or any combination thereof.

Aspect 88. A population of cells prepared by the method of any one of aspects 1 to 87.

Aspect 89. A population of cells comprising at least about 5%, at least about 10%, at least about 15%, at least about 20%, at least about 25%, at least about 30%, at least about 35%, at least about 40%, at least about 45%, at least about 50%, at least about 60%, or at least about 70% of the cells are CD3+, CD45RO−, CCR7+, CD45RA+, CD62L+, CD27+, CD28+, and TCF7+, wherein the cells are cultured according to the method of any one of aspects 1 to 87.

Aspect 90. A cell culture medium useful for the method of any one of aspects 1 to 87.

Aspect 91. A cell culture medium comprising (i) immune cells or stem cells as described in aspects 1 to 87 and (ii) a potassium ion at a concentration higher than 40 mM, wherein the culture medium is not hypertonic.

Aspect 92. The culture medium of aspect 91, wherein the concentration of the potassium ion is at least about 45 mM, at least about 50 mM, at least about 55 mM, at least about 60 mM, at least about 65 mM, at least about 70 mM, about 75 mM, about 80 mM, about 85 mM, about 90 mM, about 95 mM, or about 100 mM.

Aspect 93. The culture medium of aspect 91 or 92, wherein the concentration of the potassium ion is about 50 mM, about 60 mM, about 70 mM, or about 80 mM.

Aspect 94. The culture medium of any one of aspects 91 to 93, which further comprises one or more cytokines.

Aspect 95. The culture medium of aspect 94, wherein the one or more cytokines are selected from IL-2, IL-7, IL-15, IL-21, and any combination thereof.

Aspect 96. A method of treating a disease or condition in a subject in need thereof comprising administering the population of cells of aspect 88 or 89 to the subject.

Aspect 97. The method of aspect 96, wherein the disease or condition comprises a tumor derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, carcinoma, sarcoma, leukemia, lymphoma, myeloma, or a combination thereof.

BRIEF DESCRIPTION OF THE DRAWINGS/FIGURES

FIG. 1A shows stringent cell surface markers and transcription factors for FACS analysis that accurately define "stem cell-like" cells, e.g., T cells. FIG. 1B is an illustration of progressive differentiation of exemplary cells, e.g., T cells, annotated with the various phenotypic characteristics and biomarker expression profiles.

FIGS. 2A-2F are scatter plots showing the relative stem-like populations of cells (FIGS. 2A-2C) and the relative yields (FIGS. 2D-2F) at varying potassium concentrations, wherein the medium has a tonicity of 250 mOsmol (FIGS. 2A and 2D), 280 mOsmol (FIGS. 2B and 2E), or 320 mOsmol (FIGS. 2C and 2F) (circles: 50 mM potassium ion; squares: 60 mM potassium ion; triangles: 70 mM potassium ion; inverted triangles: 80 mM potassium ion; diamonds: 90 mM potassium ion; open circles: control). FIG. 2G is a line graph showing the relative stem-like populations following culture in control medium or hypotonic medium having a tonicity of 250 mOsmol. Tonicity of the media was calculated based on the concentrations of potassium and NaCl as shown in Table 2.

FIGS. 3A-3G show the effects of culturing T cells in elevated potassium in hypotonic culture conditions. FIG. 3A illustrates a T cell culture scheme consistent with some aspects disclosed herein. FIG. 3B shows FACS analysis of expression of CD45RA CCR7 under various culture conditions. FIG. 3C shows FACS analysis of expression of CD45RA and CD62L under various culture conditions. FIG. 3D shows FACS analysis of expression of T cell persistence associated marker CD27 and CCR7$^+$ under various culture conditions. FIG. 3E shows FACS analysis of expression of TCF7 and CD39 under various culture conditions. FIG. 3F shows FACs analysis of TCF7 expression and CD3. FIG. 3G shows the percentage of TCF7$^+$ cells from control and hypotonic modified media with elevated potassium culture conditions.

FIGS. 4A-4B show T cell yield and viability during in vitro expansion. FIG. 4A shows fold expansion ($10^6$) of T cells cultured in control media and modified (hypotonic) media, i.e., media containing elevated potassium and NaCl such that the combination of the potassium ion and NaCl is less than 140 mM. FIG. 4B shows viability of T cells cultured in control media and modified (hypotonic) media, i.e., media containing elevated potassium and NaCl such that the combination of the potassium ion and NaCl is less than 140 mM.

FIGS. 5A-5B show hypotonic conditioning medium-enriched "stem cell-like" T cells. FIG. 5A shows FACS analysis of "stem cell-like" markers from CD4 and CD8 T cells cultured in control media. FIG. 5B shows FACS analysis of "stem cell-like" markers from CD4 and CD8 T cells cultured in modified (hypotonic) media, i.e., media containing elevated potassium and NaCl such that the combination of the potassium ion and NaCl is less than 140 mM.

Figure 8A:
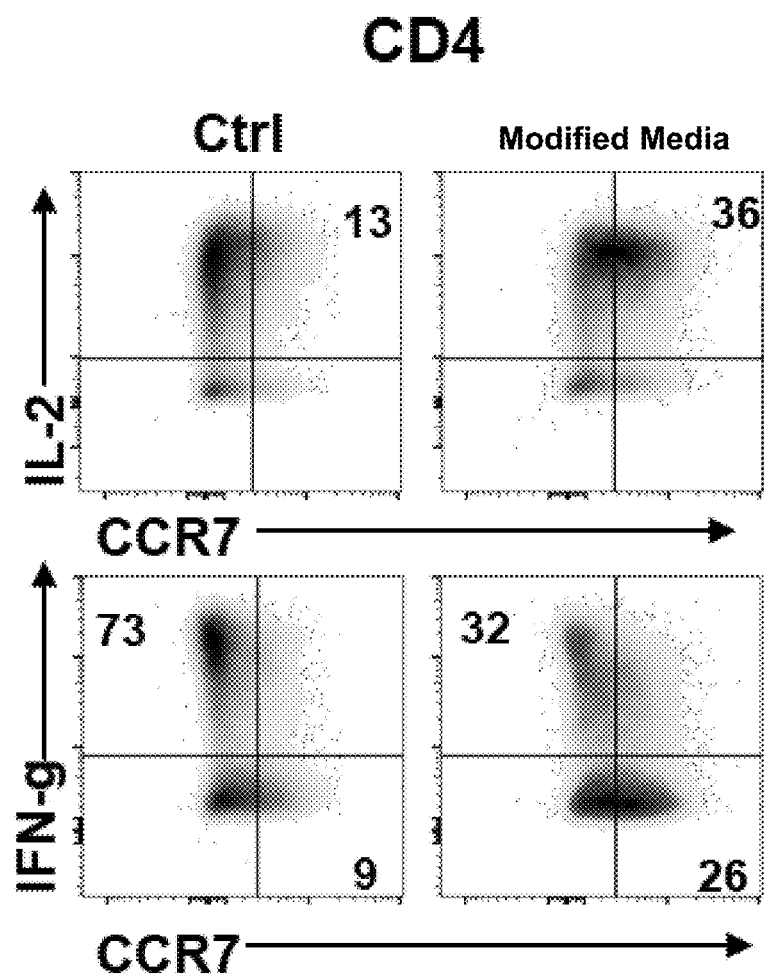
Figure 8B:
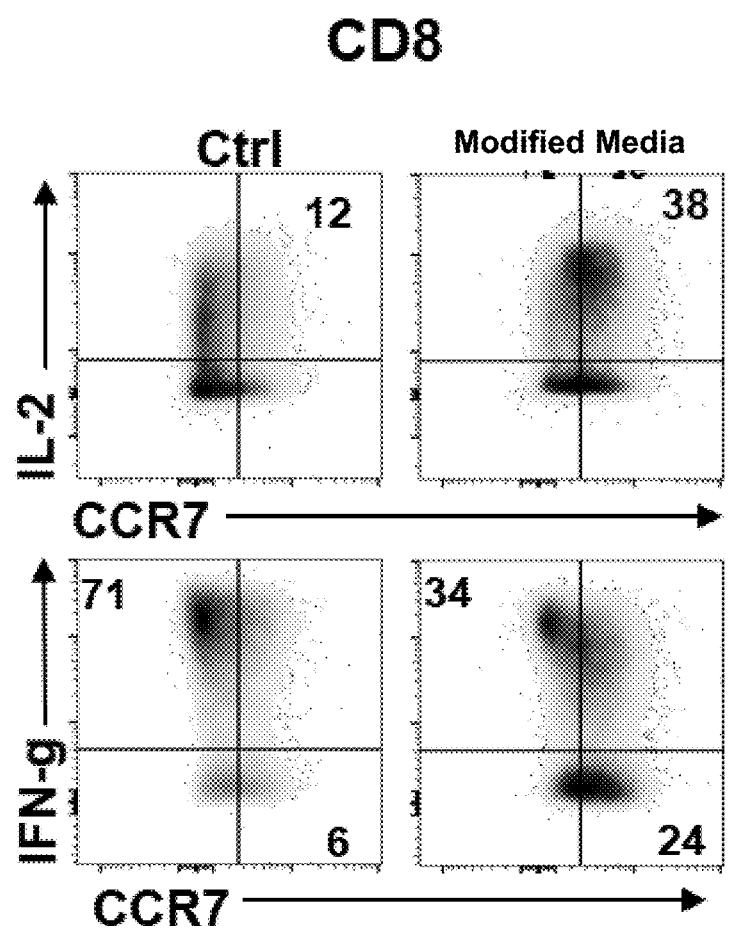
Figure 8C:
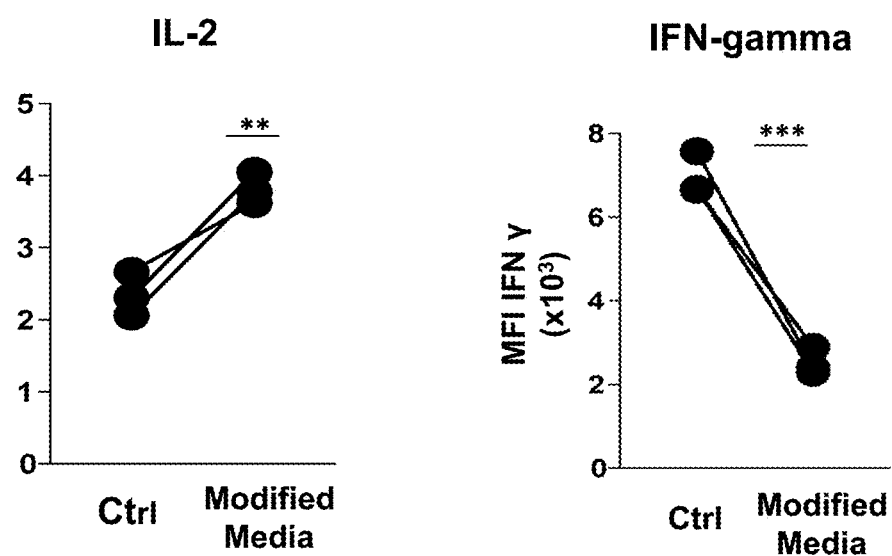

FIGS. 8A-8C show the effect of elevated potassium on the fate of effector functions of $T_{SCM}$ populations. FIG. 8A shows FACS plots showing enrichment of IL-2 expression in CCR7+ and reduction of IFN-γ in CD19-CAR engineered CD4 T cells. FIG. 8B shows FACS plots showing enrichment of IL-2 expression in CCR7+ and reduction of IFN-γ in CD19-CAR engineered CD8 T cells. FIG. 8C shows a quantification of IL-2 and IFN-γ expression in control and elevated potassium in hypotonic culture conditions.

Figure 9A:
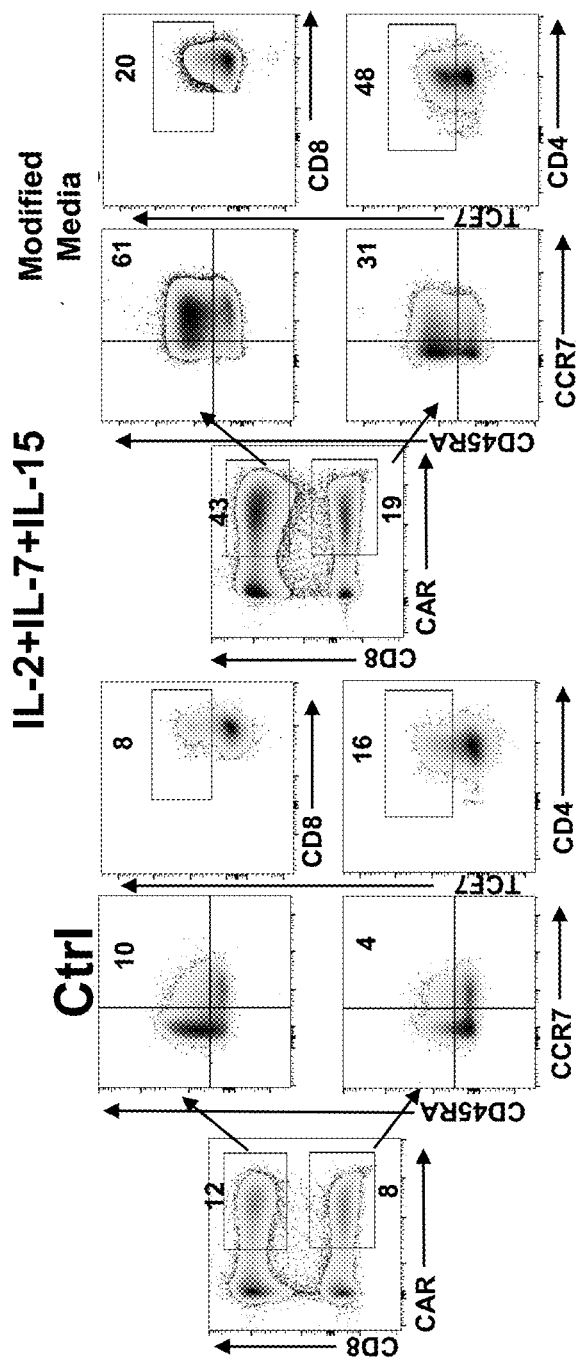
Figure 9B:
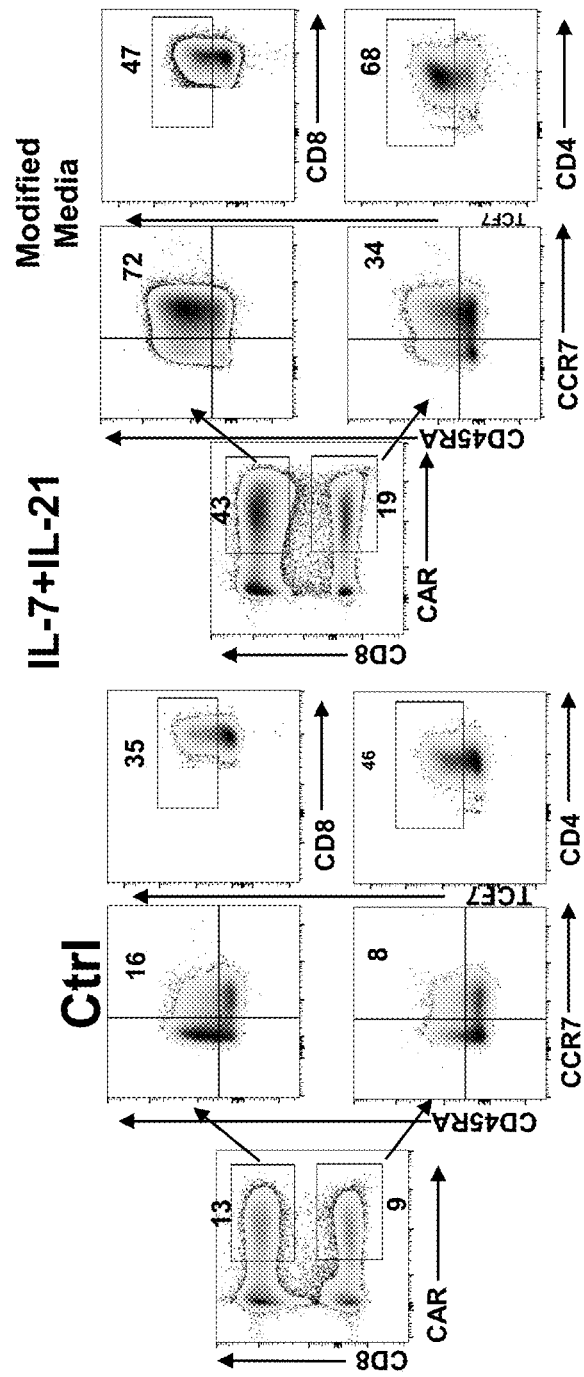

FIGS. 9A-9B show the effect of cytokines on $T_{SCM}$ populations in control (left panels) or in modified (hypotonic) media (right panels) with elevated potassium and hypotonic culture conditions. FIG. 9A shows the effect of the combination of IL-2, IL-7, and IL-15. FIG. 9B shows the effect of the combination of IL-7 and IL-21.

Figure 10A:
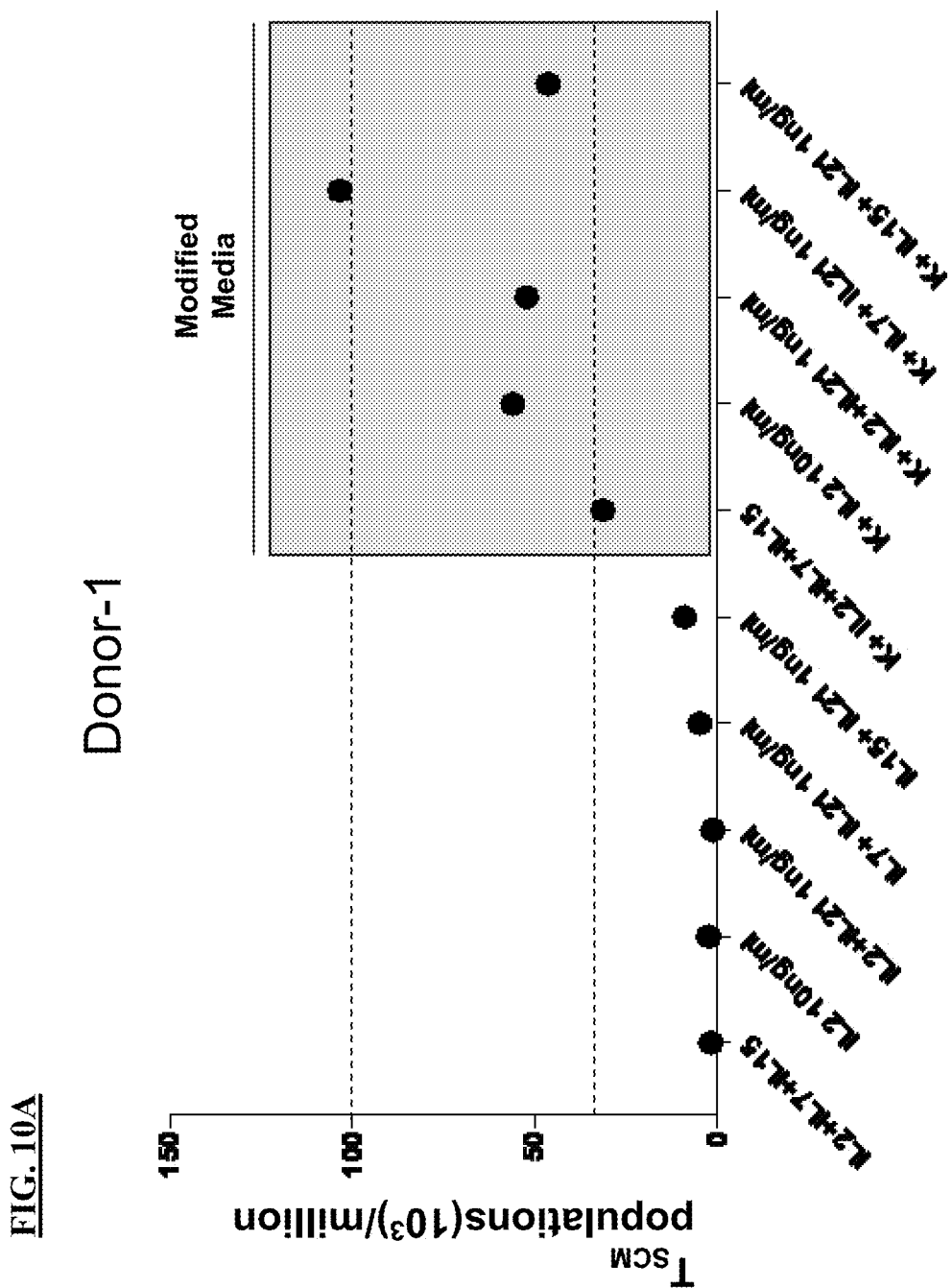
Figure 10B:
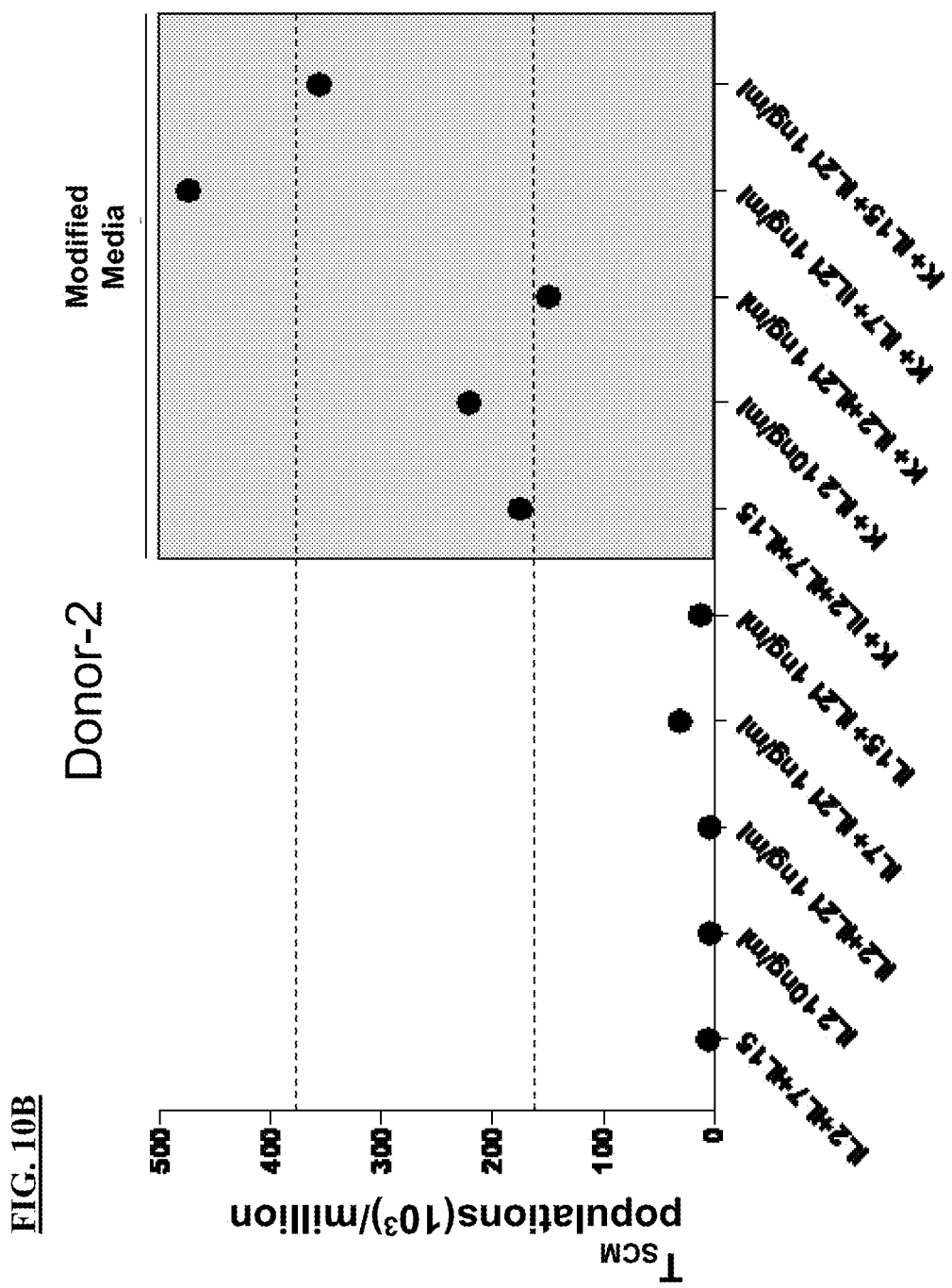

FIGS. 10A-10B show the number of $T_{SCM}$ cells in CAR engineered products cultured in control and elevated potassium in hypotonic culture conditions in modified (hypotonic) media comprising elevated potassium with cytokine combinations. FIG. 10A shows the number of $T_{SCM}$ cells in CAR engineered products from Donor 1. From left to right, cells were cultured with IL-2, IL-7, and IL-15; IL-2 (10 ng/mL); IL-2 and IL-21 (1 ng/mL); IL-7 and IL-21 (1 ng/ml); IL-15 and IL-21 (1 ng/mL); Potassium and IL-2, IL-7, and IL-15; Potassium and IL-2 (10 ng/mL); Potassium and IL-2 and IL-21 (1 ng/mL); Potassium and IL-7 and IL-21 (1 ng/mL); Potassium and IL-15 and IL-21 (1 ng/mL). FIG. 10B shows the number of $T_{SCM}$ cells in CAR engineered products from Donor 1. From left to right, cells were cultured with IL-2, IL-7, and IL-15; IL-2 (10 ng/mL); IL-2 and IL-21 (1 ng/mL); IL-7 and IL-21 (1 ng/ml); IL-15 and IL-21 (1 ng/mL); Potassium and IL-2, IL-7, and IL-15; Potassium and IL-2 (10 ng/mL); Potassium and IL-2 and IL-21 (1 ng/mL); Potassium and IL-7 and IL-21 (1 ng/mL); Potassium and IL-15 and IL-21 (1 ng/mL).

Figure 11:
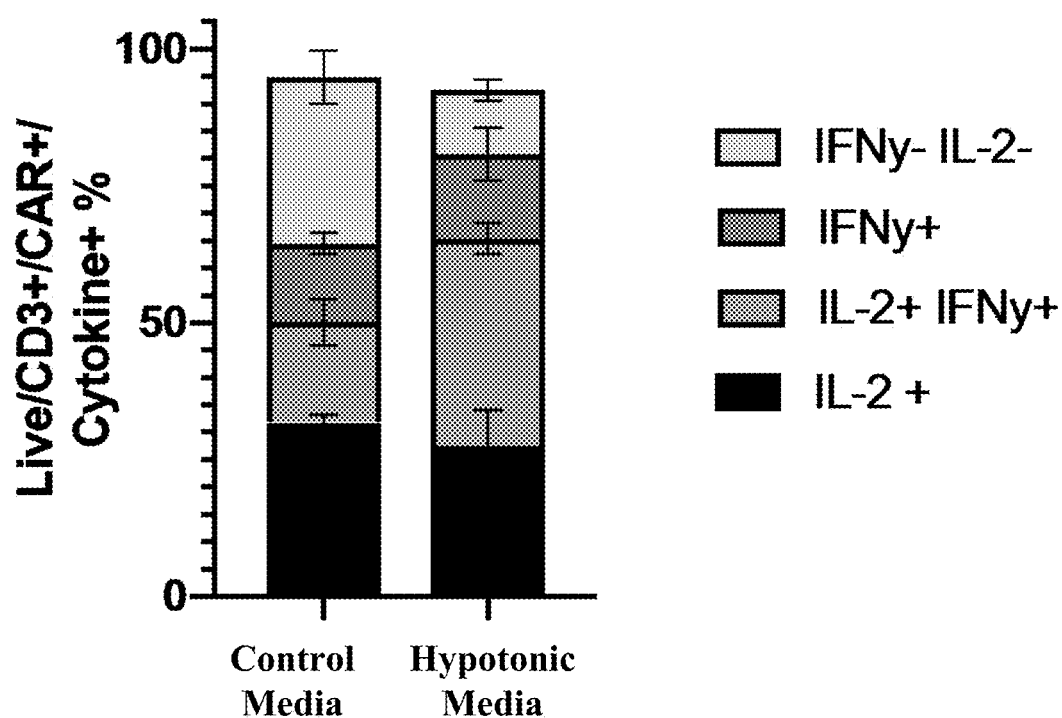

FIG. 11 is a bar graph of the percent of cells expressing IL-2 and/or IFNγ, as indicated, illustrating the differentiation status of ROR1 chimeric antigen receptor (CAR) T cells cultured in control media or in hypotonic media (i.e., modified media containing elevated potassium and NaCl such that the combination of the potassium ion and NaCl is less than 140 mM).

Figure 12:
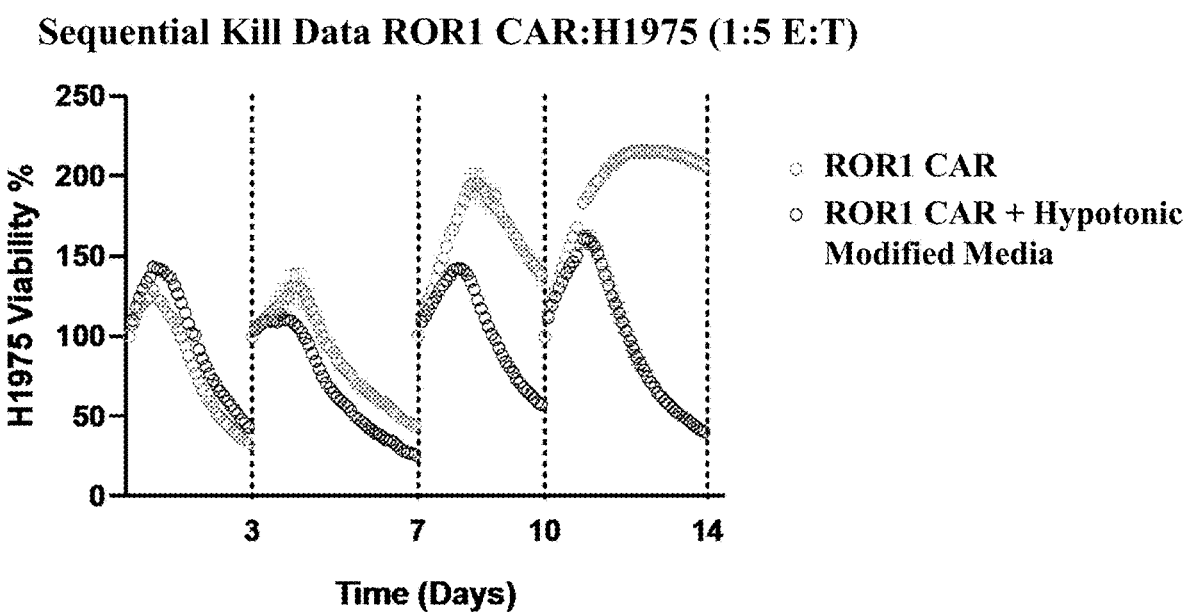

FIG. 12 is a graphical representations of sequential kill data for ROR1 CART cells co-cultured in control media ("ROR1 CAR") or in modified hypotonic media containing elevated potassium and NaCl such that the combination of the potassium ion and NaCl is less than 140 mM.

Figure 13A:
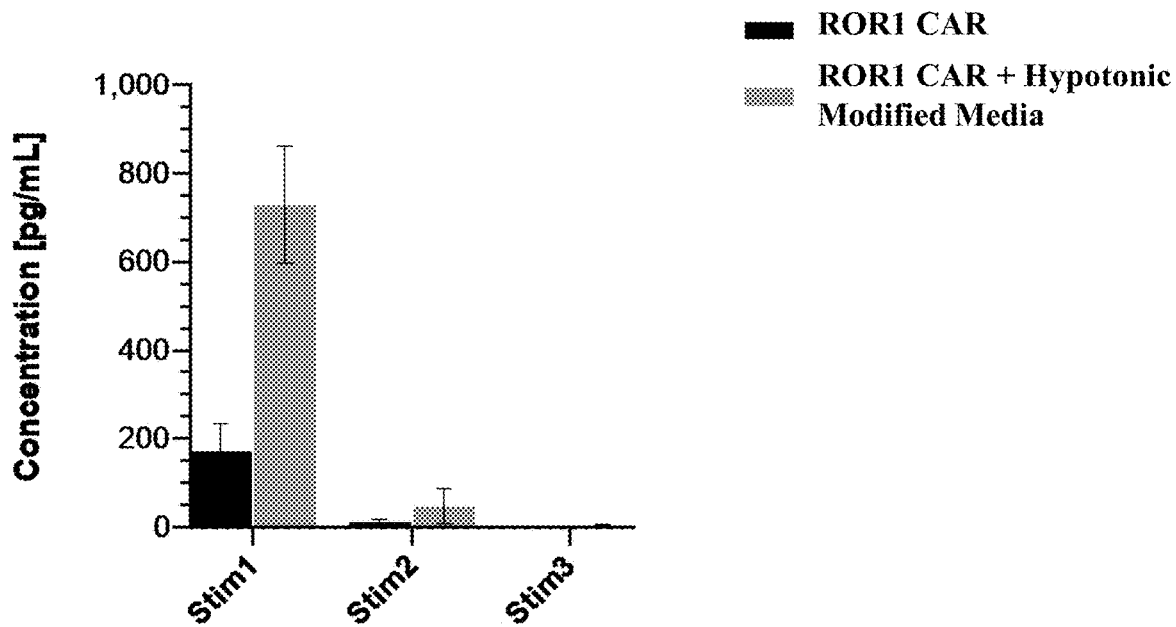
Figure 13B:
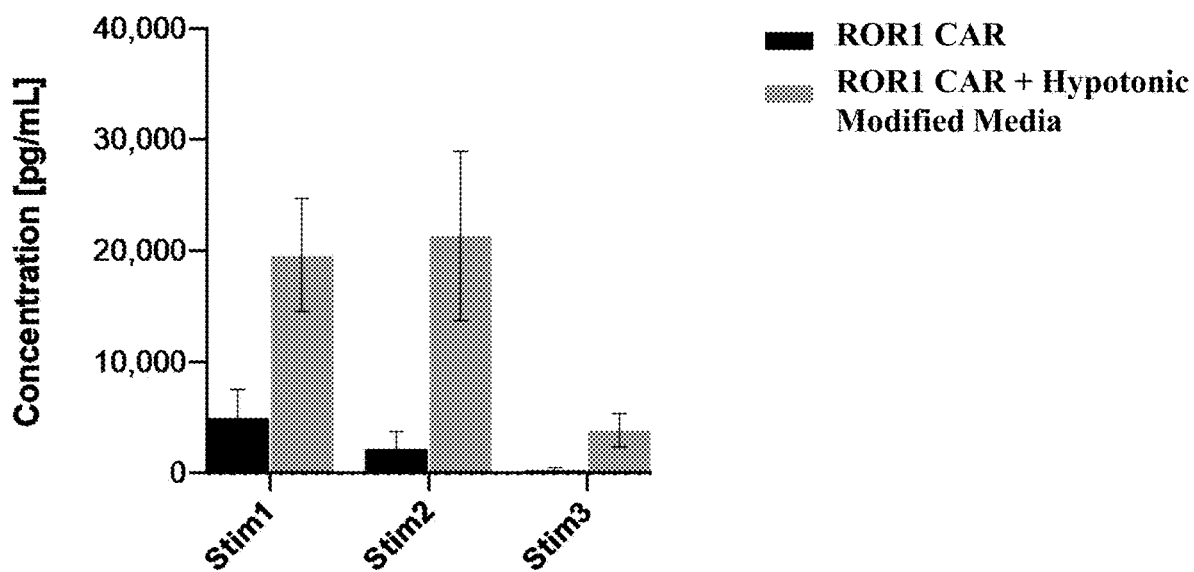

FIGS. 13A-13B are bar graphs illustrating IL-2 secretion (FIG. 13A) and IFNγ secretion (FIG. 13B) for CAR-T cells co-cultured with H1975 cells in control media or in media containing elevated potassium and NaCl such that the combination of the potassium ion and NaCl is less than 140 mM.

Figure 14:
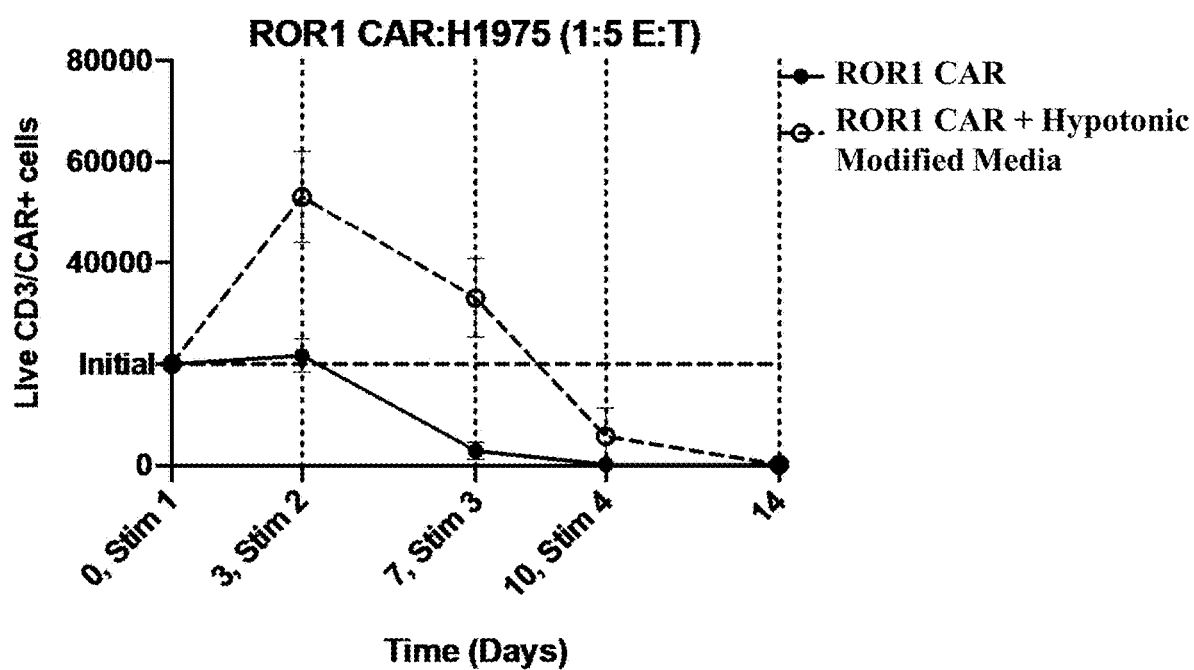

FIG. 14 is a line graph showing ROR1 CAR T cell proliferation in co-culture with H1975 target cells in control media ("ROR1 CAR") and in media containing elevated potassium and NaCl such that the combination of the potassium ion and NaCl is less than 140 mM.

DETAILED DESCRIPTION

The present disclosure is directed to methods of culturing cells, cells prepared by the methods, and/or compositions or kits for the cell culturing methods. The cell culturing methods of the present disclosure are capable of increasing multipotency and/or pluripotency of the cultured cells or increasing transduction efficiency when the cells are being transduced with a vector. In some aspects, the culturing methods are capable of reducing and/or preventing cell exhaustion when the cells are cultured and/or the cells are used in therapy in vivo. In some aspects, the culturing methods are also capable of increasing in vivo viability, in vivo persistence, in vivo effector function, or any combination thereof. In some aspects, the disclosure is directed to methods of culturing cells, e.g., pluripotent, multipotent, and/or immune cells, comprising placing the cells in a medium comprising potassium at a concentration of at least about 5 mM (e.g., higher than 5 mM), wherein the medium is not hypertonic, e.g., hypotonic or isotonic. Some aspects of the present disclosure are directed to methods of culturing cells, e.g., pluripotent, multipotent, and/or immune cells, comprising placing the cells in a medium comprising potassium at a concentration higher than 40 mM, e.g., about 50 mM-80 mM. In some aspects, the cells are immune cells. In some aspects, the immune cells comprise T cells, tumor-infiltrating lymphocytes (TILs), natural killer (NK) cells, regulatory T ($T_{reg}$) cells, or any combination thereof. In some aspects, the cells are multipotent cells. In some aspects, the cells are pluripotent cells. In some aspects, the pluripotent cells are induced pluripotent stem cells or embryonic stem cells. In some aspects, the cells are hematopoietic stem cells.

Some aspects of the present disclosure are directed to a method of increasing the yield of human immune cells and/or stem cells during ex vivo or in vitro culturing while increasing stemness of the human immune cells and/or stem cells comprising culturing human immune cells and/or stem cells in a medium comprising potassium ion at a concentration between 40 mM and 80 mM and NaCl at a concentration between 30 mM and 100 mM, wherein the total concentration of potassium ion and NaCl is between 110 and 140 mM. Some aspects of the present disclosure are directed to a method of preparing a population of human immune cells and/or stem cells for immunotherapy comprising culturing human immune cells and/or stem cells in a medium comprising potassium ion at a concentration between 40 mM and 80 mM and NaCl at a concentration between 30 mM and 100 mM, wherein the total concentration of potassium ion and NaCl is between 110 and 140 mM. Some aspects of the present disclosure are directed to a method of increasing stemness of human immune cells during ex vivo or in vitro culturing for immunotherapy comprising culturing human immune cells in a medium comprising potassium ion at a concentration between 40 mM and 80 mM and NaCl at a concentration between 30 mM and 100 mM, wherein the total concentration of potassium ion and NaCl is between 110 and 140 mM. In some aspects, the human immune cells are T cells.

In some aspects, the medium is hypotonic. In some aspects, the medium is isotonic. In certain aspects, the medium further comprises interleukin (IL)-2, IL-21, IL-7, IL-15, or any combination thereof. In some aspects, the medium comprises IL-2, IL-7 and IL-15. In some aspects, the medium comprises IL-2 and IL-21. In some aspects, the medium further comprises sodium ion, calcium ion, glucose, or any combination thereof.

Before the present disclosure is described in greater detail, it is to be understood that this disclosure is not limited to the particular compositions or process steps described, as such can, of course, vary. As will be apparent to those of skill in the art upon reading this disclosure, each of the individual aspects described and illustrated herein has discrete components and features which can be readily separated from or combined with the features of any of the other several aspects without departing from the scope or spirit of the present disclosure. Any recited method can be carried out in the order of events recited or in any other order that is logically possible.

The headings provided herein are not limitations of the various aspects of the disclosure, which can be defined by reference to the specification as a whole. It is also to be understood that the terminology used herein is for the purpose of describing particular aspects only, and is not intended to be limiting.

I. Terms

In order that the present disclosure can be more readily understood, certain terms are first defined. As used in this application, except as otherwise expressly provided herein, each of the following terms shall have the meaning set forth below. Additional definitions are set forth throughout the application.

Throughout this disclosure, the term "a" or "an" entity refers to one or more of that entity; for example, "a chimeric polypeptide," is understood to represent one or more chimeric polypeptides. As such, the terms "a" (or "an"), "one or more," and "at least one" can be used interchangeably herein. In addition, "or" is used mean an open list of the components in the list. For example, "wherein X comprises A or B" means X comprises A, X comprises B, X comprises A and B, or X comprises A or B and any other components.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range.

Abbreviations used herein are defined throughout the present disclosure. Various aspects of the disclosure are described in further detail in the following subsections.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, the term "pluripotent cell" refers to a self-replicating cell that is capable of differentiating into any cell type, e.g., in the human body.

As used herein, a "multipotent cell" refers to a self-replicating cell, which is capable of differentiating into more than one differentiated progeny cell.

As used herein, the term "immune cell" refers to a cell of the immune system. In some aspects, the immune cell is selected from a T lymphocyte ("T cell"), B lymphocyte ("B cell"), natural killer (NK) cell, macrophage, eosinophil, mast cell, dendritic cell or neutrophil). As used herein, the terms "T cell" and "T lymphocyte" are interchangeable and refer to any lymphocytes produced or processed by the thymus gland. Non-limiting classes of T cells include effector T cells and Th cells (such as CD4$^+$ or CD8$^+$ T cells). In some aspects, the immune cell is a Th1 cell. In some aspects, the immune cell is a Th2 cell. In some aspects, the immune cell is a Tc17 cell. In some aspects, the immune cell is a Th17 cell. In some aspects, the immune cell is a tumor-infiltrating cell (TIL). In some aspects, the immune cell is a $T_{reg}$ cell.

As used herein, the term "memory" T cells refers to T cells that have previously encountered and responded to their cognate antigen (e.g., in vivo, in vitro, or ex vivo) or which have been stimulated with, e.g., an anti-CD3 antibody (e.g., in vitro or ex vivo). Immune cells having a "memory-like" phenotype upon secondary exposure, such memory T cells can reproduce to mount a faster and strong immune response than during the primary exposure. In some aspects, memory T cells comprise central memory T cells ($T_{CM}$ cells), effector memory T cells ($T_{EM}$ cells), tissue resident memory T cells ($T_{RM}$ cells), stem cell-like memory T cells ($T_{SCM}$ cells), or any combination thereof.

As used herein, the term "stem cell-like memory T cells," "T memory stem cells," or "$T_{SCM}$ cells" refer to memory T cells that express CD95, CD45RA, CCR7, and CD62L and are endowed with the stem cell-like ability to self-renew and the multipotent capacity to reconstitute the entire spectrum of memory and effector T cell subsets.

As used herein, the term "central memory T cells" or "$T_{CM}$ cells" refer to memory T cells that express CD45RO, CCR7, and CD62L. Central memory T cells are generally found within the lymph nodes and in peripheral circulation.

As used herein, the term "effector memory T cells" or "$T_{EM}$ cells" refer to memory T cells that express CD45RO but lack expression of CCR7 and CD62L. Because effector memory T cells lack lymph node-homing receptors (e.g., CCR7 and CD62L), these cells are typically found in peripheral circulation and in non-lymphoid tissues.

As used herein, the term "tissue resident memory T cells" or "$T_{RM}$ cells" refer to memory T cells that do not circulate and remain resident in peripheral tissues, such as the skin, lung, and the gastrointestinal tract. In certain aspects, tissue resident memory T cells are also effector memory T cells.

As used herein, the term "naïve T cells" or "$T_N$ cells" refers to T cells that express CD45RA, CCR7, and CD62L, but which do not express CD95. $T_N$ cells represent the most undifferentiated cell in the T cell lineage. The interaction between a $T_N$ cell and an antigen-presenting cell (APC) induces differentiation of the $T_N$ cell towards an activated $T_{EFF}$ cell and an immune response.

The term "culturing" as used herein refers to the controlled growth of cells ex vivo and/or in vitro. As used herein, "culturing" includes the growth of cells, e.g., T cells and/or NK cells, during cell expansion, or cell engineering (e.g., transduction with a construct for expressing a CAR, a TCR, or a TCRm). In some aspects, the cultured cells are obtained from a subject, e.g., a human subject. In some aspects, the cultured cells comprise T cells or NK cells obtained from a human subject. In some aspects, the T cells and/or NK cells are purified prior to the culture. In some aspects, the T cells and/or NK cells are tumor-infiltrating T cells and/or NK cells. In some aspects, the cell culturing is intended to expand the number of cultured cells, e.g., to increase proliferation of the cells.

As used herein, "cell engineering" refers to the targeted modification of a cell, e.g., a pluripotent cell, a multipotent cell, or an immune cell disclosed herein. In some aspects, the cell engineering comprises viral genetic engineering, non-viral genetic engineering, introduction of receptors to allow for tumor specific targeting (e.g., a TCR, TCRm, and/or a CAR), introduction of one or more endogenous genes that improve T cell function, introduction of one or more synthetic genes that improve T cell function, or any combination thereof.

As used herein, the term "stemness," "stem cell-like," "stem-like," or "less-differentiated" refers to a cell, e.g., a pluripotent cell, a multipotent cell, or an immune cell (e.g., a T cell, an NK cell, or a TIL), that expresses markers consistent with a more naïve phenotype. For example, a less differentiated T cell can express one or more marker characteristic of a $T_N$ or a $T_{SCM}$ cell. In some aspects, a "less-differentiated" or "stem-like" T cell expresses CD45RA, CCR7, and CD62L, and does not express CD45RO. In some aspects, the methods disclosed herein promote cells, e.g., a pluripotent cell, a multipotent cell, or an immune cell (e.g., a T cell, an NK cell, or a TIL), having a less-differentiated phenotype. Without being bound by any particular mechanism, in some aspects, the methods disclosed herein block, inhibit, or limit differentiation of less-differentiated cells, e.g., a pluripotent cell, a multipotent cell, or an immune cell (e.g., a T cell, an NK cell, or a TIL), resulting in an increased number of stem-like cells in culture. For example, it is generally thought that to effectively control tumors, adoptive transfer of less-differentiated immune cells, e.g., T cells, NK cells, and/or TIL, with a stem cell-like memory or central memory phenotype are preferred. See Lynn, R. C., et al., *Nature* 576(7786): 293-300 (2019); and Gattinoni, L., et al., *Nat Med* 17(10): 1290-1297 (2011).

Stemness is characterized by the capacity to self-renew, the multipotency, and the persistence of proliferative potential. In some aspects, stemness is characterized by a particular gene signature, e.g., a combined pattern of expression across a multitude of genes. In some aspects, the gene signature comprises one or more genes selected from ACTN1, DSC1, TSHZ2, MYB, LEF1, TIMD4, MAL, KRT73, SESN3, CDCA7L, LOC283174, TCF7, SLC16A10, LASS6, UBE2E2, IL7R, GCNT4, TAF4B, SULT1B1, SELP, KRT72, STXBP1, TCEA3, FCGBP, CXCRS, GPA33, NELL2, APBA2, SELL, VIPR1, FAM153B, PPFIBP2, FCER1G, GJB6, OCM2, GCET2, LRRN1, IL6ST, LRRC16A, IGSF9B, EFHA2, LOC129293, APP, PKIA, ZC3H12D, CHMP7, KIAA0748, SLC22A17, FLJ13197, NRCAM, C5orf13, GIPC3, WNT7A, FAM117B, BEND5, LGMN, FAM63A, FAM153B, ARHGEF11, RBM11, RIC3, LDLRAP1, PELI1, PTK2, KCTD12, LMO7, CEP68, SDK2, MCOLN3, ZNF238, EDAR, FAM153C, FAAH2, BCL9, C17orf48, MAP1D, ZSWIM1, SORBS3, IL4R, SERPINF1, C16orf45, SPTBN1, KCNQ1, LDHB, BZW2, NBEA, GAL3ST4, CRTC3, MAP3K1, HLA-DOA, RAB43, SGTB, CNN3, CWH43, KLHL3, PIM2, RGMB, C16orf74, AEBP1, SNORD115-11, SNORD115-11, GRAP, and any combination thereof (see, e.g., Gattinoni (2011)). In some aspects, the gene signature comprises one or more gene selected from NOG, TIMD4, MYB, UBE2E2, FCER1G, HAVCR1, FCGBP, PPFIBP2, TPST1, ACTN1, IGF1R, KRT72, SLC16A10, GJB6, LRRN1, PRAGMIN, GIPC3, FLNB, ARRB1, SLC7A8, NUCB2, LRRC7, MYO15B, MAL, AEBP1, SDK2, BZW2, GAL3 ST4, PITPNM2, ZNF496, FAM117B, C16orf74, TDRD6, TSPAN32, C18orf22, C3orf44, LOC129293, ZC3H12D, MLXIP, C7orf10, STXBP1, KCNQ1, FLJ13197, LDLRAP1, RAB43, RIN3, SLC22A17, AGBL3, TCEA3, NCRNA00185, FAM153B, FAM153C, VIPR1, MMP19, HBS1L, EEF2K, SNORA5C, UBASH3A, FLJ43390, RP6-213H19.1, INPP5A, PIM2, TNFRSF10D, SNRK, LOC100128288, PIGV, LOC100129858, SPTBN1, PROS1, MMP28, HES1, CACHD1, NSUN5C, LEF1, TTTY14, SNORA54, HSF2, C16orf67, NSUN5B, KIAA1257, NRG2, CAD, TARBP1, STRADB, MT1F, TMEM41B, PDHX, KDM6B, LOC100288322, UXS1, LGMN, NANOS2, PYGB, RAS-GRP2, C14orf80, XPO6, SLC24A6, FAM113A, MRM1, FBXW8, NDUFS2, KCTD12, and any combination thereof (see, e.g., Gattinoni, L., et al., *Nat Med* 17(10): 1290-1297 (2011)).

In the presence of prolonged antigen exposure, such as in many cancers, more differentiated immune cells, e.g., effector and effector memory T cells, often become exhausted and lose their anti-tumor function. Biomarkers, e.g., T cell markers, can be measured using any methods. In some aspects, T cells are identified using antibody-staining following by gated flow cytometry.

As used herein, the term "tonicity" refers to the measure of the effective osmotic pressure gradient across a cell membrane. Tonicity can be expressed in terms of the osmolality of the solution, e.g., the media. As used herein, a solution, e.g., medium, is considered "isotonic" when the concentration of solutes in the media is equivalent to the concentration of solutes inside the cell. As used herein, an isotonic medium has an osmolality of about 280 mOsm/L. As used herein, a solution, e.g., a medium, is considered "hypotonic" if the concentration of solutes in the solution is lower than the concentration of solutes in the cell. As used herein, a hypotonic solution has a tonicity of less than 280 mOsm/L. In some aspects, a hypotonic medium has a tonicity from at least about 220 mOsm/L to less than about 280 mOsm/L. In some aspects, a hypotonic medium has a tonicity from at least about 230 mOsm/L to less than about 280 mOsm/L. In some aspects, a hypotonic medium has a tonicity from at least about 240 mOsm/L to less than about 280 mOsm/L. In some aspects, a hypotonic medium described herein has a tonicity of about 250 mOsm/L. As used herein, a solution, e.g., a medium, is considered "hypertonic" if the concentration of solutes in the solution is higher than the concentration of solutes in the cell. As used herein, a hypertonic solution has an osmolality of greater than 300 mOsm/L. In some aspects, a hypertonic medium described herein has an osmolality of about 320 mOsm/L. In certain aspects, the tonicity of the solution, e.g., medium is adjusted by increasing or decreasing the concentration of one or more solute selected from potassium ions, sodium ions, glucose, and any combination thereof. In some aspects, the tonicity of the solution, e.g., medium is adjusted by increasing or decreasing the concentration of potassium ions and NaCl. In some aspects, the tonicity of a medium can be maintained by offsetting the increase of one solute with a decrease in a second solute. For example, increasing the concentration of potassium ion in a medium without changing the concentration of sodium ions can increase the tonicity of the medium. However, if the concentration of potassium ions is increased and the concentration of sodium ions is decreased, the tonicity of the original medium can be maintained. As used herein, the tonicity of a medium is defined by the sum of the potassium concentration and the NaCl concentration, multiplied by two. See, e.g., Table 2.

As used herein, the terms "potassium," "potassium ion," "potassium cation," and "K+" are used interchangeably to refer to elemental potassium. Elemental potassium exists in solution as a positive ion. However, it would be readily apparent to a person of ordinary skill in the art that standard means of preparing a solution comprising potassium ion include diluting a potassium containing salt (e.g., KCl) into a solution. As such, a solution, e.g., a medium, comprising a molar (M) concentration of potassium ion, can be described as comprising an equal molar (M) concentration of a salt comprising potassium.

As used herein, the term "basal" media refers to any starting media that is supplemented with one or more of the additional elements disclosed herein, e.g., potassium, sodium, calcium, glucose, IL-2, IL-7, IL-15, IL-21, and any combination thereof. The basal media can be any media for culturing immune cells, e.g., T cells. In some aspects, the basal media is selected from a balanced salt solution (e.g., PBS, DPBS, HBSS, EBSS), Dulbecco's Modified Eagle's Medium (DMEM), Minimal Essential Medium (MEM), Basal Medium Eagle (BME), F-10, F-12, RPMI 1640, Glasgow Minimal Essential Medium (GMEM), alpha Minimal Essential Medium (alpha MEM), Iscove's Modified Dulbecco's Medium (IMDM), M199, OPTMIZER™ CTS™ T-Cell Expansion Basal Medium (ThermoFisher), OPTMIZER™ Complete, IMMUNOCULT™ XF (STEMCELL™ Technologies), IMMUNOCULT™ XF, AIM V, TEXMACS™ medium, and any combination thereof. In some aspects, the basal media comprises PRIME-XV T cell CDM. In some aspects, the basal media comprises OPTMIZER™. In some aspects, the basal media comprises OPTMIZER™ Pro. In some aspects, the basal media comprises X-VIVO™ 15 (LONZA). In some aspects, the basal media comprises IMMUNOCULT™. In some aspects, the basal media comprises Click's medium. In some aspects, the basal media comprises TRANSACT™ TIL expansion medium. In some aspects, the basal media comprises TIL rapid expansion medium. In some aspects, the basal medium is serum free. In some aspects, the basal medium further comprises immune cell serum replacement (ICSR). For example, in some aspects, the basal medium comprises OPTMIZER™ Complete supplemented with ICSR, AIM V supplemented with ICSR, IMMUNOCULT™ XF supplemented with ICSR, RPMI supplemented with ICSR, TEXMACS™ supplemented with ICSR, or any combination thereof. In some aspects, suitable basal media include Click's medium, OpTimizer® (CTS®) medium, Stemline® T cell expansion medium (Sigma-Aldrich), AIM V® medium (CTS®), TexMACS® medium (Miltenyi Biotech), ImmunoCult® medium (Stem Cell Technologies), PRIME-XV® T-Cell Expansion XSFM (Irvine Scientific), Iscoves medium, and/or RPMI-1640 medium. In some aspects, the basal media comprises NaCl free CTS™ OpTimizer™. In some aspects, the basal media comprises one or more sodium salt in addition to the NaCl that is added to control the tonicity, e.g., NaCl added in combination with potassium ion.

As used herein, the term "cytokine" refers to small, secreted proteins released by cells that have a specific effect on the interactions and communications between cells. Non-limiting examples of cytokines include interleukins (e.g., interleukin (IL)-1, IL-2, IL-4, IL-7, IL-9, IL-13, IL-15, IL-3, IL-5, IL-6, IL-11, IL-10, IL-20, IL-14, IL-16, IL-17, IL-21 and IL-23), interferons (IFN; e.g., IFN-α, IFN-β, and IFN-γ), tumor necrosis factor (TNF) family members, and transforming growth factor (TGF) family members. Certain aspects of the present disclosure are directed to methods of culturing cells, e.g., T cells and/or NK cells, in a medium comprising a cytokine. In some aspects, the cytokine is an interleukin. In some aspects, the cytokine is selected from IL-2, IL-7, IL-15, IL-21 and any combination thereof. IL-2 (UniProtKB—P60568) is produced by T cells in response to antigenic or mitogenic stimulation. IL-2 is known to stimulate T cell proliferation and other activities crucial to regulation of the immune response. IL-7 (UniProtKB—P13232) is a hematopoietic growth factor capable of stimulating the proliferation of lymphoid progenitors. IL-7 is believed to play a role in proliferation during certain stages of B-cell maturation. IL-15 (UniProtKB—P40933), like IL-2, is a cytokine that stimulates the proliferation of T-lymphocytes. IL-21 (UniProtKB—Q9HBE4) is a cytokine with immunoregulatory activity. IL-21 is thought to promote the transition between innate and adaptive immunity and to induce the production of IgG1 and IgG3 in B-cells. IL-21 may also play a role in proliferation and maturation of natural killer (NK) cells in synergy with IL-15, and IL-21 may regulate proliferation of mature B- and T-cells in response to activating stimuli. In synergy with IL-15 and IL-18, IL-15 also stimulates interferon gamma production in T-cells and NK cells, and IL-21 may also inhibit dendritic cell activation and maturation during a T-cell-mediated immune response.

As used herein, the term "higher than" means greater than but not equal to. For example, "higher than 4 mM" means any amount that is more than 4 mM, but which does not include 4 mM.

As used herein, "administering" refers to the physical introduction of a therapeutic agent or a composition comprising a therapeutic agent to a subject, using any of the various methods and delivery systems. The different routes of administration for a therapeutic agent described herein (e.g., T cell or an NK cell cultured as described herein) include intravenous, intraperitoneal, intramuscular, subcutaneous, spinal or other parenteral routes of administration, for example by injection or infusion.

The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, intratracheal, pulmonary, subcutaneous, subcuticular, intraarticular, subcapsular, subarachnoid, intraventricular, intravitreal, epidural, and intrasternal injection and infusion, as well as in vivo electroporation.

Alternatively, a therapeutic agent described herein (e.g., a T cell or an NK cell cultured as described herein) can be administered via a non-parenteral route, such as a topical, epidermal, or mucosal route of administration, for example, intranasally, orally, vaginally, rectally, sublingually, or topically. Administering can also be performed, for example, once, a plurality of times, and/or over one or more extended periods.

As used herein, the term "antigen" refers to any natural or synthetic immunogenic substance, such as a protein, peptide, or hapten. As used herein, the term "cognate antigen" refers to an antigen which an immune cell (e.g., T cell) recognizes and thereby, induces the activation of the immune cell (e.g., triggering intracellular signals that induce effector functions, such as cytokine production, and/or for proliferation of the cell).

A "cancer" refers a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

The term "hematological malignancy" or "hematological cancer" refers to mammalian cancers and tumors of the hematopoietic and lymphoid tissues. Non-limiting examples of hematological malignancies include those affecting tissues of the blood, bone marrow, lymph nodes, and lymphatic system, including acute lymphoblastic leukemia (ALL), chronic lymphocytic lymphoma (CLL), small lymphocytic lymphoma (SLL), acute myelogenous leukemia (AML), chronic myelogenous leukemia (CIVIL), acute monocytic leukemia (AMoL), Hodgkin's lymphoma, and non-Hodgkin's lymphomas. Hematological malignancies are also referred to as "liquid tumors." Liquid tumor cancers include, but are not limited to, leukemias, myelomas, and lymphomas, as well as other hematological malignancies.

A "solid tumor," as used herein, refers to an abnormal mass of tissue. Solid tumors may be benign or malignant. Nonlimiting examples of solid tumors include sarcomas, carcinomas, and lymphomas, such as cancers of the lung, breast, prostate, colon, rectum, and bladder. The tissue structure of a solid tumor includes interdependent tissue compartments including the parenchyma (cancer cells) and the supporting stromal cells in which the cancer cells are dispersed, and which may provide a supporting microenvironment.

In some aspects, the cancer is selected from adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment. In some aspects, the cancer is selected from chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma. In some aspects, the cancer is selected from acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma. In some aspects, the cancer is selected from acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum. In some aspects, the cancer is selected from Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

As used herein, the term "immune response" refers to a biological response within a vertebrate against foreign agents, which response protects the organism against these agents and diseases caused by them. An immune response is mediated by the action of a cell of the immune system (e.g., a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4$^+$ or CD8$^+$ T cell, or the inhibition of a Treg cell. As used herein, the terms "T cell" and "T lymphocytes" are interchangeable and refer to any lymphocytes produced or processed by the thymus gland. In some aspects, a T cell is a CD4+ T cell. In some aspects, a T cell is a CD8+ T cell. In some aspects, a T cell is a NKT cell.

As used herein, the term "anti-tumor immune response" refers to an immune response against a tumor antigen.

A "subject" includes any human or nonhuman animal. The term "nonhuman animal" includes, but is not limited to, vertebrates such as nonhuman primates, sheep, dogs, and rodents such as mice, rats and guinea pigs. In some aspects, the subject is a human. The terms "subject" and "patient" are used interchangeably herein. As used herein, the phrase "subject in need thereof" includes subjects, such as mammalian subjects, that would benefit, e.g., from administration of T cells cultured as described herein to control tumor growth.

The term "therapeutically effective amount" or "therapeutically effective dosage" refers to an amount of an agent (e.g., a T cell or NK cell cultured as described herein) that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some aspects, an effective amount is an amount sufficient to delay tumor development. In some aspects, an effective amount is an amount sufficient to prevent or delay tumor recurrence. An effective amount can be administered in one or more administrations.

The effective amount of the composition (e.g., cells cultured as described herein) can, for example, (i) reduce the number of cancer cells; (ii) reduce tumor size; (iii) inhibit, delay, slow to some extent and can stop cancer cell infiltration into peripheral organs; (iv) inhibit (i.e., slow to some extent and can stop tumor metastasis); (v) inhibit tumor growth; (vi) prevent or delay occurrence and/or recurrence of tumor; and/or (vii) relieve to some extent one or more of the symptoms associated with the cancer.

In some aspects, a "therapeutically effective amount" is the amount of a composition disclosed herein (e.g., T cells cultured as described herein), which is clinically proven to effect a significant decrease in cancer or slowing of progression (regression) of cancer, such as an advanced solid tumor. The ability of a therapeutic agent of the present disclosure (e.g., T cells cultured as described herein) to promote disease regression can be evaluated using a variety of methods known to the skilled practitioner, such as in human subjects during clinical trials, in animal model systems predictive of efficacy in humans, or by assaying the activity of the agent in in vitro assays.

The terms "effective" and "effectiveness" with regard to a treatment include both pharmacological effectiveness and physiological safety. Pharmacological effectiveness refers to the ability of a composition disclosed herein (e.g., cells cultured as described herein) to promote cancer regression in the patient. Physiological safety refers to the level of toxicity, or other adverse physiological effects at the cellular, organ, and/or organism level (adverse effects) resulting from administration of a composition disclosed herein (e.g., cells cultured as described herein).

The terms "chimeric antigen receptor" and "CAR," as used herein, refer to a recombinant fusion protein that has an antigen-specific extracellular domain coupled to an intracellular domain that directs the cell to perform a specialized function upon binding of an antigen to the extracellular domain. In some aspects, a chimeric antigen receptor disclosed herein comprises a chimeric polypeptide of the present disclosure.

The terms "artificial T cell receptor," "chimeric T-cell receptor," and "chimeric immunoreceptor" can each be used interchangeably herein with the term "chimeric antigen receptor." Chimeric antigen receptors are distinguished from other antigen-binding agents by their ability to both bind MHC-independent antigen and transduce activation signals via their intracellular domain.

The antigen-specific extracellular domain of a chimeric antigen receptor recognizes and specifically binds an antigen, typically a surface-expressed antigen of a malignancy. An antigen-specific extracellular domain specifically binds an antigen when, for example, it binds the antigen with an affinity constant or affinity of interaction (KD) between about 0.1 pM to about 10 for example, about 0.1 pM to about 1 µM or about 0.1 pM to about 100 nM. Methods for determining the affinity of interaction are known in the art. An antigen-specific extracellular domain suitable for use in a CAR of the present disclosure can be any antigen-binding polypeptide, a wide variety of which are known in the art. In some aspects, the antigen-binding domain is a single chain Fv (scFv). Other antibody-based recognition domains such as cAb VHH (camelid antibody variable domains) and humanized versions thereof, lgNAR VH (shark antibody variable domains) and humanized versions thereof, sdAb VH (single domain antibody variable domains), and "camelized" antibody variable domains are also suitable for use in a CAR of the present disclosure. In some aspects, T cell receptor (TCR) based recognition domains, such as single chain TCR (scTv, i.e., single chain two-domain TCR containing V.alpha.V.beta.) are also suitable for use in a TCR of the present disclosure.

As used herein, the term "T cell receptor" or "TCR" refers to a heterodimer composed of 2 different transmembrane polypeptide chains: an α chain and a β chain, each consisting of a constant region, which anchors the chain inside the T-cell surface membrane, and a variable region, which recognizes and binds to the antigen presented by MHCs. The TCR complex is associated with 6 polypeptides forming 2 heterodimers, CD3γε and CD3δε, and 1 homodimer CD3ζ, which together forms the CD3 complex. T-cell receptor-engineered T-cell therapy utilizes the modification of T cells that retain these complexes to specifically target the antigens expressed by particular tumor cells. As used herein, the term "TCR" includes naturally occurring TCRs and engineered TCRs.

As used herein, an "engineered TCR" or "engineered T-cell receptor" refers to a T-cell receptor (TCR) engineered to specifically bind with a desired affinity to a major histocompatibility complex (MHC)/peptide target antigen that is selected, cloned, and/or subsequently introduced into a population of immune cells, e.g., T cells, NK cells, and/or TILs.

A "TCR mimic" or a "TCRm" refers to a type of antibody that recognize epitopes comprising both the peptide and the MHC-I molecule, similar to the recognition of such complexes by the TCR on T cells.

As used herein, the terms "ug" and "uM" are used interchangeably with "µg" and "µM," respectively.

Various aspects described herein are described in further detail in the following subsections.

II. Methods of the Disclosure

The present disclosure is directed to methods of culturing cells ex vivo or in vitro. In some aspects, the methods of the present disclosure comprise culturing or placing cells, e.g., a pluripotent cell, a multipotent cell, or an immune cell (e.g., a T cell, an NK cell, or a TIL) in a culture condition, wherein the culture (e.g., tonicity of the medium, cytokines, and or any combination thereof) is capable of limiting or preventing the differentiation of the cells, thereby affecting or improving their use in a cell therapy.

Cell culture media are useful for the in vitro expansion of cell products used to expand and activate cells for the treatments of varieties of maladies. One of the most urgent unmet needs is for the expansion of cells that can be used in therapy, e.g., cells that can destroy cancer cells. Metastatic solid tumors are responsible for >500,000 deaths in the United States alone. It is known that T lymphocytes are capable of killing tumors in settings where other available treatments are ineffective. For example, surgery, chemotherapy, radiation therapy and 'targeted' or small molecule therapies are not effective for many common types of metastatic cancers such as those of the colon, breast, lung, pancreas, prostate, bile duct and other histologies. Cell-based cancer immunotherapies can represent curative therapy in these histologies.

The efficacy of cellular immunotherapy is dependent on the persistence, multipotency, and asymmetric cell division in vivo (phenotypic characteristics of T cell stemness). The media that are employed in the culturing and/or engineering of therapeutic cells can profoundly affect the metabolic, epigenetic, and phenotypic attributes of the cells. The formulations of media currently in use have not undergone significant change in approximately 40 years (see Moore et al., *JAMA* 199(8): 519-24 (1967), which is incorporated by reference herein in its entirety)). However, robust preclinical data disclosed herein demonstrate that the concentration of ions, especially potassium (K+), nutrients, and/or cytokines can significantly affect the multipotency of T cells during ex vivo manipulations. This effect is multifactorial and depends on the target of the therapeutic cells, cell function within the tumor microenvironment, and the quality of the therapeutic cells prior to transfer. Disclosed herein are strategies to promote antitumor cell stemness, e.g., prior to adoptive transfer.

Some aspects of the disclosure are directed to methods of culturing cells, e.g., pluripotent, multipotent, and/or immune cells (e.g., T cells, NK cells, and/or TILs), in medium comprising an increased concentration of potassium ion (e.g., greater than about 40 mM, greater than about 45 mM, greater than about 50 mM, greater than about 55 mM, greater than about 60 mM, greater than about 65 mM, or greater than about 70 mM), relative to conventional immune cell culture media. In some aspects, the media with elevated potassium is hypotonic or isotonic.

Some aspects of the present disclosure are directed to a method of increasing the yield of human immune cells and/or stem cells during ex vivo or in vitro culturing while increasing stemness of the human immune cells and/or stem cells comprising culturing human immune cells and/or stem cells in a medium comprising potassium ion at a concentration between 40 mM and 80 mM and NaCl at a concentration between 30 mM and 100 mM, wherein the total concentration of potassium ion and NaCl is between 110 and 140 mM. Some aspects of the present disclosure are directed to a method of preparing a population of human immune cells and/or stem cells for immunotherapy comprising culturing human immune cells and/or stem cells in a medium comprising potassium ion at a concentration between 40 mM and 80 mM and NaCl at a concentration between 30 mM and 100 mM, wherein the total concentration of potassium ion and NaCl is between 110 and 140 mM. Some aspects of the present disclosure are directed to a method of increasing stemness of human immune cells during ex vivo or in vitro culturing for immunotherapy comprising culturing human immune cells in a medium comprising potassium ion at a concentration between 40 mM and 80 mM and NaCl at a concentration between 30 mM and 100 mM, wherein the total concentration of potassium ion and NaCl is between 110 and 140 mM.

In some aspects, the method of the present disclosure comprises placing, growing, or culturing the cells, e.g., immune cells, e.g., T cells, NK cells, and/or TILs, in a medium comprising potassium ion at a concentration of at least about 5 mM, wherein the medium is hypotonic. In certain aspects, the concentration of potassium ion is at least about 50 mM. In some aspects, the method of the present disclosure comprises placing, growing, or culturing the cells, e.g., T cells, in a medium comprising potassium ion at a concentration of higher than about 40 mM, wherein the medium is hypotonic or isotonic. In certain aspects, the concentration of potassium ion is at least about 50 mM. In some aspects, the method of the present disclosure comprises placing, growing, or culturing the cells, e.g., T cells, in a medium comprising potassium ion at a concentration of at least about 50 mM, wherein the medium is hypotonic or isotonic. Some aspects of the present disclosure are directed to a method of preparing a population of chimeric antigen receptor (CAR) or TCR-expressing immune cells, e.g., T cells, NK cells, and/or TILs, comprising placing the cells into a medium comprising potassium ion at a concentration of at least about 5 mM, wherein the medium is hypotonic. In certain aspects, the concentration of potassium ion is at least about 50 mM. Some aspects of the present disclosure are directed to a method of preparing a population of chimeric antigen receptor (CAR) or TCR-expressing immune cells, e.g., T cells, NK cells, and/or TIL, comprising placing the cells into a medium comprising potassium ion at a concentration of at least about 5 mM, wherein the medium is not hypertonic, e.g., wherein the medium is hypotonic or isotonic. Some aspects of the present disclosure are directed to a method of preparing a population of chimeric antigen receptor (CAR) or TCR-expressing immune cells, e.g., T cells, NK cells, and/or TIL, comprising placing the cells into a medium comprising potassium ion at a concentration of at least about 50 mM. In some aspects, the medium is hypotonic or isotonic. The medium can be prepared by adding a sufficient amount of a potassium salt. The tonicity of the medium can be modified by controlling the concentration of NaCl in the medium relative to the concentration of potassium ion. In some aspects, the total concentration of potassium ion and NaCl is between 110 mM and 140 mM.

In some aspects, the present disclosure also provides that cells, e.g., pluripotent, multipotent, and/or immune cells (e.g., T cells, NK cells, and/or TILs), grown in a medium having a high concentration of potassium ion (e.g., higher than about 5 mM, e.g., higher than 40 mM, e.g., between 55 mM and 70 mM), but being isotonic or hypotonic, are capable of preserving a more stem-like phenotype of minimal differentiation than cells grown in a medium being hypertonic. In some aspects, therefore, the medium is not hypertonic after adding the potassium salt. In some aspects, the medium is hypotonic. In some aspects, the medium is isotonic. In certain aspects, the medium further comprises interleukin (IL)-2, IL-21, IL-7, IL-15, or any combination thereof. In some aspects, the medium further comprises sodium ion, calcium ion, glucose, or any combination thereof.

In certain aspects, a population of cells, e.g., pluripotent, multipotent, and/or immune cells (e.g., T cells, NK cells, and/or TILs), cultured using the methods disclosed herein exhibits an increased number of stem-like cells relative to a population of cells cultured using conventional methods, e.g., in a medium having less than 5 mM potassium ion or under hypertonic conditions. In some aspects, the cells, e.g., pluripotent, multipotent, and/or immune cells (e.g., T cells, NK cells, and/or TILs), exhibit increased expression of markers characteristic of stem-like cells relative to the starting population of cells. In some aspects, the starting population of cells comprises cells obtained from a human subject. In some aspects, the starting population of cells comprises T cells obtained from a human subject. In some aspects, the starting population of T cells comprises $T_N$ cells, $T_{SCM}$ cells, $T_{CM}$ cells, $T_{EM}$ cells, or any combination thereof.

Increased cell multipotency can be measured using any methods known in the art. In certain aspects, cell stemness is measured by antibody staining followed by gated flow cytometry. In some aspects, the cell stemness is measured by autophagy flux. In some aspects, the cell stemness is measured by glucose uptake. In some aspects, the cell stemness is measured by fatty acid uptake. In some aspects, the cell stemness is measured by mitochondrial biomass. In some aspects, the cell stemness is measured by RNA quantification/expression analysis (e.g., microarray, qPCR (taqman), RNA-Seq., single-cell RNA-Seq., or any combinations thereof). In some aspects, the cell stemness is measured by a metabolism assay (e.g., a Seahorse metabolism assay, analysis of extracellular acidification rate (ECAR); analysis of oxygen consumption rate (OCR); analysis of spare respiratory capacity; and/or analysis of mitochondrial membrane potential (TMRM)). In some aspects, stemness is measured using one or more in vivo functional assays (e.g., assaying cell persistence, antitumor capacity, antitumor clearance, viral clearance, multipotency, and any combination thereof).

In some aspects, the differentiation status of the cells, e.g., the pluripotent cells, the multipotent cells, and/or the immune cells (e.g., T cells, NK cells, and/or TILs), is characterized by increased numbers of cells expressing markers typical of less differentiated cells. In some aspects, an increase in the number of stem-like T cells is characterized by increased numbers of T cells expressing markers typical of $T_N$ and/or $T_{SCM}$ cells. In certain aspects, an increase in the number of stem-like T cells is characterized by increased numbers of T cells expressing markers typical of $T_{SCM}$ cells. In some aspects, the T cells exhibit an increased number of T cells that express CD45RA. In some aspects, the T cells exhibit an increased number of T cells that express CCR7. In some aspects, the T cells exhibit an increased number of T cells that express CD62L. In some aspects, the T cells exhibit an increased number of T cells that express CD28. In some aspects, the T cells exhibit an increased number of T cells that express CD95. In some aspects, the T cells do not express CD45RO. In some aspects, the T cells exhibit an increased number of T cells that are $CD95^+$, $CD45RA^+$, $CCR7^+$, and $CD62L^+$. In some aspects, the T cells exhibit an increased number of cells that express TCF7. In some aspects, the T cells exhibit an increased number of T cells that are $CD95^+$, $CD45RA^+$, $CCR7^+$, $CD62L^+$, and $TCF7^+$. In some aspects, the T cells express CD3. In some aspects, the T cells exhibit an increased number of T cells that are $CD3^+$, $CD95^+$, $CD45RA^+$, $CCR7^+$, $CD62L^+$, and $TCF7^+$. In some aspects, the T cells express CD27. In some aspects, the T cells exhibit an increased number of T cells that are $CD27^+$, $CD3^+$, $CD95^+$, $CD45RA^+$, $CCR7^+$, $CD62L^+$, and $TCF7^+$. In some aspects, the T cells exhibit an increased number of $T_{SCM}$ cells. In some aspects, the T cells exhibit an increased number of $T_N$ cells. In some aspects, the T cells exhibit an increased number of $T_{SCM}$ and $T_N$ cells.

In some aspects, the number of stem-like cells in the culture is increased by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 100%, relative to the number of stem-like cells prior to culture. In some aspects, the number of stem-like cells in the culture is increased by at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, at least about 10-fold, at least about 15-fold, or at least about 20-fold, relative to the number of stem-like cells prior to culture.

In some aspects, following culture of T cells according to the methods disclosed herein, stem-like T cells constitute at least about 1%, at least about 2%, at least about 3%, at least about 4%, at least about 5%, at least about 10%, at least about 15%, of the total number of $CD8^+$ T cells in the culture.

In some aspects, following culture of T cells according to the methods disclosed herein, stem-like T constitute at least about 1%, at least about 2%, at least about 3%, at least about 4%, at least about 5%, at least about 10%, at least about 15%, of the total number of $CD4^+$ T cells in the culture.

In some aspects, the cells, e.g., pluripotent, multipotent, and/or immune cells (e.g., T cells, NK cells, and/or TILs), cultured according to the methods disclosed herein exhibit increased transduction efficiency. In some aspects, a greater percentage of cells express a target transgene, e.g., encoding a CAR, a TCR, or a TCRm, following transduction, wherein the cells are cultured according to the methods disclosed herein as compared to cells similarly transduced and cultured using conventional methods. In certain aspects, the cells, e.g., pluripotent, multipotent, and/or immune cells (e.g., T cells, NK cells, and/or TILs), are transduced using a viral vector. In some aspects, the viral vector comprises an AAV. In some aspects, the viral vector comprises a retrovirus. In some aspects, the viral vector comprises a lentivirus. In certain aspects, a greater percentage of cells cultured according to the methods disclosed herein express a CAR or a TCR following lentiviral transduction of the cells, as compared to similarly transduced cells cultured using conventional methods. In some aspects, transduction efficiency is increased at least 1.5-fold relative to similarly transduced cells cultured using conventional methods. In some aspects, transduction efficiency is increase at least 2-fold relative to similarly transduced cells cultured using conventional methods.

In some aspects, the cells, e.g., pluripotent, multipotent, and/or immune cells (e.g., T cells, NK cells, and/or TILs), are transduced before culturing according to the methods disclosed herein. In some aspects, the cells, e.g., pluripotent, multipotent, and/or immune cells (e.g., T cells, NK cells, and/or TILs), are transduced after culturing according to the methods disclosed herein. In some aspects, the cells, e.g., pluripotent, multipotent, and/or immune cells (e.g., T cells, NK cells, and/or TILs), are cultured according to the methods disclosed herein, e.g., in a hypotonic or isotonic medium comprising at least 50 mM potassium ion, prior to, during, and after transduction.

In certain aspects, upon adoptive transfer of the cells, e.g., T cells, NK cells, and/or TILs, cultured according to the methods disclosed herein, the transferred cells exhibit decreased cell exhaustion, as compared to cells cultured using conventional culture conditions. In certain aspects, upon adoptive transfer of the cultured cells, the transferred cells persist for a longer period of time in vivo, as compared to cells cultured using conventional culture conditions. In some aspects, the transferred cells, e.g., T cells, NK cells, and/or TILs, have a greater in vivo efficacy, e.g., tumor-killing activity, as compared to cells cultured using conventional culture conditions. In some aspects, a lower dose of the cells cultured according to the methods disclosed herein is needed to elicit a response, e.g., decreased tumor volume, in a subject as compared to cells cultured using conventional culture conditions.

Certain aspects of the disclosure are directed to methods of culturing cells, e.g., pluripotent, multipotent, and/or immune cells (e.g., T cells, NK cells, and/or TILs), in medium comprising potassium ion at a concentration of at least about 5 mM, wherein the medium is hypotonic. Some aspects of the disclosure are directed to methods of culturing cells, e.g., pluripotent, multipotent, and/or immune cells (e.g., T cells, NK cells, and/or TILs), in medium comprising potassium ion at a concentration higher than 40 mM. Some aspects of the disclosure are directed to methods of culturing cells, e.g., pluripotent, multipotent, and/or immune cells (e.g., T cells, NK cells, and/or TILs), in medium comprising potassium ion at a concentration of at least about 50 mM. Some aspects of the disclosure are directed to methods of culturing cells, e.g., pluripotent, multipotent, and/or immune cells (e.g., T cells, NK cells, and/or TILs), in medium comprising potassium ion at a concentration of at least about 50 mM, wherein the medium is hypotonic or isotonic. In some aspects, the cells, e.g., the T cells, NK cells, or TILs, are cultured in a medium disclosed herein, e.g., comprising potassium ion at a concentration of at least about 50 mM, immediately upon isolation from a subject. In some aspects, the cells, e.g., the T cells, NK cells, or TILs, are cultured in a medium disclosed herein, e.g., comprising potassium ion at a concentration of at least about 50 mM, during expansion of the cells. In some aspects, the cells, e.g., the T cells, NK cells, or TILs, are cultured in a medium disclosed herein, e.g., comprising potassium ion at a concentration of at least about 50 mM, during engineering of the cells, e.g., during transduction with a construct encoding a CAR or a TCR. In some aspects, the cells, e.g., the T cells, NK cells, or TILs, are cultured in a medium disclosed herein, e.g., comprising potassium ion at a concentration of at least about 50 mM, following engineering of the cells, e.g., following transduction with a construct encoding a CAR or a TCR. In some aspects, the cells, e.g., the T cells, NK cells, or TILs, are cultured in a medium disclosed herein, e.g., comprising potassium ion at a concentration of at least about 50 mM, throughout expansion and engineering. In certain aspects, the cells, e.g., the T cells, NK cells, or TILs, are cultured in a medium disclosed herein, e.g., comprising potassium ion at a concentration of at least about 50 mM, throughout viral genetic engineering. In certain aspects, the cells, e.g., the T cells, NK cells, or TILs, are cultured in a medium disclosed herein, e.g., comprising potassium ion at a concentration of at least about 50 mM, throughout non-viral genetic engineering. In certain aspects, the cells, e.g., the T cells, NK cells, or TILs, are cultured in a medium disclosed herein, e.g., comprising potassium ion at a concentration of at least about 50 mM, during introduction of receptors to allow for tumor specific targeting (e.g., a TCR, a TCRm, and/or a CAR). In certain aspects, the cells, e.g., the T cells, NK cells, or TILs, are cultured in a medium disclosed herein, e.g., comprising potassium ion at a concentration of at least about 50 mM, throughout introduction of one or more endogenous genes that improve T cell function. In certain aspects, the cells, e.g., the T cells, NK cells, or TILs, are cultured in a medium disclosed herein, e.g., comprising potassium ion at a concentration of at least about 50 mM, throughout introduction of one or more synthetic genes that improve T cell function.

In some aspects, the concentration of potassium ion is at least about 5 mM, at least about 10 mM, at least about 15 mM, at least about 20 mM, at least about 25 mM, at least about 30 mM, at least about 35 mM, at least about 40 mM, or at least about 45 mM. In some aspects, the concentration of potassium ion is at least about 50 mM. In some aspects, the concentration of potassium ion is about 5 mM, about 10 mM, about 15 mM, about 20 mM, about 25 mM, about 30 mM, about 35 mM, about 40 mM, or about 45 mM. In some aspects, the concentration of potassium ion is about 40 mM. In some aspects, the concentration of potassium ion is about 45 mM. In some aspects, the concentration of potassium ion is about 50 mM.

In some aspects, the concentration of potassium ion is at least about 55 mM, at least about 60 mM, at least about 65 mM, at least about 70 mM, at least about 75 mM, at least about 80 mM, at least about 85 mM, at least about 90 mM, at least about 95 mM, at least about 100 mM, at least about 105 mM, at least about 110 mM, at least about 115 mM, at least about 120 mM. In some aspects, the concentration of potassium ion is about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM. In some aspects, the concentration of potassium ion is about 55 mM. In some aspects, the concentration of potassium ion is about 60 mM. In some aspects, the concentration of potassium ion is about 65 mM. In some aspects, the concentration of potassium ion is about 70 mM.

In some aspects, the concentration of potassium ion is about 5 mM to about 100 mM, wherein the medium is hypotonic. In some aspects, the concentration of potassium ion is about 5 mM to about 90 mM, about 5 mM to about 80 mM, about 5 mM to about 70 mM, about 5 mM to about 60 mM, or about 5 mM to about 50 mM, wherein the medium is hypotonic. In some aspects, the concentration of potassium ion is about 25 mM to about 100 mM, wherein the medium is hypotonic. In some aspects, the concentration of potassium ion is about 25 mM to about 90 mM, about 25 mM to about 80 mM, about 25 mM to about 70 mM, about 25 mM to about 60 mM, or about 25 mM to about 50 mM, wherein the medium is hypotonic. In some aspects, the concentration of potassium ion is about 40 mM to about 100 mM, wherein the medium is hypotonic. In some aspects, the concentration of potassium ion is about 40 mM to about 90 mM, about 40 mM to about 85 mM, about 40 mM to about 80 mM, about 40 mM to about 75 mM, about 40 mM to about 70 mM, about 40 mM to about 65 mM, about 40 mM to about 60 mM, about 40 mM to about 55 mM, or about 40 mM to about 50 mM, wherein the medium is hypotonic. In some aspects, the concentration of potassium ion is about 50 mM to about 90 mM, about 50 mM to about 85 mM, about 50 mM to about 80 mM, about 50 mM to about 75 mM, about 50 mM to about 70 mM, about 50 mM to about 65 mM, about 50 mM to about 60 mM, or about 50 mM to about 55 mM. In some aspects, the medium is hypotonic. In some aspects, the medium comprises at least about 50 mM potassium ion and less than about 90 mM NaCl. In some aspects, the total concentration of potassium ion and NaCl is between 110 mM and 140 mM.

In some aspects, the concentration of potassium ion is about 50 mM to about 120 mM. In some aspects, the concentration of potassium ion is about 50 mM to about 115 mM, about 50 mM to about 110 mM, about 50 mM to about 105 mM, about 50 mM to about 100 mM, about 50 mM to about 95 mM, about 50 mM to about 90 mM, about 50 mM to about 85 mM, about 50 mM to about 80 mM, about 50 mM to about 75 mM, about 50 mM to about 70 mM, about 50 mM to about 65 mM, about 50 mM to about 60 mM, or about 50 mM to about 55 mM. In some aspects, the medium is hypotonic. In some aspects, the medium comprises at least about 50 mM to about 120 mM potassium ion and less than about 90 mM to about 20 mM NaCl. In some aspects, the total concentration of potassium ion and NaCl is between 110 mM and 140 mM.

In some aspects, the concentration of potassium ion is about 55 mM to about 120 mM. In some aspects, the concentration of potassium ion is about 55 mM to about 115 mM, about 55 mM to about 110 mM, about 55 mM to about 105 mM, about 55 mM to about 100 mM, about 55 mM to about 95 mM, about 55 mM to about 90 mM, about 55 mM to about 85 mM, about 55 mM to about 80 mM, about 55 mM to about 75 mM, about 55 mM to about 70 mM, about 55 mM to about 65 mM, or about 55 mM to about 60 mM. In some aspects, the medium is hypotonic. In some aspects, the medium comprises at least about 55 mM to about 120 mM potassium ion and less than about 85 mM to about 20 mM NaCl. In some aspects, the total concentration of potassium ion and NaCl is between 110 mM and 140 mM.

In some aspects, the concentration of potassium ion is about 60 mM to about 120 mM. In some aspects, the concentration of potassium ion is about 60 mM to about 115 mM, about 60 mM to about 110 mM, about 60 mM to about 105 mM, about 60 mM to about 100 mM, about 60 mM to about 95 mM, about 60 mM to about 90 mM, about 60 mM to about 85 mM, about 60 mM to about 80 mM, about 60 mM to about 75 mM, about 60 mM to about 70 mM, or about 60 mM to about 65 mM. In some aspects, the medium is hypotonic. In some aspects, the medium comprises at least about 60 mM to about 120 mM potassium ion and less than about 80 mM to about 20 mM NaCl. In some aspects, the total concentration of potassium ion and NaCl is between 110 mM and 140 mM.

In some aspects, the concentration of potassium ion is about 65 mM to about 120 mM. In some aspects, the concentration of potassium ion is about 65 mM to about 115 mM, about 65 mM to about 110 mM, about 65 mM to about 105 mM, about 65 mM to about 100 mM, about 65 mM to about 95 mM, about 65 mM to about 90 mM, about 65 mM to about 85 mM, about 65 mM to about 80 mM, about 65 mM to about 75 mM, or about 65 mM to about 70 mM. In some aspects, the medium is hypotonic. In some aspects, the medium comprises at least about 65 mM to about 120 mM potassium ion and less than about 75 mM to about 20 mM NaCl. In some aspects, the total concentration of potassium ion and NaCl is between 110 mM and 140 mM.

In some aspects, the concentration of potassium ion is about 70 mM to about 120 mM. In some aspects, the concentration of potassium ion is about 70 mM to about 115 mM, about 70 mM to about 110 mM, about 70 mM to about 105 mM, about 70 mM to about 100 mM, about 70 mM to about 95 mM, about 70 mM to about 90 mM, about 70 mM to about 85 mM, about 70 mM to about 80 mM, or about 70 mM to about 75 mM. In some aspects, the medium is hypotonic. In some aspects, the medium comprises at least about 70 mM to about 120 mM potassium ion and less than about 70 mM to about 20 mM NaCl. In some aspects, the total concentration of potassium ion and NaCl is between 110 mM and 140 mM.

In some aspects, the concentration of potassium ion is about 75 mM to about 120 mM. In some aspects, the concentration of potassium ion is about 75 mM to about 115 mM, about 75 mM to about 110 mM, about 75 mM to about 105 mM, about 75 mM to about 100 mM, about 75 mM to about 95 mM, about 75 mM to about 90 mM, about 75 mM to about 85 mM, or about 75 mM to about 80 mM. In some aspects, the medium is hypotonic. In some aspects, the medium comprises at least about 75 mM to about 120 mM potassium ion and less than about 65 mM to about 20 mM NaCl. In some aspects, the total concentration of potassium ion and NaCl is between 110 mM and 140 mM.

In some aspects, the concentration of potassium ion is about 80 mM to about 120 mM. In some aspects, the concentration of potassium ion is about 80 mM to about 115 mM, about 80 mM to about 110 mM, about 80 mM to about 105 mM, about 80 mM to about 100 mM, about 80 mM to about 95 mM, about 80 mM to about 90 mM, or about 80 mM to about 85 mM. In some aspects, the medium is hypotonic. In some aspects, the medium comprises at least about 80 mM to about 120 mM potassium ion and less than about 60 mM to about 20 mM NaCl. In some aspects, the total concentration of potassium ion and NaCl is between 110 mM and 140 mM.

In some aspects, the concentration of potassium ion is about 85 mM to about 120 mM. In some aspects, the concentration of potassium ion is about 85 mM to about 115 mM, about 85 mM to about 110 mM, about 85 mM to about 105 mM, about 85 mM to about 100 mM, about 85 mM to about 95 mM, or about 85 mM to about 90 mM. In some aspects, the medium is hypotonic. In some aspects, the medium comprises at least about 85 mM to about 120 mM potassium ion and less than about 65 mM to about 20 mM NaCl. In some aspects, the total concentration of potassium ion and NaCl is between 110 mM and 140 mM.

In some aspects, the concentration of potassium ion is about 90 mM to about 120 mM. In some aspects, the concentration of potassium ion is about 90 mM to about 115 mM, about 90 mM to about 110 mM, about 90 mM to about 105 mM, about 90 mM to about 100 mM, or about 90 mM to about 95 mM. In some aspects, the medium is hypotonic. In some aspects, the medium comprises at least about 90 mM to about 120 mM potassium ion and less than about 50 mM to about 20 mM NaCl. In some aspects, the total concentration of potassium ion and NaCl is between 110 mM and 140 mM.

In some aspects, the concentration of potassium ion is about 95 mM to about 120 mM. In some aspects, the concentration of potassium ion is about 95 mM to about 115 mM, about 95 mM to about 110 mM, about 95 mM to about 105 mM, or about 95 mM to about 100 mM. In some aspects, the medium is hypotonic. In some aspects, the medium comprises at least about 95 mM to about 120 mM potassium ion and less than about 55 mM to about 20 mM NaCl. In some aspects, the total concentration of potassium ion and NaCl is between 110 mM and 140 mM.

In some aspects, the concentration of potassium ion is about 100 mM to about 120 mM. In some aspects, the concentration of potassium ion is about 100 mM to about 115 mM, about 100 mM to about 110 mM, or about 100 mM to about 105 mM. In some aspects, the medium is hypotonic. In some aspects, the medium comprises at least about 100 mM to about 120 mM potassium ion and less than about 50 mM to about 20 mM NaCl. In some aspects, the total concentration of potassium ion and NaCl is between 110 mM and 140 mM.

In some aspects, the concentration of potassium ion is about 105 mM to about 120 mM. In some aspects, the concentration of potassium ion is about 105 mM to about 115 mM, or about 105 mM to about 110 mM. In some aspects, the medium is hypotonic. In some aspects, the medium comprises at least about 105 mM to about 120 mM potassium ion and less than about 35 mM to about 20 mM NaCl. In some aspects, the total concentration of potassium ion and NaCl is between 110 mM and 140 mM.

In some aspects, the concentration of potassium ion is about 110 mM to about 120 mM. In some aspects, the concentration of potassium ion is about 110 mM to about 115 mM. In some aspects, the medium is hypotonic. In some aspects, the medium comprises at least about 110 mM to about 120 mM potassium ion and less than about 30 mM to about 20 mM NaCl. In some aspects, the total concentration of potassium ion and NaCl is between 110 mM and 140 mM.

In some aspects, the concentration of potassium ion is about 50 mM to about 90 mM. In some aspects, the concentration of potassium ion is about 50 mM to about 80 mM. In some aspects, the concentration of potassium ion is about 60 mM to about 90 mM. In some aspects, the concentration of potassium ion is about 60 mM to about 80 mM. In some aspects, the concentration of potassium ion is about 70 mM to about 90 mM. In some aspects, the concentration of potassium ion is about 70 mM to about 80 mM. In some aspects, the concentration of potassium ion is about 80 mM to about 90 mM.

In some aspects, the concentration of potassium ion is about 50 mM to about 90 mM, and the concentration of NaCl is less than about 90 mM to about 50 mM. In some aspects, the concentration of potassium ion is about 50 mM to about 80 mM, and the concentration of NaCl is less than about 90 mM to about 60 mM. In some aspects, the concentration of potassium ion is about 60 mM to about 90 mM, and the concentration of NaCl is less than about 90 mM to about 60 mM. In some aspects, the concentration of potassium ion is about 60 mM to about 80 mM, and the concentration of NaCl is less than about 80 mM to about 60 mM. In some aspects, the concentration of potassium ion is about 70 mM to about 90 mM, and the concentration of NaCl is less than about 70 mM to about 50 mM. In some aspects, the concentration of potassium ion is about 70 mM to about 80 mM, and the concentration of NaCl is less than about 70 mM to about 60 mM. In some aspects, the concentration of potassium ion is about 80 mM to about 90 mM, and the concentration of NaCl is less than about 60 mM to about 50 mM. In some aspects, the total concentration of potassium ion and NaCl is between 110 mM and 140 mM.

In some aspects, the concentration of potassium ion is about 50 mM to about 55 mM. In some aspects, the concentration of potassium ion is about 50 mM to about 55 mM, and the concentration of NaCl is less than about 90 to about 85. In some aspects, the concentration of potassium ion is about 55 mM to about 60 mM. In some aspects, the concentration of potassium ion is about 55 mM to about 60 mM, and the concentration of NaCl is less than about 85 to about 80. In some aspects, the concentration of potassium ion is about 60 mM to about 65 mM. In some aspects, the concentration of potassium ion is about 60 mM to about 65 mM, and the concentration of NaCl is less than about 80 mM to about 75 mM. In some aspects, the concentration of potassium ion is about 65 mM to about 70 mM. In some aspects, the concentration of potassium ion is about 65 mM to about 70 mM, and the concentration of NaCl is less than about 75 mM to about 70 mM. In some aspects, the concentration of potassium ion is about 70 mM to about 75 mM. In some aspects, the concentration of potassium ion is about 70 mM to about 75 mM, and the concentration of NaCl is less than about 70 mM to about 65 mM. In some aspects, the concentration of potassium ion is about 75 mM to about 80 mM. In some aspects, the concentration of potassium ion is about 75 mM to about 80 mM, and the concentration of NaCl is less than about 65 to about 60. In some aspects, the concentration of potassium ion is about 80 mM to about 85 mM. In some aspects, the concentration of potassium ion is about 80 mM to about 85 mM, and the concentration of NaCl is less than about 60 mM to about 55 mM. In some aspects, the concentration of potassium ion is about 85 mM to about 90 mM. In some aspects, the concentration of potassium ion is about 85 mM to about 90 mM, and the concentration of NaCl is less than about 55 mM to about 50 mM. In some aspects, the concentration of potassium ion is about 90 mM to about 95 mM. In some aspects, the concentration of potassium ion is about 90 mM to about 95 mM, and the concentration of NaCl is less than about 50 to about 45. In some aspects, the concentration of potassium ion is about 95 mM to about 100 mM. In some aspects, the concentration of potassium ion is about 95 mM to about 100 mM, and the concentration of NaCl is less than about 45 mM to about 40 mM. In some aspects, the concentration of potassium ion is about 100 mM to about 105 mM. In some aspects, the concentration of potassium ion is about 100 mM to about 105 mM, and the concentration of NaCl is less than about 40 mM to about 35 mM. In some aspects, the concentration of potassium ion is about 105 mM to about 110 mM. In some aspects, the concentration of potassium ion is about 105 mM to about 110 mM, and the concentration of NaCl is less than about 35 to about 30. In some aspects, the concentration of potassium ion is about 110 mM to about 115 mM. In some aspects, the concentration of potassium ion is about 110 mM to about 115 mM, and the concentration of NaCl is less than about 30 mM to about 25 mM. In some aspects, the concentration of potassium ion is about 115 mM to about 120 mM. In some aspects, the concentration of potassium ion is about 115 mM to about 120 mM, and the concentration of NaCl is less than about 25 mM to about 20 mM. In some aspects, the total concentration of potassium ion and NaCl is between 110 mM and 140 mM.

In certain aspects, the concentration of potassium ion is about 40 mM to about 90 mM, wherein the medium is hypotonic. In certain aspects, the concentration of potassium ion is about 40 mM to about 80 mM, wherein the medium is hypotonic. In certain aspects, the concentration of potassium ion is about 40 mM to about 70 mM, wherein the medium is hypotonic. In certain aspects, the concentration of potassium ion is about 50 mM to about 90 mM, wherein the medium is hypotonic. In certain aspects, the concentration of potassium ion is about 50 mM to about 80 mM, wherein the medium is hypotonic. In certain aspects, the concentration of potassium ion is about 50 mM to about 70 mM, wherein the medium is hypotonic. In certain aspects, the concentration of potassium ion is about 55 mM to about 90 mM, wherein the medium is hypotonic. In certain aspects, the concentration of potassium ion is about 55 mM to about 80 mM, wherein the medium is hypotonic. In certain aspects, the concentration of potassium ion is about 55 mM to about 70 mM, wherein the medium is hypotonic. In certain aspects, the concentration of potassium ion is about 60 mM to about 90 mM, wherein the medium is hypotonic. In certain aspects, the concentration of potassium ion is about 60 mM to about 80 mM, wherein the medium is hypotonic. In certain aspects, the concentration of potassium ion is about 60 mM to about 70 mM, wherein the medium is hypotonic. In certain aspects, the concentration of potassium ion is about 65 mM to about 90 mM, wherein the medium is hypotonic. In certain aspects, the concentration of potassium ion is about 65 mM to about 80 mM, wherein the medium is hypotonic. In certain aspects, the concentration of potassium ion is about 65 mM to about 70 mM, wherein the medium is hypotonic.

In some aspects, the concentration of potassium ion is higher than about 40 mM, wherein the medium is hypotonic. In some aspects, the concentration of potassium ion is about 40 mM, wherein the medium is hypotonic. In some aspects, the concentration of potassium ion is higher than about 41 mM, wherein the medium is hypotonic. In some aspects, the concentration of potassium ion is about 41 mM, wherein the medium is hypotonic. In some aspects, the concentration of potassium ion is higher than about 42 mM, wherein the medium is hypotonic. In some aspects, the concentration of potassium ion is about 42 mM, wherein the medium is hypotonic. In some aspects, the concentration of potassium ion is higher than about 43 mM, wherein the medium is hypotonic. In some aspects, the concentration of potassium ion is about 43 mM, wherein the medium is hypotonic. In some aspects, the concentration of potassium ion is higher than about 44 mM, wherein the medium is hypotonic. In some aspects, the concentration of potassium ion is about 44 mM, wherein the medium is hypotonic. In some aspects, the concentration of potassium ion is higher than about 45 mM, wherein the medium is hypotonic. In some aspects, the concentration of potassium ion is about 45 mM, wherein the medium is hypotonic. In some aspects, the concentration of potassium ion is higher than about 46 mM, wherein the medium is hypotonic. In some aspects, the concentration of potassium ion is about 46 mM, wherein the medium is hypotonic. In some aspects, the concentration of potassium ion is higher than about 47 mM, wherein the medium is hypotonic. In some aspects, the concentration of potassium ion is about 47 mM, wherein the medium is hypotonic. In some aspects, the concentration of potassium ion is higher than about 48 mM, wherein the medium is hypotonic. In some aspects, the concentration of potassium ion is about 48 mM, wherein the medium is hypotonic. In some aspects, the concentration of potassium ion is higher than about 49 mM, wherein the medium is hypotonic. In some aspects, the concentration of potassium ion is about 49 mM, wherein the medium is hypotonic.

In some aspects, the concentration of potassium ion is higher than about 40 mM, wherein the total concentration of potassium ion and NaCl in the medium is between 110 mM and 140 mM. In some aspects, the concentration of potassium ion is about 40 mM, wherein the total concentration of potassium ion and NaCl in the medium is between 110 mM and 140 mM. In some aspects, the concentration of potassium ion is higher than about 41 mM, wherein the total concentration of potassium ion and NaCl in the medium is between 110 mM and 140 mM. In some aspects, the concentration of potassium ion is about 41 mM, wherein the total concentration of potassium ion and NaCl in the medium is between 110 mM and 140 mM. In some aspects, the concentration of potassium ion is higher than about 42 mM, wherein the total concentration of potassium ion and NaCl in the medium is between 110 mM and 140 mM. In some aspects, the concentration of potassium ion is about 42 mM, wherein the total concentration of potassium ion and NaCl in the medium is between 110 mM and 140 mM. In some aspects, the concentration of potassium ion is higher than about 43 mM, wherein the total concentration of potassium ion and NaCl in the medium is between 110 mM and 140 mM. In some aspects, the concentration of potassium ion is about 43 mM, wherein the total concentration of potassium ion and NaCl in the medium is between 110 mM and 140 mM. In some aspects, the concentration of potassium ion is higher than about 44 mM, wherein the total concentration of potassium ion and NaCl in the medium is between 110 mM and 140 mM. In some aspects, the concentration of potassium ion is about 44 mM, wherein the total concentration of potassium ion and NaCl in the medium is between 110 mM and 140 mM. In some aspects, the concentration of potassium ion is higher than about 45 mM, wherein the total concentration of potassium ion and NaCl in the medium is between 110 mM and 140 mM. In some aspects, the concentration of potassium ion is about 45 mM, wherein the total concentration of potassium ion and NaCl in the medium is between 110 mM and 140 mM. In some aspects, the concentration of potassium ion is higher than about 46 mM, wherein the total concentration of potassium ion and NaCl in the medium is between 110 mM and 140 mM. In some aspects, the concentration of potassium ion is about 46 mM, wherein the total concentration of potassium ion and NaCl in the medium is between 110 mM and 140 mM. In some aspects, the concentration of potassium ion is higher than about 47 mM, wherein the total concentration of potassium ion and NaCl in the medium is between 110 mM and 140 mM. In some aspects, the concentration of potassium ion is about 47 mM, wherein the total concentration of potassium ion and NaCl in the medium is between 110 mM and 140 mM. In some aspects, the concentration of potassium ion is higher than about 48 mM, wherein the total concentration of potassium ion and NaCl in the medium is between 110 mM and 140 mM. In some aspects, the concentration of potassium ion is about 48 mM, wherein the total concentration of potassium ion and NaCl in the medium is between 110 mM and 140 mM. In some aspects, the concentration of potassium ion is higher than about 49 mM, wherein the total concentration of potassium ion and NaCl in the medium is between 110 mM and 140 mM. In some aspects, the concentration of potassium ion is about 49 mM, wherein the total concentration of potassium ion and NaCl in the medium is between 110 mM and 140 mM.

In some aspects, the concentration of potassium ion is higher than about 50 mM. In some aspects, the concentration of potassium ion is about 50 mM. In some aspects, the concentration of potassium ion is higher than about 51 mM. In some aspects, the concentration of potassium ion is about 51 mM. In some aspects, the concentration of potassium ion is higher than about 52 mM. In some aspects, the concentration of potassium ion is about 52 mM. In some aspects, the concentration of potassium ion is higher than about 53 mM. In some aspects, the concentration of potassium ion is about 53 mM. In some aspects, the concentration of potassium ion is higher than about 54 mM. In some aspects, the concentration of potassium ion is about 54 mM. In some aspects, the concentration of potassium ion is higher than about 55 mM. In some aspects, the concentration of potassium ion is about 55 mM. In some aspects, the concentration of potassium ion is higher than about 56 mM. In some aspects, the concentration of potassium ion is about 56 mM. In some aspects, the concentration of potassium ion is higher than about 57 mM. In some aspects, the concentration of potassium ion is about 57 mM. In some aspects, the concentration of potassium ion is higher than about 58 mM. In some aspects, the concentration of potassium ion is about 58 mM. In some aspects, the concentration of potassium ion is higher than about 59 mM. In some aspects, the concentration of potassium ion is about 59 mM. In certain aspects, the medium is hypotonic. In certain aspects, the medium is isotonic.

In some aspects, the concentration of potassium ion is higher than about 50 mM, wherein the total concentration of potassium ion and NaCl in the medium is between 110 mM and 140 mM. In some aspects, the concentration of potassium ion is about 50 mM, wherein the total concentration of potassium ion and NaCl in the medium is between 110 mM and 140 mM. In some aspects, the concentration of potassium ion is higher than about 51 mM, wherein the total concentration of potassium ion and NaCl in the medium is between 110 mM and 140 mM. In some aspects, the concentration of potassium ion is about 51 mM, wherein the total concentration of potassium ion and NaCl in the medium is between 110 mM and 140 mM. In some aspects, the concentration of potassium ion is higher than about 52 mM, wherein the total concentration of potassium ion and NaCl in the medium is between 110 mM and 140 mM. In some aspects, the concentration of potassium ion is about 52 mM, wherein the total concentration of potassium ion and NaCl in the medium is between 110 mM and 140 mM. In some aspects, the concentration of potassium ion is higher than about 53 mM, wherein the total concentration of potassium ion and NaCl in the medium is between 110 mM and 140 mM. In some aspects, the concentration of potassium ion is about 53 mM, wherein the total concentration of potassium ion and NaCl in the medium is between 110 mM and 140 mM. In some aspects, the concentration of potassium ion is higher than about 54 mM, wherein the total concentration of potassium ion and NaCl in the medium is between 110 mM and 140 mM. In some aspects, the concentration of potassium ion is about 54 mM, wherein the total concentration of potassium ion and NaCl in the medium is between 110 mM and 140 mM. In some aspects, the concentration of potassium ion is higher than about 55 mM, wherein the total concentration of potassium ion and NaCl in the medium is between 110 mM and 140 mM. In some aspects, the concentration of potassium ion is about 55 mM, wherein the total concentration of potassium ion and NaCl in the medium is between 110 mM and 140 mM. In some aspects, the concentration of potassium ion is higher than about 56 mM, wherein the total concentration of potassium ion and NaCl in the medium is between 110 mM and 140 mM. In some aspects, the concentration of potassium ion is about 56 mM, wherein the total concentration of potassium ion and NaCl in the medium is between 110 mM and 140 mM. In some aspects, the concentration of potassium ion is higher than about 57 mM, wherein the total concentration of potassium ion and NaCl in the medium is between 110 mM and 140 mM. In some aspects, the concentration of potassium ion is about 57 mM, wherein the total concentration of potassium ion and NaCl in the medium is between 110 mM and 140 mM. In some aspects, the concentration of potassium ion is higher than about 58 mM, wherein the total concentration of potassium ion and NaCl in the medium is between 110 mM and 140 mM. In some aspects, the concentration of potassium ion is about 58 mM, wherein the total concentration of potassium ion and NaCl in the medium is between 110 mM and 140 mM. In some aspects, the concentration of potassium ion is higher than about 59 mM, wherein the total concentration of potassium ion and NaCl in the medium is between 110 mM and 140 mM. In some aspects, the concentration of potassium ion is about 59 mM, wherein the total concentration of potassium ion and NaCl in the medium is between 110 mM and 140 mM.

In some aspects, the concentration of potassium ion is higher than about 60 mM. In some aspects, the concentration of potassium ion is about 60 mM. In some aspects, the concentration of potassium ion is higher than about 61 mM. In some aspects, the concentration of potassium ion is about 61 mM. In some aspects, the concentration of potassium ion is higher than about 62 mM. In some aspects, the concentration of potassium ion is about 62 mM. In some aspects, the concentration of potassium ion is higher than about 63 mM. In some aspects, the concentration of potassium ion is about 63 mM. In some aspects, the concentration of potassium ion is higher than about 64 mM. In some aspects, the concentration of potassium ion is about 64 mM. In some aspects, the concentration of potassium ion is higher than about 65 mM. In some aspects, the concentration of potassium ion is about 65 mM. In some aspects, the concentration of potassium ion is higher than about 66 mM. In some aspects, the concentration of potassium ion is about 66 mM. In some aspects, the concentration of potassium ion is higher than about 67 mM. In some aspects, the concentration of potassium ion is about 67 mM. In some aspects, the concentration of potassium ion is higher than about 68 mM. In some aspects, the concentration of potassium ion is about 68 mM. In some aspects, the concentration of potassium ion is higher than about 69 mM. In some aspects, the concentration of potassium ion is about 69 mM. In certain aspects, the medium is hypotonic. In certain aspects, the medium is isotonic.

In some aspects, the concentration of potassium ion is higher than about 60 mM, wherein the total concentration of potassium ion and NaCl in the medium is between 110 mM and 140 mM. In some aspects, the concentration of potassium ion is about 60 mM, wherein the total concentration of potassium ion and NaCl in the medium is between 110 mM and 140 mM. In some aspects, the concentration of potassium ion is higher than about 61 mM, wherein the total concentration of potassium ion and NaCl in the medium is between 110 mM and 140 mM. In some aspects, the concentration of potassium ion is about 61 mM, wherein the total concentration of potassium ion and NaCl in the medium is between 110 mM and 140 mM. In some aspects, the concentration of potassium ion is higher than about 62 mM, wherein the total concentration of potassium ion and NaCl in the medium is between 110 mM and 140 mM. In some aspects, the concentration of potassium ion is about 62 mM, wherein the total concentration of potassium ion and NaCl in the medium is between 110 mM and 140 mM. In some aspects, the concentration of potassium ion is higher than about 63 mM, wherein the total concentration of potassium ion and NaCl in the medium is between 110 mM and 140 mM. In some aspects, the concentration of potassium ion is about 63 mM, wherein the total concentration of potassium ion and NaCl in the medium is between 110 mM and 140 mM. In some aspects, the concentration of potassium ion is higher than about 64 mM, wherein the total concentration of potassium ion and NaCl in the medium is between 110 mM and 140 mM. In some aspects, the concentration of potassium ion is about 64 mM, wherein the total concentration of potassium ion and NaCl in the medium is between 110 mM and 140 mM. In some aspects, the concentration of potassium ion is higher than about 65 mM, wherein the total concentration of potassium ion and NaCl in the medium is between 110 mM and 140 mM. In some aspects, the concentration of potassium ion is about 65 mM, wherein the total concentration of potassium ion and NaCl in the medium is between 110 mM and 140 mM. In some aspects, the concentration of potassium ion is higher than about 66 mM, wherein the total concentration of potassium ion and NaCl in the medium is between 110 mM and 140 mM. In some aspects, the concentration of potassium ion is about 66 mM, wherein the total concentration of potassium ion and NaCl in the medium is between 110 mM and 140 mM. In some aspects, the concentration of potassium ion is higher than about 67 mM, wherein the total concentration of potassium ion and NaCl in the medium is between 110 mM and 140 mM. In some aspects, the concentration of potassium ion is about 67 mM, wherein the total concentration of potassium ion and NaCl in the medium is between 110 mM and 140 mM. In some aspects, the concentration of potassium ion is higher than about 68 mM, wherein the total concentration of potassium ion and NaCl in the medium is between 110 mM and 140 mM. In some aspects, the concentration of potassium ion is about 68 mM, wherein the total concentration of potassium ion and NaCl in the medium is between 110 mM and 140 mM. In some aspects, the concentration of potassium ion is higher than about 69 mM, wherein the total concentration of potassium ion and NaCl in the medium is between 110 mM and 140 mM. In some aspects, the concentration of potassium ion is about 69 mM, wherein the total concentration of potassium ion and NaCl in the medium is between 110 mM and 140 mM.

In some aspects, the concentration of potassium ion is higher than about 70 mM. In some aspects, the concentration of potassium ion is about 70 mM. In some aspects, the concentration of potassium ion is higher than about 71 mM. In some aspects, the concentration of potassium ion is about 71 mM. In some aspects, the concentration of potassium ion is higher than about 72 mM. In some aspects, the concentration of potassium ion is about 72 mM. In some aspects, the concentration of potassium ion is higher than about 73 mM. In some aspects, the concentration of potassium ion is about 73 mM. In some aspects, the concentration of potassium ion is higher than about 74 mM. In some aspects, the concentration of potassium ion is about 74 mM. In some aspects, the concentration of potassium ion is higher than about 75 mM. In some aspects, the concentration of potassium ion is about 75 mM. In some aspects, the concentration of potassium ion is higher than about 76 mM. In some aspects, the concentration of potassium ion is about 76 mM. In some aspects, the concentration of potassium ion is higher than about 77 mM. In some aspects, the concentration of potassium ion is about 77 mM. In some aspects, the concentration of potassium ion is higher than about 78 mM. In some aspects, the concentration of potassium ion is about 78 mM. In some aspects, the concentration of potassium ion is higher than about 79 mM. In some aspects, the concentration of potassium ion is about 79 mM. In certain aspects, the medium is hypotonic. In certain aspects, the medium is isotonic.

In some aspects, the concentration of potassium ion is higher than about 70 mM, wherein the total concentration of potassium ion and NaCl in the medium is between 110 mM and 140 mM. In some aspects, the concentration of potassium ion is about 70 mM, wherein the total concentration of potassium ion and NaCl in the medium is between 110 mM and 140 mM. In some aspects, the concentration of potassium ion is higher than about 71 mM, wherein the total concentration of potassium ion and NaCl in the medium is between 110 mM and 140 mM. In some aspects, the concentration of potassium ion is about 71 mM, wherein the total concentration of potassium ion and NaCl in the medium is between 110 mM and 140 mM. In some aspects, the concentration of potassium ion is higher than about 72 mM, wherein the total concentration of potassium ion and NaCl in the medium is between 110 mM and 140 mM. In some aspects, the concentration of potassium ion is about 72 mM, wherein the total concentration of potassium ion and NaCl in the medium is between 110 mM and 140 mM. In some aspects, the concentration of potassium ion is higher than about 73 mM, wherein the total concentration of potassium ion and NaCl in the medium is between 110 mM and 140 mM. In some aspects, the concentration of potassium ion is about 73 mM, wherein the total concentration of potassium ion and NaCl in the medium is between 110 mM and 140 mM. In some aspects, the concentration of potassium ion is higher than about 74 mM, wherein the total concentration of potassium ion and NaCl in the medium is between 110 mM and 140 mM. In some aspects, the concentration of potassium ion is about 74 mM, wherein the total concentration of potassium ion and NaCl in the medium is between 110 mM and 140 mM. In some aspects, the concentration of potassium ion is higher than about 75 mM, wherein the total concentration of potassium ion and NaCl in the medium is between 110 mM and 140 mM. In some aspects, the concentration of potassium ion is about 75 mM, wherein the total concentration of potassium ion and NaCl in the medium is between 110 mM and 140 mM. In some aspects, the concentration of potassium ion is higher than about 76 mM, wherein the total concentration of potassium ion and NaCl in the medium is between 110 mM and 140 mM. In some aspects, the concentration of potassium ion is about 76 mM, wherein the total concentration of potassium ion and NaCl in the medium is between 110 mM and 140 mM. In some aspects, the concentration of potassium ion is higher than about 77 mM, wherein the total concentration of potassium ion and NaCl in the medium is between 110 mM and 140 mM. In some aspects, the concentration of potassium ion is about 77 mM, wherein the total concentration of potassium ion and NaCl in the medium is between 110 mM and 140 mM. In some aspects, the concentration of potassium ion is higher than about 78 mM, wherein the total concentration of potassium ion and NaCl in the medium is between 110 mM and 140 mM. In some aspects, the concentration of potassium ion is about 78 mM, wherein the total concentration of potassium ion and NaCl in the medium is between 110 mM and 140 mM. In some aspects, the concentration of potassium ion is higher than about 79 mM, wherein the total concentration of potassium ion and NaCl in the medium is between 110 mM and 140 mM. In some aspects, the concentration of potassium ion is about 79 mM, wherein the total concentration of potassium ion and NaCl in the medium is between 110 mM and 140 mM.

In some aspects, the concentration of potassium ion is higher than about 80 mM. In some aspects, the concentration of potassium ion is about 80 mM. In some aspects, the concentration of potassium ion is higher than about 81 mM. In some aspects, the concentration of potassium ion is about 81 mM. In some aspects, the concentration of potassium ion is higher than about 82 mM. In some aspects, the concentration of potassium ion is about 82 mM. In some aspects, the concentration of potassium ion is higher than about 83 mM. In some aspects, the concentration of potassium ion is about 83 mM. In some aspects, the concentration of potassium ion is higher than about 84 mM. In some aspects, the concentration of potassium ion is about 84 mM. In some aspects, the concentration of potassium ion is higher than about 85 mM. In some aspects, the concentration of potassium ion is about 85 mM. In some aspects, the concentration of potassium ion is higher than about 86 mM. In some aspects, the concentration of potassium ion is about 86 mM. In some aspects, the concentration of potassium ion is higher than about 87 mM. In some aspects, the concentration of potassium ion is about 87 mM. In some aspects, the concentration of potassium ion is higher than about 88 mM. In some aspects, the concentration of potassium ion is about 88 mM. In some aspects, the concentration of potassium ion is higher than about 89 mM. In some aspects, the concentration of potassium ion is about 89 mM. In certain aspects, the medium is hypotonic. In certain aspects, the medium is isotonic.

In some aspects, the concentration of potassium ion is higher than about 80 mM, wherein the total concentration of potassium ion and NaCl in the medium is between 110 mM and 140 mM. In some aspects, the concentration of potassium ion is about 80 mM, wherein the total concentration of potassium ion and NaCl in the medium is between 110 mM and 140 mM. In some aspects, the concentration of potassium ion is higher than about 81 mM, wherein the total concentration of potassium ion and NaCl in the medium is between 110 mM and 140 mM. In some aspects, the concentration of potassium ion is about 81 mM, wherein the total concentration of potassium ion and NaCl in the medium is between 110 mM and 140 mM. In some aspects, the concentration of potassium ion is higher than about 82 mM, wherein the total concentration of potassium ion and NaCl in the medium is between 110 mM and 140 mM. In some aspects, the concentration of potassium ion is about 82 mM, wherein the total concentration of potassium ion and NaCl in the medium is between 110 mM and 140 mM. In some aspects, the concentration of potassium ion is higher than about 83 mM, wherein the total concentration of potassium ion and NaCl in the medium is between 110 mM and 140 mM. In some aspects, the concentration of potassium ion is about 83 mM, wherein the total concentration of potassium ion and NaCl in the medium is between 110 mM and 140 mM. In some aspects, the concentration of potassium ion is higher than about 84 mM, wherein the total concentration of potassium ion and NaCl in the medium is between 110 mM and 140 mM. In some aspects, the concentration of potassium ion is about 84 mM, wherein the total concentration of potassium ion and NaCl in the medium is between 110 mM and 140 mM. In some aspects, the concentration of potassium ion is higher than about 85 mM, wherein the total concentration of potassium ion and NaCl in the medium is between 110 mM and 140 mM. In some aspects, the concentration of potassium ion is about 85 mM, wherein the total concentration of potassium ion and NaCl in the medium is between 110 mM and 140 mM. In some aspects, the concentration of potassium ion is higher than about 86 mM, wherein the total concentration of potassium ion and NaCl in the medium is between 110 mM and 140 mM. In some aspects, the concentration of potassium ion is about 86 mM, wherein the total concentration of potassium ion and NaCl in the medium is between 110 mM and 140 mM. In some aspects, the concentration of potassium ion is higher than about 87 mM, wherein the total concentration of potassium ion and NaCl in the medium is between 110 mM and 140 mM. In some aspects, the concentration of potassium ion is about 87 mM, wherein the total concentration of potassium ion and NaCl in the medium is between 110 mM and 140 mM. In some aspects, the concentration of potassium ion is higher than about 88 mM, wherein the total concentration of potassium ion and NaCl in the medium is between 110 mM and 140 mM. In some aspects, the concentration of potassium ion is about 88 mM, wherein the total concentration of potassium ion and NaCl in the medium is between 110 mM and 140 mM. In some aspects, the concentration of potassium ion is higher than about 89 mM, wherein the total concentration of potassium ion and NaCl in the medium is between 110 mM and 140 mM. In some aspects, the concentration of potassium ion is about 89 mM, wherein the total concentration of potassium ion and NaCl in the medium is between 110 mM and 140 mM.

In some aspects, the concentration of potassium ion is higher than about 90 mM. In some aspects, the concentration of potassium ion is about 90 mM. In some aspects, the concentration of potassium ion is higher than about 91 mM. In some aspects, the concentration of potassium ion is about 91 mM. In some aspects, the concentration of potassium ion is higher than about 92 mM. In some aspects, the concentration of potassium ion is about 92 mM. In some aspects, the concentration of potassium ion is higher than about 93 mM. In some aspects, the concentration of potassium ion is about 93 mM. In some aspects, the concentration of potassium ion is higher than about 94 mM. In some aspects, the concentration of potassium ion is about 94 mM. In some aspects, the concentration of potassium ion is higher than about 95 mM. In some aspects, the concentration of potassium ion is about 95 mM. In some aspects, the concentration of potassium ion is higher than about 96 mM. In some aspects, the concentration of potassium ion is about 96 mM. In some aspects, the concentration of potassium ion is higher than about 97 mM. In some aspects, the concentration of potassium ion is about 97 mM. In some aspects, the concentration of potassium ion is higher than about 98 mM. In some aspects, the concentration of potassium ion is about 98 mM. In some aspects, the concentration of potassium ion is higher than about 99 mM. In some aspects, the concentration of potassium ion is about 99 mM. In certain aspects, the medium is hypotonic. In certain aspects, the medium is isotonic.

In some aspects, the concentration of potassium ion is higher than about 90 mM, wherein the total concentration of potassium ion and NaCl in the medium is between 110 mM and 140 mM. In some aspects, the concentration of potassium ion is about 90 mM, wherein the total concentration of potassium ion and NaCl in the medium is between 110 mM and 140 mM. In some aspects, the concentration of potassium ion is higher than about 91 mM, wherein the total concentration of potassium ion and NaCl in the medium is between 110 mM and 140 mM. In some aspects, the concentration of potassium ion is about 91 mM, wherein the total concentration of potassium ion and NaCl in the medium is between 110 mM and 140 mM. In some aspects, the concentration of potassium ion is higher than about 92 mM, wherein the total concentration of potassium ion and NaCl in the medium is between 110 mM and 140 mM. In some aspects, the concentration of potassium ion is about 92 mM, wherein the total concentration of potassium ion and NaCl in the medium is between 110 mM and 140 mM. In some aspects, the concentration of potassium ion is higher than about 93 mM, wherein the total concentration of potassium ion and NaCl in the medium is between 110 mM and 140 mM. In some aspects, the concentration of potassium ion is about 93 mM, wherein the total concentration of potassium ion and NaCl in the medium is between 110 mM and 140 mM. In some aspects, the concentration of potassium ion is higher than about 94 mM, wherein the total concentration of potassium ion and NaCl in the medium is between 110 mM and 140 mM. In some aspects, the concentration of potassium ion is about 94 mM, wherein the total concentration of potassium ion and NaCl in the medium is between 110 mM and 140 mM. In some aspects, the concentration of potassium ion is higher than about 95 mM, wherein the total concentration of potassium ion and NaCl in the medium is between 110 mM and 140 mM. In some aspects, the concentration of potassium ion is about 95 mM, wherein the total concentration of potassium ion and NaCl in the medium is between 110 mM and 140 mM. In some aspects, the concentration of potassium ion is higher than about 96 mM, wherein the total concentration of potassium ion and NaCl in the medium is between 110 mM and 140 mM. In some aspects, the concentration of potassium ion is about 96 mM, wherein the total concentration of potassium ion and NaCl in the medium is between 110 mM and 140 mM. In some aspects, the concentration of potassium ion is higher than about 97 mM, wherein the total concentration of potassium ion and NaCl in the medium is between 110 mM and 140 mM. In some aspects, the concentration of potassium ion is about 97 mM, wherein the total concentration of potassium ion and NaCl in the medium is between 110 mM and 140 mM. In some aspects, the concentration of potassium ion is higher than about 98 mM, wherein the total concentration of potassium ion and NaCl in the medium is between 110 mM and 140 mM. In some aspects, the concentration of potassium ion is about 98 mM, wherein the total concentration of potassium ion and NaCl in the medium is between 110 mM and 140 mM. In some aspects, the concentration of potassium ion is higher than about 99 mM, wherein the total concentration of potassium ion and NaCl in the medium is between 110 mM and 140 mM. In some aspects, the concentration of potassium ion is about 99 mM, wherein the total concentration of potassium ion and NaCl in the medium is between 110 mM and 140 mM.

In some aspects, the concentration of potassium ion is higher than about 100 mM. In some aspects, the concentration of potassium ion is about 100 mM. In some aspects, the concentration of potassium ion is higher than about 101 mM. In some aspects, the concentration of potassium ion is about 101 mM. In some aspects, the concentration of potassium ion is higher than about 102 mM. In some aspects, the concentration of potassium ion is about 102 mM. In some aspects, the concentration of potassium ion is higher than about 103 mM. In some aspects, the concentration of potassium ion is about 103 mM. In some aspects, the concentration of potassium ion is higher than about 104 mM. In some aspects, the concentration of potassium ion is about 104 mM. In some aspects, the concentration of potassium ion is higher than about 105 mM. In some aspects, the concentration of potassium ion is about 105 mM. In some aspects, the concentration of potassium ion is higher than about 106 mM. In some aspects, the concentration of potassium ion is about 106 mM. In some aspects, the concentration of potassium ion is higher than about 107 mM. In some aspects, the concentration of potassium ion is about 107 mM. In some aspects, the concentration of potassium ion is higher than about 108 mM. In some aspects, the concentration of potassium ion is about 108 mM. In some aspects, the concentration of potassium ion is higher than about 109 mM. In some aspects, the concentration of potassium ion is about 109 mM. In certain aspects, the medium is hypotonic. In certain aspects, the medium is isotonic.

In some aspects, the concentration of potassium ion is higher than about 100 mM, wherein the total concentration of potassium ion and NaCl in the medium is between 110 mM and 140 mM. In some aspects, the concentration of potassium ion is about 100 mM, wherein the total concentration of potassium ion and NaCl in the medium is between 110 mM and 140 mM. In some aspects, the concentration of potassium ion is higher than about 101 mM, wherein the total concentration of potassium ion and NaCl in the medium is between 110 mM and 140 mM. In some aspects, the concentration of potassium ion is about 101 mM, wherein the total concentration of potassium ion and NaCl in the medium is between 110 mM and 140 mM. In some aspects, the concentration of potassium ion is higher than about 102 mM, wherein the total concentration of potassium ion and NaCl in the medium is between 110 mM and 140 mM. In some aspects, the concentration of potassium ion is about 102 mM, wherein the total concentration of potassium ion and NaCl in the medium is between 110 mM and 140 mM. In some aspects, the concentration of potassium ion is higher than about 103 mM, wherein the total concentration of potassium ion and NaCl in the medium is between 110 mM and 140 mM. In some aspects, the concentration of potassium ion is about 103 mM, wherein the total concentration of potassium ion and NaCl in the medium is between 110 mM and 140 mM. In some aspects, the concentration of potassium ion is higher than about 104 mM, wherein the total concentration of potassium ion and NaCl in the medium is between 110 mM and 140 mM. In some aspects, the concentration of potassium ion is about 104 mM, wherein the total concentration of potassium ion and NaCl in the medium is between 110 mM and 140 mM. In some aspects, the concentration of potassium ion is higher than about 105 mM, wherein the total concentration of potassium ion and NaCl in the medium is between 110 mM and 140 mM. In some aspects, the concentration of potassium ion is about 105 mM, wherein the total concentration of potassium ion and NaCl in the medium is between 110 mM and 140 mM. In some aspects, the concentration of potassium ion is higher than about 106 mM, wherein the total concentration of potassium ion and NaCl in the medium is between 110 mM and 140 mM. In some aspects, the concentration of potassium ion is about 106 mM, wherein the total concentration of potassium ion and NaCl in the medium is between 110 mM and 140 mM. In some aspects, the concentration of potassium ion is higher than about 107 mM, wherein the total concentration of potassium ion and NaCl in the medium is between 110 mM and 140 mM. In some aspects, the concentration of potassium ion is about 107 mM, wherein the total concentration of potassium ion and NaCl in the medium is between 110 mM and 140 mM. In some aspects, the concentration of potassium ion is higher than about 108 mM, wherein the total concentration of potassium ion and NaCl in the medium is between 110 mM and 140 mM. In some aspects, the concentration of potassium ion is about 108 mM, wherein the total concentration of potassium ion and NaCl in the medium is between 110 mM and 140 mM. In some aspects, the concentration of potassium ion is higher than about 109 mM, wherein the total concentration of potassium ion and NaCl in the medium is between 110 mM and 140 mM. In some aspects, the concentration of potassium ion is about 109 mM, wherein the total concentration of potassium ion and NaCl in the medium is between 110 mM and 140 mM.

In some aspects, the concentration of potassium ion is higher than about 110 mM. In some aspects, the concentration of potassium ion is about 110 mM. In some aspects, the concentration of potassium ion is higher than about 111 mM. In some aspects, the concentration of potassium ion is about 111 mM. In some aspects, the concentration of potassium ion is higher than about 112 mM. In some aspects, the concentration of potassium ion is about 112 mM. In some aspects, the concentration of potassium ion is higher than about 113 mM. In some aspects, the concentration of potassium ion is about 113 mM. In some aspects, the concentration of potassium ion is higher than about 114 mM. In some aspects, the concentration of potassium ion is about 114 mM. In some aspects, the concentration of potassium ion is higher than about 115 mM. In some aspects, the concentration of potassium ion is about 115 mM. In some aspects, the concentration of potassium ion is higher than about 116 mM. In some aspects, the concentration of potassium ion is about 116 mM. In some aspects, the concentration of potassium ion is higher than about 117 mM. In some aspects, the concentration of potassium ion is about 117 mM. In some aspects, the concentration of potassium ion is higher than about 118 mM. In some aspects, the concentration of potassium ion is about 118 mM. In some aspects, the concentration of potassium ion is higher than about 119 mM. In some aspects, the concentration of potassium ion is about 119 mM. In certain aspects, the medium is hypotonic. In certain aspects, the medium is isotonic.

In some aspects, the concentration of potassium ion is higher than about 110 mM, wherein the total concentration of potassium ion and NaCl in the medium is between 110 mM and 140 mM. In some aspects, the concentration of potassium ion is about 110 mM, wherein the total concentration of potassium ion and NaCl in the medium is between 110 mM and 140 mM. In some aspects, the concentration of potassium ion is higher than about 111 mM, wherein the total concentration of potassium ion and NaCl in the medium is between 110 mM and 140 mM. In some aspects, the concentration of potassium ion is about 111 mM, wherein the total concentration of potassium ion and NaCl in the medium is between 110 mM and 140 mM. In some aspects, the concentration of potassium ion is higher than about 112 mM, wherein the total concentration of potassium ion and NaCl in the medium is between 110 mM and 140 mM. In some aspects, the concentration of potassium ion is about 112 mM, wherein the total concentration of potassium ion and NaCl in the medium is between 110 mM and 140 mM. In some aspects, the concentration of potassium ion is higher than about 113 mM, wherein the total concentration of potassium ion and NaCl in the medium is between 110 mM and 140 mM. In some aspects, the concentration of potassium ion is about 113 mM, wherein the total concentration of potassium ion and NaCl in the medium is between 110 mM and 140 mM. In some aspects, the concentration of potassium ion is higher than about 114 mM, wherein the total concentration of potassium ion and NaCl in the medium is between 110 mM and 140 mM. In some aspects, the concentration of potassium ion is about 114 mM, wherein the total concentration of potassium ion and NaCl in the medium is between 110 mM and 140 mM. In some aspects, the concentration of potassium ion is higher than about 115 mM, wherein the total concentration of potassium ion and NaCl in the medium is between 110 mM and 140 mM. In some aspects, the concentration of potassium ion is about 115 mM, wherein the total concentration of potassium ion and NaCl in the medium is between 110 mM and 140 mM. In some aspects, the concentration of potassium ion is higher than about 116 mM, wherein the total concentration of potassium ion and NaCl in the medium is between 110 mM and 140 mM. In some aspects, the concentration of potassium ion is about 116 mM, wherein the total concentration of potassium ion and NaCl in the medium is between 110 mM and 140 mM. In some aspects, the concentration of potassium ion is higher than about 117 mM, wherein the total concentration of potassium ion and NaCl in the medium is between 110 mM and 140 mM. In some aspects, the concentration of potassium ion is about 117 mM, wherein the total concentration of potassium ion and NaCl in the medium is between 110 mM and 140 mM. In some aspects, the concentration of potassium ion is higher than about 118 mM, wherein the total concentration of potassium ion and NaCl in the medium is between 110 mM and 140 mM. In some aspects, the concentration of potassium ion is about 118 mM, wherein the total concentration of potassium ion and NaCl in the medium is between 110 mM and 140 mM. In some aspects, the concentration of potassium ion is higher than about 119 mM, wherein the total concentration of potassium ion and NaCl in the medium is between 110 mM and 140 mM. In some aspects, the concentration of potassium ion is about 119 mM, wherein the total concentration of potassium ion and NaCl in the medium is between 110 mM and 140 mM.

In some aspects, the concentration of potassium ion is higher than about 120 mM. In some aspects, the concentration of potassium ion is about 120 mM. In some aspects, the concentration of potassium ion is higher than about 121 mM. In some aspects, the concentration of potassium ion is about 121 mM. In some aspects, the concentration of potassium ion is higher than about 122 mM. In some aspects, the concentration of potassium ion is about 122 mM. In some aspects, the concentration of potassium ion is higher than about 123 mM. In some aspects, the concentration of potassium ion is about 123 mM. In some aspects, the concentration of potassium ion is higher than about 124 mM. In some aspects, the concentration of potassium ion is about 124 mM. In some aspects, the concentration of potassium ion is higher than about 125 mM. In some aspects, the concentration of potassium ion is about 125 mM. In some aspects, the concentration of potassium ion is higher than about 126 mM. In some aspects, the concentration of potassium ion is about 126 mM. In some aspects, the concentration of potassium ion is higher than about 127 mM. In some aspects, the concentration of potassium ion is about 127 mM. In some aspects, the concentration of potassium ion is higher than about 128 mM. In some aspects, the concentration of potassium ion is about 128 mM. In some aspects, the concentration of potassium ion is higher than about 129 mM. In some aspects, the concentration of potassium ion is about 129 mM. In some aspects, the concentration of potassium ion is higher than about 130 mM. In some aspects, the concentration of potassium ion is about 130 mM. In certain aspects, the medium is hypotonic. In certain aspects, the medium is isotonic.

In some aspects, the concentration of potassium ion is higher than about 120 mM, wherein the total concentration of potassium ion and NaCl in the medium is between 110 mM and 140 mM. In some aspects, the concentration of potassium ion is about 120 mM, wherein the total concentration of potassium ion and NaCl in the medium is between 110 mM and 140 mM. In some aspects, the concentration of potassium ion is higher than about 121 mM, wherein the total concentration of potassium ion and NaCl in the medium is between 110 mM and 140 mM. In some aspects, the concentration of potassium ion is about 121 mM, wherein the total concentration of potassium ion and NaCl in the medium is between 110 mM and 140 mM. In some aspects, the concentration of potassium ion is higher than about 122 mM, wherein the total concentration of potassium ion and NaCl in the medium is between 110 mM and 140 mM. In some aspects, the concentration of potassium ion is about 122 mM, wherein the total concentration of potassium ion and NaCl in the medium is between 110 mM and 140 mM. In some aspects, the concentration of potassium ion is higher than about 123 mM, wherein the total concentration of potassium ion and NaCl in the medium is between 110 mM and 140 mM. In some aspects, the concentration of potassium ion is about 123 mM, wherein the total concentration of potassium ion and NaCl in the medium is between 110 mM and 140 mM. In some aspects, the concentration of potassium ion is higher than about 124 mM, wherein the total concentration of potassium ion and NaCl in the medium is between 110 mM and 140 mM. In some aspects, the concentration of potassium ion is about 124 mM, wherein the total concentration of potassium ion and NaCl in the medium is between 110 mM and 140 mM. In some aspects, the concentration of potassium ion is higher than about 125 mM, wherein the total concentration of potassium ion and NaCl in the medium is between 110 mM and 140 mM. In some aspects, the concentration of potassium ion is about 125 mM, wherein the total concentration of potassium ion and NaCl in the medium is between 110 mM and 140 mM. In some aspects, the concentration of potassium ion is higher than about 126 mM, wherein the total concentration of potassium ion and NaCl in the medium is between 110 mM and 140 mM. In some aspects, the concentration of potassium ion is about 126 mM, wherein the total concentration of potassium ion and NaCl in the medium is between 110 mM and 140 mM. In some aspects, the concentration of potassium ion is higher than about 127 mM, wherein the total concentration of potassium ion and NaCl in the medium is between 110 mM and 140 mM. In some aspects, the concentration of potassium ion is about 127 mM, wherein the total concentration of potassium ion and NaCl in the medium is between 110 mM and 140 mM. In some aspects, the concentration of potassium ion is higher than about 128 mM, wherein the total concentration of potassium ion and NaCl in the medium is between 110 mM and 140 mM. In some aspects, the concentration of potassium ion is about 128 mM, wherein the total concentration of potassium ion and NaCl in the medium is between 110 mM and 140 mM. In some aspects, the concentration of potassium ion is higher than about 129 mM, wherein the total concentration of potassium ion and NaCl in the medium is between 110 mM and 140 mM. In some aspects, the concentration of potassium ion is about 129 mM, wherein the total concentration of potassium ion and NaCl in the medium is between 110 mM and 140 mM. In some aspects, the concentration of potassium ion is higher than about 130 mM, wherein the total concentration of potassium ion and NaCl in the medium is between 110 mM and 140 mM. In some aspects, the concentration of potassium ion is about 130 mM, wherein the total concentration of potassium ion and NaCl in the medium is between 110 mM and 140 mM.

In some aspects, the medium comprising a high concentration of potassium ion can be prepared by adding a sufficient amount of a potassium salt in a medium. In some aspects, non-limiting examples of potassium salt include potassium aminetrichloroplatinate, potassium aquapentachlororuthenate, potassium bis(oxalato)platinate(II) dihydrate, potassium bi sulfate, potassium borohydride, potassium bromide, potassium carbonate, potassium chloride, potassium chromate, potassium dichromate, potassium dicyanoargentate, potassium dicyanoaurate, potassium fluoride, potassium fluorosulfate, potassium hexachloroiridate, potassium hexachloroosmate, potassium hexachloropalladate, potassium hexachloroplatinate, potassium hexachlororhenate, potassium hexacyanochromate, potassium hexacyanoferrate, potassium hexacyanoruthenate(II) hydrate, potassium hexafluoroantimonate, potassium hexafluoronickelate, potassium hexafluorophosphate, potassium hexafluorotitanate, potassium hexafluorozirconate, potassium hexahydroxoantimonate, potassium hexaiodoplatinate, potassium hexaiodorhenate, potassium hydroxide, potassium iodate, potassium iodide, potassium manganate, potassium metavanadate, potassium molybdate, potassium nitrate, potassium nitrosodisulfonate, potassium osmate(VI) dihydrate, potassium pentachloronitrosylruthenate, potassium perchlorate, potassium perrhenate, potassium perruthenate, potassium persulfate, potassium phosphate dibasic, potassium phosphate monobasic, potassium pyrophosphate, potassium selenocyanate, potassium selenocyanate, potassium stannate trihydrate, potassium sulfate, potassium tellurate hydrate, potassium tellurite, potassium tetraborate tetrahydrate, potassium tetrabromoaurate, potassium tetrabromopalladate, potassium tetrachloropalladate, potassium tetrachloroplatinate, potassium tetracyanopalladate, potassium tetracyanoplatinate, potassium tetrafluoroborate, potassium tetranitroplatinate, potassium tetrathionate, potassium p-toluenethiosulfonate, and potassium hydroxycitrate tribasic monohydrate. In certain aspects, the potassium salt comprises potassium chloride (KCl). In certain aspects, the potassium salt comprises potassium gluconate. In certain aspects, the potassium salt comprises potassium citrate. In certain aspects, the potassium salt comprises potassium hydroxycitrate.

In some aspects, the medium comprises potassium ion at a concentration disclosed herein, and the medium has an osmolality of about 250 mOsmol. In some aspects, the medium comprises potassium ion at a concentration disclosed herein, and the medium has an osmolality of about 280 mOsmol.

In some aspects, the medium comprises about 50 mM potassium ion, and the medium has an osmolality of about 255 mOsmol. In some aspects, the medium comprises about 50 mM potassium ion, and the medium has an osmolality of about 250 mOsmol to about 260 mOsmol. In some aspects, the medium comprises about 50 mM potassium ion, and the medium has an osmolality of about 254 mOsmol to about 256 mOsmol. In some aspects, the medium comprises about 50 mM potassium ion, and the medium has an osmolality of about 254.7 mOsmol.

In some aspects, the medium comprises about 51 mM, about 52 mM, about 53 mM, or about 54 mM potassium ion, and the medium has an osmolality of about 255 mOsmol. In some aspects, the medium comprises about 51 mM, about 52 mM, about 53 mM, or about 54 mM potassium ion, and the medium has an osmolality of about 250 mOsmol to about 260 mOsmol. In some aspects, the medium comprises about 51 mM, about 52 mM, about 53 mM, or about 54 mM potassium ion, and the medium has an osmolality of about 254 mOsmol to about 256 mOsmol. In some aspects, the medium comprises about 51 mM, about 52 mM, about 53 mM, or about 54 mM potassium ion, and the medium has an osmolality of about 254.7 mOsmol. In some aspects, the medium comprises about 51 mM, about 52 mM, about 53 mM, or about 54 mM potassium ion, and the medium has an osmolality of about 255.2 mOsmol.

In some aspects, the medium comprises about 55 mM potassium ion, and the medium has an osmolality of about 255 mOsmol. In some aspects, the medium comprises about 55 mM potassium ion, and the medium has an osmolality of about 250 mOsmol to about 260 mOsmol. In some aspects, the medium comprises about 55 mM potassium ion, and the medium has an osmolality of about 254 mOsmol to about 256 mOsmol. In some aspects, the medium comprises about 55 mM potassium ion, and the medium has an osmolality of about 255.2 mOsmol.

In some aspects, the medium comprises about 56 mM, about 57 mM, about 58 mM, or about 59 mM potassium ion, and the medium has an osmolality of about 256 mOsmol. In some aspects, the medium comprises about 56 mM, about 57 mM, about 58 mM, or about 59 mM potassium ion, and the medium has an osmolality of about 250 mOsmol to about 260 mOsmol. In some aspects, the medium comprises about 56 mM, about 57 mM, about 58 mM, or about 59 mM potassium ion, and the medium has an osmolality of about 255 mOsmol to about 258 mOsmol. In some aspects, the medium comprises about 60 mM potassium ion, and the medium has an osmolality of about 257.2 mOsmol.

In some aspects, the medium comprises about 60 mM potassium ion, and the medium has an osmolality of about 257 mOsmol. In some aspects, the medium comprises about 60 mM potassium ion, and the medium has an osmolality of about 250 mOsmol to about 260 mOsmol. In some aspects, the medium comprises about 60 mM potassium ion, and the medium has an osmolality of about 256 mOsmol to about 258 mOsmol. In some aspects, the medium comprises about 60 mM potassium ion, and the medium has an osmolality of about 257.2 mOsmol.

In some aspects, the medium comprises about 61 mM, about 62 mM, about 63 mM, or about 64 mM potassium ion, and the medium has an osmolality of about 257 mOsmol. In some aspects, the medium comprises about 61 mM, about 62 mM, about 63 mM, or about 64 mM potassium ion, and the medium has an osmolality of about 250 mOsmol to about 260 mOsmol. In some aspects, the medium comprises about 61 mM, about 62 mM, about 63 mM, or about 64 mM potassium ion, and the medium has an osmolality of about 256 mOsmol to about 258 mOsmol. In some aspects, the medium comprises about 61 mM, about 62 mM, about 63 mM, or about 64 mM potassium ion, and the medium has an osmolality of about 257.2 mOsmol. In some aspects, the medium comprises about 61 mM, about 62 mM, about 63 mM, or about 64 mM potassium ion, and the medium has an osmolality of about 257.5 mOsmol.

In some aspects, the medium comprises about 65 mM potassium ion, and the medium has an osmolality of about 257 mOsmol. In some aspects, the medium comprises about 65 mM potassium ion, and the medium has an osmolality of about 250 mOsmol to about 260 mOsmol. In some aspects, the medium comprises about 65 mM potassium ion, and the medium has an osmolality of about 257 mOsmol to about 258 mOsmol. In some aspects, the medium comprises about 65 mM potassium ion, and the medium has an osmolality of about 257.5 mOsmol.

In some aspects, the medium comprises about 66 mM, about 67 mM, about 68 mM, or about 69 mM potassium ion, and the medium has an osmolality of about 257 mOsmol. In some aspects, the medium comprises about 66 mM, about 67 mM, about 68 mM, or about 69 mM potassium ion, and the medium has an osmolality of about 255 mOsmol to about 265 mOsmol. In some aspects, the medium comprises about 66 mM, about 67 mM, about 68 mM, or about 69 mM potassium ion, and the medium has an osmolality of about 257 mOsmol to about 260 mOsmol. In some aspects, the medium comprises about 66 mM, about 67 mM, about 68 mM, or about 69 mM potassium ion, and the medium has an osmolality of about 257.5 mOsmol. In some aspects, the medium comprises about 66 mM, about 67 mM, about 68 mM, or about 69 mM potassium ion, and the medium has an osmolality of about 259.7 mOsmol.

In some aspects, the medium comprises about 70 mM potassium ion, and the medium has an osmolality of about 259 mOsmol. In some aspects, the medium comprises about 70 mM potassium ion, and the medium has an osmolality of about 255 mOsmol to about 265 mOsmol. In some aspects, the medium comprises about 70 mM potassium ion, and the medium has an osmolality of about 259 mOsmol to about 261 mOsmol. In some aspects, the medium comprises about 70 mM potassium ion, and the medium has an osmolality of about 259.7 mOsmol.

In some aspects, the medium comprises about 71 mM, about 72 mM, about 73 mM, or about 74 mM potassium ion, and the medium has an osmolality of about 259 mOsmol. In some aspects, the medium comprises about 71 mM, about 72 mM, about 73 mM, or about 74 mM potassium ion, and the medium has an osmolality of about 255 mOsmol to about 265 mOsmol. In some aspects, the medium comprises about 71 mM, about 72 mM, about 73 mM, or about 74 mM potassium ion, and the medium has an osmolality of about 259 mOsmol to about 261 mOsmol. In some aspects, the medium comprises about 71 mM, about 72 mM, about 73 mM, or about 74 mM potassium ion, and the medium has an osmolality of about 259.7 mOsmol. In some aspects, the medium comprises about 71 mM, about 72 mM, about 73 mM, or about 74 mM potassium ion, and the medium has an osmolality of about 260 mOsmol.

In some aspects, the medium comprises about 75 mM potassium ion, and the medium has an osmolality of about 260 mOsmol. In some aspects, the medium comprises about 75 mM potassium ion, and the medium has an osmolality of about 255 mOsmol to about 265 mOsmol. In some aspects, the medium comprises about 75 mM potassium ion, and the medium has an osmolality of about 259 mOsmol to about 261 mOsmol. In some aspects, the medium comprises about 75 mM potassium ion, and the medium has an osmolality of about 260 mOsmol.

In some aspects, the medium comprises about 81 mM, about 82 mM, about 83 mM, or about 84 mM potassium ion, and the medium has an osmolality of about 260 mOsmol. In some aspects, the medium comprises about 81 mM, about 82 mM, about 83 mM, or about 84 mM potassium ion, and the medium has an osmolality of about 261 mOsmol. In some aspects, the medium comprises about 81 mM, about 82 mM, about 83 mM, or about 84 mM potassium ion, and the medium has an osmolality of about 262 mOsmol. In some aspects, the medium comprises about 81 mM, about 82 mM, about 83 mM, or about 84 mM potassium ion, and the medium has an osmolality of about 263 mOsmol. In some aspects, the medium comprises about 81 mM, about 82 mM, about 83 mM, or about 84 mM potassium ion, and the medium has an osmolality of about 255 mOsmol to about 265 mOsmol. In some aspects, the medium comprises about 81 mM, about 82 mM, about 83 mM, or about 84 mM potassium ion, and the medium has an osmolality of about 261 mOsmol to about 263 mOsmol. In some aspects, the medium comprises about 81 mM, about 82 mM, about 83 mM, or about 84 mM potassium ion, and the medium has an osmolality of about 262.26 mOsmol.

In some aspects, the medium comprises about 80 mM potassium ion, and the medium has an osmolality of about 262 mOsmol. In some aspects, the medium comprises about 80 mM potassium ion, and the medium has an osmolality of about 255 mOsmol to about 265 mOsmol. In some aspects, the medium comprises about 80 mM potassium ion, and the medium has an osmolality of about 261 mOsmol to about 263 mOsmol. In some aspects, the medium comprises about 80 mM potassium ion, and the medium has an osmolality of about 262.26 mOsmol.

In some aspects, the medium comprises about 81 mM, about 82 mM, about 83 mM, about 84 mM, or about 85 mM potassium ion, and the medium has an osmolality of about 262 mOsmol. In some aspects, the medium comprises about 81 mM, about 82 mM, about 83 mM, about 84 mM, or about 85 mM potassium ion, and the medium has an osmolality of about 263 mOsmol. In some aspects, the medium comprises about 81 mM, about 82 mM, about 83 mM, about 84 mM, or about 85 mM potassium ion, and the medium has an osmolality of about 264 mOsmol. In some aspects, the medium comprises about 81 mM, about 82 mM, about 83 mM, about 84 mM, or about 85 mM potassium ion, and the medium has an osmolality of about 265 mOsmol. In some aspects, the medium comprises about 81 mM, about 82 mM, about 83 mM, about 84 mM, or about 85 mM potassium ion, and the medium has an osmolality of about 255 mOsmol to about 265 mOsmol. In some aspects, the medium comprises about 81 mM, about 82 mM, about 83 mM, about 84 mM, or about 85 mM potassium ion, and the medium has an osmolality of about 260 mOsmol to about 270 mOsmol. In some aspects, the medium comprises about 81 mM, about 82 mM, about 83 mM, about 84 mM, or about 85 mM potassium ion, and the medium has an osmolality of about 261 mOsmol to about 263 mOsmol. In some aspects, the medium comprises about 81 mM, about 82 mM, about 83 mM, about 84 mM, or about 85 mM potassium ion, and the medium has an osmolality of about 263 mOsmol to about 265 mOsmol.

In some aspects, the medium further comprises a cell expansion agent. As used herein, a "cell expansion agent" refers to an agent, e.g., small molecule, polypeptide, or any combination thereof, that promotes the in vitro and/or ex vivo growth and proliferation of cultured cells, e.g., pluripotent, multipotent, and/or immune cells (e.g., T cells, NK cells, and/or TILs). In some aspects, the cell expansion agent comprises a PI3K inhibitor. In some aspects, the medium further comprises an AKT inhibitor. In some aspects, the medium further comprises a PI3K inhibitor and an AKT inhibitor. In some aspects, the PI3K inhibitor comprises LY294002. In some aspects, the PI3K inhibitor comprises IC87114. In some aspects, the PI3K inhibitor comprises idelalisib (see, e.g., Peterson et al., Blood Adv. 2(3):210-23 (2018)). In some aspects, the medium further comprises a GSK3B inhibitor. In some aspects, the GSK3B inhibitor comprises TWS119. In some aspects, the medium further comprises an ACLY inhibitor. In some aspects, the ACLY inhibitor comprises potassium hydroxycitrate tribasic monohydrate. In some aspects, the PI3K inhibitor comprises hydroxyl citrate. In some aspects, the PI3K inhibitor comprises pictilisib. In some aspects, the PI3K inhibitor comprises CAL-101. In some aspects, the AKT inhibitor comprises MK2206, A443654, or AKTi-VIII (CAS 612847-09-3).

In some aspects, the cells, e.g., pluripotent, multipotent, and/or immune cells (e.g., T cells, NK cells, and/or TILs), are cultured in the medium disclosed herein for the entirety of ex vivo culture, e.g., from the time the T cells are isolated form a subject, through growing, expansion, engineering, and until administration. In some aspects, the cells, e.g., pluripotent, multipotent, and/or immune cells (e.g., T cells, NK cells, and/or TILs), are cultured in the medium disclosed herein for the duration of expansion. In some aspects, the cells, e.g., pluripotent, multipotent, and/or immune cells (e.g., T cells, NK cells, and/or TILs), are cultured in the medium disclosed herein for the duration of expansion. In some aspects, the cells, e.g., pluripotent, multipotent, and/or immune cells (e.g., T cells, NK cells, and/or TILs), are cultured in the medium disclosed herein until the total number of viable cells, e.g., pluripotent, multipotent, and/or immune cells (e.g., T cells, NK cells, and/or TILs), is at least about $10^4$, $5 \times 10^4$, $10^5$, $5 \times 10^5$, $10^6$, or $5 \times 10^6$ total cells.

II.A. Sodium

Certain aspects of the present disclosure are directed to methods of culturing cells, e.g., pluripotent, multipotent, or immune cells (e.g., T cells, NK cells, and/or TILs), comprising placing the cells in a medium comprising (i) potassium ion at a concentration of at least about 5 mM and (ii) sodium ion at a concentration of less than about 115 mM, wherein the medium is hypotonic or isotonic. Some aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration higher than 40 mM and (ii) sodium ion at a concentration of less than about 115 mM. Certain aspects of the present disclosure are directed to methods of culturing T cells, comprising placing the T cells in a medium comprising (i) potassium ion at a concentration of at least about 50 mM and (ii) sodium ion at a concentration of less than about 115 mM. In some aspects, the medium is hypotonic. In some aspects, the medium is isotonic.

In some aspects, the target concentration of sodium is reached by starting with a basal medium comprising a higher concentration of sodium ion, and diluting the solution to reach the target concentration of sodium ion. In some aspects, the target concentration of sodium is reached by raising the concentration of sodium ion by adding one or more sodium salts. Non-limiting examples of sodium salts include sodium (meta)periodate, sodium arsenyl tartrate hydrate, sodium azide, sodium benzyloxide, sodium bromide, sodium carbonate, sodium chloride, sodium chromate, sodium cyclohexanebutyrate, sodium ethanethiolate, sodium fluoride, sodium fluorophosphate, sodium formate, sodium hexachloroiridate(III) hydrate, sodium hexachloroiridate(IV) hexahydrate, sodium hexachloroplatinate(IV) hexahydrate, sodium hexachlororhodate(III), sodium hexafluoroaluminate, sodium hexafluoroantimonate(V), sodium hexafluoroarsenate(V), sodium hexafluoroferrate (III), sodium hexafluorophosphate, sodium hexafluorosilicate, sodium hexahydroxyplatinate(IV), sodium hexametaphosphate, sodium hydrogen difluoride, sodium hydrogen sulfate, sodium hydrogencyanamide, sodium hydroxide, sodium iodide, sodium metaborate tetrahydrate, sodium metasilicate nonahydrate, sodium metavanadate, sodium molybdate, sodium nitrate, sodium nitrite, sodium oxalate, sodium perborate monohydrate, sodium percarbonate, sodium perchlorate, sodium periodate, sodium permanganate, sodium perrhenate, sodium phosphate, sodium pyrophosphate, sodium selenate, sodium selenite, sodium stannate, sodium sulfate, sodium tellurite, sodium tetraborate, sodium tetrachloroaluminate, sodium tetrachloroaurate(III), sodium tetrachloropalladate(II), sodium tetrachloroplatinate (II), sodium thiophosphate tribasic, sodium thiosulfate, sodium thiosulfate pentahydrate, sodium yttrium oxyfluoride, Trisodium trimetaphosphate, and any combination thereof. In certain aspects, the sodium salt comprises sodium chloride (NaCl). In certain aspects, the sodium salt comprises sodium gluconate. In certain aspects, the sodium salt comprises sodium bicarbonate. In certain aspects, the sodium salt comprises sodium hydroxycitrate. In certain aspects, the sodium salt comprises sodium phosphate.

In some aspects, the concentration of the sodium ion is less than that of the basal medium. In some aspects, the concentration of the sodium ion is reduced as the concentration of potassium ion is increased. In some aspects, the concentration of the sodium ion is from about 25 mM to about 115 mM. In some aspects, the concentration of the sodium ion is from about 25 mM to about 100 mM, about 30 mM to about 40 mM, about 30 mM to about 50 mM, about 30 mM to about 60 mM, about 30 mM to about 70 mM, about 30 mM to about 80 mM, about 40 mM to about 50 mM, about 40 mM to about 60 mM, about 40 mM to about 70 mM, about 40 mM to about 80 mM, about 50 mM to about 55 mM, about 50 mM to about 60 mM, about 50 mM to about 65 mM, about 50 mM to about 70 mM, about 50 mM to about 75 mM, about 50 mM to about 80 mM, about 55 mM to about 60 mM, about 55 mM to about 65 mM, about 55 mM to about 70 mM, about 55 mM to about 75 mM, about 55 mM to about 80 mM, about 60 mM to about 65 mM, about 60 mM to about 70 mM, about 60 mM to about 75 mM, about 60 mM to about 80 mM, about 70 mM to about 75 mM, about 70 mM to about 80 mM, or about 75 mM to about 80 mM. In certain aspects, the concentration of the sodium ion is from about 40 mM to about 80 mM. In certain aspects, the concentration of the sodium ion is from about 50 mM to about 85 mM. In certain aspects, the concentration of the sodium ion is from about 55 mM to about 80 mM. In certain aspects, the concentration of the sodium ion is from about 30 mM to about 35 mM. In certain aspects, the concentration of the sodium ion is from about 35 mM to about 40 mM. In certain aspects, the concentration of the sodium ion is from about 40 mM to about 45 mM. In certain aspects, the concentration of the sodium ion is from about 45 mM to about 50 mM. In certain aspects, the concentration of the sodium ion is from about 50 mM to about 55 mM. In certain aspects, the concentration of the sodium ion is from about 55 mM to about 60 mM. In certain aspects, the concentration of the sodium ion is from about 60 mM to about 65 mM. In certain aspects, the concentration of the sodium ion is from about 65 mM to about 70 mM. In certain aspects, the concentration of the sodium ion is from about 70 mM to about 75 mM. In certain aspects, the concentration of the sodium ion is from about 75 mM to about 80 mM. In certain aspects, the concentration of the sodium ion is from about 80 mM to about 85 mM. In certain aspects, the concentration of the sodium ion is from about 80 mM to about 90 mM.

In some aspects, the concentration of the sodium ion is about 30 mM, about 35 mM, about 40 mM, about 45 mM, about 50 mM, about 55 mM, about 60 mM, about 65 mM, about 70 mM, about 75 mM, about 80 mM, about 85 mM, or about 90 mM. In certain aspects, the concentration of sodium ion is about 40 mM. In certain aspects, the concentration of sodium ion is about 45 mM. In certain aspects, the concentration of sodium ion is about 50 mM. In certain aspects, the concentration of sodium ion is about 55 mM. In certain aspects, the concentration of sodium ion is about 55.6 mM. In certain aspects, the concentration of sodium ion is about 59.3 mM. In certain aspects, the concentration of sodium ion is about 60 mM. In certain aspects, the concentration of sodium ion is about 63.9 mM. In certain aspects, the concentration of sodium ion is about 65 mM. In certain aspects, the concentration of sodium ion is about 67.6 mM. In certain aspects, the concentration of sodium ion is about 70 mM. In certain aspects, the concentration of sodium ion is about 72.2 mM. In certain aspects, the concentration of sodium ion is about 75 mM. In certain aspects, the concentration of sodium ion is about 76 mM. In certain aspects, the concentration of sodium ion is about 80 mM. In certain aspects, the concentration of sodium ion is about 80.5 mM.

In some aspects, the medium comprises about 50 mM to about 75 mM potassium ion and about 80 mM to about 90 mM sodium ion. In some aspects, the medium comprises about 55 mM to about 75 mM potassium ion and about 80 mM to about 90 mM sodium ion. In some aspects, the medium comprises about 60 mM to about 75 mM potassium ion and about 80 mM to about 90 mM sodium ion. In some aspects, the medium comprises about 65 mM to about 75 mM potassium ion and about 80 mM to about 85 mM sodium ion. In some aspects, the medium comprises about 65 mM potassium ion and about 80 mM to about 85 mM sodium ion. In some aspects, the medium comprises about 66 mM potassium ion and about 80 mM to about 85 mM sodium ion. In some aspects, the medium comprises about 67 mM potassium ion and about 80 mM to about 85 mM sodium ion. In some aspects, the medium comprises about 68 mM potassium ion and about 80 mM to about 85 mM sodium ion. In some aspects, the medium comprises about 69 mM potassium ion and about 80 mM to about 85 mM sodium ion. In some aspects, the medium comprises about 70 mM potassium ion and about 80 mM to about 85 mM sodium ion. In some aspects, the medium comprises about 71 mM potassium ion and about 80 mM to about 85 mM sodium ion. In some aspects, the medium comprises about 72 mM potassium ion and about 80 mM to about 85 mM sodium ion. In some aspects, the medium comprises about 73 mM potassium ion and about 80 mM to about 85 mM sodium ion. In some aspects, the medium comprises about 74 mM potassium ion and about 80 mM to about 85 mM sodium ion. In some aspects, the medium comprises about 75 mM potassium ion and about 80 mM to about 85 mM sodium ion. In some aspects, the medium comprises about 65 mM potassium ion and about 80 mM sodium ion. In some aspects, the medium comprises about 65 mM potassium ion and about 85 mM sodium ion. In some aspects, the medium comprises about 65 mM potassium ion and about 90 mM sodium ion. In some aspects, the medium comprises about 70 mM potassium ion and about 80 mM sodium ion. In some aspects, the medium comprises about 70 mM potassium ion and about 85 mM sodium ion. In some aspects, the medium comprises about 70 mM potassium ion and about 90 mM sodium ion. In some aspects, the medium comprises about 75 mM potassium ion and about 80 mM sodium ion. In some aspects, the medium comprises about 75 mM potassium ion and about 85 mM sodium ion. In some aspects, the medium comprises about 75 mM potassium ion and about 90 mM sodium ion.

In some aspects, the medium comprises about 40 mM to about 90 mM potassium ion and about 30 mM to about 109 mM NaCl, wherein the concentration of NaCl (mM) is equal to or lower than (135−potassium ion concentration). In some aspects, the medium comprises about 40 mM potassium ion and less than or equal to about 95 mM NaCl (e.g., about 95 mM, about 94 mM, about 93 mM, about 92 mM, about 91 mM, about 90 mM, about 85 mM, about 80 mM, about 75 mM, about 70 mM, about 65 mM, about 60 mM, about 55 mM, or about 50 mM NaCl). In some aspects, the medium comprises about 45 mM potassium ion and less than or equal to about 90 mM NaCl (e.g., about 90 mM, about 89 mM, about 88 mM, about 87 mM, about 86 mM, about 85 mM, about 80 mM, about 75 mM, about 70 mM, about 65 mM, about 60 mM, about 55 mM, or about 50 mM NaCl). In some aspects, the medium comprises about 50 mM potassium ion and less than or equal to about 85 mM NaCl (e.g., about 85 mM, about 84 mM, about 83 mM, about 82 mM, about 81 mM, about 80 mM, about 75 mM, about 70 mM, about 65 mM, about 60 mM, about 55 mM, or about 50 mM NaCl). In some aspects, the medium comprises about 55 mM potassium ion and less than or equal to about 80 mM NaCl (e.g., about 80 mM, about 79 mM, about 78 mM, about 77 mM, about 76 mM, about 75 mM, about 70 mM, about 65 mM, about 60 mM, about 55 mM, or about 50 mM NaCl). In some aspects, the medium comprises about 60 mM potassium ion and less than or equal to about 75 mM NaCl (e.g., about 75 mM, about 74 mM, about 73 mM, about 72 mM, about 71 mM, about 70 mM, about 65 mM, about 60 mM, about 55 mM, or about 50 mM NaCl). In some aspects, the medium comprises about 65 mM potassium ion and less than or equal to about 70 mM NaCl (e.g., about 70 mM, about 69 mM, about 68 mM, about 67 mM, about 66 mM, about 65 mM, about 60 mM, about 55 mM, or about 50 mM NaCl). In some aspects, the medium comprises about 70 mM potassium ion and less than or equal to about 70 mM NaCl (e.g., about 65 mM, about 64 mM, about 63 mM, about 62 mM, about 61 mM, about 60 mM, about 55 mM, or about 50 mM NaCl). In some aspects, the medium comprises about 75 mM potassium ion and less than or equal to about 60 mM NaCl (e.g., about 60 mM, about 59 mM, about 58 mM, about 57 mM, about 56 mM, about 55 mM, about 50 mM, about 45 mM, or about 40 mM NaCl). In some aspects, the medium comprises about 80 mM potassium ion and less than or equal to about 55 mM NaCl (e.g., about 55 mM, about 54 mM, about 53 mM, about 52 mM, about 51 mM, about 50 mM, about 45 mM, about 40 mM, or about 35 mM NaCl). In some aspects, the medium comprises about 85 mM potassium ion and less than or equal to about 50 mM NaCl (e.g., about 50 mM, about 49 mM, about 48 mM, about 47 mM, about 46 mM, about 45 mM, about 40 mM, about 35 mM, or about 30 mM NaCl). In some aspects, the medium comprises about 90 mM potassium ion and less than or equal to about 45 mM NaCl (e.g., about 45 mM, about 44 mM, about 43 mM, about 42 mM, about 41 mM, about 40 mM, about 35 mM, about 30 mM, or about 25 mM NaCl). In some aspects, the medium comprises about 70 mM potassium ion and about 60 mM NaCl. In some aspects, the medium comprises about 70 mM potassium ion and about 61 mM NaCl. In some aspects, the medium comprises about 70 mM potassium ion and about 62 mM NaCl.

In some aspects, the medium comprises about 50 mM potassium ion and about 80.5 mM sodium ion. In some aspects, the medium is hypotonic. In some aspects, the medium is isotonic. In some aspects, the medium comprises about 50 mM potassium ion and about 80.5 mM sodium ion, and the medium has an osmolality of about 254.7 mOsmol.

In some aspects, the medium comprises about 55 mM potassium ion and about 76 mM sodium ion. In some aspects, the medium is hypotonic. In some aspects, the medium is isotonic. In some aspects, the medium comprises about 55 mM potassium ion and about 76 mM sodium ion, and the medium has an osmolality of about 255.2 mOsmol.

In some aspects, the medium comprises about 60 mM potassium ion and about 72.2 mM sodium ion. In some aspects, the medium is hypotonic. In some aspects, the medium is isotonic. In some aspects, the medium comprises about 60 mM potassium ion and about 72.2 mM sodium ion, and the medium has an osmolality of about 257.2 mOsmol.

In some aspects, the medium comprises about 65 mM potassium ion and about 67.6 mM sodium ion. In some aspects, the medium is hypotonic. In some aspects, the medium is isotonic. In some aspects, the medium comprises about 65 mM potassium ion and about 67.6 mM sodium ion, and the medium has an osmolality of about 257.5 mOsmol.

In some aspects, the medium comprises about 70 mM potassium ion and about 63.9 mM sodium ion. In some aspects, the medium is hypotonic. In some aspects, the medium is isotonic. In some aspects, the medium comprises about 70 mM potassium ion and about 63.9 mM sodium ion, and the medium has an osmolality of about 259.7 mOsmol.

In some aspects, the medium comprises about 75 mM potassium ion and about 59.3 mM sodium ion. In some aspects, the medium is hypotonic. In some aspects, the medium is isotonic. In some aspects, the medium comprises about 75 mM potassium ion and about 59.3 mM sodium ion, and the medium has an osmolality of about 260 mOsmol.

In some aspects, the medium comprises about 80 mM potassium ion and about 55.6 mM sodium ion. In some aspects, the medium is hypotonic. In some aspects, the medium is isotonic. In some aspects, the medium comprises about 80 mM potassium ion and about 55.6 mM sodium ion, and the medium has an osmolality of about 262.26 mOsmol.

In some aspects, the medium comprises about 50 mM potassium ion and about 75 mM sodium ion. In some aspects, the medium is hypotonic. In some aspects, the medium is isotonic.

Some aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration higher than 40 mM and (ii) NaCl at a concentration of less than about 100 mM. Certain aspects of the present disclosure are directed to methods of culturing T cells, comprising placing the T cells in a medium comprising (i) potassium ion at a concentration of at least about 50 mM and (ii) NaCl at a concentration of less than about 90 mM.

II.B. Saccharides

Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 5 mM and (ii) a saccharide, wherein the medium is hypotonic or isotonic. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration higher than 40 mM and (ii) a saccharide. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 50 mM and (ii) a saccharide. In some aspects, the medium is hypotonic. In some aspects, the medium is isotonic. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 50 mM and (ii) a saccharide; wherein the total concentration of potassium ion and NaCl is between 110 mM and 140 mM.

In some aspects, the target concentration of the saccharide is reached by starting with a basal medium comprising a higher concentration of the saccharide, and diluting the solution to reach the target concentration of the saccharide. In some aspects, the target concentration of the saccharide is reached by raising the concentration of the saccharide by adding the saccharide until the desired concentration is reached.

In some aspects, the saccharide is a monosaccharide, a disaccharide, or a polysaccharide. In some aspects, the saccharide is selected from glucose, fructose, galactose, mannose, maltose, sucrose, lactose, trehalose, and any combination thereof. In certain aspects, the saccharide is glucose. In some aspects, the medium comprises (i) potassium ion at a concentration of at least about 5 mM and (ii) glucose. In some aspects, the medium comprises (i) potassium ion at a concentration higher than 40 mM and (ii) glucose. In some aspects, the medium comprises (i) potassium ion at a concentration of at least about 5 mM and (ii) mannose. In some aspects, the medium comprises (i) potassium ion at a concentration of at least about 50 mM and (ii) mannose. In some aspects, the medium is hypotonic. In some aspects, the medium is isotonic. In some aspects, the medium comprises (i) potassium ion at a concentration higher than 40 mM and (ii) glucose; wherein the total concentration of potassium ion and NaCl is between 110 mM and 140 mM. In some aspects, the medium comprises (i) potassium ion at a concentration higher than 50 mM and (ii) glucose; wherein the total concentration of potassium ion and NaCl is between 110 mM and 140 mM. In some aspects, the medium comprises (i) potassium ion at a concentration of at least about 40 mM and (ii) mannose; wherein the total concentration of potassium ion and NaCl is between 110 mM and 140 mM. In some aspects, the medium comprises (i) potassium ion at a concentration of at least about 50 mM and (ii) mannose; wherein the total concentration of potassium ion and NaCl is between 110 mM and 140 mM.

In some aspects, the concentration of the saccharide, e.g., glucose, is less than about 4.29 g/L. In some aspects, the concentration of the saccharide, e.g., glucose, is less than about 24 mM. In some aspects, the concentration of the saccharide, e.g., glucose, is more than about 5 mM. In some aspects, the concentration of the saccharide, e.g., glucose, is about 5 mM. In some aspects, the concentration of the saccharide, e.g., glucose, is from about 5 mM to about 20 mM. In some aspects, the concentration of the saccharide, e.g., glucose, is from about 10 mM to about 20 mM. In some aspects, the concentration of the saccharide, e.g., glucose, is from about 10 mM to about 25 mM, about 10 mM to about 20 mM, about 10 mM to about 5 mM, about 15 mM to about 25 mM, about 15 mM to about 20 mM, about 15 mM to about 19 mM, about 15 mM to about 18 mM, about 15 mM to about 17 mM, about 15 mM to about 16 mM, about 16 mM to about 20 mM, about 16 mM to about 19 mM, about 16 mM to about 18 mM, about 16 mM to about 17 mM, about 17 mM to about 20 mM, about 17 mM to about 19 mM, or about 17 mM to about 18 mM. In some aspects, the concentration of the saccharide, e.g., glucose, is from about 5 mM to about 20 mM. In some aspects, the concentration of the saccharide, e.g., glucose, is from about 10 mM to about 20 mM. In some aspects, the concentration of the saccharide, e.g., glucose, is from about 10 mM to about 15 mM. In some aspects, the concentration of the saccharide, e.g., glucose, is from about 14 mM to about 14.5 mM. In some aspects, the concentration of the saccharide, e.g., glucose, is from about 14.5 mM to about 15 mM. In some aspects, the concentration of the saccharide, e.g., glucose, is from about 15 mM to about 15.5 mM. In some aspects, the concentration of the saccharide, e.g., glucose, is from about 15.5 mM to about 16 mM. In some aspects, the concentration of the saccharide, e.g., glucose, is from about 16 mM to about 16.5 mM. In some aspects, the concentration of the saccharide, e.g., glucose, is from about 16.5 mM to about 17 mM. In some aspects, the concentration of the saccharide, e.g., glucose, is from about 17 mM to about 17.5 mM. In some aspects, the concentration of the saccharide, e.g., glucose, is from about 17.5 mM to about 18 mM.

In some aspects, the concentration of the saccharide, e.g., glucose, is about 5 mM, about 6 mM, about 7 mM, about 8 mM, about 9 mM, about 10 mM, is about 10.5 mM, about 11 mM, about 11.5 mM, about 12 mM, about 12.5 mM, about 13 mM, about 13.5 mM, about 14 mM, about 14.5 mM, about 15 mM, about 15.5 mM, about 16 mM, about 16.5 mM, about 17 mM, about 17.5 mM, about 18 mM, about 18.5 mM, about 19 mM, about 19.5 mM, about 20 mM, about 20.5 mM, about 21 mM, about 22 mM, about 23 mM, about 24 mM, or about 25 mM.

In some aspects, the concentration of the saccharide, e.g., glucose, is about 5 mM. In some aspects, the concentration of the saccharide, e.g., glucose, is about 6 mM. In some aspects, the concentration of the saccharide, e.g., glucose, is about 7 mM. In some aspects, the concentration of the saccharide, e.g., glucose, is about 8 mM. In some aspects, the concentration of the saccharide, e.g., glucose, is about 9 mM. In some aspects, the concentration of the saccharide, e.g., glucose, is about 10 mM. In some aspects, the concentration of the saccharide, e.g., glucose, is about 10.5 mM. In some aspects, the concentration of the saccharide, e.g., glucose, is about 11 mM. In some aspects, the concentration of the saccharide, e.g., glucose, is about 11.5 mM. In some aspects, the concentration of the saccharide, e.g., glucose, is about 12 mM. In some aspects, the concentration of the saccharide, e.g., glucose, is about 12.5 mM. In some aspects, the concentration of the saccharide, e.g., glucose, is about 13 mM. In some aspects, the concentration of the saccharide, e.g., glucose, is about 13.5 mM. In some aspects, the concentration of the saccharide, e.g., glucose, is about 14 mM. In some aspects, the concentration of the saccharide, e.g., glucose, is about 14.5 mM. In some aspects, the concentration of the saccharide, e.g., glucose, is about 15 mM. In some aspects, the concentration of the saccharide, e.g., glucose, is about 15.4 mM. In some aspects, the concentration of the saccharide, e.g., glucose, is about 15.9 mM. In some aspects, the concentration of the saccharide, e.g., glucose, is about 16.3 mM. In some aspects, the concentration of the saccharide, e.g., glucose, is about 16.8 mM. In some aspects, the concentration of the saccharide, e.g., glucose, is about 17.2 mM. In some aspects, the concentration of the saccharide, e.g., glucose, is about 17.7 mM.

In some aspects, the medium comprises about 50 mM potassium ion and about 17.7 mM glucose. In some aspects, the medium is hypotonic. In some aspects, the medium is isotonic. In some aspects, the medium comprises about 50 mM potassium ion and about 17.7 mM glucose, and the medium has an osmolality of about 254.7 mOsmol.

In some aspects, the medium comprises about 55 mM potassium ion and about 17.2 mM glucose. In some aspects, the medium is hypotonic. In some aspects, the medium is isotonic. In some aspects, the medium comprises about 55 mM potassium ion and about 17.2 mM glucose, and the medium has an osmolality of about 255.2 mOsmol.

In some aspects, the medium comprises about 60 mM potassium ion and about 16.8 mM glucose. In some aspects, the medium comprises about 60 mM potassium ion and about 16.8 mM glucose, and the medium is hypotonic. In some aspects, the medium is isotonic. In some aspects, the medium has an osmolality of about 257.2 mOsmol.

In some aspects, the medium comprises about 65 mM potassium ion and about 16.3 mM glucose. In some aspects, the medium is hypotonic. In some aspects, the medium is isotonic. In some aspects, the medium comprises about 65 mM potassium ion and about 16.3 mM glucose, and the medium has an osmolality of about 257.5 mOsmol.

In some aspects, the medium comprises about 70 mM potassium ion and about 15.9 mM glucose. In some aspects, the medium is hypotonic. In some aspects, the medium is isotonic. In some aspects, the medium comprises about 70 mM potassium ion and about 15.9 mM glucose, and the medium has an osmolality of about 259.7 mOsmol.

In some aspects, the medium comprises about 75 mM potassium ion and about 15.4 mM glucose. In some aspects, the medium is hypotonic. In some aspects, the medium is isotonic. In some aspects, the medium comprises about 75 mM potassium ion and about 15.4 mM glucose, and the medium has an osmolality of about 260 mOsmol.

In some aspects, the medium comprises about 80 mM potassium ion and about 15 mM glucose. In some aspects, the medium is hypotonic. In some aspects, the medium is isotonic. In some aspects, the medium comprises about 80 mM potassium ion and about 15 mM glucose, and the medium has an osmolality of about 262.26 mOsmol.

II.C. Calcium

Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 5 mM and (ii) sodium ion, wherein the medium is hypotonic or isotonic. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration higher than 40 mM and (ii) sodium ion. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 50 mM and (ii) sodium ion. In some aspects, the medium is hypotonic. In some aspects, the medium is isotonic. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 40 mM and (ii) NaCl; wherein the total concentration of potassium ion and NaCl is between 110 mM and 140 mM. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 50 mM and (ii) NaCl; wherein the total concentration of potassium ion and NaCl is between 110 mM and 140 mM.

In some aspects, the target concentration of calcium is reached by starting with a basal medium comprising a higher concentration of calcium ion, and diluting the solution to reach the target concentration of calcium ion. In some aspects, the target concentration of calcium is reached by raising the concentration of calcium ion by adding one or more calcium salts. Non-limiting examples of calcium salts include calcium bromide, calcium carbonate, calcium chloride, calcium cyanamide, calcium fluoride, calcium hydride, calcium hydroxide, calcium iodate, calcium iodide, calcium nitrate, calcium nitrite, calcium oxalate, calcium perchlorate tetrahydrate, calcium phosphate monobasic, calcium phosphate tribasic, calcium sulfate, calcium thiocyanate tetrahydrate, hydroxyapatite, and any combination thereof. In some aspects, the calcium salt comprises calcium chloride ($CaCl_2$)). In some aspects, the calcium salt comprises calcium gluconate.

In some aspects, the concentration of the calcium ion is less than that of the basal medium. In some aspects, the concentration of the calcium ion is greater than that of the basal medium. In some aspects, the concentration of calcium ion is more than about 0.4 mM. In some aspects, the concentration of calcium ion is less than about 2.8 mM. In some aspects, the concentration of calcium ion is less than about 2.5 mM. In some aspects, the concentration of calcium ion is less than about 2.0 mM. In some aspects, the concentration of calcium ion is less than about 1.9 mM. In some aspects, the concentration of calcium ion is less than about 1.8 mM. In some aspects, the concentration of calcium ion is less than about 1.7 mM. In some aspects, the concentration of calcium ion is less than about 1.6 mM. In some aspects, the concentration of calcium ion is less than about 1.5 mM. In some aspects, the concentration of calcium ion is less than about 1.4 mM. In some aspects, the concentration of calcium ion is less than about 1.3 mM. In some aspects, the concentration of calcium ion is less than about 1.2 mM. In some aspects, the concentration of calcium ion is less than about 1.1 mM. In some aspects, the concentration of calcium ion is less than about 1.0 mM.

In some aspects, the concentration of calcium ion is from about 0.4 mM to about 2.8 mM, about 0.4 mM to about 2.7 mM, about 0.4 mM to about 2.5 mM, about 0.5 mM to about 2.0 mM, about 1.0 mM to about 2.0 mM, about 1.1 mM to about 2.0 mM, about 1.2 mM to about 2.0 mM, about 1.3 mM to about 2.0 mM, about 1.4 mM to about 2.0 mM, about 1.5 mM to about 2.0 mM, about 1.6 mM to about 2.0 mM, about 1.7 mM to about 2.0 mM, about 1.8 mM to about 2.0 mM, about 0.8 to about 0.9 mM, about 0.8 to about 1.0 mM, about 0.8 to about 1.1 mM, about 0.8 to about 1.2 mM, about 0.8 to about 1.3 mM, about 0.8 to about 1.4 mM, about 0.8 to about 1.5 mM, about 0.8 to about 1.6 mM, about 0.8 to about 1.7 mM, about 0.8 to about 1.8 mM, about 0.9 to about 1.0 mM, about 0.9 to about 1.1 mM, about 0.9 to about 1.2 mM, about 0.9 to about 1.3 mM, about 0.9 to about 1.4 mM, about 0.9 to about 1.5 mM, about 0.9 to about 1.6 mM, about 0.9 to about 1.7 mM, about 0.9 to about 1.8 mM, about 1.0 to about 1.1 mM, about 1.0 to about 1.2 mM, about 1.0 to about 1.3 mM, about 1.0 to about 1.4 mM, about 1.0 to about 1.5 mM, about 1.0 to about 1.6 mM, about 1.0 to about 1.7 mM, about 1.0 to about 1.8 mM, about 1.1 to about 1.2 mM, about 1.1 to about 1.3 mM, about 1.1 to about 1.4 mM, about 1.1 to about 1.5 mM, about 1.1 to about 1.6 mM, about 1.1 to about 1.7 mM, about 1.1 to about 1.8 mM, about 1.2 to about 1.3 mM, about 1.2 to about 1.4 mM, about 1.2 to about 1.5 mM, about 1.2 to about 1.6 mM, about 1.2 to about 1.7 mM, about 1.2 to about 1.8 mM, about 1.3 to about 1.4 mM, about 1.3 to about 1.5 mM, about 1.3 to about 1.6 mM, about 1.3 to about 1.7 mM, about 1.3 to about 1.8 mM, about 1.4 to about 1.5 mM, about 1.4 to about 1.6 mM, about 1.4 to about 1.7 mM, about 1.4 to about 1.8 mM, about 1.5 to about 1.6 mM, about 1.5 to about 1.7 mM, about 1.5 to about 1.8 mM, about 1.6 to about 1.7 mM, about 1.6 to about 1.8 mM, or about 1.7 to about 1.8 mM.

In some aspects, the concentration of calcium ion is from about 0.8 mM to about 1.8 mM. In some aspects, the concentration of calcium ion is from about 0.9 mM to about 1.8 mM. In some aspects, the concentration of calcium ion is from about 1.0 mM to about 1.8 mM. In some aspects, the concentration of calcium ion is from about 1.1 mM to about 1.8 mM. In some aspects, the concentration of calcium ion is from about 1.2 mM to about 1.8 mM. In some aspects, the concentration of calcium ion is from about 0.8 mM to about 1.8 mM. In some aspects, the concentration of calcium ion is from about 0.8 mM to about 0.9 mM. In some aspects, the concentration of calcium ion is from about 0.9 mM to about 1.0 mM. In some aspects, the concentration of calcium ion is from about 1.0 mM to about 1.1 mM. In some aspects, the concentration of calcium ion is from about 1.1 mM to about 1.2 mM. In some aspects, the concentration of calcium ion is from about 1.2 mM to about 1.3 mM. In some aspects, the concentration of calcium ion is from about 1.3 mM to about 1.4 mM. In some aspects, the concentration of calcium ion is from about 1.4 mM to about 1.5 mM. In some aspects, the concentration of calcium ion is from about 1.5 mM to about 1.6 mM. In some aspects, the concentration of calcium ion is from about 1.7 mM to about 1.8 mM.

In some aspects, the concentration of calcium ion is about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, or about 2.0 mM. In some aspects, the concentration of calcium ion is about 0.6 mM. In some aspects, the concentration of calcium ion is about 0.7 mM. In some aspects, the concentration of calcium ion is about 0.8 mM. In some aspects, the concentration of calcium ion is about 0.9 mM. In some aspects, the concentration of calcium ion is about 1.0 mM. In some aspects, the concentration of calcium ion is about 1.1 mM. In some aspects, the concentration of calcium ion is about 1.2 mM. In some aspects, the concentration of calcium ion is about 1.3 mM. In some aspects, the concentration of calcium ion is about 1.4 mM. In some aspects, the concentration of calcium ion is about 1.5 mM. In some aspects, the concentration of calcium ion is about 1.6 mM. In some aspects, the concentration of calcium ion is about 1.7 mM. In some aspects, the concentration of calcium ion is about 1.8 mM.

In some aspects, the medium comprises about 50 mM potassium ion and about 1.8 mM calcium ion. In some aspects, the medium is hypotonic. In some aspects, the medium is isotonic. In some aspects, the medium comprises about 50 mM potassium ion and about 1.8 mM calcium ion, and the medium has an osmolality of about 254.7 mOsmol. In some aspects, the medium comprises about 50 mM potassium ion, about 1.8 mM calcium ion, and NaCl; wherein the total concentration of potassium ion and NaCl is between 110 mM and 140 mM.

In some aspects, the medium comprises about 55 mM potassium ion and about 1.7 mM calcium ion. In some aspects, the medium is hypotonic. In some aspects, the medium is isotonic. In some aspects, the medium comprises about 55 mM potassium ion and about 1.7 mM calcium ion, and the medium has an osmolality of about 255.2 mOsmol. In some aspects, the medium is isotonic. In some aspects, the medium comprises about 55 mM potassium ion, about 1.7 mM calcium ion, and NaCl; wherein the total concentration of potassium ion and NaCl is between 110 mM and 140 mM.

In some aspects, the medium comprises about 60 mM potassium ion and about 1.6 mM calcium ion. In some aspects, the medium is hypotonic. In some aspects, the medium is isotonic. In some aspects, the medium comprises about 60 mM potassium ion and about 1.6 mM calcium ion, and the medium has an osmolality of about 257.2 mOsmol. In some aspects, the medium comprises about 60 mM potassium ion, about 1.6 mM calcium ion, and NaCl; wherein the total concentration of potassium ion and NaCl is between 110 mM and 140 mM.

In some aspects, the medium comprises about 65 mM potassium ion and about 1.5 mM calcium ion. In some aspects, the medium is hypotonic. In some aspects, the medium is isotonic. In some aspects, the medium comprises about 65 mM potassium ion and about 1.5 mM calcium ion, and the medium has an osmolality of about 257.5 mOsmol. In some aspects, the medium comprises about 65 mM potassium ion, about 1.5 mM calcium ion, and NaCl; wherein the total concentration of potassium ion and NaCl is between 110 mM and 140 mM.

In some aspects, the medium comprises about 70 mM potassium ion and about 1.4 mM calcium ion. In some aspects, the medium is hypotonic. In some aspects, the medium is isotonic. In some aspects, the medium comprises about 70 mM potassium ion and about 1.4 mM calcium ion, and the medium has an osmolality of about 259.7 mOsmol. In some aspects, the medium comprises about 70 mM potassium ion, about 1.4 mM calcium ion, and NaCl; wherein the total concentration of potassium ion and NaCl is between 110 mM and 140 mM.

In some aspects, the medium comprises about 75 mM potassium ion and about 1.3 mM calcium ion. In some aspects, the medium is hypotonic. In some aspects, the medium is isotonic. In some aspects, the medium comprises about 75 mM potassium ion and about 1.3 mM calcium ion, and the medium has an osmolality of about 260 mOsmol. In some aspects, the medium comprises about 75 mM potassium ion, about 1.3 mM calcium ion, and NaCl; wherein the total concentration of potassium ion and NaCl is between 110 mM and 140 mM.

In some aspects, the medium comprises about 80 mM potassium ion and about 1.2 mM calcium ion. In some aspects, the medium is hypotonic. In some aspects, the medium is isotonic. In some aspects, the medium comprises about 80 mM potassium ion and about 1.2 mM calcium ion, and the medium has an osmolality of about 262.26 mOsmol. In some aspects, the medium comprises about 80 mM potassium ion, about 1.2 mM calcium ion, and NaCl; wherein the total concentration of potassium ion and NaCl is between 110 mM and 140 mM.

II.D. Tonicity

Certain aspects of the present disclosure are directed to methods of culturing a cell, e.g., a pluripotent cell, a multipotent cell, or an immune cell (e.g., a T cell, an NK cell, or a TIL), in a medium comprising a higher concentration of potassium ion than conventional medium (e.g., greater than about 5 mM potassium ion), wherein the medium is not hypertonic. It was surprisingly found that culturing pluripotent/multipotent/immune cells in a non-hypertonic medium having a high potassium ion concentration (e.g., greater than 5 mM potassium ion) results in an increase in the number of stem-like (e.g., less differentiated or undifferentiated) cells in the culture. This effect is most pronounced if (i) the medium has a high concentration of potassium (e.g., greater than 5 mM, e.g., greater than 50 mM) and the medium is hypotonic or isotonic. Thus, though increasing potassium ion in a culture medium might otherwise increase tonicity, the data disclosed herein suggest that an increase in potassium ion alone is not as effective at promoting stem-like properties in a population of cells as increasing potassium ion under hypotonic or isotonic conditions.

In some aspects of the present disclosure, the tonicity of the medium is adjusted. In some aspects, the tonicity of the medium is lower than that of the basal medium. In some aspects, the tonicity of the medium is higher than that of the basal medium. In some aspect, the tonicity of the medium is the same as that of the basal medium.

Medium used in the present disclosure can be hypotonic or isotonic. The tonicity of the medium can be affected by a number of factors, including the concentration of potassium ion in the media. In some aspects, increased potassium ion concentration is paired with an increase or a decrease in the concentration of one or more other factors. In some aspects, this pairing affects the tonicity of the medium. In some aspects, the concentration of potassium ion is increased while the concentration of sodium ion, e.g., NaCl, is decreased.

In some aspects, the media useful for the present media can be prepared based on the function of potassium ion and tonicity. See Table 2. For example, in some aspects, if the media useful for the present disclosure is hypotonic (e.g., less than 280 mOsm) and comprises at least about 50 mM of potassium ion, a concentration of NaCl that is sufficient to maintain the media as hypotonic can be determined based on the following formula: NaCl concentration=(desired tonicity (280)/2)−potassium ion concentration (i.e., the concentration of NaCl (mM) is equal to or lower than (140−potassium ion concentration)). In some aspects, the hypotonic media disclosed herein comprises a total concentration of potassium ion and NaCl between 110 mM and 140 mM. Therefore, for hypotonic media, the concentration of potassium ion can be set at a concentration between 50 mM and 90 mM, and the sodium ion concentration can be between 90 mM and 50 mM, or lower, so long as the total concentration of potassium ion and NaCl is between 110 mM and 140 mM. In some aspects, the hypotonic media disclosed herein comprises a total concentration of potassium ion and NaCl between 115 mM and 140 mM. In some aspects, the hypotonic media disclosed herein comprises a total concentration of potassium ion and NaCl between 120 mM and 140 mM.

In some aspects, the media is isotonic (between 280 mOsm and 300 mOsm) and comprises a concentration of potassium ion between about 50 mM and 70 mM. The corresponding concentration of sodium ion can be again calculated based on the formula: NaCl concentration=(desired tonicity/2)−potassium ion concentration. For example, if the concentration of potassium ion is 50 mM and the desired tonicity is 300 mOsm, the sodium concentration can be 100 mM.

In some aspects, the medium is isotonic. In some aspects, the medium has a tonicity of about 280 mOsm/L. In some aspects, the medium has a tonicity of 280 mOsm/L. In some aspects, the medium has a tonicity of 280 mOsm/L±1 mOsm/L. In some aspects, the medium has a tonicity of 280 mOsm/L±2 mOsm/L. In some aspects, the medium has a tonicity of 280 mOsm/L±3 mOsm/L. In some aspects, the medium has a tonicity of 280 mOsm/L±4 mOsm/L. In some aspects, the medium has a tonicity of 280 mOsm/L±5 mOsm/L. In some aspects, the medium has a tonicity of 280 mOsm/L±6 mOsm/L. In some aspects, the medium has a tonicity of 280 mOsm/L±7 mOsm/L. In some aspects, the medium has a tonicity of 280 mOsm/L±8 mOsm/L. In some aspects, the medium has a tonicity of 280 mOsm/L±9 mOsm/L. In some aspects, the medium has a tonicity of 280 mOsm/L±10 mOsm/L. In some aspects, the medium has a tonicity of about 280 mOsm/L to about 285 mOsm/L, about 280 mOsm/L to about 290 mOsm/L, about 280 mOsm/L to about 295 mOsm/L, about 280 mOsm/L to about 300 mOsm/L, about 280 mOsm/L to about 305 mOsm/L, about 280 mOsm/L to about 310 mOsm/L, about 280 mOsm/L to about 315 mOsm/L, or about 280 mOsm/L to less than 320 mOsm/L. In some aspects, the medium has a tonicity of about 285 mOsm/L, about 290 mOsm/L, about 295 mOsm/L, about 300 mOsm/L, about 305 mOsm/L, about 310 mOsm/L, or about 315 mOsm/L.

In some aspects, the medium is hypotonic. In some aspects, the medium has a tonicity lower than about 280 mOsm/L. In some aspects, the medium has a tonicity lower than about 280 mOsm/L; as measured by adding the potassium ion concentration and the NaCl concentration, and multiplying by two (see Table 2). In some aspects, the medium has a tonicity lower than 280 mOsm/L. In some aspects, the medium has a tonicity lower than 280 mOsm/L; as measured by adding the potassium ion concentration and the NaCl concentration, and multiplying by two. In some aspects, the medium has a tonicity lower than 275 mOsm/L. In some aspects, the medium has a tonicity lower than 275 mOsm/L; as measured by adding the potassium ion concentration and the NaCl concentration, and multiplying by two; as measured by adding the potassium ion concentration and the NaCl concentration, and multiplying by two. In some aspects, the medium has a tonicity lower than 270 mOsm/L. In some aspects, the medium has a tonicity lower than 270 mOsm/L; as measured by adding the potassium ion concentration and the NaCl concentration, and multiplying by two. In some aspects, the medium has a tonicity lower than 265 mOsm/L. In some aspects, the medium has a tonicity lower than 265 mOsm/L; as measured by adding the potassium ion concentration and the NaCl concentration, and multiplying by two. In some aspects, the medium has a tonicity lower than 260 mOsm/L. In some aspects, the medium has a tonicity lower than 260 mOsm/L; as measured by adding the potassium ion concentration and the NaCl concentration, and multiplying by two. In some aspects, the medium has a tonicity lower than 265 mOsm/L. In some aspects, the medium has a tonicity lower than 265 mOsm/L; as measured by adding the potassium ion concentration and the NaCl concentration, and multiplying by two. In some aspects, the medium has a tonicity lower than 260 mOsm/L. In some aspects, the medium has a tonicity lower than 260 mOsm/L; as measured by adding the potassium ion concentration and the NaCl concentration, and multiplying by two. In some aspects, the medium has a tonicity lower than 255 mOsm/L. In some aspects, the medium has a tonicity lower than 255 mOsm/L; as measured by adding the potassium ion concentration and the NaCl concentration, and multiplying by two. In some aspects, the medium has a tonicity lower than about 250 mOsm/L. In some aspects, the medium has a tonicity lower than about 250 mOsm/L; as measured by adding the potassium ion concentration and the NaCl concentration, and multiplying by two. In some aspects, the medium has a tonicity lower than about 245 mOsm/L. In some aspects, the medium has a tonicity lower than about 245 mOsm/L; as measured by adding the potassium ion concentration and the NaCl concentration, and multiplying by two. In some aspects, the medium has a tonicity lower than about 240 mOsm/L. In some aspects, the medium has a tonicity lower than about 240 mOsm/L; as measured by adding the potassium ion concentration and the NaCl concentration, and multiplying by two. In some aspects, the medium has a tonicity lower than about 235 mOsm/L. In some aspects, the medium has a tonicity lower than about 235 mOsm/L; as measured by adding the potassium ion concentration and the NaCl concentration, and multiplying by two. In some aspects, the medium has a tonicity lower than about 230 mOsm/L. In some aspects, the medium has a tonicity lower than about 230 mOsm/L; as measured by adding the potassium ion concentration and the NaCl concentration, and multiplying by two. In some aspects, the medium has a tonicity lower than about 225 mOsm/L. In some aspects, the medium has a tonicity lower than about 225 mOsm/L. In some aspects, the tonicity is higher than about 220 mOsm/L; as measured by adding the potassium ion concentration and the NaCl concentration, and multiplying by two. In some aspects, the medium has a tonicity from about 230 mOsm/L to about 280 mOsm/L. In some aspects, the medium has a tonicity from about 240 mOsm/L to about 280 mOsm/L.

In some aspects, the medium has a tonicity lower than about 220 mOsm/L. In some aspects, the medium has a tonicity lower than about 215 mOsm/L. In some aspects, the medium has a tonicity lower than about 210 mOsm/L. In some aspects, the medium has a tonicity lower than about 205 mOsm/L. In some aspects, the medium has a tonicity lower than about 200 mOsm/L.

In some aspects, the medium has a tonicity from about 100 mOsm/L to about 280 mOsm/L, about 125 mOsm/L to about 280 mOsm/L, about 150 mOsm/L to about 280 mOsm/L, about 175 mOsm/L to about 280 mOsm/L, about 200 mOsm/L to about 280 mOsm/L, about 210 mOsm/L to about 280 mOsm/L, about 220 mOsm/L to about 280 mOsm/L, about 225 mOsm/L to about 280 mOsm/L, about 230 mOsm/L to about 280 mOsm/L, about 235 mOsm/L to about 280 mOsm/L, about 240 mOsm/L to about 280 mOsm/L, about 245 mOsm/L to about 280 mOsm/L, about 250 mOsm/L to about 280 mOsm/L, about 255 mOsm/L to about 280 mOsm/L, about 260 mOsm/L to about 280 mOsm/L, about 265 mOsm/L to about 280 mOsm/L, about 270 mOsm/L to about 280 mOsm/L, or about 275 mOsm/L to about 280 mOsm/L. In some aspects, the medium has a tonicity from about 250 mOsm/L to about 270 mOsm/L. In some aspects, the medium has a tonicity from about 250 mOsm/L to about 255 mOsm/L, about 250 mOsm/L to about 260 mOsm/L, about 250 mOsm/L to about 265 mOsm/L, about 255 mOsm/L to about 260 mOsm/L, about 255 mOsm/L to about 265 mOsm/L, about 255 mOsm/L to about 265 mOsm/L, about 260 mOsm/L to about 265 mOsm/L, or about 254 mOsm/L to about 263 mOsm/L. In some aspects, the medium has a tonicity from about 254 mOsm/L to about 255 mOsm/L. In some aspects, the medium has a tonicity from about 255 mOsm/L to about 256 mOsm/L. In some aspects, the medium has a tonicity from about 256 mOsm/L to about 257 mOsm/L. In some aspects, the medium has a tonicity from about 257 mOsm/L to about 258 mOsm/L. In some aspects, the medium has a tonicity from about 258 mOsm/L to about 259 mOsm/L. In some aspects, the medium has a tonicity from about 260 mOsm/L to about 261 mOsm/L. In some aspects, the medium has a tonicity from about 261 mOsm/L to about 262 mOsm/L. In some aspects, the medium has a tonicity from about 262 mOsm/L to about 263 mOsm/L. In some aspects, the medium has a tonicity from about 263 mOsm/L to about 264 mOsm/L. In some aspects, the medium has a tonicity from about 264 mOsm/L to about 265 mOsm/L. In some aspects, the medium has a tonicity from about 220 mOsm/L to about 280 mOsm/L; as measured by adding the potassium ion concentration and the NaCl concentration, and multiplying by two.

In some aspects, the medium has a tonicity of about 100 mOsm/L, about 125 mOsm/L, about 150 mOsm/L, about 175 mOsm/L, about 200 mOsm/L, about 210 mOsm/L, about 220 mOsm/L, about 225 mOsm/L, about 230 mOsm/L, about 235 mOsm/L, about 240 mOsm/L, about 245 mOsm/L, about 250 mOsm/L, about 255 mOsm/L, about 260 mOsm/L, about 265 mOsm/L, about 270 mOsm/L, or about 275 mOsm/L. In some aspects, the tonicity is measured by adding the potassium ion concentration and the NaCl concentration, and multiplying by two.

In some aspects, the medium has a tonicity of about 250 mOsm/L. In some aspects, the medium has a tonicity of about 262.26 mOsm/L. In some aspects, the medium has a tonicity of about 260 mOsm/L. In some aspects, the medium has a tonicity of about 259.7 mOsm/L. In some aspects, the medium has a tonicity of about 257.5 mOsm/L. In some aspects, the medium has a tonicity of about 257.2 mOsm/L. In some aspects, the medium has a tonicity of about 255.2 mOsm/L. In some aspects, the medium has a tonicity of about 254.7. In some aspects, the medium has a tonicity of about 255 mOsm/L. In some aspects, the medium has a tonicity of about 260 mOsm/L. In some aspects, the tonicity is measured by adding the potassium ion concentration and the NaCl concentration, and multiplying by two.

In some aspects, the medium comprises about 50 mM potassium ion and (i) about 80.5 mM sodium ion; (ii) about 17.7 mM glucose; (iii) about 1.8 mM calcium ion; or (iv) any combination of (i)-(iii). In some aspects, the medium is hypotonic. In some aspects, the medium is isotonic. In some aspects, the medium comprises about 50 mM potassium ion and (i) about 80.5 mM sodium ion; (ii) about 17.7 mM glucose; (iii) about 1.8 mM calcium ion; or (iv) any combination of (i)-(iii); and the medium has an osmolality of about 254.7 mOsmol. In some aspects, the medium comprises about 50 mM potassium ion and (i) about 80.5 mM NaCl; (ii) about 17.7 mM glucose; (iii) about 1.8 mM calcium ion; or (iv) any combination of (i)-(iii). In some aspects, the medium comprises about 50 mM potassium ion and (i) about 80.5 mM NaCl; (ii) about 17.7 mM glucose; and (iii) about 1.8 mM calcium ion.

In some aspects, the medium comprises about 55 mM potassium ion and (i) about 76 mM sodium ion; (ii) about 17.2 mM glucose; (iii) about 1.7 mM calcium ion; or (iv) any combination of (i)-(iii). In some aspects, the medium is hypotonic. In some aspects, the medium is isotonic. In some aspects, the medium comprises about 55 mM potassium ion and (i) about 76 mM sodium ion; (ii) about 17.2 mM glucose; (iii) about 1.7 mM calcium ion; or (iv) any combination of (i)-(iii); and the medium has an osmolality of about 255.2 mOsmol. In some aspects, the medium comprises about 55 mM potassium ion and (i) about 76 mM NaCl; (ii) about 17.2 mM glucose; (iii) about 1.7 mM calcium ion; or (iv) any combination of (i)-(iii). In some aspects, the medium comprises about 55 mM potassium ion and (i) about 76 mM NaCl; (ii) about 17.2 mM glucose; and (iii) about 1.7 mM calcium ion.

In some aspects, the medium comprises about 60 mM potassium ion and (i) about 72.2 mM sodium ion; (ii) about 16.8 mM glucose; (iii) about 1.6 mM calcium ion; or (iv) any combination of (i)-(iii). In some aspects, the medium is hypotonic. In some aspects, the medium is isotonic. In some aspects, the medium comprises about 60 mM potassium ion and (i) about 72.2 mM sodium ion; (ii) about 16.8 mM glucose; (iii) about 1.6 mM calcium ion; or (iv) any combination of (i)-(iii); and the medium has an osmolality of about 257.2 mOsmol. In some aspects, the medium comprises about 60 mM potassium ion and (i) about 72.2 mM NaCl; (ii) about 16.8 mM glucose; (iii) about 1.6 mM calcium ion; or (iv) any combination of (i)-(iii). In some aspects, the medium comprises about 60 mM potassium ion and (i) about 72.2 mM NaCl; (ii) about 16.8 mM glucose; and (iii) about 1.6 mM calcium ion.

In some aspects, the medium comprises about 65 mM potassium ion and (i) about 67.6 mM sodium ion; (ii) about 16.3 mM glucose; (iii) about 1.5 mM calcium ion; or (iv) any combination of (i)-(iii). In some aspects, the medium is hypotonic. In some aspects, the medium is isotonic. In some aspects, the medium comprises about 65 mM potassium ion and (i) about 67.6 mM sodium ion; (ii) about 16.3 mM glucose; (iii) about 1.5 mM calcium ion; or (iv) any combination of (i)-(iii); and the medium has an osmolality of about 257.5 mOsmol. In some aspects, the medium comprises about 65 mM potassium ion and (i) about 67.6 mM NaCl; (ii) about 16.3 mM glucose; (iii) about 1.5 mM calcium ion; or (iv) any combination of (i)-(iii). In some aspects, the medium comprises about 65 mM potassium ion and (i) about 67.6 mM NaCl; (ii) about 16.3 mM glucose; and (iii) about 1.5 mM calcium ion.

In some aspects, the medium comprises about 70 mM potassium ion and (i) about 63.9 mM sodium ion; (ii) about 15.9 mM glucose; (iii) about 1.4 mM calcium ion; or (iv) any combination of (i)-(iii). In some aspects, the medium is hypotonic. In some aspects, the medium is isotonic. In some aspects, the medium comprises about 70 mM potassium ion and (i) about 63.9 mM sodium ion; (ii) about 15.9 mM glucose; (iii) about 1.4 mM calcium ion; or (iv) any combination of (i)-(iii); and the medium has an osmolality of about 259.7 mOsmol. In some aspects, the medium comprises about 70 mM potassium ion and (i) about 63.9 mM NaCl; (ii) about 15.9 mM glucose; (iii) about 1.4 mM calcium ion; or (iv) any combination of (i)-(iii). In some aspects, the medium comprises about 70 mM potassium ion and (i) about 63.9 mM NaCl; (ii) about 15.9 mM glucose; and (iii) about 1.4 mM calcium ion.

In some aspects, the medium comprises about 75 mM potassium ion and (i) about 59.3 mM sodium ion; (ii) about 15.4 mM glucose; (iii) about 1.3 mM calcium ion; or (iv) any combination of (i)-(iii). In some aspects, the medium is hypotonic. In some aspects, the medium is isotonic. In some aspects, the medium comprises about 75 mM potassium ion and (i) about 59.3 mM sodium ion; (ii) about 15.4 mM glucose; (iii) about 1.3 mM calcium ion; or (iv) any combination of (i)-(iii); and the medium has an osmolality of about 260 mOsmol. In some aspects, the medium comprises about 75 mM potassium ion and (i) about 59.3 mM NaCl; (ii) about 15.4 mM glucose; (iii) about 1.3 mM calcium ion; or (iv) any combination of (i)-(iii). In some aspects, the medium comprises about 75 mM potassium ion and (i) about 59.3 mM NaCl; (ii) about 15.4 mM glucose; and (iii) about 1.3 mM calcium ion.

In some aspects, the medium comprises about 80 mM potassium ion and (i) about 55.6 mM sodium ion; (ii) about 15 mM glucose; (iii) about 1.2 mM calcium ion; or (iv) any combination of (i)-(iii). In some aspects, the medium is hypotonic. In some aspects, the medium is isotonic. In some aspects, the medium comprises about 80 mM potassium ion and (i) about 55.6 mM sodium ion; (ii) about 15 mM glucose; (iii) about 1.2 mM calcium ion; or (iv) any combination of (i)-(iii); and the medium has an osmolality of about 262.26 mOsmol. In some aspects, the medium comprises about 80 mM potassium ion and (i) about 55.6 mM NaCl; (ii) about 15 mM glucose; (iii) about 1.2 mM calcium ion; or (iv) any combination of (i)-(iii). In some aspects, the medium comprises about 80 mM potassium ion and (i) about 55.6 mM NaCl; (ii) about 15 mM glucose; and (iii) about 1.2 mM calcium ion.

The osmolality of the medium can be adjusted, e.g., to an isotonic or hypotonic state disclosed herein, at any point. In some aspects, the osmolality of the medium can be adjusted, e.g., to an isotonic or hypotonic state disclosed herein, before the cells are added to the medium. In some aspects, the cells are cultured in the hypotonic or isotonic medium prior to cell engineering, e.g., prior to transduction with a construct expressing a CAR or a TCR. In some aspects, the cells are cultured in the hypotonic or isotonic medium during cell engineering, e.g., during transduction with a construct expressing a CAR or a TCR. In some aspects the cells are cultured in the hypotonic or isotonic medium after cell engineering, e.g., after transduction with a construct expressing a CAR or a TCR. In some aspects, the cells are cultured in the hypotonic or isotonic medium throughout cell expansion.

II.E. Cytokines

Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 5 mM, as disclosed herein, and (ii) a cytokine, wherein the medium is hypotonic or isotonic. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration higher than 40 mM, as disclosed herein, and (ii) a cytokine. Certain aspects of the present disclosure are directed to methods of culturing cells, e.g., pluripotent, multipotent, and/or immune cells (e.g., T cells, NK cells, and/or TILs), comprising placing the cells in a medium comprising (i) potassium ion at a concentration of at least about 50 mM, as disclosed herein, and (ii) a cytokine. In some aspects, the medium is hypotonic. In some aspects, the medium is isotonic.

Some aspects of the present disclosure are directed to methods of increasing a number of less-differentiated immune cells, e.g., stem-like T cells, NK cells, or TILs, e.g., cells having one or more $T_{SCM}$-like phenotype and/or function, in immune cells ex vivo or in vitro, comprising placing the cells in a medium comprising (i) potassium at a concentration of at least about 5 mM, as disclosed herein, and (ii) a cytokine, wherein the medium is hypotonic or isotonic. Some aspects of the present disclosure are directed to methods of increasing a number of less-differentiated immune cells, e.g., stem-like T cells, NK cells, or TILs, e.g., cells having one or more $T_{SCM}$-like phenotype and/or function, in immune cells ex vivo or in vitro, comprising placing the cells in a medium comprising (i) potassium at a concentration of at least about 50 mM, as disclosed herein, and (ii) a cytokine. In some aspects, the medium is hypotonic. In some aspects, the medium is isotonic. In some aspects, the cytokine is selected from IL-2, IL-7, IL-15, IL-21, and any combination thereof.

The cytokine can be added to the medium at any point. In some aspects, the cytokine is added to the medium before the cells are added to the medium. In some aspects, the cells are cultured in the medium comprising (i) potassium at a concentration disclosed herein, and (ii) a cytokine prior to cell engineering, e.g., prior to transduction with a construct expressing a CAR or a TCR. In some aspects, the cells are cultured in the medium comprising (i) potassium at a concentration disclosed herein, and (ii) a cytokine during cell engineering, e.g., during transduction with a construct expressing a CAR or a TCR. In some aspects, the cells are cultured in the medium comprising (i) potassium at a concentration disclosed herein, and (ii) a cytokine after cell engineering, e.g., after transduction with a construct expressing a CAR or a TCR. In some aspects, the cells are cultured in the medium comprising (i) potassium at a concentration disclosed herein, and (ii) a cytokine throughout cell expansion.

In some aspects, the medium comprises (i) at least about 5 mM potassium ion and (ii) IL-2. In some aspects, the medium comprises (i) more than 40 mM potassium ion and (ii) IL-2. In some aspects, the medium comprises (i) at least about 50 mM potassium ion and (ii) IL-2. In some aspects, the medium comprises (i) at least about 5 mM potassium ion and (ii) IL-7. In some aspects, the medium comprises (i) more than 40 mM potassium ion and (ii) IL-7. In some aspects, the medium comprises (i) at least about 50 mM potassium ion and (ii) IL-7. In some aspects, the medium comprises (i) at least about 5 mM potassium ion and (ii) IL-15. In some aspects, the medium comprises (i) more than 40 mM potassium ion and (ii) IL-15. In some aspects, the medium comprises (i) at least about 50 mM potassium ion and (ii) IL-15. In some aspects, the medium comprises (i) at least about 5 mM potassium ion and (ii) IL-21. In some aspects, the medium comprises (i) more than 40 mM potassium ion and (ii) IL-21. In some aspects, the medium comprises (i) at least about 50 mM potassium ion and (ii) IL-21. In some aspects, the medium comprises (i) at least about 5 mM potassium ion and (ii) IL-2, and the medium does not comprise IL-7. In some aspects, the medium comprises (i) more than 40 mM potassium ion and (ii) IL-2, and the medium does not comprise IL-7. In some aspects, the medium comprises (i) at least about 50 mM potassium ion and (ii) IL-2, and the medium does not comprise IL-7. In some aspects, the medium comprises (i) at least about 5 mM potassium ion and (ii) IL-2, and the medium does not comprise IL-15. In some aspects, the medium comprises (i) more than 40 mM potassium ion and (ii) IL-2, and the medium does not comprise IL-15. In some aspects, the medium comprises (i) at least about 50 mM potassium ion and (ii) IL-2, and the medium does not comprise IL-15. In some aspects, the medium comprises (i) at least about 5 mM potassium ion and (ii) IL-2, and the medium does not comprise IL-7 and IL-15. In some aspects, the medium comprises (i) more than 40 mM potassium ion and (ii) IL-2, and the medium does not comprise IL-7 and IL-15. In some aspects, the medium comprises (i) at least about 50 mM potassium ion and (ii) IL-2, and the medium does not comprise IL-7 and IL-15. In some aspects, the medium comprises (i) at least about 5 mM potassium ion and (ii) IL-2 and IL-21. In some aspects, the medium comprises (more than 40 mM potassium ion and (ii) IL-2 and IL-21. In some aspects, the medium comprises (i) at least about 50 mM potassium ion and (ii) IL-2 and IL-21. In some aspects, the medium comprises (i) at least about 5 mM potassium ion and (ii) IL-7 and IL-21. In some aspects, the medium comprises (i) more than 40 mM potassium ion and (ii) IL-7 and IL-21. In some aspects, the medium comprises (i) at least about 50 mM potassium ion and (ii) IL-7 and IL-21. In some aspects, the medium comprises (i) at least about 5 mM potassium ion and (ii) IL-15 and IL-21. In some aspects, the medium comprises (i) more than 40 mM potassium ion and (ii) IL-15 and IL-21. In some aspects, the medium comprises (i) at least about 50 mM potassium ion and (ii) IL-15 and IL-21. In some aspects, the medium is hypotonic. In some aspects, the medium is isotonic. In some aspects, the medium further comprises NaCl, wherein the total concentration of potassium ion and NaCl is from 110 mM to 140 mM.

Certain aspects of the present disclosure are directed to a method of increasing a number of less-differentiated immune cells, e.g., stem-like T cells, NK cells, or TILs, e.g., cells having a $T_{SCM}$-like phenotype, in immune cells ex vivo or in vitro comprising culturing the cells in a medium comprising potassium ion at a concentration of at least about 50 mM, wherein the medium comprises IL-2. In some aspects, the medium does not comprise IL-7 and/or IL-15. In some aspects, the number of less-differentiated-cells, e.g., stem-like T cells, NK cells, or TILs, e.g., cells having a $T_{SCM}$-like phenotype, following culture in the medium is higher than the number of less-differentiated cells cultured in a medium comprising IL-2, IL-7, and IL-15.

In some aspects, the medium comprises at least about 0.1 ng/mL IL-2. In some aspects, the medium comprises from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL IL-2.

In some aspects, the medium comprises at least about 0.1 ng/mL, at least about 0.5 ng/mL, at least about 1 ng/mL, at least about 2 ng/mL, at least about 3 ng/mL, at least about 4 ng/mL, at least about 5 ng/mL, at least about 6 ng/mL, at least about 7 ng/mL, at least about 8 ng/mL, at least about 9 ng/mL, at least about 10 ng/mL, at least about 11 ng/mL, at least about 12 ng/mL, at least about 13 ng/mL, at least about 14 ng/mL, at least about 15 ng/mL, at least about 16 ng/mL, at least about 17 ng/mL, at least about 18 ng/mL, at least about 19 ng/mL, or at least about 20 ng/mL IL-2. In some aspects, the medium comprises at least about 1.0 ng/mL IL-2. In some aspects, the medium comprises at least about 2.0 ng/mL IL-2. In some aspects, the medium comprises at least about 3.0 ng/mL IL-2. In some aspects, the medium comprises at least about 4.0 ng/mL IL-2. In some aspects, the medium comprises at least about 5.0 ng/mL IL-2. In some aspects, the medium comprises at least about 6.0 ng/mL IL-2. In some aspects, the medium comprises at least about 7.0 ng/mL IL-2. In some aspects, the medium comprises at least about 8.0 ng/mL IL-2. In some aspects, the medium comprises at least about 9.0 ng/mL IL-2. In some aspects, the medium comprises at least about 10 ng/mL IL-2.

In some aspects, the medium comprises at least about 0.1 ng/mL. In some aspects, the medium comprises from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL IL-21.

In some aspects, the medium comprises at least about 0.1 ng/mL, at least about 0.5 ng/mL, at least about 1 ng/mL, at least about 2 ng/mL, at least about 3 ng/mL, at least about 4 ng/mL, at least about 5 ng/mL, at least about 6 ng/mL, at least about 7 ng/mL, at least about 8 ng/mL, at least about 9 ng/mL, at least about 10 ng/mL, at least about 11 ng/mL, at least about 12 ng/mL, at least about 13 ng/mL, at least about 14 ng/mL, at least about 15 ng/mL, at least about 16 ng/mL, at least about 17 ng/mL, at least about 18 ng/mL, at least about 19 ng/mL, or at least about 20 ng/mL IL-21. In some aspects, the medium comprises at least about 1.0 ng/mL IL-21. In some aspects, the medium comprises at least about 2.0 ng/mL IL-21. In some aspects, the medium comprises at least about 3.0 ng/mL IL-21. In some aspects, the medium comprises at least about 4.0 ng/mL IL-21. In some aspects, the medium comprises at least about 5.0 ng/mL IL-21. In some aspects, the medium comprises at least about 6.0 ng/mL IL-21. In some aspects, the medium comprises at least about 7.0 ng/mL IL-21. In some aspects, the medium comprises at least about 8.0 ng/mL IL-21. In some aspects, the medium comprises at least about 9.0 ng/mL IL-21. In some aspects, the medium comprises at least about 10 ng/mL IL-21.

In some aspects, the medium comprises at least about 0.1 ng/mL IL-7. In some aspects, the medium comprises from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL IL-7.

In some aspects, the medium comprises at least about 0.1 ng/mL, at least about 0.5 ng/mL, at least about 1 ng/mL, at least about 2 ng/mL, at least about 3 ng/mL, at least about 4 ng/mL, at least about 5 ng/mL, at least about 6 ng/mL, at least about 7 ng/mL, at least about 8 ng/mL, at least about 9 ng/mL, at least about 10 ng/mL, at least about 11 ng/mL, at least about 12 ng/mL, at least about 13 ng/mL, at least about 14 ng/mL, at least about 15 ng/mL, at least about 16 ng/mL, at least about 17 ng/mL, at least about 18 ng/mL, at least about 19 ng/mL, or at least about 20 ng/mL IL-7. In some aspects, the medium comprises at least about 1.0 ng/mL IL-7. In some aspects, the medium comprises at least about 2.0 ng/mL IL-7. In some aspects, the medium comprises at least about 3.0 ng/mL IL-7. In some aspects, the medium comprises at least about 4.0 ng/mL IL-7. In some aspects, the medium comprises at least about 5.0 ng/mL IL-7. In some aspects, the medium comprises at least about 6.0 ng/mL IL-7. In some aspects, the medium comprises at least about 7.0 ng/mL IL-7. In some aspects, the medium comprises at least about 8.0 ng/mL IL-7. In some aspects, the medium comprises at least about 9.0 ng/mL IL-7. In some aspects, the medium comprises at least about 10 ng/mL IL-7.

In some aspects, the medium comprises at least about 0.1 ng/mL IL-15. In some aspects, the medium comprises from about 0.1 ng/mL to about 20 ng/mL, about 1 ng/mL to about 20 ng/mL, about 1 ng/mL to about 15 ng/mL, about 1 ng/mL to about 14 ng/mL, about 1 ng/mL to about 13 ng/mL, about 1 ng/mL to about 12 ng/mL, about 1 ng/mL to about 11 ng/mL, about 1 ng/mL to about 10 ng/mL, about 1 ng/mL to about 9 ng/mL, about 1 ng/mL to about 8 ng/mL, about 1 ng/mL to about 7 ng/mL, about 1 ng/mL to about 6 ng/mL, about 1 ng/mL to about 5 ng/mL, about 1 ng/mL to about 4 ng/mL, about 1 ng/mL to about 3 ng/mL, about 1 ng/mL to about 2 ng/mL, about 5 ng/mL to about 15 ng/mL, about 5 ng/mL to about 10 ng/mL, about 10 ng/mL to about 20 ng/mL, about 10 ng/mL to about 15 ng/mL, or about 15 ng/mL to about 20 ng/mL IL-15.

In some aspects, the medium comprises at least about 0.1 ng/mL, at least about 0.5 ng/mL, at least about 1 ng/mL, at least about 2 ng/mL, at least about 3 ng/mL, at least about 4 ng/mL, at least about 5 ng/mL, at least about 6 ng/mL, at least about 7 ng/mL, at least about 8 ng/mL, at least about 9 ng/mL, at least about 10 ng/mL, at least about 11 ng/mL, at least about 12 ng/mL, at least about 13 ng/mL, at least about 14 ng/mL, at least about 15 ng/mL, at least about 16 ng/mL, at least about 17 ng/mL, at least about 18 ng/mL, at least about 19 ng/mL, or at least about 20 ng/mL IL-15. In some aspects, the medium comprises at least about 1.0 ng/mL IL-15. In some aspects, the medium comprises at least about 2.0 ng/mL IL-15. In some aspects, the medium comprises at least about 3.0 ng/mL IL-15. In some aspects, the medium comprises at least about 4.0 ng/mL IL-15. In some aspects, the medium comprises at least about 5.0 ng/mL IL-15. In some aspects, the medium comprises at least about 6.0 ng/mL IL-15. In some aspects, the medium comprises at least about 7.0 ng/mL IL-15. In some aspects, the medium comprises at least about 8.0 ng/mL IL-15. In some aspects, the medium comprises at least about 9.0 ng/mL IL-15. In some aspects, the medium comprises at least about 10 ng/mL IL-15. In some aspects, the medium further comprises NaCl, wherein the total concentration of potassium ion and NaCl is from 110 mM to 140 mM.

In certain aspects, the medium comprises more than 40 mM potassium ion and about 10 ng/mL IL-2, wherein the medium is hypotonic. In certain aspects, the medium comprise at least about 45 mM potassium ion and about 10 ng/mL IL-2, wherein the medium is hypotonic. In certain aspects, the medium comprise at least about 50 mM potassium ion and about 10 ng/mL IL-2, wherein the medium is hypotonic. In certain aspects, the medium comprise at least about 55 mM potassium ion and about 10 ng/mL IL-2, wherein the medium is hypotonic. In certain aspects, the medium comprise at least about 60 mM potassium ion and about 10 ng/mL IL-2, wherein the medium is hypotonic. In certain aspects, the medium comprise at least about 65 mM potassium ion and about 10 ng/mL IL-2, wherein the medium is hypotonic. In certain aspects, the medium comprise at least about 70 mM potassium ion and about 10 ng/mL IL-2, wherein the medium is hypotonic. In certain aspects, the medium comprise at least about 75 mM potassium ion and about 10 ng/mL IL-2, wherein the medium is hypotonic. In certain aspects, the medium comprise at least about 80 mM potassium ion and about 10 ng/mL IL-2, wherein the medium is hypotonic. In certain aspects, the medium comprise at least about 85 mM potassium ion and about 10 ng/mL IL-2, wherein the medium is hypotonic. In certain aspects, the medium comprise at least about 90 mM potassium ion and about 10 ng/mL IL-2, wherein the medium is hypotonic. In certain aspects, the medium comprises (i) at least about 70 mM potassium ion, (ii) about 60 mM sodium, (iii) about 1.4 mM calcium, (iv) about 16 mM glucose, and (v) about 10 ng/mL IL-2, wherein the medium is hypotonic.

In certain aspects, the medium comprises more than 40 mM potassium ion and about 10 ng/mL IL-2 and about 1 ng/mL IL-7, wherein the medium is hypotonic. In certain aspects, the medium comprise at least about 45 mM potassium ion and about 10 ng/mL IL-2 and about 1 ng/mL IL-7, wherein the medium is hypotonic. In certain aspects, the medium comprise at least about 40 mM potassium ion and about 50 ng/mL IL-2 and about 1 ng/mL IL-7, wherein the medium is hypotonic. In certain aspects, the medium comprise at least about 55 mM potassium ion and about 10 ng/mL IL-2 and about 1 ng/mL IL-7, wherein the medium is hypotonic. In certain aspects, the medium comprise at least about 60 mM potassium ion and about 10 ng/mL IL-2 and about 1 ng/mL IL-7, wherein the medium is hypotonic. In certain aspects, the medium comprise at least about 65 mM potassium ion and about 10 ng/mL IL-2 and about 1 ng/mL IL-7, wherein the medium is hypotonic. In certain aspects, the medium comprise at least about 70 mM potassium ion and about 10 ng/mL IL-2 and about 1 ng/mL IL-7, wherein the medium is hypotonic. In certain aspects, the medium comprise at least about 75 mM potassium ion and about 10 ng/mL IL-2 and about 1 ng/mL IL-7, wherein the medium is hypotonic. In certain aspects, the medium comprise at least about 80 mM potassium ion and about 10 ng/mL IL-2 and about 1 ng/mL IL-7, wherein the medium is hypotonic. In certain aspects, the medium comprise at least about 85 mM potassium ion and about 10 ng/mL IL-2 and about 1 ng/mL IL-7, wherein the medium is hypotonic. In certain aspects, the medium comprise at least about 90 mM potassium ion and about 10 ng/mL IL-2 and about 1 ng/mL IL-7, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 10 ng/mL IL-2, and (vi) about 1 ng/mL IL-7, wherein the medium is hypotonic.

In certain aspects, the medium comprises more than 40 mM potassium ion and about 10 ng/mL IL-2 and about 1 ng/mL IL-15, wherein the medium is hypotonic. In certain aspects, the medium comprise at least about 45 mM potassium ion and about 10 ng/mL IL-2 and about 1 ng/mL IL-15, wherein the medium is hypotonic. In certain aspects, the medium comprise at least about 50 mM potassium ion and about 10 ng/mL IL-2 and about 1 ng/mL IL-15, wherein the medium is hypotonic. In certain aspects, the medium comprise at least about 55 mM potassium ion and about 10 ng/mL IL-2 and about 1 ng/mL IL-15, wherein the medium is hypotonic. In certain aspects, the medium comprise at least about 60 mM potassium ion and about 10 ng/mL IL-2 and about 1 ng/mL IL-15, wherein the medium is hypotonic. In certain aspects, the medium comprise at least about 65 mM potassium ion and about 10 ng/mL IL-2 and about 1 ng/mL IL-15, wherein the medium is hypotonic. In certain aspects, the medium comprise at least about 70 mM potassium ion and about 10 ng/mL IL-2 and about 1 ng/mL IL-15, wherein the medium is hypotonic. In certain aspects, the medium comprise at least about 75 mM potassium ion and about 10 ng/mL IL-2 and about 1 ng/mL IL-15, wherein the medium is hypotonic. In certain aspects, the medium comprise at least about 80 mM potassium ion and about 10 ng/mL IL-2 and about 1 ng/mL IL-15, wherein the medium is hypotonic. In certain aspects, the medium comprise at least about 85 mM potassium ion and about 10 ng/mL IL-2 and about 1 ng/mL IL-15, wherein the medium is hypotonic. In certain aspects, the medium comprise at least about 90 mM potassium ion and about 10 ng/mL IL-2 and about 1 ng/mL IL-15, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 10 ng/mL IL-2, and (vi) about 1 ng/mL IL-15, wherein the medium is hypotonic.

In certain aspects, the medium comprises more than 40 mM potassium ion and about 10 ng/mL IL-2, about 1 ng/mL IL-7, and about 1 ng/mL IL-15, wherein the medium is hypotonic. In certain aspects, the medium comprise at least about 45 mM potassium ion and about 10 ng/mL IL-2, about 1 ng/mL IL-7, and about 1 ng/mL IL-15, wherein the medium is hypotonic. In certain aspects, the medium comprise at least about 50 mM potassium ion and about 10 ng/mL IL-2, about 1 ng/mL IL-7, and about 1 ng/mL IL-15, wherein the medium is hypotonic. In certain aspects, the medium comprise at least about 55 mM potassium ion and about 10 ng/mL IL-2, about 1 ng/mL IL-7, and about 1 ng/mL IL-15, wherein the medium is hypotonic. In certain aspects, the medium comprise at least about 60 mM potassium ion and about 10 ng/mL IL-2, about 1 ng/mL IL-7, and about 1 ng/mL IL-15, wherein the medium is hypotonic. In certain aspects, the medium comprise at least about 65 mM potassium ion and about 10 ng/mL IL-2, about 1 ng/mL IL-7, and about 1 ng/mL IL-15, wherein the medium is hypotonic. In certain aspects, the medium comprise at least about 70 mM potassium ion and about 10 ng/mL IL-2, about 1 ng/mL IL-7, and about 1 ng/mL IL-15, wherein the medium is hypotonic. In certain aspects, the medium comprise at least about 75 mM potassium ion and about 10 ng/mL IL-2, about 1 ng/mL IL-7, and about 1 ng/mL IL-15, wherein the medium is hypotonic. In certain aspects, the medium comprise at least about 80 mM potassium ion and about 10 ng/mL IL-2, about 1 ng/mL IL-7, and about 1 ng/mL IL-15, wherein the medium is hypotonic. In certain aspects, the medium comprise at least about 85 mM potassium ion and about 10 ng/mL IL-2, about 1 ng/mL IL-7, and about 1 ng/mL IL-15, wherein the medium is hypotonic. In certain aspects, the medium comprise at least about 90 mM potassium ion and about 10 ng/mL IL-2, about 1 ng/mL IL-7, and about 1 ng/mL IL-15, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 10 ng/mL IL-2, (vi) about 1 ng/mL IL-7, and (vii) about 1 ng/mL IL-15, wherein the medium is hypotonic.

In certain aspects, the medium comprises more than 40 mM potassium ion and about 10 ng/mL IL-2 and about 1 ng/mL IL-21, wherein the medium is hypotonic. In certain aspects, the medium comprise at least about 45 mM potassium ion and about 10 ng/mL IL-2 and about 1 ng/mL IL-21, wherein the medium is hypotonic. In certain aspects, the medium comprise at least about 50 mM potassium ion and about 10 ng/mL IL-2 and about 1 ng/mL IL-21, wherein the medium is hypotonic. In certain aspects, the medium comprise at least about 55 mM potassium ion and about 10 ng/mL IL-2 and about 1 ng/mL IL-21, wherein the medium is hypotonic. In certain aspects, the medium comprise at least about 60 mM potassium ion and about 10 ng/mL IL-2 and about 1 ng/mL IL-21, wherein the medium is hypotonic. In certain aspects, the medium comprise at least about 65 mM potassium ion and about 10 ng/mL IL-2 and about 1 ng/mL IL-21, wherein the medium is hypotonic. In certain aspects, the medium comprise at least about 70 mM potassium ion and about 10 ng/mL IL-2 and about 1 ng/mL IL-21, wherein the medium is hypotonic. In certain aspects, the medium comprise at least about 75 mM potassium ion and about 10 ng/mL IL-2 and about 1 ng/mL IL-21, wherein the medium is hypotonic. In certain aspects, the medium comprise at least about 80 mM potassium ion and about 10 ng/mL IL-2 and about 1 ng/mL IL-21, wherein the medium is hypotonic. In certain aspects, the medium comprise at least about 85 mM potassium ion and about 10 ng/mL IL-2 and about 1 ng/mL IL-21, wherein the medium is hypotonic. In certain aspects, the medium comprise at least about 90 mM potassium ion and about 10 ng/mL IL-2 and about 1 ng/mL IL-21, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 10 ng/mL IL-2, and (vi) about 1 ng/mL IL-21, wherein the medium is hypotonic.

In certain aspects, the medium comprises more than 40 mM potassium ion and about 1 ng/mL IL-7 and about 1 ng/mL IL-21, wherein the medium is hypotonic. In certain aspects, the medium comprise at least about 45 mM potassium ion and about 1 ng/mL IL-7 and about 1 ng/mL IL-21, wherein the medium is hypotonic. In certain aspects, the medium comprise at least about 50 mM potassium ion and about 1 ng/mL IL-7 and about 1 ng/mL IL-21, wherein the medium is hypotonic. In certain aspects, the medium comprise at least about 55 mM potassium ion and about 1 ng/mL IL-7 and about 1 ng/mL IL-21, wherein the medium is hypotonic. In certain aspects, the medium comprise at least about 60 mM potassium ion and about 1 ng/mL IL-7 and about 1 ng/mL IL-21, wherein the medium is hypotonic. In certain aspects, the medium comprise at least about 65 mM potassium ion and about 1 ng/mL IL-7 and about 1 ng/mL IL-21, wherein the medium is hypotonic. In certain aspects, the medium comprise at least about 70 mM potassium ion and about 1 ng/mL IL-7 and about 1 ng/mL IL-21, wherein the medium is hypotonic. In certain aspects, the medium comprise at least about 75 mM potassium ion and about 1 ng/mL IL-7 and about 1 ng/mL IL-21, wherein the medium is hypotonic. In certain aspects, the medium comprise at least about 80 mM potassium ion and about 1 ng/mL IL-7 and about 1 ng/mL IL-21, wherein the medium is hypotonic. In certain aspects, the medium comprise at least about 85 mM potassium ion and about 1 ng/mL IL-7 and about 1 ng/mL IL-21, wherein the medium is hypotonic. In certain aspects, the medium comprise at least about 90 mM potassium ion and about 1 ng/mL IL-7 and about 1 ng/mL IL-21, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 1 ng/mL IL-7, and (vi) about 1 ng/mL IL-21, wherein the medium is hypotonic.

In certain aspects, the medium comprises more than 40 mM potassium ion and about 1 ng/mL IL-15 and about 1 ng/mL IL-21, wherein the medium is hypotonic. In certain aspects, the medium comprise at least about 45 mM potassium ion and about 1 ng/mL IL-15 and about 1 ng/mL IL-21, wherein the medium is hypotonic. In certain aspects, the medium comprise at least about 50 mM potassium ion and about 1 ng/mL IL-15 and about 1 ng/mL IL-21, wherein the medium is hypotonic. In certain aspects, the medium comprise at least about 55 mM potassium ion and about 1 ng/mL IL-15 and about 1 ng/mL IL-21, wherein the medium is hypotonic. In certain aspects, the medium comprise at least about 60 mM potassium ion and about 1 ng/mL IL-15 and about 1 ng/mL IL-21, wherein the medium is hypotonic. In certain aspects, the medium comprise at least about 65 mM potassium ion and about 1 ng/mL IL-15 and about 1 ng/mL IL-21, wherein the medium is hypotonic. In certain aspects, the medium comprise at least about 70 mM potassium ion and about 1 ng/mL IL-15 and about 1 ng/mL IL-21, wherein the medium is hypotonic. In certain aspects, the medium comprise at least about 75 mM potassium ion and about 1 ng/mL IL-15 and about 1 ng/mL IL-21, wherein the medium is hypotonic. In certain aspects, the medium comprise at least about 80 mM potassium ion and about 1 ng/mL IL-15 and about 1 ng/mL IL-21, wherein the medium is hypotonic. In certain aspects, the medium comprise at least about 85 mM potassium ion and about 1 ng/mL IL-15 and about 1 ng/mL IL-21, wherein the medium is hypotonic. In certain aspects, the medium comprise at least about 90 mM potassium ion and about 1 ng/mL IL-15 and about 1 ng/mL IL-21, wherein the medium is hypotonic. In certain aspects, the medium comprises (i) at least about 70 mM potassium ion, (ii) about 60 mM sodium, (iii) about 1.4 mM calcium, (iv) about 16 mM glucose, (v) about 1 ng/mL IL-15, and (vi) about 1 ng/mL IL-2111, wherein the medium is hypotonic.

In certain aspects, the medium comprises more than 40 mM potassium ion, NaCl, and about 10 ng/mL IL-2, wherein the total concentration of potassium ion and NaCl in the medium is between 110 mM and 140 mM. In certain aspects, the medium comprise at least about 45 mM potassium ion, NaCl, and about 10 ng/mL IL-2, wherein the total concentration of potassium ion and NaCl in the medium is between 110 mM and 140 mM. In certain aspects, the medium comprise at least about 50 mM potassium ion, NaCl, and about 10 ng/mL IL-2, wherein the total concentration of potassium ion and NaCl in the medium is between 110 mM and 140 mM. In certain aspects, the medium comprise at least about 55 mM potassium ion, NaCl, and about 10 ng/mL IL-2, wherein the total concentration of potassium ion and NaCl in the medium is between 110 mM and 140 mM. In certain aspects, the medium comprise at least about 60 mM potassium ion, NaCl, and about 10 ng/mL IL-2, wherein the total concentration of potassium ion and NaCl in the medium is between 110 mM and 140 mM. In certain aspects, the medium comprise at least about 65 mM potassium ion, NaCl, and about 10 ng/mL IL-2, wherein the total concentration of potassium ion and NaCl in the medium is between 110 mM and 140 mM. In certain aspects, the medium comprise at least about 70 mM potassium ion, NaCl, and about 10 ng/mL IL-2, wherein the total concentration of potassium ion and NaCl in the medium is between 110 mM and 140 mM. In certain aspects, the medium comprise at least about 75 mM potassium ion, NaCl, and about 10 ng/mL IL-2, wherein the total concentration of potassium ion and NaCl in the medium is between 110 mM and 140 mM. In certain aspects, the medium comprise at least about 80 mM potassium ion, NaCl, and about 10 ng/mL IL-2, wherein the total concentration of potassium ion and NaCl in the medium is between 110 mM and 140 mM. In certain aspects, the medium comprise at least about 85 mM potassium ion, NaCl, and about 10 ng/mL IL-2, wherein the total concentration of potassium ion and NaCl in the medium is between 110 mM and 140 mM. In certain aspects, the medium comprise at least about 90 mM potassium ion, NaCl, and about 10 ng/mL IL-2, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, and (v) about 10 ng/mL IL-2.

In certain aspects, the medium comprises more than 40 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 45 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 40 mM potassium ion, NaCl, and about 50 ng/mL IL-2 and about 1 ng/mL IL-7, wherein the total concentration of potassium ion and NaCl in the medium is between 110 mM and 140 mM. In certain aspects, the medium comprise at least about 55 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 60 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 65 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 70 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 75 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 80 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 85 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprise at least about 90 mM potassium ion, NaCl, and about 10 ng/mL IL-2 and about 1 ng/mL IL-7, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 10 ng/mL IL-2, and (vi) about 1 ng/mL IL-7.

In certain aspects, the medium comprises more than 40 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 45 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 50 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 55 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 60 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 65 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 70 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 75 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 80 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 85 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprise at least about 90 mM potassium ion, NaCl, and about 10 ng/mL IL-2 and about 1 ng/mL IL-15, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 10 ng/mL IL-2, and (vi) about 1 ng/mL IL-15.

In certain aspects, the medium comprises more than 40 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 45 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 50 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 55 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 60 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 65 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 70 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 75 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 80 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 85 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprise at least about 90 mM potassium ion, NaCl, and about 10 ng/mL IL-2, about 1 ng/mL IL-7, and about 1 ng/mL IL-15, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 10 ng/mL IL-2, (vi) about 1 ng/mL IL-7, and (vii) about 1 ng/mL IL-15.

In certain aspects, the medium comprises more than 40 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 45 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 50 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 55 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 60 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 65 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 70 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 75 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 80 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 85 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprise at least about 90 mM potassium ion, NaCl, and about 10 ng/mL IL-2 and about 1 ng/mL IL-21, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 10 ng/mL IL-2, and (vi) about 1 ng/mL IL-21.

In certain aspects, the medium comprises more than 40 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 45 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 50 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 55 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 60 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 65 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 70 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 75 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 80 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 85 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprise at least about 90 mM potassium ion, NaCl, and about 1 ng/mL IL-7 and about 1 ng/mL IL-21, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 1 ng/mL IL-7, and (vi) about 1 ng/mL IL-21.

In certain aspects, the medium comprises more than 40 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 45 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 50 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 55 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 60 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 65 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 70 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 75 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 80 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 85 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprise at least about 90 mM potassium ion, NaCl, and about 1 ng/mL IL-15 and about 1 ng/mL IL-21, wherein the total concentration of potassium ion and NaCl in the medium is between 110 mM and 140 mM. In certain aspects, the medium comprises (i) at least about 70 mM potassium ion, (ii) about 60 mM NaCl, (iii) about 1.4 mM calcium, (iv) about 16 mM glucose, (v) about 1 ng/mL IL-15, and (vi) about 1 ng/mL IL-21, wherein the total concentration of potassium ion and NaCl in the medium is between 110 mM and 140 mM.

In some aspects, the media comprises more than 40 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 50 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 55 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 60 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 65 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 70 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 75 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM. In some aspects, the media comprises about 80 mM potassium ion, NaCl, about 200 IU/mL IL-2, about 1200 IU/mL IL-7, about 200 IU/mL IL-15, wherein the total concentration of potassium ion and NaCl in the medium is between 110 mM and 140 mM.

II.F. Basal Media

Certain aspects of the present disclosure are directed to methods of culturing cells, e.g., pluripotent, multipotent, and/or immune cells (e.g., T cells, NK cells, and/or TILs), comprising placing the cells in a medium comprising potassium ion at a concentration of at least about 5 mM, wherein the media is hypotonic or isotonic. Some aspects of the present disclosure are directed to methods of culturing cells, e.g., pluripotent, multipotent, and/or immune cells (e.g., T cells, NK cells, and/or TILs), comprising placing the cells in a medium comprising potassium ion at a concentration higher than 40 mM. Some aspects of the present disclosure are directed to methods of culturing cells, e.g., pluripotent, multipotent, and/or immune cells (e.g., T cells, NK cells, and/or TILs), comprising placing the cells in a medium comprising potassium ion at a concentration higher than 40 mM and NaCl at a concentration less than 100 mM. Some aspects of the present disclosure are directed to methods of culturing cells, e.g., pluripotent, multipotent, and/or immune cells (e.g., T cells, NK cells, and/or TILs), comprising placing the cells in a medium comprising potassium ion at a concentration of at least about 50 mM. Some aspects of the present disclosure are directed to methods of culturing cells, e.g., pluripotent, multipotent, and/or immune cells (e.g., T cells, NK cells, and/or TILs), comprising placing the cells in a medium comprising potassium ion at a concentration of at least about 50 mM and NaCl at a concentration of less than 90 mM. In some aspects, the medium is prepared by adding potassium ion to a basal medium. Any basal medium known in the art that is used to culture cells, e.g., pluripotent, multipotent, and/or immune cells (e.g., T cells, NK cells, and/or TILs), can be used.

In some aspects, the basal medium further comprises one or more essential amino acids. In some aspects, the basal media comprises one or more essential amino acids selected form L-arginine, L-cystine, L-isoleucine, L-leucine, L-lysine, L-methionine, L-phenylalanine, L-threonine, L-tryptophan, L-histidine, L-tyrosine, L-valine, and L-glutamine, or any combination thereof. In some aspects, the basal media comprises L-glutamine.

In some aspects, the basal media comprises at least about 0.01 mM of one or more essential amino acids. In some aspects, the basal media comprises about 0.01 mM to about 10 mM of one or more essential amino acids. In some aspects, the basal media comprises about 0.01 mM to about 10 mM, about 0.01 mM to about 9 mM, about 0.01 mM to about 8 mM, about 0.01 mM to about 7 mM, about 0.01 mM to about 6 mM, about 0.01 mM to about 5 mM, about 0.01 mM to about 4 mM, about 0.01 mM to about 3 mM, about 0.01 mM to about 2 mM, about 0.01 mM to about 1 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 4 mM, about 1 mM to about 3 mM, or about 1 mM to about 2 mM of one or more essential amino acids.

In some aspects, the basal media comprises at least about 0.01 mM, at least about 0.1 mM, at least about 0.5 mM, at least about 1.0 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, or at least about 15 mM or at least about 50 mM of one or more essential amino acids.

In certain aspects, the basal medium comprises about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.1 mM, about 5.2 mM, about 5.3 mM, about 5.4 mM, about 5.5 mM, about 5.6 mM, about 5.7 mM, about 5.8 mM, about 5.9 mM, about 6.0 mM, about 6.1 mM, about 6.2 mM, about 6.3 mM, about 6.4 mM, about 6.5 mM, about 6.6 mM, about 6.7 mM, about 6.8 mM, about 6.9 mM, or about 7.0 mM of one or more essential amino acids.

In some aspects, the basal medium comprises L-glutamine. In some aspects, the basal media comprises at least about 0.01 mM L-glutamine. In some aspects, the basal media comprises about 0.01 mM to about 10 mM L-glutamine. In some aspects, the basal media comprises about 0.01 mM to about 10 mM, about 0.01 mM to about 9 mM, about 0.01 mM to about 8 mM, about 0.01 mM to about 7 mM, about 0.01 mM to about 6 mM, about 0.01 mM to about 5 mM, about 0.01 mM to about 4 mM, about 0.01 mM to about 3 mM, about 0.01 mM to about 2 mM, about 0.01 mM to about 1 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 4 mM, about 1 mM to about 3 mM, or about 1 mM to about 2 mM L-glutamine.

In some aspects, the basal media comprises at least about 0.01 mM, at least about 0.1 mM, at least about 0.5 mM, at least about 1.0 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, or at least about 15 mM or at least about 50 mM L-glutamine.

In certain aspects, the basal medium comprises about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.1 mM, about 5.2 mM, about 5.3 mM, about 5.4 mM, about 5.5 mM, about 5.6 mM, about 5.7 mM, about 5.8 mM, about 5.9 mM, about 6.0 mM, about 6.1 mM, about 6.2 mM, about 6.3 mM, about 6.4 mM, about 6.5 mM, about 6.6 mM, about 6.7 mM, about 6.8 mM, about 6.9 mM, or about 7.0 mM L-glutamine. In some aspects, the basal medium comprises about 1.7 mM L-glutamine. In certain aspects, the basal medium comprises about 1.68 mM L-glutamine.

In some aspects, the basal media comprises about 0.14 mM L-glutamine. In some aspects, the basal media comprises about 0.15 mM L-glutamine. In some aspects, the basal media comprises about 1.76 mM L-glutamine. In some aspects, the basal media comprises about 1.83 mM L-glutamine. In some aspects, the basal media comprises about 1.84 mM L-glutamine. In some aspects, the basal media comprises about 1.97 mM L-glutamine. In some aspects, the basal media comprises about 2.05 mM L-glutamine. In some aspects, the basal media comprises about 2.11 mM L-glutamine. In some aspects, the basal media comprises about 2.18 mM L-glutamine. In some aspects, the basal media comprises about 5.41 mM L-glutamine. In some aspects, the basal media comprises about 5.47 mM L-glutamine. In some aspects, the basal media comprises about <0.10 mM L-glutamine.

In some aspects, the basal medium comprises L-glutamic acid. In some aspects, the basal media comprises at least about 0.01 mM L-glutamic acid. In some aspects, the basal media comprises about 0.01 mM to about 10 mM L-glutamic acid. In some aspects, the basal media comprises about 0.01 mM to about 10 mM, about 0.01 mM to about 9 mM, about 0.01 mM to about 8 mM, about 0.01 mM to about 7 mM, about 0.01 mM to about 6 mM, about 0.01 mM to about 5 mM, about 0.01 mM to about 4 mM, about 0.01 mM to about 3 mM, about 0.01 mM to about 2 mM, about 0.01 mM to about 1 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 4 mM, about 1 mM to about 3 mM, or about 1 mM to about 2 mM L-glutamic acid.

In some aspects, the basal media comprises at least about 0.01 mM, at least about 0.1 mM, at least about 0.5 mM, at least about 1.0 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, or at least about 15 mM or at least about 50 mM L-glutamic acid.

In certain aspects, the basal medium comprises about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.1 mM, about 5.2 mM, about 5.3 mM, about 5.4 mM, about 5.5 mM, about 5.6 mM, about 5.7 mM, about 5.8 mM, about 5.9 mM, about 6.0 mM, about 6.1 mM, about 6.2 mM, about 6.3 mM, about 6.4 mM, about 6.5 mM, about 6.6 mM, about 6.7 mM, about 6.8 mM, about 6.9 mM, or about 7.0 mM L-glutamic acid.

In some aspects, the basal media comprises about 0.15 mM L-glutamic acid. In some aspects, the basal media comprises about 0.17 mM L-glutamic acid. In some aspects, the basal media comprises about 0.18 mM L-glutamic acid. In some aspects, the basal media comprises about 0.19 mM L-glutamic acid. In some aspects, the basal media comprises about 0.85 mM L-glutamic acid. In some aspects, the basal media comprises about 0.86 mM L-glutamic acid. In some aspects, the basal media comprises about 0.9 mM L-glutamic acid. In some aspects, the basal media comprises about 0.95 mM L-glutamic acid. In some aspects, the basal media comprises about 1.06 mM L-glutamic acid. In some aspects, the basal media comprises about 1.09 mM L-glutamic acid. In some aspects, the basal media comprises about <0.10 mM L-glutamic acid.

In some aspects, the basal medium comprises a dipeptide. In some aspects, the basal medium comprises glutamine-glutamine (Gln-Gln). In some aspects, the basal medium comprises alanyl-glutamine (Ala-Gln).

In some aspects, the basal media comprises at least about 0.1 mM dipeptide (e.g., Ala-Gln). In some aspects, the basal media comprises about 0.1 mM to about 50 mM dipeptide (e.g., Ala-Gln). In some aspects, the basal media comprises about 0.1 mM to about 40 mM, about 0.1 mM to about 35 mM, about 0.1 mM to about 30 mM, about 0.1 mM to about 25 mM, about 0.1 mM to about 20 mM, about 1 mM to about 20 mM, about 2 mM to about 20 mM, about 3 mM to about 20 mM, about 4 mM to about 20 mM, about 5 mM to about 20 mM, about 6 mM to about 20 mM, about 7 mM to about 20 mM, about 8 mM to about 20 mM, about 9 mM to about 20 mM, about 10 mM to about 20 mM, about 1 mM to about 10 mM, about 2 mM to about 10 mM, about 3 mM to about 10 mM, about 4 mM to about 10 mM, about 5 mM to about 10 mM, about 6 mM to about 10 mM, about 7 mM to about 10 mM, about 8 mM to about 10 mM, or about 9 mM to about 10 mM dipeptide (e.g., Ala-Gln).

In some aspects, the basal media comprises at least about 0.1 mM, at least about 1.0 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, at least about 20 mM, at least about 25 mM, at least about 30 mM, or at least about 50 mM dipeptide (e.g., Ala-Gln).

In certain aspects, the basal medium comprises about 1 mM, about 1.1 mM, about 1.2 mM, about 1.3 mM, about 1.4 mM, about 1.5 mM, about 1.6 mM, about 1.7 mM, about 1.8 mM, about 1.9 mM, or about 2.0 mM dipeptide (e.g., Ala-Gln). In some aspects, the basal medium comprises about 1.7 mM dipeptide (e.g., Ala-Gln). In certain aspects, the basal medium comprises about 1.68 mM dipeptide (e.g., Ala-Gln).

In certain aspects, the basal medium comprises about 6 mM, about 6.1 mM, about 6.2 mM, about 6.3 mM, about 6.4 mM, about 6.5 mM, about 6.6 mM, about 6.7 mM, about 6.8 mM, about 6.9 mM, about 7.0 mM, about 7.1 mM, or about 7.2 mM dipeptide (e.g., Ala-Gln). In some aspects, the basal medium comprises about 6.8 mM dipeptide (e.g., Ala-Gln). In some aspects, the basal medium comprises about 6.81 mM dipeptide (e.g., Ala-Gln). In some aspects, the basal medium comprises about 6.9 mM dipeptide (e.g., Ala-Gln). In some aspects, the basal medium comprises about 6.96 mM dipeptide (e.g., Ala-Gln). In certain aspects, the basal medium comprises about 7.0 mM dipeptide (e.g., Ala-Gln).

In certain aspects, the basal media comprises less than about 5 mM ammonia ($NH_3$). In some aspects, the basal media comprises less than about 4 mM, less than about 3.5 mM, less than about 3 mM, less than about 2.5 mM, less than about 2 mM, less than about 1.5 mM, less than about 1 mM, less than about 0.5 mM, less than about 0.4 mM, less than about 0.3 mM, less than about 0.2 mM, or less than about 0.1 mM ammonia. In certain aspects, the basal media comprises about 0.01 mM ammonia to less than about 2 mM ammonia, about 0.01 mM ammonia to less than about 1.9 mM ammonia, about 0.01 mM ammonia to less than about 1.8 mM ammonia, about 0.01 mM ammonia to less than about 1.7 mM ammonia, about 0.01 mM ammonia to less than about 1.6 mM ammonia, about 0.01 mM ammonia to less than about 1.5 mM ammonia, about 0.01 mM ammonia to less than about 1.4 mM ammonia, about 0.01 mM ammonia to less than about 1.3 mM ammonia, about 0.01 mM ammonia to less than about 1.2 mM ammonia, about 0.01 mM ammonia to less than about 1.1 mM ammonia, about 0.01 mM ammonia to less than about 1 mM ammonia, about 0.01 mM ammonia to less than about 0.9 mM ammonia, about 0.01 mM ammonia to less than about 0.8 mM ammonia, about 0.01 mM ammonia to less than about 0.7 mM ammonia, about 0.01 mM ammonia to less than about 0.6 mM ammonia, about 0.01 mM ammonia to less than about 0.5 mM ammonia, about 0.01 mM ammonia to less than about 0.4 mM ammonia, about 0.01 mM ammonia to less than about 0.3 mM ammonia, about 0.01 mM ammonia to less than about 0.2 mM ammonia, or about 0.01 mM ammonia to less than about 0.1 mM ammonia. In some aspects, the basal media comprises about 1.2 mM ammonia. In some aspects, the basal media comprises about 1.25 mM ammonia. In some aspects, the basal media comprises about 1.259 mM ammonia.

In some aspects, the basal media comprises about 1.28 mM ammonia. In some aspects, the basal media comprises about 1.3 mM ammonia. In some aspects, the basal media comprises about 0.3 mM ammonia. In some aspects, the basal media comprises about 0.34 mM ammonia. In some aspects, the basal media comprises about 0.35 mM ammonia. In some aspects, the basal media comprises about 0.36 mM ammonia. In some aspects, the basal media comprises about 0.37 mM ammonia. In some aspects, the basal media comprises less than about 0.3 mM ammonia. In some aspects, the basal media comprises less than about 0.29 mM ammonia. In some aspects, the basal media comprises less than about 0.28 mM ammonia. In some aspects, the basal media comprises less than about 0.278 mM ammonia. In some aspects, the basal media does not comprise ammonia.

In some aspects, the basal media comprises lactate. In certain aspects, the basal media does not comprise lactate.

In some aspects, the basal media comprises potassium, e.g., the basal media comprises potassium prior to addition of potassium, as described herein. In some aspects, the basal media comprises less than about 10 mM potassium ion. In some aspects, the basal media comprises about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.1 mM, about 5.2 mM, about 5.3 mM, about 5.4 mM, about 5.5 mM, about 5.6 mM, about 5.7 mM, about 5.8 mM, about 5.9 mM, or about 6.0 mM potassium ion. In certain aspects, the basal media comprises about 4 mM potassium ion.

In some aspects, the basal medium is selected from a balanced salt solution (e.g., PBS, DPBS, HBSS, EBSS), Dulbecco's Modified Eagle's Medium (DMEM), Minimal Essential Medium (MEM), Basal Medium Eagle (BME), F-10, F-12, RPMI 1640, Glasgow Minimal Essential Medium (GMEM), alpha Minimal Essential Medium (alpha MEM), Iscove's Modified Dulbecco's Medium (IMDM), M199, OpTmizer™ CTS™ T-Cell Expansion Basal Medium (ThermoFisher), OPTMIZER™ Complete, IMMUNOCULT™ XF (STEMCELL™ Technologies), IMMUNOCULT™ XF, AIM V, TEXMACS™ medium, and any combination thereof. In some aspects, the basal media comprises PRIME-XV T cell CDM. In some aspects, the basal media comprises OPTMIZER™. In some aspects, the basal media comprises OPTMIZER™ Pro. In some aspects, the basal media comprises X-VIVO™ 15 (LONZA). In some aspects, the basal media comprises IMMUNOCULT™. In some aspects, the basal medium is serum free. In some aspects, the basal medium further comprises immune cell serum replacement (ICSR). For example, in some aspects, the basal medium comprises OPTMIZER™ Complete supplemented with ICSR, AIM V supplemented with ICSR, IMMUNOCULT™ XF supplemented with ICSR, RPMI supplemented with ICSR, TEXMACS™ supplemented with ICSR, or any combination thereof. In particular aspects, the basal media comprises OPTMIZER™ complete.

II.G. Cells

Some aspects of the present disclosure are directed to methods of culturing cells, comprising placing the cells in a hypotonic or isotonic medium comprising potassium ion at a concentration of at least about 5 mM, as disclosed herein. Certain aspects of the present disclosure are directed to methods of culturing cells, comprising placing the cells in a medium comprising potassium ion at a concentration higher than 40 mM, as disclosed herein. Certain aspects of the present disclosure are directed to methods of culturing cells, comprising placing the cells in a medium comprising potassium ion at a concentration of at least about 50 mM, as disclosed herein.

Some aspects of the present disclosure are directed to methods of culturing cells (e.g., human immune cells and/or stem cells disclosed herein), comprising placing the cells in a medium comprising potassium ion at a concentration of at least about 40 mM and NaCl at a concentration of less than 100 mM, as disclosed herein. Certain aspects of the present disclosure are directed to methods of culturing cells (e.g., human immune cells and/or stem cells disclosed herein), comprising placing the cells in a medium comprising potassium ion at a concentration of at least about 50 mM and NaCl at a concentration of less than 90 mM, as disclosed herein.

The cells that are placed in the medium can be cells that are collected and/or isolated from a subject in need of a therapy. In some aspects, the cells that are placed in the medium have been engineered prior to the culturing. In some aspects, the cells that are placed in the medium have been expanded. The cells that are placed in the medium can be referred to as starting (initial, i.e., patient sample, apheresis sample, buffy coat) cells. The cells that result from culturing them in the media disclosed herein can be referred to as resulting (cultured) cells.

The methods disclosed herein provide culture conditions that promote a less-differentiated phenotype for cultured pluripotent or multipotent cells. As such, the methods and media disclosed herein are useful for the culture of multipotent (e.g., pluripotent) cell type. In some aspects, the cell culturable using the methods disclosed herein is a multipotent cell. In some aspects, the cells are pluripotent cells. In certain aspects, the pluripotent cells comprise embryonic stem cells (ESCs). In certain aspects, the pluripotent cells comprise induced pluripotent stem cells (iPSCs). In some aspects, the cells are hematopoietic stem cells.

In certain aspects, the cells are immune cells. In some aspects, the starting immune cells are isolated from a human subject. In some aspects, the starting immune cells are isolated from a human subject for allogeneic cell therapy. In some aspects, the starting immune cells are isolated from a human subject for autologous cell therapy. In some aspects, the cells are T cells. In some aspects, the cells are NK cells. In some aspects, the cells are TILs. In some aspects, the cells are Tregs. In some aspects, the cells, e.g., T cells, NK cells, and/or TILs, are isolated from a human subject. In some aspects, the immune cells are tumor-infiltrating T cells or tumor-infiltrating NK cells. In certain aspects, the cells, e.g., T cells, NK cells, and/or TILs, are engineered. In some aspects, the immune cells, e.g., T cells, NK cells, and/or TILs, are engineered to comprise a chimeric antigen receptor (CAR). In some aspects, the immune cells, e.g., T cells, NK cells, and/or TILs, are engineered to comprise an engineered T cell receptor (TCR).

In some aspects, the cells, e.g., T cells, NK cells, and/or TILs, are engineered before culturing according to the methods disclosed herein. In some aspects, the cells, e.g., T cells, NK cells, and/or TILs, are engineered after culturing according to the methods disclosed herein. In some aspects, the cells, e.g., T cells, NK cells, and/or TILs, are cultured according to the methods disclosed herein, e.g., in a hypotonic or isotonic medium comprising at least 50 mM potassium ion, prior to, during, and after cell engineering. In some aspects, the cells, e.g., T cells, NK cells, and/or TILs, are engineered to express a chimeric antigen receptor (CAR). In some aspects, the cells, e.g., T cells, NK cells, and/or TILs, are engineered to express an engineered T cell receptor (TCR). In certain aspects, culturing the cells, e.g., T cells, NK cells, and/or TILs, under the conditions disclosed herein, e.g., in a hypotonic or isotonic medium comprising at least about 50 mM potassium ion, results in higher transduction efficiency. In some aspects, transduction efficiency is at least about 2-fold greater in cells, e.g., T cells, NK cells, and/or TILs, cultured in hypotonic or isotonic medium comprising at least about 60 mM potassium ion, according to the methods disclosed herein, as compared to cells, e.g., T cells, NK cells, and/or TILs, cultured in medium comprising 4 mM potassium ion or less. In some aspects, transduction efficiency is at least about 2.5-fold greater in cells, e.g., T cells, NK cells, and/or TILs, cultured in hypotonic or isotonic medium comprising at least about 65 mM potassium ion, according to the methods disclosed herein, as compared to cells, e.g., T cells, NK cells, and/or TILs, cultured in medium comprising 4 mM potassium ion or less.

In some aspects, the cell comprises a construct expressing an antigen receptor and/or another additional polypeptide. In some aspects, the antigen receptor comprises an antibody, an engineered antibody such as scFv, a CAR, an engineered TCR, a TCR mimic (e.g., an antibody-T cell receptor (abTCR) or a chimeric antibody-T cell receptor (caTCR)), or a chimeric signaling receptor (CSR). By way of example, a TCR can comprise an engineered TCR in which the antigen-binding domain of a TCR (e.g., an alpha/beta TCR or a gamma/delta TCR) has been replaced by that of an antibody (with or without the antibody's constant domains); the engineered TCR then becomes specific for the antibody's antigen while retaining the TCR's signaling functions. A chimeric signaling receptor can comprise (1) an extracellular binding domain (e.g., natural/modified receptor extracellular domain, natural/modified ligand extracellular domain, scFv, nanobody, Fab, DARPin, and affibody), (2) a transmembrane domain, and (3) an intracellular signaling domain (e.g., a domain that activates transcription factors, or recruits and/or activates JAK/STAT, kinases, phosphatases, and ubiquitin; SH3; SH2; and PDZ). See, e.g., EP340793B1, WO 2017/070608, WO 2018/200582, WO 2018/200583, WO 2018/200585, and Xu et al., Cell Discovery (2018) 4:62.

In some aspects, the antigen receptor targets an antigen of interest (e.g., a tumor antigen or an antigen of a pathogen). The antigens can include, without limitation, AFP (alpha-fetoprotein), αvβ6 or another integrin, BCMA, B7-H3, B7-H6, Braf, CA9 (carbonic anhydrase 9), CCL-1 (C-C motif chemokine ligand 1), CD5, CD19, CD20, CD21, CD22, CD23, CD24, CD30, CD33, CD38, CD40, CD44, CD44v6, CD44v7/8, CD45, CD47, CD56, CD66e, CD70, CD74, CD79a, CD79b, CD98, CD123, CD138, CD171, CD352, CEA (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-a (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRCSD (G Protein Coupled Receptor 5D), HER2, HER3, HER4, hepatitis B surface antigen, HLA-A1 (human leukocyte antigen A1), HLA-A2 (human leukocyte antigen A2), HMW-MAA (human high molecular weight-melanoma-associated antigen), IGF1R (insulin-like growth factor 1 receptor), Ig kappa, Ig lambda, IL-22Ra (IL-22 receptor alpha), IL-13Ra2 (IL-13 receptor alpha 2), KDR (kinase insert domain receptor), LI cell adhesion molecule (LI-CAM), Liv-1, LRRC8A (leucine rich repeat containing 8 Family member A), Lewis Y, melanoma-associated antigen (MAGE)-A1, MAGE-A3, MAGE-A6, MART-1 (melan A), murine cytomegalovirus (MCMV), MCSP (melanoma-associated chondroitin sulfate proteoglycan), mesothelin, mucin 1 (MUC1), MUC16, MHC/peptide complexes (e.g., HLA-A complexed with peptides derived from AFP, KRAS, NY-ESO, MAGE-A, and WT1), NCAM (neural cell adhesion molecule), Nectin-4, NKG2D (natural killer group 2 member D) ligands, NY-ESO, oncofetal antigen, PD-1, PD-L1, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), STEAP1 (six transmembrane epithelial antigen of the prostate 1), survivin, TAG72 (tumor-associated glycoprotein 72), TPBG (trophoblast glycoprotein), Trop-2, VEGFR1 (vascular endothelial growth factor receptor 1), VEGFR2, and antigens from HIV, HBV, HCV, HPV, and other pathogens.

In certain aspects, the antigen receptor targets hTERT. In some aspects, the antigen receptor targets KRAS. In some aspects, the antigen receptor targets Braf. In some aspects, the antigen receptor targets TGFβRII. In some aspects, the antigen receptor targets MAGE A10/A4. In some aspects, the antigen receptor targets AFP. In some aspects, the antigen receptor targets PRAME. In some aspects, the antigen receptor targets MAGE A1. In some aspects, the antigen receptor targets WT-1. In some aspects, the antigen receptor targets NY-ESO. In some aspects, the antigen receptor targets PRAME. In some aspects, the antigen receptor targets NY-ESO. In some aspects, the antigen receptor targets CD19.

In some aspects, the antigen receptor targets BCMA. In some aspects, the antigen receptor targets CD147. In some aspects, the antigen receptor targets CD19. In some aspects, the antigen receptor targets CD19 and CD22. In some aspects, the antigen receptor targets CD19 and CD28. In some aspects, the antigen receptor targets CD20. In some aspects, the antigen receptor targets CD20 and CD19. In some aspects, the antigen receptor targets CD22. In some aspects, the antigen receptor targets CD30. In some aspects, the antigen receptor targets CEA. In some aspects, the antigen receptor targets DLL3. In some aspects, the antigen receptor targets EGFRvIII. In some aspects, the antigen receptor targets GD2. In some aspects, the antigen receptor targets HER2. In some aspects, the antigen receptor targets IL-1RAP. In some aspects, the antigen receptor targets mesothelin. In some aspects, the antigen receptor targets methothelin. In some aspects, the antigen receptor targets NKG2D. In some aspects, the antigen receptor targets PSMA. In some aspects, the antigen receptor targets TnMUC1.

II.G.1. Chimeric Antigen Receptor (CAR)

In some aspects, the cell, e.g., T cell, NK cell, and/or TIL, comprises a CAR. In some aspects, the cell that can be prepared to express a CAR (e.g., a CAR T cell) is, e.g., a CD8+ T cell or CD4+ T cell. In some aspects, a CAR-expressing cell disclosed herein is a CAR T cell, e.g., a mono CAR T cell, a genome-edited CAR T cell, a dual CAR T cell, or a tandem CAR T cell. Examples of such CAR T cells are provided in International Application No. PCT/US2019/044195.

In some aspects, the CAR specifically binds (i.e., target) one or more antigens expressed on a tumor cell, such as a malignant B cell, a malignant T cell, or a malignant plasma cell.

In some aspects, the CAR specifically binds to (i.e., targets) an antigen selected from the group consisting of CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

In some aspects, the CAR targets BCMA. In some aspects, the CAR targets CD147. In some aspects, the CAR targets CD19. In some aspects, the CAR targets ROR1. In some aspects, the CAR targets GPC3. In some aspects, the CAR targets GPC2. In some aspects, the CAR targets CD19 and CD22. In some aspects, the CAR targets CD19 and CD28. In some aspects, the CAR targets CD20. In some aspects, the CAR targets CD20 and CD19. In some aspects, the CAR targets CD22. In some aspects, the CAR targets CD30. In some aspects, the CAR targets CEA. In some aspects, the CAR targets DLL3. In some aspects, the CAR targets EGFRvIII. In some aspects, the CAR targets GD2. In some aspects, the CAR targets HER2. In some aspects, the CAR targets IL-1RAP. In some aspects, the CAR targets mesothelin. In some aspects, the CAR targets methothelin. In some aspects, the CAR targets NKG2D. In some aspects, the CAR targets PSMA. In some aspects, the CAR targets TnMUC1.

In certain aspects, the CAR comprises an antigen-binding domain that specifically binds an antigen in complex with an MHC. In some aspects, the CAR comprises an antigen-binding domain from a TCRm, e.g., any TCRm disclosed herein.

II.G.2. T Cell Receptor-Engineered (TCR) Cells

In some aspects, an immune cell, e.g., a T cell, an NK cell, or a TIL, disclosed herein comprises a T cell receptor (TCR), e.g., an engineered TCR. In some aspects, the TCR specifically binds to a tumor antigen. As used herein, the term "engineered TCR" or "engineered T-cell receptor" refers to a T-cell receptor (TCR) engineered to specifically bind with a desired affinity to a major histocompatibility complex (MHC)/peptide target antigen that is selected, cloned, and/or subsequently introduced into a population of immune cells, e.g., T cells, NK cells, and/or TILs. In some aspects, the TCR specifically binds a neoantigen identified from a cancer patient.

In some aspects, the TCR specifically binds (i.e., target) one or more antigens expressed on a tumor cell, such as a malignant B cell, a malignant T cell, or a malignant plasma cell.

In certain aspects, an engineered cell of the present disclosure can express a T cell receptor (TCR) targeting an antigen. In some aspects, the TCR engineered cells can target main types: shared tumor-associated antigens (shared TAAs) and unique tumor-associated antigens (unique TAAs), or tumor-specific antigens. The former can include, without any limitation, cancer-testis (CT) antigens, overexpressed antigens, and differentiation antigens, while the latter can include, without any limitation, neoantigens and oncoviral antigens. Human papillomavirus (HPV) E6 protein and HPV E7 protein belong to the category of oncoviral antigens.

In some aspects, the TCR engineered cells can target a CT antigen, e.g., melanoma-associated antigen (MAGE) including, but not limited to, MAGE-Al, MAGE-A2, MAGE-A3, MAGE-A4, MAGE-A6, MAGE-A8, MAGE-A9.23, MAGE-A10, and MAGE-A12. In some aspects, the TCR engineered cells can target glycoprotein (gp100), melanoma antigen recognized by T cells (MART-1), and/or tyrosinase, which are mainly found in melanomas and normal melanocytes. In some aspects, the TCR engineered cells can target Wilms tumor 1 (WT1), i.e., one kind of overexpressed antigen that is highly expressed in most acute myeloid leukemia (AML), acute lymphoid leukemia, almost every type of solid tumor and several critical tissues, such as heart tissues. In some aspects, the TCR engineered cells can target mesothelin, another kind of overexpressed antigen that is highly expressed in mesothelioma but is also present on mesothelial cells of several tissues, including trachea.

In some aspects, the TCR engineered cells can target any neoantigen, which can be formed by random somatic mutations specific to individual tumors. In some aspects, the TCR specifically binds to (i.e., targets) a cancer antigen selected from the group consisting of AFP, Braf, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-Al, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

In certain aspects, the TCR specifically binds (i.e., targets) hTERT. In some aspects, the TCR specifically binds (i.e., targets) KRAS. In some aspects, the TCR specifically binds (i.e., targets) Braf. In some aspects, the TCR specifically binds (i.e., targets) TGFβRII. In some aspects, the TCR specifically binds (i.e., targets) MAGE A10/A4. In some aspects, the TCR specifically binds (i.e., targets) AFP. In some aspects, the TCR specifically binds (i.e., targets) PRAME. In some aspects, the TCR specifically binds (i.e., targets) MAGE A1. In some aspects, the TCR specifically binds (i.e., targets) WT-1. In some aspects, the TCR specifically binds (i.e., targets) NY-ESO. In some aspects, the TCR specifically binds (i.e., targets) PRAME. In some aspects, the TCR specifically binds (i.e., targets) NY-ESO. In some aspects, the TCR specifically binds (i.e., targets) CD19. In certain aspects, the TCR specifically binds a neoantigen identified from a cancer patient.

In some aspects, the TCR comprises an intracellular gamma/delta domain. In some aspects, the TCR is an antibody-T-cell receptor (AbTCR) (see, e.g., Xu et al., *Cell Discovery* 4:62 (2018), which is incorporated by reference herein in its entirety.

II.G.3. T Cell Receptor Mimics (TCRm)

In some aspects, an immune cell, e.g., a T cell, an NK cell, and/or a TIL, disclosed herein comprises a T cell receptor mimic (TCRm), also known as a TCR-like antibody. TCRm are a type of antibody that recognize epitopes comprising both the peptide and the MHC-I molecule, similar to the recognition of such complexes by the TCR on T cells (see, e.g., Traneska et al., *Front. Immunol.* 8(1001):1-12 (2017), which is incorporated by reference herein in its entirety). In some aspects, the TCRm specifically binds to a tumor antigen. In certain aspects, the TCRm specifically binds a neoantigen identified from a cancer patient.

In some aspects, the TCRm specifically binds (i.e., target) one or more antigens expressed on a tumor cell, such as a malignant B cell, a malignant T cell, or a malignant plasma cell. In some aspects, the TCRm is a monoclonal antibody. In some aspects, the TCRm specifically binds to WT1. In some aspects, the TCRm specifically binds to a fragment of WT1. In some aspects, the TCRm comprises ESK1 (see, e.g., Ataie et al., *J. Mol. Biol.* 428(1):194-205 (2016), which is incorporated by reference herein in its entirety). In some aspects, the TCRm specifically binds to MAGE-Al. In some aspects, the TCRm specifically binds to p68 RNA helicase/HLA-A*02:01. In some aspects, the TCRm specifically binds to hCG-b/HLAA*02:01. In some aspects, the TCRm specifically binds to Her2-E75/HLA-A*02:01. In some aspects, the TCRm specifically binds to PR-1 in context of HLA-A*02:01 (see, e.g., *Oncoimmunology* 5(1):e1049803 (June 2015), which is incorporated by reference herein in its entirety). In some aspects, the TCRm specifically binds to the survivin-2B-derived nonamer peptide, AYACNTSTL (SV2B80-88), presented on HLA-A*24 (SV2B80-88/HLA-A*24) (see, e.g., Kurosawa et al., *Nature Scientific Reports* 9(9827):1-11 (2019), which is incorporated by reference herein in its entirety). In some aspects, the TCRm specifically binds one or more tumor-associated PRAME peptide/HLA-I antigens (see, e.g., *J Clin Invest.* 127(7):2705-18 (2017), which is incorporated by reference herein in its entirety). In some aspects, the TCRm specifically binds to tyrosinase. In some aspects, the TCRm specifically binds telomerase catalytic subunit. In some aspects, the TCRm specifically binds to glycoprotein 100 (gp100). In some aspects, the TCRm specifically binds to mucin 1 (MUC1). In some aspects, the TCRm specifically binds to human telomerase reverse transcriptase (hTERT). In some aspects, the TCRm specifically binds to NYESO-1. In some aspects, the TCRm specifically binds to MART-1. In some aspects, the TCRm specifically binds to PRAME.

In some aspects, the TCRm specifically binds to a viral antigen. In some aspects, the TCRm specifically binds to Env183/A2 (Hep B/HLA-A*02:01). In some aspects, the TCRm specifically binds to KP14/1 and KP15/11 (HIV envelope gp160/HLAA*02:01). In some aspects, the TCRm specifically binds to RL36A (West Nile Virus/mouse H-2Db). In some aspects, the TCRm specifically binds to a viral epitope derived from HTLV. In some aspects, the TCRm specifically binds to a viral epitope derived from influenza. In some aspects, the TCRm specifically binds to a viral epitope derived from CMV. In some aspects, the TCRm specifically binds to a viral epitope derived from HIV.

III. Compositions of the Disclosure

III.A. Cell Culture Medium

Some aspects of the present disclosure are directed to a hypotonic or isotonic cell culture medium comprising at least about 5 mM potassium ion, as disclosed herein. Certain aspects of the present disclosure are directed to a cell culture medium comprising higher than 40 mM potassium ion, as disclosed herein. Certain aspects of the present disclosure are directed to a cell culture medium comprising at least about 50 mM potassium ion, as disclosed herein. In some aspects, the medium is hypotonic. In some aspects, the medium is isotonic.

Some aspects of the present disclosure are directed to a cell culture medium comprising at least about 50 mM potassium ion and less than 90 mM NaCl, as disclosed herein. In some aspects, the total concentration of potassium ion and NaCl is at least 110 mM.

In some aspects, the medium comprises about 40 mM potassium ion, and the medium has a tonicity of about 250 mOsmol. In some aspects, the medium comprises about 41 mM potassium ion, and the medium has a tonicity of about 250 mOsmol. In some aspects, the medium comprises about 42 mM potassium ion, and the medium has a tonicity of about 250 mOsmol. In some aspects, the medium comprises about 43 mM potassium ion, and the medium has a tonicity of about 250 mOsmol. In some aspects, the medium comprises about 44 mM potassium ion, and the medium has a tonicity of about 250 mOsmol. In some aspects, the medium comprises about 45 mM potassium ion, and the medium has a tonicity of about 250 mOsmol. In some aspects, the medium comprises about 46 mM potassium ion, and the medium has a tonicity of about 250 mOsmol. In some aspects, the medium comprises about 47 mM potassium ion, and the medium has a tonicity of about 250 mOsmol. In some aspects, the medium comprises about 48 mM potassium ion, and the medium has a tonicity of about 250 mOsmol. In some aspects, the medium comprises about 49 mM potassium ion, and the medium has a tonicity of about 250 mOsmol.

In some aspects, the medium comprises about 50 mM potassium ion, and the medium has a tonicity of about 255 mOsmol. In some aspects, the medium comprises about 50 mM potassium ion, and the medium has a tonicity of about 250 mOsmol to about 260 mOsmol. In some aspects, the medium comprises about 50 mM potassium ion, and the medium has a tonicity of about 254 mOsmol to about 256 mOsmol. In some aspects, the medium comprises about 50 mM potassium ion, and the medium has a tonicity of about 254.7 mOsmol.

In some aspects, the medium comprises about 51 mM, about 52 mM, about 53 mM, or about 54 mM potassium ion, and the medium has a tonicity of about 255 mOsmol. In some aspects, the medium comprises about 51 mM, about 52 mM, about 53 mM, or about 54 mM potassium ion, and the medium has a tonicity of about 250 mOsmol to about 260 mOsmol. In some aspects, the medium comprises about 51 mM, about 52 mM, about 53 mM, or about 54 mM potassium ion, and the medium has a tonicity of about 254 mOsmol to about 256 mOsmol. In some aspects, the medium comprises about 51 mM, about 52 mM, about 53 mM, or about 54 mM potassium ion, and the medium has a tonicity of about 254.7 mOsmol. In some aspects, the medium comprises about 51 mM, about 52 mM, about 53 mM, or about 54 mM potassium ion, and the medium has a tonicity of about 255.2 mOsmol.

In some aspects, the medium comprises about 55 mM potassium ion, and the medium has a tonicity of about 255 mOsmol. In some aspects, the medium comprises about 55 mM potassium ion, and the medium has a tonicity of about 250 mOsmol to about 260 mOsmol. In some aspects, the medium comprises about 55 mM potassium ion, and the medium has a tonicity of about 254 mOsmol to about 256 mOsmol. In some aspects, the medium comprises about 55 mM potassium ion, and the medium has a tonicity of about 255.2 mOsmol.

In some aspects, the medium comprises about 56 mM, about 57 mM, about 58 mM, or about 59 mM potassium ion, and the medium has a tonicity of about 256 mOsmol. In some aspects, the medium comprises about 56 mM, about 57 mM, about 58 mM, or about 59 mM potassium ion, and the medium has a tonicity of about 250 mOsmol to about 260 mOsmol. In some aspects, the medium comprises about 56 mM, about 57 mM, about 58 mM, or about 59 mM potassium ion, and the medium has a tonicity of about 255 mOsmol to about 258 mOsmol. In some aspects, the medium comprises about 60 mM potassium ion, and the medium has a tonicity of about 257.2 mOsmol.

In some aspects, the medium comprises about 60 mM potassium ion, and the medium has a tonicity of about 257 mOsmol. In some aspects, the medium comprises about 60 mM potassium ion, and the medium has a tonicity of about 250 mOsmol to about 260 mOsmol. In some aspects, the medium comprises about 60 mM potassium ion, and the medium has a tonicity of about 256 mOsmol to about 258 mOsmol. In some aspects, the medium comprises about 60 mM potassium ion, and the medium has a tonicity of about 257.2 mOsmol.

In some aspects, the medium comprises about 61 mM, about 62 mM, about 63 mM, or about 64 mM potassium ion, and the medium has a tonicity of about 257 mOsmol. In some aspects, the medium comprises about 61 mM, about 62 mM, about 63 mM, or about 64 mM potassium ion, and the medium has a tonicity of about 250 mOsmol to about 260 mOsmol. In some aspects, the medium comprises about 61 mM, about 62 mM, about 63 mM, or about 64 mM potassium ion, and the medium has a tonicity of about 256 mOsmol to about 258 mOsmol. In some aspects, the medium comprises about 61 mM, about 62 mM, about 63 mM, or about 64 mM potassium ion, and the medium has a tonicity of about 257.2 mOsmol. In some aspects, the medium comprises about 61 mM, about 62 mM, about 63 mM, or about 64 mM potassium ion, and the medium has a tonicity of about 257.5 mOsmol.

In some aspects, the medium comprises about 65 mM potassium ion, and the medium has a tonicity of about 257 mOsmol. In some aspects, the medium comprises about 65 mM potassium ion, and the medium has a tonicity of about 250 mOsmol to about 260 mOsmol. In some aspects, the medium comprises about 65 mM potassium ion, and the medium has a tonicity of about 257 mOsmol to about 258 mOsmol. In some aspects, the medium comprises about 65 mM potassium ion, and the medium has a tonicity of about 257.5 mOsmol.

In some aspects, the medium comprises about 66 mM, about 67 mM, about 68 mM, or about 69 mM potassium ion, and the medium has a tonicity of about 257 mOsmol. In some aspects, the medium comprises about 66 mM, about 67 mM, about 68 mM, or about 69 mM potassium ion, and the medium has a tonicity of about 255 mOsmol to about 265 mOsmol. In some aspects, the medium comprises about 66 mM, about 67 mM, about 68 mM, or about 69 mM potassium ion, and the medium has a tonicity of about 257 mOsmol to about 260 mOsmol. In some aspects, the medium comprises about 66 mM, about 67 mM, about 68 mM, or about 69 mM potassium ion, and the medium has a tonicity of about 257.5 mOsmol. In some aspects, the medium comprises about 66 mM, about 67 mM, about 68 mM, or about 69 mM potassium ion, and the medium has a tonicity of about 259.7 mOsmol.

In some aspects, the medium comprises about 70 mM potassium ion, and the medium has a tonicity of about 259 mOsmol. In some aspects, the medium comprises about 70 mM potassium ion, and the medium has a tonicity of about 255 mOsmol to about 265 mOsmol. In some aspects, the medium comprises about 70 mM potassium ion, and the medium has a tonicity of about 259 mOsmol to about 261 mOsmol. In some aspects, the medium comprises about 70 mM potassium ion, and the medium has a tonicity of about 259.7 mOsmol.

In some aspects, the medium comprises about 71 mM, about 72 mM, about 73 mM, or about 74 mM potassium ion, and the medium has a tonicity of about 259 mOsmol. In some aspects, the medium comprises about 71 mM, about 72 mM, about 73 mM, or about 74 mM potassium ion, and the medium has a tonicity of about 255 mOsmol to about 265 mOsmol. In some aspects, the medium comprises about 71 mM, about 72 mM, about 73 mM, or about 74 mM potassium ion, and the medium has a tonicity of about 259 mOsmol to about 261 mOsmol. In some aspects, the medium comprises about 71 mM, about 72 mM, about 73 mM, or about 74 mM potassium ion, and the medium has a tonicity of about 259.7 mOsmol. In some aspects, the medium comprises about 71 mM, about 72 mM, about 73 mM, or about 74 mM potassium ion, and the medium has a tonicity of about 260 mOsmol.

In some aspects, the medium comprises about 75 mM potassium ion, and the medium has a tonicity of about 260 mOsmol. In some aspects, the medium comprises about 75 mM potassium ion, and the medium has a tonicity of about 255 mOsmol to about 265 mOsmol. In some aspects, the medium comprises about 75 mM potassium ion, and the medium has a tonicity of about 259 mOsmol to about 261 mOsmol. In some aspects, the medium comprises about 75 mM potassium ion, and the medium has a tonicity of about 260 mOsmol.

In some aspects, the medium comprises about 81 mM, about 82 mM, about 83 mM, or about 84 mM potassium ion, and the medium has a tonicity of about 260 mOsmol. In some aspects, the medium comprises about 81 mM, about 82 mM, about 83 mM, or about 84 mM potassium ion, and the medium has a tonicity of about 261 mOsmol. In some aspects, the medium comprises about 81 mM, about 82 mM, about 83 mM, or about 84 mM potassium ion, and the medium has a tonicity of about 262 mOsmol. In some aspects, the medium comprises about 81 mM, about 82 mM, about 83 mM, or about 84 mM potassium ion, and the medium has a tonicity of about 263 mOsmol. In some aspects, the medium comprises about 81 mM, about 82 mM, about 83 mM, or about 84 mM potassium ion, and the medium has a tonicity of about 255 mOsmol to about 265 mOsmol. In some aspects, the medium comprises about 81 mM, about 82 mM, about 83 mM, or about 84 mM potassium ion, and the medium has a tonicity of about 261 mOsmol to about 263 mOsmol. In some aspects, the medium comprises about 81 mM, about 82 mM, about 83 mM, or about 84 mM potassium ion, and the medium has a tonicity of about 262.26 mOsmol.

In some aspects, the medium comprises about 80 mM potassium ion, and the medium has a tonicity of about 262 mOsmol. In some aspects, the medium comprises about 80 mM potassium ion, and the medium has a tonicity of about 255 mOsmol to about 265 mOsmol. In some aspects, the medium comprises about 80 mM potassium ion, and the medium has a tonicity of about 261 mOsmol to about 263 mOsmol. In some aspects, the medium comprises about 80 mM potassium ion, and the medium has a tonicity of about 262.26 mOsmol.

In some aspects, the medium comprises about 81 mM, about 82 mM, about 83 mM, about 84 mM, or about 85 mM potassium ion, and the medium has a tonicity of about 262 mOsmol. In some aspects, the medium comprises about 81 mM, about 82 mM, about 83 mM, about 84 mM, or about 85 mM potassium ion, and the medium has a tonicity of about 263 mOsmol. In some aspects, the medium comprises about 81 mM, about 82 mM, about 83 mM, about 84 mM, or about 85 mM potassium ion, and the medium has a tonicity of about 264 mOsmol. In some aspects, the medium comprises about 81 mM, about 82 mM, about 83 mM, about 84 mM, or about 85 mM potassium ion, and the medium has a tonicity of about 265 mOsmol. In some aspects, the medium comprises about 81 mM, about 82 mM, about 83 mM, about 84 mM, or about 85 mM potassium ion, and the medium has a tonicity of about 255 mOsmol to about 265 mOsmol. In some aspects, the medium comprises about 81 mM, about 82 mM, about 83 mM, about 84 mM, or about 85 mM potassium ion, and the medium has a tonicity of about 260 mOsmol to about 270 mOsmol. In some aspects, the medium comprises about 81 mM, about 82 mM, about 83 mM, about 84 mM, or about 85 mM potassium ion, and the medium has a tonicity of about 261 mOsmol to about 263 mOsmol. In some aspects, the medium comprises about 81 mM, about 82 mM, about 83 mM, about 84 mM, or about 85 mM potassium ion, and the medium has a tonicity of about 263 mOsmol to about 265 mOsmol.

In some aspects, the medium comprises sodium ion. In some aspects, the concentration of the sodium ion is less than that of the basal medium. In some aspects, the concentration of the sodium ion is reduced as the concentration of potassium ion is increased. In some aspects, the concentration of the sodium ion is from about 25 mM to about 115 mM. In some aspects, the concentration of the sodium ion is from about 25 mM to about 100 mM, about 30 mM to about 40 mM, about 30 mM to about 50 mM, about 30 mM to about 60 mM, about 30 mM to about 70 mM, about 30 mM to about 80 mM, about 40 mM to about 50 mM, about 40 mM to about 60 mM, about 40 mM to about 70 mM, about 40 mM to about 80 mM, about 50 mM to about 55 mM, about 50 mM to about 60 mM, about 50 mM to about 65 mM, about 50 mM to about 70 mM, about 50 mM to about 75 mM, about 50 mM to about 80 mM, about 55 mM to about 60 mM, about 55 mM to about 65 mM, about 55 mM to about 70 mM, about 55 mM to about 75 mM, about 55 mM to about 80 mM, about 60 mM to about 65 mM, about 60 mM to about 70 mM, about 60 mM to about 75 mM, about 60 mM to about 80 mM, about 70 mM to about 75 mM, about 70 mM to about 80 mM, or about 75 mM to about 80 mM. In certain aspects, the concentration of the sodium ion is from about 50 mM to about 85 mM. In certain aspects, the concentration of the sodium ion is from about 55 mM to about 80 mM. In certain aspects, the concentration of the sodium ion is from about 30 mM to about 35 mM. In certain aspects, the concentration of the sodium ion is from about 35 mM to about 40 mM. In certain aspects, the concentration of the sodium ion is from about 40 mM to about 45 mM. In certain aspects, the concentration of the sodium ion is from about 45 mM to about 50 mM. In certain aspects, the concentration of the sodium ion is from about 50 mM to about 55 mM. In certain aspects, the concentration of the sodium ion is from about 55 mM to about 60 mM. In certain aspects, the concentration of the sodium ion is from about 60 mM to about 65 mM. In certain aspects, the concentration of the sodium ion is from about 65 mM to about 70 mM. In certain aspects, the concentration of the sodium ion is from about 70 mM to about 75 mM. In certain aspects, the concentration of the sodium ion is from about 75 mM to about 80 mM. In certain aspects, the concentration of the sodium ion is from about 80 mM to about 85 mM.

In some aspects, the concentration of the sodium ion is about 30 mM, about 35 mM, about 40 mM, about 45 mM, about 50 mM, about 55 mM, about 60 mM, about 65 mM, about 70 mM, about 75 mM, about 80 mM, about 85 mM, or about 90 mM. In certain aspects, the concentration of sodium ion is about 55 mM. In certain aspects, the concentration of sodium ion is about 55.6 mM. In certain aspects, the concentration of sodium ion is about 59.3 mM. In certain aspects, the concentration of sodium ion is about 60 mM. In certain aspects, the concentration of sodium ion is about 63.9 mM. In certain aspects, the concentration of sodium ion is about 65 mM. In certain aspects, the concentration of sodium ion is about 67.6 mM. In certain aspects, the concentration of sodium ion is about 70 mM. In certain aspects, the concentration of sodium ion is about 72.2 mM. In certain aspects, the concentration of sodium ion is about 75 mM. In certain aspects, the concentration of sodium ion is about 76 mM. In certain aspects, the concentration of sodium ion is about 80 mM. In certain aspects, the concentration of sodium ion is about 80.5 mM.

In some aspects, the medium comprises about 50 mM potassium ion and about 80.5 mM sodium ion. In some aspects, the medium has a tonicity of about 254.7 mOsmol. In some aspects, the medium comprises about 55 mM potassium ion and about 76 mM sodium ion. In some aspects, the medium has a tonicity of about 255.2 mOsmol. In some aspects, the medium comprises about 60 mM potassium ion and about 72.2 mM sodium ion. In some aspects, the medium has a tonicity of about 257.2 mOsmol. In some aspects, the medium comprises about 65 mM potassium ion and about 67.6 mM sodium ion. In some aspects, the medium has a tonicity of about 257.5 mOsmol. In some aspects, the medium comprises about 70 mM potassium ion and about 63.9 mM sodium ion. In some aspects, the medium has a tonicity of about 259.7 mOsmol. In some aspects, the medium comprises about 75 mM potassium ion and about 59.3 mM sodium ion. In some aspects, the medium has a tonicity of about 260 mOsmol. In some aspects, the medium comprises about 80 mM potassium ion and about 55.6 mM sodium ion. In some aspects, the medium has a tonicity of about 262.26 mOsmol.

In some aspects, the medium comprises about 40 mM potassium ion and an NaCl concentration of 100 mM. In some aspects, the medium comprises about 41 mM potassium ion and an NaCl concentration of 99 mM. In some aspects, the medium comprises about 42 mM potassium ion and an NaCl concentration of 98 mM. In some aspects, the medium comprises about 43 mM potassium ion and an NaCl concentration of 97 mM. In some aspects, the medium comprises about 44 mM potassium ion and an NaCl concentration of 96 mM. In some aspects, the medium comprises about 45 mM potassium ion and an NaCl concentration of 95 mM. In some aspects, the medium comprises about 46 mM potassium ion and an NaCl concentration of 94 mM. In some aspects, the medium comprises about 47 mM potassium ion and an NaCl concentration of 93 mM. In some aspects, the medium comprises about 48 mM potassium ion and an NaCl concentration of 92 mM. In some aspects, the medium comprises about 49 mM potassium ion and an NaCl concentration of 91 mM.

In some aspects, the medium comprises about 50 mM potassium ion and an NaCl concentration of 90 mM. In some aspects, the medium comprises about 51 mM potassium ion and an NaCl concentration of 89 mM. In some aspects, the medium comprises about 52 mM potassium ion and an NaCl concentration of 88 mM. In some aspects, the medium comprises about 53 mM potassium ion and an NaCl concentration of 87 mM. In some aspects, the medium comprises about 54 mM potassium ion and an NaCl concentration of 86 mM. In some aspects, the medium comprises about 55 mM potassium ion and an NaCl concentration of 85 mM. In some aspects, the medium comprises about 56 mM potassium ion and an NaCl concentration of 84 mM. In some aspects, the medium comprises about 57 mM potassium ion and an NaCl concentration of 83 mM. In some aspects, the medium comprises about 58 mM potassium ion and an NaCl concentration of 82 mM. In some aspects, the medium comprises about 59 mM potassium ion and an NaCl concentration of 81 mM.

In some aspects, the medium comprises about 60 mM potassium ion and an NaCl concentration of 80 mM. In some aspects, the medium comprises about 61 mM potassium ion and an NaCl concentration of 79 mM. In some aspects, the medium comprises about 62 mM potassium ion and an NaCl concentration of 78 mM. In some aspects, the medium comprises about 63 mM potassium ion and an NaCl concentration of 77 mM. In some aspects, the medium comprises about 64 mM potassium ion and an NaCl concentration of 76 mM. In some aspects, the medium comprises about 65 mM potassium ion and an NaCl concentration of 75 mM. In some aspects, the medium comprises about 66 mM potassium ion and an NaCl concentration of 74 mM. In some aspects, the medium comprises about 67 mM potassium ion and an NaCl concentration of 73 mM. In some aspects, the medium comprises about 68 mM potassium ion and an NaCl concentration of 72 mM. In some aspects, the medium comprises about 69 mM potassium ion and an NaCl concentration of 71 mM.

In some aspects, the medium comprises about 70 mM potassium ion and an NaCl concentration of 70 mM. In some aspects, the medium comprises about 71 mM potassium ion and an NaCl concentration of 69 mM. In some aspects, the medium comprises about 72 mM potassium ion and an NaCl concentration of 68 mM. In some aspects, the medium comprises about 73 mM potassium ion and an NaCl concentration of 67 mM. In some aspects, the medium comprises about 74 mM potassium ion and an NaCl concentration of 66 mM. In some aspects, the medium comprises about 75 mM potassium ion and an NaCl concentration of 65 mM. In some aspects, the medium comprises about 76 mM potassium ion and an NaCl concentration of 64 mM. In some aspects, the medium comprises about 77 mM potassium ion and an NaCl concentration of 63 mM. In some aspects, the medium comprises about 78 mM potassium ion and an NaCl concentration of 62 mM. In some aspects, the medium comprises about 79 mM potassium ion and an NaCl concentration of 61 mM.

In some aspects, the medium comprises about 80 mM potassium ion and an NaCl concentration of 60 mM. In some aspects, the medium comprises about 81 mM potassium ion and an NaCl concentration of 59 mM. In some aspects, the medium comprises about 82 mM potassium ion and an NaCl concentration of 58 mM. In some aspects, the medium comprises about 83 mM potassium ion and an NaCl concentration of 57 mM. In some aspects, the medium comprises about 84 mM potassium ion and an NaCl concentration of 56 mM. In some aspects, the medium comprises about 85 mM potassium ion and an NaCl concentration of 55 mM. In some aspects, the medium comprises about 86 mM potassium ion and an NaCl concentration of 54 mM. In some aspects, the medium comprises about 87 mM potassium ion and an NaCl concentration of 53 mM. In some aspects, the medium comprises about 88 mM potassium ion and an NaCl concentration of 52 mM. In some aspects, the medium comprises about 89 mM potassium ion and an NaCl concentration of 51 mM.

In some aspects, the medium comprises about 890 mM potassium ion and an NaCl concentration of 50 mM. In some aspects, the medium comprises about 91 mM potassium ion and an NaCl concentration of 49 mM. In some aspects, the medium comprises about 92 mM potassium ion and an NaCl concentration of 48 mM. In some aspects, the medium comprises about 93 mM potassium ion and an NaCl concentration of 47 mM. In some aspects, the medium comprises about 94 mM potassium ion and an NaCl concentration of 46 mM. In some aspects, the medium comprises about 95 mM potassium ion and an NaCl concentration of 45 mM. In some aspects, the medium comprises about 96 mM potassium ion and an NaCl concentration of 44 mM. In some aspects, the medium comprises about 97 mM potassium ion and an NaCl concentration of 43 mM. In some aspects, the medium comprises about 98 mM potassium ion and an NaCl concentration of 42 mM. In some aspects, the medium comprises about 99 mM potassium ion and an NaCl concentration of 41 mM.

In some aspects, the medium comprises NaCl. In some aspects, the concentration of the NaCl is less than that of the basal medium. In some aspects, the concentration of the NaCl is reduced as the concentration of potassium ion is increased. In some aspects, the concentration of the NaCl is from about 25 mM to about 115 mM. In some aspects, the concentration of the NaCl is from about 25 mM to about 100 mM, about 30 mM to about 40 mM, about 30 mM to about 50 mM, about 30 mM to about 60 mM, about 30 mM to about 70 mM, about 30 mM to about 80 mM, about 40 mM to about 50 mM, about 40 mM to about 60 mM, about 40 mM to about 70 mM, about 40 mM to about 80 mM, about 50 mM to about 55 mM, about 50 mM to about 60 mM, about 50 mM to about 65 mM, about 50 mM to about 70 mM, about 50 mM to about 75 mM, about 50 mM to about 80 mM, about 55 mM to about 60 mM, about 55 mM to about 65 mM, about 55 mM to about 70 mM, about 55 mM to about 75 mM, about 55 mM to about 80 mM, about 60 mM to about 65 mM, about 60 mM to about 70 mM, about 60 mM to about 75 mM, about 60 mM to about 80 mM, about 70 mM to about 75 mM, about 70 mM to about 80 mM, or about 75 mM to about 80 mM. In certain aspects, the concentration of the NaCl is from about 50 mM to about 85 mM. In certain aspects, the concentration of the NaCl is from about 55 mM to about 80 mM. In certain aspects, the concentration of the NaCl is from about 30 mM to about 35 mM. In certain aspects, the concentration of the NaCl is from about 35 mM to about 40 mM. In certain aspects, the concentration of the NaCl is from about 40 mM to about 45 mM. In certain aspects, the concentration of the NaCl is from about 45 mM to about 50 mM. In certain aspects, the concentration of the NaCl is from about 50 mM to about 55 mM. In certain aspects, the concentration of the NaCl is from about 55 mM to about 60 mM. In certain aspects, the concentration of the NaCl is from about 60 mM to about 65 mM. In certain aspects, the concentration of the NaCl is from about 65 mM to about 70 mM. In certain aspects, the concentration of the NaCl is from about 70 mM to about 75 mM. In certain aspects, the concentration of the NaCl is from about 75 mM to about 80 mM. In certain aspects, the concentration of the NaCl is from about 80 mM to about 85 mM.

In some aspects, the medium comprises calcium ion. In some aspects, the concentration of calcium ion is more than about 0.4 mM. In some aspects, the concentration of calcium ion is less than about 2.8 mM. In some aspects, the concentration of calcium ion is less than about 2.5 mM. In some aspects, the concentration of calcium ion is less than about 2.0 mM. In some aspects, the concentration of calcium ion is less than about 1.9 mM. In some aspects, the concentration of calcium ion is less than about 1.8 mM. In some aspects, the concentration of calcium ion is less than about 1.7 mM. In some aspects, the concentration of calcium ion is less than about 1.6 mM. In some aspects, the concentration of calcium ion is less than about 1.5 mM. In some aspects, the concentration of calcium ion is less than about 1.4 mM. In some aspects, the concentration of calcium ion is less than about 1.3 mM. In some aspects, the concentration of calcium ion is less than about 1.2 mM. In some aspects, the concentration of calcium ion is less than about 1.1 mM. In some aspects, the concentration of calcium ion is less than about 1.0 mM.

In some aspects, the concentration of calcium ion is from about 0.4 mM to about 2.8 mM, about 0.4 mM to about 2.7 mM, about 0.4 mM to about 2.5 mM, about 0.5 mM to about 2.0 mM, about 1.0 mM to about 2.0 mM, about 1.1 mM to about 2.0 mM, about 1.2 mM to about 2.0 mM, about 1.3 mM to about 2.0 mM, about 1.4 mM to about 2.0 mM, about 1.5 mM to about 2.0 mM, about 1.6 mM to about 2.0 mM, about 1.7 mM to about 2.0 mM, about 1.8 mM to about 2.0 mM, about 0.8 to about 0.9 mM, about 0.8 to about 1.0 mM, about 0.8 to about 1.1 mM, about 0.8 to about 1.2 mM, about 0.8 to about 1.3 mM, about 0.8 to about 1.4 mM, about 0.8 to about 1.5 mM, about 0.8 to about 1.6 mM, about 0.8 to about 1.7 mM, about 0.8 to about 1.8 mM, about 0.9 to about 1.0 mM, about 0.9 to about 1.1 mM, about 0.9 to about 1.2 mM, about 0.9 to about 1.3 mM, about 0.9 to about 1.4 mM, about 0.9 to about 1.5 mM, about 0.9 to about 1.6 mM, about 0.9 to about 1.7 mM, about 0.9 to about 1.8 mM, about 1.0 to about 1.1 mM, about 1.0 to about 1.2 mM, about 1.0 to about 1.3 mM, about 1.0 to about 1.4 mM, about 1.0 to about 1.5 mM, about 1.0 to about 1.6 mM, about 1.0 to about 1.7 mM, about 1.0 to about 1.8 mM, about 1.1 to about 1.2 mM, about 1.1 to about 1.3 mM, about 1.1 to about 1.4 mM, about 1.1 to about 1.5 mM, about 1.1 to about 1.6 mM, about 1.1 to about 1.7 mM, about 1.1 to about 1.8 mM, about 1.2 to about 1.3 mM, about 1.2 to about 1.4 mM, about 1.2 to about 1.5 mM, about 1.2 to about 1.6 mM, about 1.2 to about 1.7 mM, about 1.2 to about 1.8 mM, about 1.3 to about 1.4 mM, about 1.3 to about 1.5 mM, about 1.3 to about 1.6 mM, about 1.3 to about 1.7 mM, about 1.3 to about 1.8 mM, about 1.4 to about 1.5 mM, about 1.4 to about 1.6 mM, about 1.4 to about 1.7 mM, about 1.4 to about 1.8 mM, about 1.5 to about 1.6 mM, about 1.5 to about 1.7 mM, about 1.5 to about 1.8 mM, about 1.6 to about 1.7 mM, about 1.6 to about 1.8 mM, or about 1.7 to about 1.8 mM.

In some aspects, the concentration of calcium ion is from about 0.8 mM to about 1.8 mM. In some aspects, the concentration of calcium ion is from about 0.9 mM to about 1.8 mM. In some aspects, the concentration of calcium ion is from about 1.0 mM to about 1.8 mM. In some aspects, the concentration of calcium ion is from about 1.1 mM to about 1.8 mM. In some aspects, the concentration of calcium ion is from about 1.2 mM to about 1.8 mM. In some aspects, the concentration of calcium ion is from about 0.8 mM to about 1.8 mM. In some aspects, the concentration of calcium ion is from about 0.8 mM to about 0.9 mM. In some aspects, the concentration of calcium ion is from about 0.9 mM to about 1.0 mM. In some aspects, the concentration of calcium ion is from about 1.0 mM to about 1.1 mM. In some aspects, the concentration of calcium ion is from about 1.1 mM to about 1.2 mM. In some aspects, the concentration of calcium ion is from about 1.2 mM to about 1.3 mM. In some aspects, the concentration of calcium ion is from about 1.3 mM to about 1.4 mM. In some aspects, the concentration of calcium ion is from about 1.4 mM to about 1.5 mM. In some aspects, the concentration of calcium ion is from about 1.5 mM to about 1.6 mM. In some aspects, the concentration of calcium ion is from about 1.7 mM to about 1.8 mM.

In some aspects, the concentration of calcium ion is about 0.6 mM, about 0.7 mM, about 0.8 mM, about 0.9 mM, 1.0 mM, about 1.1 mM, about 1.2 mM, about 1.3 mM, about 1.4 mM, about 1.5 mM, about 1.6 mM, about 1.7 mM, about 1.8 mM, about 1.9 mM, or about 2.0 mM. In some aspects, the concentration of calcium ion is about 0.6 mM. In some aspects, the concentration of calcium ion is about 0.7 mM. In some aspects, the concentration of calcium ion is about 0.8 mM. In some aspects, the concentration of calcium ion is about 0.9 mM. In some aspects, the concentration of calcium ion is about 1.0 mM. In some aspects, the concentration of calcium ion is about 1.1 mM. In some aspects, the concentration of calcium ion is about 1.2 mM. In some aspects, the concentration of calcium ion is about 1.3 mM. In some aspects, the concentration of calcium ion is about 1.4 mM. In some aspects, the concentration of calcium ion is about 1.5 mM. In some aspects, the concentration of calcium ion is about 1.6 mM. In some aspects, the concentration of calcium ion is about 1.7 mM. In some aspects, the concentration of calcium ion is about 1.8 mM.

In some aspects, the medium comprises about 50 mM potassium ion and about 1.8 mM calcium ion. In some aspects, the medium further comprises less than 90 mM NaCl.

In some aspects, the medium comprises about 55 mM potassium ion and about 1.7 mM calcium ion. In some aspects, the medium further comprises less than 85 mM NaCl.

In some aspects, the medium comprises about 60 mM potassium ion and about 1.6 mM calcium ion. In some aspects, the medium has an osmolality of about 257.2 mOsmol. In some aspects, the medium further comprises less than 80 mM NaCl.

In some aspects, the medium comprises about 65 mM potassium ion and about 1.5 mM calcium ion. In some aspects, the medium further comprises less than 75 mM NaCl.

In some aspects, the medium comprises about 70 mM potassium ion and about 1.4 mM calcium ion. In some aspects, the medium further comprises less than 70 mM NaCl.

In some aspects, the medium comprises about 75 mM potassium ion and about 1.3 mM calcium ion. In some aspects, the medium further comprises less than 65 mM NaCl.

In some aspects, the medium comprises about 80 mM potassium ion and about 1.2 mM calcium ion. In some aspects, the medium further comprises less than 60 mM NaCl.

In some aspects, the medium comprises a saccharide. In some aspects, the saccharide is a monosaccharide, a disaccharide, or a polysaccharide. In some aspects, the saccharide is selected from glucose, fructose, galactose, mannose, maltose, sucrose, lactose, trehalose, and any combination thereof. In certain aspects, the saccharide is glucose. In some aspects, the medium comprises (i) potassium ion at a concentration of at least about 50 mM and (ii) glucose. In some aspects, the medium comprises (i) potassium ion at a concentration of at least about 50 mM and (ii) mannose. In some aspects, the medium comprises more than one saccharide. In some aspects, the medium comprises glucose and galactose. In some aspects, the medium comprises glucose and fructose. In some aspects, the medium comprises glucose and mannose. In some aspects, the medium comprises glucose and maltose. In some aspects, the medium comprises glucose and sucrose. In some aspects, the medium comprises glucose and lactose. In some aspects, the medium comprises glucose and trehalose.

In some aspects, the concentration of the saccharide, e.g., glucose, is less than about 4.29 g/L. In some aspects, the concentration of the saccharide, e.g., glucose, is less than about 24 mM. In some aspects, the concentration of the saccharide, e.g., glucose, is more than about 5 mM. In some aspects, the concentration of the saccharide, e.g., glucose, is more than about 5 mM. In some aspects, the concentration of the saccharide, e.g., glucose, is from about 5 mM to about 20 mM. In some aspects, the concentration of the saccharide, e.g., glucose, is from about 10 mM to about 20 mM. In some aspects, the concentration of the saccharide, e.g., glucose, is from about 10 mM to about 25 mM, about 10 mM to about 20 mM, about 10 mM to about 5 mM, about 15 mM to about 25 mM, about 15 mM to about 20 mM, about 15 mM to about 19 mM, about 15 mM to about 18 mM, about 15 mM to about 17 mM, about 15 mM to about 16 mM, about 16 mM to about 20 mM, about 16 mM to about 19 mM, about 16 mM to about 18 mM, about 16 mM to about 17 mM, about 17 mM to about 20 mM, about 17 mM to about 19 mM, or about 17 mM to about 18 mM. In some aspects, the concentration of the saccharide, e.g., glucose, is from about 5 mM to about 20 mM. In some aspects, the concentration of the saccharide, e.g., glucose, is from about 10 mM to about 20 mM. In some aspects, the concentration of the saccharide, e.g., glucose, is from about 10 mM to about 15 mM. In some aspects, the concentration of the saccharide, e.g., glucose, is from about 14 mM to about 14.5 mM. In some aspects, the concentration of the saccharide, e.g., glucose, is from about 14.5 mM to about 15 mM. In some aspects, the concentration of the saccharide, e.g., glucose, is from about 15 mM to about 15.5 mM. In some aspects, the concentration of the saccharide, e.g., glucose, is from about 15.5 mM to about 16 mM. In some aspects, the concentration of the saccharide, e.g., glucose, is from about 16 mM to about 16.5 mM.

In some aspects, the concentration of the saccharide, e.g., glucose, is from about 16.5 mM to about 17 mM. In some aspects, the concentration of the saccharide, e.g., glucose, is from about 17 mM to about 17.5 mM. In some aspects, the concentration of the saccharide, e.g., glucose, is from about 17.5 mM to about 18 mM.

In some aspects, the concentration of the saccharide, e.g., glucose, is about 5 mM, about 6 mM, about 7 mM, about 8 mM, about 9 mM, about 10 mM, is about 10.5 mM, about 11 mM, about 11.5 mM, about 12 mM, about 12.5 mM, about 13 mM, about 13.5 mM, about 14 mM, about 14.5 mM, about 15 mM, about 15.5 mM, about 16 mM, about 16.5 mM, about 17 mM, about 17.5 mM, about 18 mM, about 18.5 mM, about 19 mM, about 19.5 mM, about 20 mM, about 20.5 mM, about 21 mM, about 22 mM, about 23 mM, about 24 mM, or about 25 mM.

In some aspects, the concentration of the saccharide, e.g., glucose, is about 13 mM. In some aspects, the concentration of the saccharide, e.g., glucose, is about 13.5 mM. In some aspects, the concentration of the saccharide, e.g., glucose, is about 14 mM. In some aspects, the concentration of the saccharide, e.g., glucose, is about 14.5 mM. In some aspects, the concentration of the saccharide, e.g., glucose, is about 15 mM. In some aspects, the concentration of the saccharide, e.g., glucose, is about 15.4 mM. In some aspects, the concentration of the saccharide, e.g., glucose, is about 15.9 mM. In some aspects, the concentration of the saccharide, e.g., glucose, is about 16.3 mM. In some aspects, the concentration of the saccharide, e.g., glucose, is about 16.8 mM. In some aspects, the concentration of the saccharide, e.g., glucose, is about 17.2 mM. In some aspects, the concentration of the saccharide, e.g., glucose, is about 17.7 mM.

In some aspects, the medium comprises about 50 mM potassium ion and about 17.7 mM glucose. In some aspects, the medium further comprises less than 90 mM NaCl.

In some aspects, the medium comprises about 55 mM potassium ion and about 17.2 mM glucose. In some aspects, the medium further comprises less than 85 mM NaCl.

In some aspects, the medium comprises about 60 mM potassium ion and about 16.8 mM glucose. In some aspects, the medium further comprises less than 80 mM NaCl.

In some aspects, the medium comprises about 65 mM potassium ion and about 16.3 mM glucose. In some aspects, the medium further comprises less than 75 mM NaCl.

In some aspects, the medium comprises about 70 mM potassium ion and about 15.9 mM glucose. In some aspects, the medium further comprises less than 70 mM NaCl.

In some aspects, the medium comprises about 75 mM potassium ion and about 15.4 mM glucose. In some aspects, the medium further comprises less than 65 mM NaCl.

In some aspects, the medium comprises about 80 mM potassium ion and about 15 mM glucose. In some aspects, the medium further comprises less than 60 mM NaCl.

In some aspects, the medium is isotonic. In some aspects, the medium has a tonicity of about 280 mOsm/L. In some aspects, the medium has a tonicity of 280 mOsm/L. In some aspects, the medium has a tonicity of 280 mOsm/L±1 mOsm/L. In some aspects, the medium has a tonicity of 280 mOsm/L±2 mOsm/L. In some aspects, the medium has a tonicity of 280 mOsm/L±3 mOsm/L. In some aspects, the medium has a tonicity of 280 mOsm/L±4 mOsm/L. In some aspects, the medium has a tonicity of 280 mOsm/L±5 mOsm/L. In some aspects, the medium has a tonicity of 280 mOsm/L±6 mOsm/L. In some aspects, the medium has a tonicity of 280 mOsm/L±7 mOsm/L. In some aspects, the medium has a tonicity of 280 mOsm/L±8 mOsm/L. In some aspects, the medium has a tonicity of 280 mOsm/L±9 mOsm/L. In some aspects, the medium has a tonicity of 280 mOsm/L±10 mOsm/L. In some aspects, the medium has a tonicity of about 280 mOsm/L to about 285 mOsm/L, about 280 mOsm/L to about 290 mOsm/L, about 280 mOsm/L to about 295 mOsm/L, about 280 mOsm/L to about 300 mOsm/L, about 280 mOsm/L to about 305 mOsm/L, about 280 mOsm/L to about 310 mOsm/L, about 280 mOsm/L to about 315 mOsm/L, or about 280 mOsm/L to less than 320 mOsm/L. In some aspects, the medium has a tonicity of about 285 mOsm/L, about 290 mOsm/L, about 295 mOsm/L, about 300 mOsm/L, about 305 mOsm/L, about 310 mOsm/L, or about 315 mOsm/L. In some aspects, tonicity is measured by adding the concentrations of potassium ion and NaCl, and multiplying by two.

In some aspects, the medium is hypotonic. In some aspects, the medium has a tonicity lower than about 280 mOsm/L. In some aspects, the medium has a tonicity lower than 280 mOsm/L. In some aspects, the medium has a tonicity lower than 275 mOsm/L. In some aspects, the medium has a tonicity lower than 270 mOsm/L. In some aspects, the medium has a tonicity lower than 265 mOsm/L. In some aspects, the medium has a tonicity lower than 260 mOsm/L. In some aspects, the medium has a tonicity lower than 265 mOsm/L. In some aspects, the medium has a tonicity lower than 260 mOsm/L. In some aspects, the medium has a tonicity lower than 255 mOsm/L. In some aspects, the medium has a tonicity lower than about 250 mOsm/L. In some aspects, the medium has a tonicity lower than about 245 mOsm/L. In some aspects, the medium has a tonicity lower than about 240 mOsm/L. In some aspects, the medium has a tonicity lower than about 235 mOsm/L. In some aspects, the medium has a tonicity lower than about 230 mOsm/L. In some aspects, the medium has a tonicity lower than about 225 mOsm/L. In some aspects, the medium has a tonicity lower than about 220 mOsm/L. In some aspects, the medium has a tonicity lower than about 215 mOsm/L. In some aspects, the medium has a tonicity lower than about 210 mOsm/L. In some aspects, the medium has a tonicity lower than about 205 mOsm/L. In some aspects, the medium has a tonicity lower than about 200 mOsm/L. In some aspects, tonicity is measured by adding the concentrations of potassium ion and NaCl, and multiplying by two.

In some aspects, the medium has a tonicity from about 100 mOsm/L to about 280 mOsm/L, about 125 mOsm/L to about 280 mOsm/L, about 150 mOsm/L to about 280 mOsm/L, about 175 mOsm/L to about 280 mOsm/L, about 200 mOsm/L to about 280 mOsm/L, about 210 mOsm/L to about 280 mOsm/L, about 220 mOsm/L to about 280 mOsm/L, about 225 mOsm/L to about 280 mOsm/L, about 230 mOsm/L to about 280 mOsm/L, about 235 mOsm/L to about 280 mOsm/L, about 240 mOsm/L to about 280 mOsm/L, about 245 mOsm/L to about 280 mOsm/L, about 250 mOsm/L to about 280 mOsm/L, about 255 mOsm/L to about 280 mOsm/L, about 260 mOsm/L to about 280 mOsm/L, about 265 mOsm/L to about 280 mOsm/L, about 270 mOsm/L to about 280 mOsm/L, or about 275 mOsm/L to about 280 mOsm/L. In some aspects, the medium has a tonicity from about 250 mOsm/L to about 270 mOsm/L. In some aspects, the medium has a tonicity from about 250 mOsm/L to about 255 mOsm/L, about 250 mOsm/L to about 260 mOsm/L, about 250 mOsm/L to about 265 mOsm/L, about 255 mOsm/L to about 260 mOsm/L, about 255 mOsm/L to about 265 mOsm/L, about 255 mOsm/L to about 265 mOsm/L, about 260 mOsm/L to about 265 mOsm/L, or about 254 mOsm/L to about 263 mOsm/L. In some aspects, the medium has a tonicity from about 254 mOsm/L to about 255 mOsm/L. In some aspects, the medium has a tonicity from about 255 mOsm/L to about 256 mOsm/L. In some aspects, the medium has a tonicity from about 256 mOsm/L to about 257 mOsm/L. In some aspects, the medium has a tonicity from about 257 mOsm/L to about 258 mOsm/L. In some aspects, the medium has a tonicity from about 258 mOsm/L to about 259 mOsm/L. In some aspects, the medium has a tonicity from about 260 mOsm/L to about 261 mOsm/L. In some aspects, the medium has a tonicity from about 261 mOsm/L to about 262 mOsm/L. In some aspects, the medium has a tonicity from about 262 mOsm/L to about 263 mOsm/L. In some aspects, the medium has a tonicity from about 263 mOsm/L to about 264 mOsm/L. In some aspects, the medium has a tonicity from about 264 mOsm/L to about 265 mOsm/L. In some aspects, tonicity is measured by adding the concentrations of potassium ion and NaCl, and multiplying by two.

In some aspects, the medium has a tonicity of about 100 mOsm/L, about 125 mOsm/L, about 150 mOsm/L, about 175 mOsm/L, about 200 mOsm/L, about 210 mOsm/L, about 220 mOsm/L, about 225 mOsm/L, about 230 mOsm/L, about 235 mOsm/L, about 240 mOsm/L, about 245 mOsm/L, about 250 mOsm/L, about 255 mOsm/L, about 260 mOsm/L, about 265 mOsm/L, about 270 mOsm/L, or about 275 mOsm/L. In some aspects, tonicity is measured by adding the concentrations of potassium ion and NaCl, and multiplying by two.

In some aspects, the medium has a tonicity of about 250 mOsm/L. In some aspects, the medium has a tonicity of about 262.26 mOsm/L. In some aspects, the medium has a tonicity of about 260 mOsm/L. In some aspects, the medium has a tonicity of about 259.7 mOsm/L. In some aspects, the medium has a tonicity of about 257.5 mOsm/L. In some aspects, the medium has a tonicity of about 257.2 mOsm/L. In some aspects, the medium has a tonicity of about 255.2 mOsm/L. In some aspects, the medium has a tonicity of about 254.7. In some aspects, the medium has a tonicity of about 255 mOsm/L. In some aspects, the medium has a tonicity of about 260 mOsm/L. In some aspects, tonicity is measured by adding the concentrations of potassium ion and NaCl, and multiplying by two.

In some aspects, the medium comprises about 50 mM potassium ion and (i) about 80.5 mM sodium ion; (ii) about 17.7 mM glucose; (iii) about 1.8 mM calcium ion; or (iv) any combination of (i)-(iii). In some aspects, the medium has a tonicity of about 254.7 mOsmol. In some aspects, the medium comprises about 50 mM potassium ion and (i) about 80.5 mM NaCl; (ii) about 17.7 mM glucose; (iii) about 1.8 mM calcium ion; or (iv) any combination of (i)-(iii).

In some aspects, the medium comprises about 55 mM potassium ion and (i) about 76 mM sodium ion; (ii) about 17.2 mM glucose; (iii) about 1.7 mM calcium ion; or (iv) any combination of (i)-(iii). In some aspects, the medium has a tonicity of about 255.2 mOsmol. In some aspects, the medium comprises about 55 mM potassium ion and (i) about 76 mM sodium ion; (ii) about 17.2 mM glucose; (iii) and about 1.7 mM calcium ion; wherein the medium has a tonicity of about 255.2 mOsmol. In some aspects, the medium comprises about 55 mM potassium ion and (i) about 76 mM NaCl; (ii) about 17.2 mM glucose; (iii) about 1.7 mM calcium ion; or (iv) any combination of (i)-(iii).

In some aspects, the medium comprises about 60 mM potassium ion and (i) about 72.2 mM sodium ion; (ii) about 16.8 mM glucose; (iii) about 1.6 mM calcium ion; or (iv) any combination of (i)-(iii). In some aspects, the medium has a tonicity of about 257.2 mOsmol. In some aspects, the medium comprises about 60 mM potassium ion and (i) about 72.2 mM sodium ion; (ii) about 16.8 mM glucose; and (iii) about 1.6 mM calcium ion; wherein the medium has a tonicity of about 257.2 mOsmol. In some aspects, the medium comprises about 60 mM potassium ion and (i) about 72.2 mM NaCl; (ii) about 16.8 mM glucose; (iii) about 1.6 mM calcium ion; or (iv) any combination of (i)-(iii).

In some aspects, the medium comprises about 65 mM potassium ion and (i) about 67.6 mM sodium ion; (ii) about 16.3 mM glucose; (iii) about 1.5 mM calcium ion; or (iv) any combination of (i)-(iii). In some aspects, the medium has a tonicity of about 257.5 mOsmol. In some aspects, the medium comprises about 65 mM potassium ion and (i) about 67.6 mM sodium ion; (ii) about 16.3 mM glucose; and (iii) about 1.5 mM calcium ion; wherein the medium has a tonicity of about 257.5 mOsmol. In some aspects, the medium comprises about 65 mM potassium ion and (i) about 67.6 mM NaCl; (ii) about 16.3 mM glucose; (iii) about 1.5 mM calcium ion; or (iv) any combination of (i)-(iii).

In some aspects, the medium comprises about 70 mM potassium ion and (i) about 63.9 mM sodium ion; (ii) about 15.9 mM glucose; (iii) about 1.4 mM calcium ion; or (iv) any combination of (i)-(iii). In some aspects, the medium has a tonicity of about 259.7 mOsmol. In some aspects, the medium comprises about 70 mM potassium ion and (i) about 63.9 mM sodium ion; (ii) about 15.9 mM glucose; and (iii) about 1.4 mM calcium ion; wherein the medium has a tonicity of about 259.7 mOsmol. In some aspects, the medium comprises about 70 mM potassium ion and (i) about 63.9 mM NaCl; (ii) about 15.9 mM glucose; (iii) about 1.4 mM calcium ion; or (iv) any combination of (i)-(iii).

In some aspects, the medium comprises about 75 mM potassium ion and (i) about 59.3 mM sodium ion; (ii) about 15.4 mM glucose; (iii) about 1.3 mM calcium ion; or (iv) any combination of (i)-(iii). In some aspects, the medium has a tonicity of about 260 mOsmol. In some aspects, the medium comprises about 75 mM potassium ion and (i) about 59.3 mM sodium ion; (ii) about 15.4 mM glucose; and (iii) about 1.3 mM calcium ion; wherein the medium has a tonicity of about 260 mOsmol. In some aspects, the medium comprises about 75 mM potassium ion and (i) about 59.3 mM NaCl; (ii) about 15.4 mM glucose; (iii) about 1.3 mM calcium ion; or (iv) any combination of (i)-(iii).

In some aspects, the medium comprises about 80 mM potassium ion and (i) about 55.6 mM sodium ion; (ii) about 15 mM glucose; (iii) about 1.2 mM calcium ion; or (iv) any combination of (i)-(iii). In some aspects, the medium has a tonicity of about 262.26 mOsmol. In some aspects, the medium comprises about 80 mM potassium ion and (i) about 55.6 mM sodium ion; (ii) about 15 mM glucose; and (iii) about 1.2 mM calcium ion; wherein the medium has a tonicity of about 262.26 mOsmol. In some aspects, the medium comprises about 80 mM potassium ion and (i) about 55.6 mM NaCl; (ii) about 15 mM glucose; (iii) about 1.2 mM calcium ion; or (iv) any combination of (i)-(iii).

III.B. Cells Prepared According to the Methods

Certain aspects of the present disclosure are directed to a cell composition comprising one or more pluripotent, multipotent, and/or immune cell (e.g., T cell, NK cell, and/or TIL) cultured according to the methods disclosed herein. Some aspects of the present disclosure are directed to a cell composition produced by a method of increasing the yield of human immune cells and/or stem cells during ex vivo or in vitro culturing while increasing stemness of the human immune cells and/or stem cells comprising culturing human immune cells and/or stem cells in a medium comprising potassium ion at a concentration between 40 mM and 80 mM and NaCl at a concentration between 100 mM and 30 mM, wherein the total concentration of potassium ion and NaCl is between 110 and 140 mM. Some aspects of the present disclosure are directed to a cell composition produced by a method of preparing a population of human immune cells and/or stem cells for immunotherapy comprising culturing human immune cells and/or stem cells in a medium comprising potassium ion at a concentration between 40 mM and 80 mM and NaCl at a concentration between 100 mM and 30 mM, wherein the total concentration of potassium ion and NaCl is between 110 and 140 mM. Some aspects of the present disclosure are directed to a cell composition produced by a method of increasing stemness of human immune cells during ex vivo or in vitro culturing for immunotherapy comprising culturing human immune cells in a medium comprising potassium ion at a concentration between 40 mM and 80 mM and NaCl at a concentration between 100 mM and 30 mM, wherein the total concentration of potassium ion and NaCl is between 110 and 140 mM.

Cells cultured according to the methods and/or in the medium disclosed herein have an increased number of less-differentiated cells as compared to comparable cells cultured according to conventional methods. In some aspects, the cells cultured according to the methods disclosed herein exhibit increased expression of one or more marker typical of a stem-like phenotype. In some aspects, the cells cultured according to the methods disclosed herein exhibit increased transduction efficiency. In some aspects, the cells cultured according to the methods disclosed herein exhibit increased in vivo viability upon transplantation in a subject. In some aspects, the cells cultured according to the methods disclosed herein exhibit increased cell potency. In some aspects, the cells cultured according to the methods disclosed herein exhibit decreased cell exhaustion. In some aspects, the cells cultured according to the methods disclosed herein exhibit increased in vivo persistence upon transplantation in a subject. In some aspects, the cells cultured according to the methods disclosed herein exhibit increased in vivo activity upon transplantation in a subject. In some aspects, the cells cultured according to the methods disclosed herein exhibit a more durable in vivo response upon transplantation in a subject. In some aspects, the subject is a human.

In some aspects, at least about 5% of the cells in the cell composition have a stem-like phenotype. In some aspects, at least about 10% of the cells in the cell composition have a stem-like phenotype. In some aspects, at least about 15% of the cells in the cell composition have a stem-like phenotype. In some aspects, at least about 20% of the cells in the cell composition have a stem-like phenotype. In some aspects, at least about 25% of the cells in the cell composition have a stem-like phenotype. In some aspects, at least about 30% of the cells in the cell composition have a stem-like phenotype. In some aspects, at least about 35% of the cells in the cell composition have a stem-like phenotype. In some aspects, at least about 40% of the cells in the cell composition have a stem-like phenotype. In some aspects, at least about 45% of the cells in the cell composition have a stem-like phenotype. In some aspects, at least about 50% of the cells in the cell composition have a stem-like phenotype.

In some aspects, the number of cells having a stem-like phenotype in the cell composition is increased at least about 1.5-fold as compared to the number of cells in the cell composition prior to the culture. In some aspects, the number of cells having a stem-like phenotype in the cell composition is increased at least about 2.0-fold as compared to the number of cells in the cell composition prior to the culture. In some aspects, the number of cells having a stem-like phenotype in the cell composition is increased at least about 2.5-fold as compared to the number of cells in the cell composition prior to the culture. In some aspects, the number of cells having a stem-like phenotype in the cell composition is increased at least about 3.0-fold as compared to the number of cells in the cell composition prior to the culture. In some aspects, the number of cells having a stem-like phenotype in the cell composition is increased at least about 3.5-fold as compared to the number of cells in the cell composition prior to the culture. In some aspects, the number of cells having a stem-like phenotype in the cell composition is increased at least about 4.0-fold as compared to the number of cells in the cell composition prior to the culture. In some aspects, the number of cells having a stem-like phenotype in the cell composition is increased at least about 4.5-fold as compared to the number of cells in the cell composition prior to the culture. In some aspects, the number of cells having a stem-like phenotype in the cell composition is increased at least about 5.0-fold as compared to the number of cells in the cell composition prior to the culture. In some aspects, the number of cells having a stem-like phenotype in the cell composition is increased at least about 5.5-fold as compared to the number of cells in the cell composition prior to the culture. In some aspects, the number of cells having a stem-like phenotype in the cell composition is increased at least about 6.0-fold as compared to the number of cells in the cell composition prior to the culture. In some aspects, the number of cells having a stem-like phenotype in the cell composition is increased at least about 6.5-fold as compared to the number of cells in the cell composition prior to the culture. In some aspects, the number of cells having a stem-like phenotype in the cell composition is increased at least about 7.0-fold as compared to the number of cells in the cell composition prior to the culture. In some aspects, the number of cells having a stem-like phenotype in the cell composition is increased at least about 7.5-fold as compared to the number of cells in the cell composition prior to the culture. In some aspects, the number of cells having a stem-like phenotype in the cell composition is increased at least about 8.0-fold as compared to the number of cells in the cell composition prior to the culture. In some aspects, the number of cells having a stem-like phenotype in the cell composition is increased at least about 9.0-fold as compared to the number of cells in the cell composition prior to the culture. In some aspects, the number of cells having a stem-like phenotype in the cell composition is increased at least about 10-fold as compared to the number of cells in the cell composition prior to the culture. In some aspects, the number of cells having a stem-like phenotype in the cell composition is increased at least about 15-fold as compared to the number of cells in the cell composition prior to the culture. In some aspects, the number of cells having a stem-like phenotype in the cell composition is increased at least about 20-fold as compared to the number of cells in the cell composition prior to the culture. In some aspects, the number of cells having a stem-like phenotype in the cell composition is increased at least about 30-fold as compared to the number of cells in the cell composition prior to the culture. In some aspects, the number of cells having a stem-like phenotype in the cell composition is increased at least about 40-fold as compared to the number of cells in the cell composition prior to the culture. In some aspects, the number of cells having a stem-like phenotype in the cell composition is increased at least about 50-fold as compared to the number of cells in the cell composition prior to the culture. In some aspects, the number of cells having a stem-like phenotype in the cell composition is increased at least about 75-fold as compared to the number of cells in the cell composition prior to the culture. In some aspects, the number of cells having a stem-like phenotype in the cell composition is increased at least about 100-fold as compared to the number of cells in the cell composition prior to the culture. In some aspects, the number of cells having a stem-like phenotype in the cell composition is increased at least about 500-fold as compared to the number of cells in the cell composition prior to the culture. In some aspects, the number of cells having a stem-like phenotype in the cell composition is increased at least about 1000-fold as compared to the number of cells in the cell composition prior to the culture.

In some aspects, the cell composition comprises immune cells, e.g., T cells, NK cells, and/or TILs. In some aspects, the cell composition comprises an increase percent of immune cells, e.g., T cells, NK cells, and/or TILs, which express CD95. In some aspects, the cell composition comprises an increase percent of immune cells, e.g., T cells, NK cells, and/or TILs, which do not express CD45RO. In some aspects, the cell composition comprises an increase percent of immune cells, e.g., T cells, NK cells, and/or TILs, which express CD45RA. In some aspects, the cell composition comprises an increase percent of immune cells, e.g., T cells, NK cells, and/or TILs, which express CCR7. In some aspects, the cell composition comprises an increase percent of immune cells, e.g., T cells, NK cells, and/or TILs, which express CD62L. In some aspects, the cell composition comprises an increase percent of immune cells, e.g., T cells, NK cells, and/or TILs, which express TCF7. In some aspects, the cell composition comprises an increase percent of immune cells, e.g., T cells, NK cells, and/or TILs, which express CD3. In some aspects, the cell composition comprises an increase percent of immune cells, e.g., T cells, NK cells, and/or TILs, which express CD27. In some aspects, the cell composition comprises an increase percent of immune cells, e.g., T cells, NK cells, and/or TILs, which express CD95 and CD45RA. In some aspects, the cell composition comprises an increase percent of immune cells, e.g., T cells, NK cells, and/or TILs, which express CD95, CD45RA, and CCR7. In some aspects, the cell composition comprises an increase percent of immune cells, e.g., T cells, NK cells, and/or TILs, which express CD95, CD45RA, CCR7, and CD62L. In some aspects, the cell composition comprises an increase percent of immune cells, e.g., T cells, NK cells, and/or TILs, which express CD95, CD45RA, CCR7, CD62L, and TCF7. In some aspects, the cell composition comprises an increase percent of immune cells, e.g., T cells, NK cells, and/or TILs, which express CD95, CD45RA, CCR7, CD62L, TCF7, and CD27. In some aspects, the cell composition comprises an increase percent of immune cells, e.g., T cells, NK cells, and/or TILs, which express CD95, CD45RA, CCR7, CD62L, TCF7, and CD27, and which do not express CD45RO.

In some aspects, the cell composition comprises one or more immune cell, e.g., T cells, NK cells, and/or TILs, which is genetically engineered. In some aspects, the cell composition comprises one or more immune cell, e.g., T cells, NK cells, and/or TILs, which is engineered to express a chimeric antigen receptor (CAR). Any CAR disclosed herein, e.g., in section II.G.1., above, can be used in the cells of the cell composition.

In some aspects, the cell composition comprises one or more immune cell, e.g., T cells, NK cells, and/or TILs, which is engineered to express a T cell receptor (TCR), e.g., an engineered TCR. Any TCR disclosed herein, e.g., in section II.G.2., above, can be used in the cells of the cell composition.

In some aspects, the cell composition comprises one or more immune cell, e.g., T cells, NK cells, and/or TILs, which is engineered to express a TCRm. Any TCRm disclosed herein, e.g., in section II.G.3., above, can be used in the cells of the cell composition.

In some aspects, the cell composition, obtained by any method described herein (e.g., the yield of the final cell product for use as a therapy), comprises at least about $1\times10^5$, $5\times10^5$, $1\times10^6$, $5\times10^6$, $1\times10^7$, $5\times10^7$, $1\times10^8$, $5\times10^8$, $1\times10^9$, or $5\times10^9$ cells. In some aspects, the cell composition, obtained by any method described herein, comprises at least about $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, or $5\times10^9$ stem-like cells. In some aspects, the cell composition, obtained by any method described herein, comprises at least about $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $10\times10^{10}$, $11\times10^{10}$, $12\times10^{10}$, $13\times10^{10}$, $14\times10^{10}$, or $15\times10^{10}$ cells. In some aspects, the cell composition, obtained by any method described herein, comprises at least about $1\times10^6$ cells. In some aspects, the cell composition, obtained by any method described herein, comprises at least about $1\times10^6$ stem-like cells. In some aspects, the cell composition, obtained by any method described herein, comprises at least about $1\times10^{10}$ cells. In some aspects, the cell composition, obtained by any method described herein, comprises at least about $2\times10^{10}$ cells. In some aspects, the cell composition, obtained by any method described herein, comprises at least about $3\times10^{10}$ cells. In some aspects, the cell composition, obtained by any method described herein, comprises at least about $4\times10^{10}$ cells. In some aspects, the cell composition, obtained by any method described herein, comprises at least about $5\times10^{10}$ cells. In some aspects, the cell composition, obtained by any method described herein, comprises at least about $6\times10^{10}$ cells. In some aspects, the cell composition, obtained by any method described herein, comprises at least about $7\times10^{10}$ cells. In some aspects, the cell composition, obtained by any method described herein, comprises at least about $8\times10^{10}$ cells. In some aspects, the cell composition, obtained by any method described herein, comprises at least about $9\times10^{10}$ cells. In some aspects, the cell composition, obtained by any method described herein, comprises at least about $10\times10^{10}$ cells. In some aspects, the cell composition, obtained by any method described herein, comprises at least about $11\times10^{10}$ cells. In some aspects, the cell composition, obtained by any method described herein, comprises at least about $12\times10^{10}$ cells. In some aspects, the cell composition, obtained by any method described herein, comprises at least about $13\times10^{10}$ cells. In some aspects, the cell composition, obtained by any method described herein, comprises at least about $14\times10^{10}$ cells. In some aspects, the cell composition, obtained by any method described herein, comprises at least about $15\times10^{10}$ cells. In some aspects, cell yield represents the total number of CD3+ cells.

IV. Methods of Preparing a Cell Culture Medium

Certain aspects of the present disclosure are directed to methods of making a cell culture medium disclosed herein. Some aspects of the present disclosure are directed to methods of making a hypotonic or isotonic cell culture medium comprising at least about 5 mM potassium ion. Some aspects of the present disclosure are directed to methods of making a cell culture medium comprising at least about 50 mM potassium ion. Some aspects of the present disclosure are directed to methods of making a cell culture medium comprising at least about 50 mM potassium ion and less than 90 mM NaCl. In some aspects, the medium is prepared by modifying a commercially available medium, e.g., a basal medium disclosed herein, to potassium ion at a concentration of at least about 5 mM and one or more of a sodium ion, a calcium ion, a saccharide (e.g., glucose), and a cytokine (e.g., IL-2, IL-7, IL-15, and/or IL-21).

In some aspects, the basal medium is any basal medium disclosed herein, e.g., a basal medium described in section II.F., above. In some aspects, the basal medium comprises potassium ion at a concentration less than 5 mM. In some aspects, the basal medium comprises potassium ion at a concentration less than 50 mM. In some aspects, the basal medium comprises one or more of a sodium ion, a calcium ion, a saccharide (e.g., glucose), and a cytokine (e.g., IL-2, IL-7, IL-15, and/or IL-21).

In some aspects, the basal medium is selected from a balanced salt solution (e.g., PBS, DPBS, HBSS, EBSS), Dulbecco's Modified Eagle's Medium (DMEM), Minimal Essential Medium (MEM), Basal Medium Eagle (BME), F-10, F-12, RPMI 1640, Glasgow Minimal Essential Medium (GMEM), alpha Minimal Essential Medium (alpha MEM), Iscove's Modified Dulbecco's Medium (IMDM), M199, OPTMIZER™ CTS™ T-Cell Expansion Basal Medium (ThermoFisher), OPTMIZER™ Complete, IMMUNOCULT™ XF (STEMCELL™ Technologies), IMMUNOCULT™ XF, AIM V, TEXMACS™ medium, and any combination thereof. In some aspects, the basal media comprises PRIME-XV T cell CDM. In some aspects, the basal media comprises OPTMIZER™. In some aspects, the basal media comprises OPTMIZER' Pro. In some aspects, the basal media comprises X-VIVO™ 15 (LONZA). In some aspects, the basal media comprises IMMUNOCULT'. In some aspects, the basal medium is serum free. In some aspects, the basal medium further comprises immune cell serum replacement (ICSR). For example, in some aspects, the basal medium comprises OPTMIZER™ Complete supplemented with ICSR, AIM V supplemented with ICSR, IMMUNOCULT™ XF supplemented with ICSR, RPMI supplemented with ICSR, TEXMACS™ supplemented with ICSR, or any combination thereof. In particular aspects, the basal media comprises OPTMIZER™ complete.

In some aspects, the method of preparing the cell culture medium described herein comprises adding potassium ion to a basal medium until the desired concentration of potassium ion is reached. In some aspects, the potassium ion is added to the basal medium by adding a sufficient amount of a potassium salt in a medium. In some aspects, non-limiting examples of potassium salt include potassium aminetrichloroplatinate, potassium aquapentachlororuthenate, potassium bis(oxalato)platinate(II) dihydrate, potassium bisulfate, potassium borohydride, potassium bromide, potassium carbonate, potassium chloride, potassium chromate, potassium dichromate, potassium dicyanoargentate, potassium dicyanoaurate, potassium fluoride, potassium fluorosulfate, potassium hexachloroiridate, potassium hexachloroosmate, potassium hexachloropalladate, potassium hexachloroplatinate, potassium hexachlororhenate, potassium hexacyanochromate, potassium hexacyanoferrate, potassium hexacyanoruthenate(II) hydrate, potassium hexafluoroantimonate, potassium hexafluoronickelate, potassium hexafluorophosphate, potassium hexafluorotitanate, potassium hexafluorozirconate, potassium hexahydroxoantimonate, potassium hexaiodoplatinate, potassium hexaiodorhenate, potassium hydroxide, potassium iodate, potassium iodide, potassium manganate, potassium metavanadate, potassium molybdate, potassium nitrate, potassium nitrosodisulfonate, potassium osmate(VI) dihydrate, potassium pentachloronitrosylruthenate, potassium perchlorate, potassium perrhenate, potassium perruthenate, potassium persulfate, potassium phosphate dibasic, potassium phosphate monobasic, potassium pyrophosphate, potassium selenocyanate, potassium selenocyanate, potassium stannate trihydrate, potassium sulfate, potassium tellurate hydrate, potassium tellurite, potassium tetraborate tetrahydrate, potassium tetrabromoaurate, potassium tetrabromopalladate, potassium tetrachloropalladate, potassium tetrachloroplatinate, potassium tetracyanopalladate, potassium tetracyanoplatinate, potassium tetrafluoroborate, potassium tetranitroplatinate, potassium tetrathionate, potassium p-toluenethiosulfonate, and potassium hydroxycitrate tribasic monohydrate. In certain aspects, the potassium salt comprises potassium chloride (KCl). In certain aspects, the potassium salt comprises potassium citrate. In certain aspects, the potassium salt comprises potassium hydroxycitrate.

In some aspects of the present disclosure, the cell culture medium comprises potassium ion at a concentration of at least about 5 mM and sodium ion, wherein the medium is hypotonic or isotonic. In some aspects of the present disclosure, the cell culture medium comprises potassium ion at a concentration of at least about 50 mM and sodium ion. In some aspects, the method of preparing the cell culture medium described herein comprises adding sodium ion to a basal medium until the desired concentration of sodium ion is reached. In some aspects, the sodium ion is added to the basal medium adding one or more sodium salts. Non-limiting examples of sodium salts include sodium (meta) periodate, sodium arsenyl tartrate hydrate, sodium azide, sodium benzyloxide, sodium bromide, sodium carbonate, sodium chloride, sodium chromate, sodium cyclohexanebutyrate, sodium ethanethiolate, sodium fluoride, sodium fluorophosphate, sodium formate, sodium hexachloroiridate(III) hydrate, sodium hexachloroiridate(IV) hexahydrate, sodium hexachloroplatinate(IV) hexahydrate, sodium hexachlororhodate(III), sodium hexafluoroaluminate, sodium hexafluoroantimonate(V), sodium hexafluoroarsenate(V), sodium hexafluoroferrate(III), sodium hexafluorophosphate, sodium hexafluorosilicate, sodium hexahydroxyplatinate (IV), sodium hexametaphosphate, sodium hydrogen difluoride, sodium hydrogen sulfate, sodium hydrogencyanamide, sodium hydroxide, sodium iodide, sodium metaborate tetrahydrate, sodium metasilicate nonahydrate, sodium metavanadate, sodium molybdate, sodium nitrate, sodium nitrite, sodium oxalate, sodium perborate monohydrate, sodium percarbonate, sodium perchlorate, sodium periodate, sodium permanganate, sodium perrhenate, sodium phosphate, sodium pyrophosphate, sodium selenate, sodium selenite, sodium stannate, sodium sulfate, sodium tellurite, sodium tetraborate, sodium tetrachloroaluminate, sodium tetrachloroaurate(III), sodium tetrachloropalladate(II), sodium tetrachloroplatinate(II), sodium thiophosphate tribasic, sodium thiosulfate, sodium thiosulfate pentahydrate, sodium yttrium oxyfluoride, Trisodium trimetaphosphate, and any combination thereof. In certain aspect, the sodium salt comprises sodium chloride (NaCl). In certain aspects, the sodium salt comprises sodium bicarbonate. In certain aspects, the sodium salt comprises sodium hydroxycitrate. In certain aspects, the sodium salt comprises sodium phosphate. In some aspects of the present disclosure, the cell culture medium comprises potassium ion at a concentration of at least about 50 mM and NaCl at a concentration of less than 90 mM. In some aspects, the method of preparing the cell culture medium described herein comprises adding NaCl to a basal medium until the desired concentration of sodium ion is reached, wherein the total concentration of potassium and NaCl is more than 110 mM and less than 140 mM.

In some aspects, the desired concentration of sodium ion is lower than that of the basal medium. Therefore, in some aspects, the desired concentration of sodium ion is reached by diluting the basal medium with a suitable solution lacking sodium ion or having a lower concentration of sodium ion.

In some aspects of the present disclosure, the cell culture medium comprises potassium ion at a concentration of at least about 5 mM and calcium ion, wherein the medium is hypotonic or isotonic. In some aspects of the present disclosure, the cell culture medium comprises potassium ion at a concentration of at least about 50 mM and calcium ion. In some aspects of the present disclosure, the cell culture medium comprises potassium ion at a concentration of at least about 50 mM, NaCl at a concentration of less than 90 mM and calcium ion. In some aspects, the method of preparing the cell culture medium described herein comprises adding calcium ion to a basal medium until the desired concentration of calcium ion is reached. In some aspects, the calcium ion is added to the basal medium adding one or more calcium salts. Non-limiting examples of calcium salts include calcium bromide, calcium carbonate, calcium chloride, calcium cyanamide, calcium fluoride, calcium hydride, calcium hydroxide, calcium iodate, calcium iodide, calcium nitrate, calcium nitrite, calcium oxalate, calcium perchlorate tetrahydrate, calcium phosphate monobasic, calcium phosphate tribasic, calcium sulfate, calcium thiocyanate tetrahydrate, Hydroxyapatite, and any combination thereof. In some aspects, the calcium salt comprises calcium chloride ($CaCl_2$)).

In some aspects, the desired concentration of calcium ion is lower than that of the basal medium. Therefore, in some aspects, the desired concentration of calcium ion is reached by diluting the basal medium with a suitable solution lacking calcium ion or having a lower concentration of calcium ion.

In some aspects of the present disclosure, the cell culture medium comprises potassium ion at a concentration of at least about 5 mM and a saccharide, e.g., glucose, wherein the medium is hypotonic or isotonic. In some aspects of the present disclosure, the cell culture medium comprises potassium ion at a concentration of at least about 50 mM and a saccharide, e.g., glucose. In some aspects, the method of preparing the cell culture medium described herein comprises adding a saccharide, e.g., glucose, to a basal medium until the desired concentration of the saccharide, e.g., glucose, is reached. Non-limiting examples of saccharides include glucose, fructose, galactose, mannose, maltose, sucrose, lactose, trehalose, and any combination thereof. In some aspects, the saccharide comprises glucose.

In some aspects, the desired concentration of the saccharide, e.g., glucose, is lower than that of the basal medium. Therefore, in some aspects, the desired concentration of the saccharide, e.g., glucose, is reached by diluting the basal medium with a suitable solution lacking the saccharide, e.g., glucose, or having a lower concentration of the saccharide, e.g., glucose.

In some aspects, the tonicity of the medium is adjusted to reach a target osmolality. In some aspects, the target osmolality of the medium is lower than that of the basal medium. In some aspects, the target osmolality of the medium is higher than that of the basal medium. In some aspect, the target osmolality of the medium is the same as that of the basal medium.

The medium can be hypotonic, isotonic, or hypertonic. The tonicity of the medium can be affected by a number of factors, including the concentration of potassium ion in the media. In some aspects, increased potassium ion concentration is paired with an increase or a decrease in the concentration of one or more other factors. In some aspects, this pairing affects the tonicity of the medium. In some aspects, the concentration of potassium ion is increased while the concentration of sodium ion is decreased. In some aspects, the concentration of potassium ion is increased while the concentration of a saccharide, e.g., glucose, is decreased. In some aspects, the concentration of potassium ion is increased while the concentration of calcium ion is decreased. In some aspects, the concentration of potassium ion is increased while the concentrations of sodium ion and saccharide, e.g., glucose, are decreased. In some aspects, the concentration of potassium ion is increased while the concentrations of sodium ion and calcium ion are decreased. In some aspects, the concentration of potassium ion is increased while the concentrations of sodium ion, saccharide (e.g., glucose), and calcium ion are decreased. In some aspects, the concentration of potassium ion, sodium ion, and/or saccharide (e.g., glucose) are adjusted in order to obtain a target tonicity.

IV. Methods Treatment

Certain aspects of the present disclosure are directed to a population of cells, e.g., pluripotent, multipotent, and/or immune cells (e.g., T cells, NK cells, and/or TILs), cultured according to any of the methods disclosed herein. In certain aspects, the cells are immune cells. In some aspects, the cells are T cells. In some aspects, the cells are NK cells. In some aspects, the immune cells, e.g., T cells, NK cells, and/or TILs, are isolated from a human subject. In some aspects, the immune cells are tumor-infiltrating T cells or tumor-infiltrating NK cells. In certain aspects, the immune cells, e.g., T cells, NK cells, and/or TILs, are engineered. In some aspects, the immune cells, e.g., T cells, NK cells, and/or TILs, are engineered to comprise a chimeric antigen receptor (CAR). In some aspects, the immune cells, e.g., T cells, NK cells, and/or TILs, are engineered to comprise an engineered T cell receptor (TCR). In some aspects, the TCR recognizes a neoantigen identified in a cancer patient.

In some aspects, the immune cell, e.g., T cells, NK cells, and/or TILs, comprises a CAR. In some aspects, the T cell is a CD8+ T cell or CD4+ T cell. In some aspects, the T cell is a Th1, Th2, Th17, or Tc17 cell. In some aspects, a CAR-expressing cell is a CART cell, e.g., a mono CAR T cell, a genome-edited CAR T cell, a dual CAR T cell, or a tandem CAR T cell. Examples of such CAR T cells are provided in International Application No. PCT/US2019/044195.

In some aspects, the cell comprises construct expressing an antigen receptor and/or another additional polypeptide. In some aspects, the antigen receptor comprises an antibody, an engineered antibody such as scFv, a CAR, an engineered TCR, a TCR mimic (e.g., an antibody-T cell receptor (abTCR) or a chimeric antibody-T cell receptor (caTCR)), or a chimeric signaling receptor (CSR). By way of example, a TCR may comprise an engineered TCR in which the antigen-binding domain of a TCR (e.g., an alpha/beta TCR or a gamma/delta TCR) has been replaced by that of an antibody (with or without the antibody's constant domains); the engineered TCR then becomes specific for the antibody's antigen while retaining the TCR's signaling functions. A chimeric signaling receptor may comprise (1) an extracellular binding domain (e.g., natural/modified receptor extracellular domain, natural/modified ligand extracellular domain, scFv, nanobody, Fab, DARPin, and affibody), (2) a transmembrane domain, and (3) an intracellular signaling domain (e.g., a domain that activates transcription factors, or recruits and/or activates JAK/STAT, kinases, phosphatases, and ubiquitin; SH3; SH2; and PDZ). See, e.g., EP340793B1, WO 2017/070608, WO 2018/200582, WO 2018/200583, WO 2018/200585, and Xu et al., Cell Discovery (2018) 4:62.

In some aspects, the antigen receptor targets an antigen of interest (e.g., a tumor antigen or an antigen of a pathogen). The antigens may include, without limitation, AFP (alpha-fetoprotein), $\alpha v\beta 6$ or another integrin, BCMA, Braf, B7-H3, B7-H6, CA9 (carbonic anhydrase 9), CCL-1 (C-C motif chemokine ligand 1), CD5, CD19, CD20, CD21, CD22, CD23, CD24, CD30, CD33, CD38, CD40, CD44, CD44v6, CD44v7/8, CD45, CD47, CD56, CD66e, CD70, CD74, CD79a, CD79b, CD98, CD123, CD138, CD171, CD352, CEA (carcinoembryonic antigen), Claudin 18.2, Claudin 6, c-MET, DLL3 (delta-like protein 3), DLL4, ENPP3 (ecto-nucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, HLA-A1 (human leukocyte antigen A1), HLA-A2 (human leukocyte antigen A2), HMW-MAA (human high molecular weight-melanoma-associated antigen), IGF1R (insulin-like growth factor 1 receptor), Ig kappa, Ig lambda, IL-22Ra (IL-22 receptor alpha), IL-13Ra2 (IL-13 receptor alpha 2), KDR (kinase insert domain receptor), LI cell adhesion molecule (LI-CAM), Liv-1, LRRC8A (leucine rich repeat containing 8 Family member A), Lewis Y, melanoma-associated antigen (MAGE)-A1, MAGE-A3, MAGE-A6, MART-1 (melan A), murine cytomegalovirus (MCMV), MCSP (melanoma-associated chondroitin sulfate proteoglycan), mesothelin, mucin 1 (MUC1), MUC16, MHC/peptide complexes (e.g., HLA-A complexed with peptides derived from AFP, KRAS, NY-ESO, MAGE-A, and WT1), NCAM (neural cell adhesion molecule), Nectin-4, NKG2D (natural killer group 2 member D) ligands, NY-ESO, oncofetal antigen, PD-1, PD-L1, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), STEAP1 (six transmembrane epithelial antigen of the prostate 1), survivin, TAG72 (tumor-associated glycoprotein 72), TPBG (trophoblast glycoprotein), Trop-2, VEGFR1 (vascular endothelial growth factor receptor 1), VEGFR2, and antigens from HIV, HBV, HCV, HPV, and other pathogens.

In certain aspects, the antigen receptor targets hTERT. In some aspects, the antigen receptor targets KRAS. In some aspects, the antigen receptor targets Braf. In some aspects, the antigen receptor targets TGFβRII. In some aspects, the antigen receptor targets MAGE A10/A4. In some aspects, the antigen receptor targets AFP. In some aspects, the antigen receptor targets PRAME. In some aspects, the antigen receptor targets MAGE A1. In some aspects, the antigen receptor targets WT-1. In some aspects, the antigen receptor targets NY-ESO. In some aspects, the antigen receptor targets PRAME. In some aspects, the antigen receptor targets NY-ESO. In some aspects, the antigen receptor targets CD19.

In some aspects, the antigen receptor targets BCMA. In some aspects, the antigen receptor targets CD147. In some aspects, the antigen receptor targets CD19. In some aspects, the antigen receptor targets CD19 and CD22. In some aspects, the antigen receptor targets CD19 and CD28. In some aspects, the antigen receptor targets CD20. In some aspects, the antigen receptor targets CD20 and CD19. In some aspects, the antigen receptor targets CD22. In some aspects, the antigen receptor targets CD30. In some aspects, the antigen receptor targets CEA. In some aspects, the antigen receptor targets DLL3. In some aspects, the antigen receptor targets EGFRvIII. In some aspects, the antigen receptor targets GD2. In some aspects, the antigen receptor targets HER2. In some aspects, the antigen receptor targets IL-1RAP. In some aspects, the antigen receptor targets mesothelin. In some aspects, the antigen receptor targets methothelin. In some aspects, the antigen receptor targets NKG2D. In some aspects, the antigen receptor targets PSMA. In some aspects, the antigen receptor targets TnMUC1.

In some aspects, the CAR specifically binds (i.e., target) one or more antigens expressed on a tumor cell, such as a malignant B cell, a malignant T cell, or a malignant plasma cell. In some aspects, the CAR specifically binds to (i.e., targets) an antigen selected from the group consisting of CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

In some aspects, the CAR targets BCMA. In some aspects, the CAR targets CD147. In some aspects, the CAR targets CD19. In some aspects, the CAR targets CD19 and CD22. In some aspects, the CAR targets CD19 and CD28. In some aspects, the CAR targets CD20. In some aspects, the CAR targets CD20 and CD19. In some aspects, the CAR targets CD22. In some aspects, the CAR targets CD30. In some aspects, the CAR targets CEA. In some aspects, the CAR targets DLL3. In some aspects, the CAR targets EGFRvIII. In some aspects, the CAR targets GD2. In some aspects, the CAR targets HER2. In some aspects, the CAR targets IL-1RAP. In some aspects, the CAR targets mesothelin. In some aspects, the CAR targets methothelin. In some aspects, the CAR targets NKG2D. In some aspects, the CAR targets PSMA. In some aspects, the CAR targets TnMUC1.

In some aspects, an immune cell, e.g., T cells, NK cells, and/or TILs, disclosed herein comprises a T cell receptor (TCR), e.g., an engineered TCR. In some aspects, the engineered TCR specifically binds to a tumor antigen. As used herein, the term "engineered TCR" or "engineered T-cell receptor" refers to a T-cell receptor (TCR) engineered to specifically bind with a desired affinity to a major histocompatibility complex (MHC)/peptide target antigen that is selected, cloned, and/or subsequently introduced into a population of T-cells.

In some aspects, the TCR specifically binds (i.e., target) one or more antigens expressed on a tumor cell, such as a malignant B cell, a malignant T cell, or a malignant plasma cell.

In certain aspects, an engineered cell of the present disclosure expresses a T cell receptor (TCR) targeting an antigen. In some aspects, the TCR engineered cells target shared tumor-associated antigens (shared TAAs). In some aspects, the TCR engineered cells target unique tumor-associated antigens (unique TAAs). In some aspects, the TCR engineered cells target tumor-specific antigens. In some aspects, the TCR engineered cells can target a CT antigen, e.g., melanoma-associated antigen (MAGE) including, but not limited to, MAGE-A1, MAGE-A2, MAGE-A3, MAGE-A4, MAGE-A6, MAGE-A8, MAGE-A9.23, MAGE-A10, and MAGE-A12.

In some aspects, the TCR engineered cells can target glycoprotein (gp100), melanoma antigen recognized by T cells (MART-1), and/or tyrosinase, which are mainly found in melanomas and normal melanocytes. In some aspects, the TCR engineered cells can target Wilms tumor 1 (WT1), i.e., one kind of overexpressed antigen that is highly expressed in most acute myeloid leukemia (AML), acute lymphoid leukemia, almost every type of solid tumor and several critical tissues, such as heart tissues. In some aspects, the TCR engineered cells can target mesothelin, another kind of overexpressed antigen that is highly expressed in mesothelioma but is also present on mesothelial cells of several tissues, including trachea.

In some aspects, the TCR engineered cells can target any neoantigen, which can be formed by random somatic mutations specific to individual tumors. In some aspects, the TCR specifically binds to (i.e., targets) a cancer antigen selected from the group consisting of AFP, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof.

In certain aspects, the TCR specifically binds (i.e., targets) hTERT. In some aspects, the TCR specifically binds (i.e., targets) KRAS. In some aspects, the TCR specifically binds (i.e., targets) Braf. In some aspects, the TCR specifically binds (i.e., targets) TGFβRII. In some aspects, the TCR specifically binds (i.e., targets) MAGE A10/A4. In some aspects, the TCR specifically binds (i.e., targets) AFP. In some aspects, the TCR specifically binds (i.e., targets) PRAME. In some aspects, the TCR specifically binds (i.e., targets) MAGE A1. In some aspects, the TCR specifically binds (i.e., targets) WT-1. In some aspects, the TCR specifically binds (i.e., targets) NY-ESO. In some aspects, the TCR specifically binds (i.e., targets) PRAME. In some aspects, the TCR specifically binds (i.e., targets) NY-ESO. In some aspects, the TCR specifically binds (i.e., targets) CD19. In some aspects, the TCR specifically binds a neoantigen identified in a cancer patient.

In some aspects, the cell, e.g., a pluripotent cell, a multipotent cell, or an immune cell (e.g., a T cell, an NK cell, or a TIL), is administered to a subject in need thereof. In some aspects the cell, e.g., a pluripotent cell, a multipotent cell, or an immune cell (e.g., a T cell, an NK cell, or a TIL), prepared using the methods disclose herein is administered to a subject to treat a cancer, e.g., a tumor. In some aspects, the method of treating comprises administering to the subject an effective amount of a cell composition of the disclosure, e.g., a cell prepared according to the methods disclosed herein, e.g., a T cell expressing a chimeric polypeptide or TCR disclosed herein.

The present disclosure also provides a method of stimulating a T cell-mediated immune response to a target cell population or tissue in a subject, comprising administering an effective amount of a cell composition of the disclosure, e.g., a cell prepared according to the methods disclosed herein, e.g., a T cell expressing a chimeric polypeptide or TCR disclosed herein.

The present disclosure also provides a method of providing an anti-tumor immunity in a subject in need thereof, the method comprising administering a cell composition of the disclosure, e.g., a cell prepared according to the methods disclosed herein, e.g., a T cell expressing a chimeric polypeptide or TCR disclosed herein to the subject.

In some aspects, the cell administered in the cell composition of the disclosure is a T cell. In some aspects, the cell is an autologous T cell.

In some aspects, administering the cell composition of the disclosure (e.g., an immune cell such as a T cell expressing a CAR or TCR prepared according to the methods disclosed herein) reduces a tumor volume in the subject compared to a reference tumor volume. In some aspects, the reference tumor volume is the tumor volume in the subject prior to the administration of the engineered cell. In further aspects, the reference tumor volume is the tumor volume in a corresponding subject that did not receive the administration. In some aspects, the tumor volume in the subject is reduced by at least about 5%, at least about 10%, at least about 15%, at least about 30%, at least about 40%, at least about 50%, at least about 60%, at least about 70%, at least about 80%, at least about 90%, or at least about 100% after the administration compared to the reference tumor volume.

In some aspects, treating a tumor comprises reducing a tumor weight in the subject. In certain aspects, administering the cell composition of the disclosure (e.g., an immune cell such as a T cell expressing a CAR or TCR prepared according to the methods disclosed herein) can reduce the tumor weight in a subject when administered to the subject. In some aspects, the tumor weight is reduced by at least about 5%, at least about 10%, at least about 15%, at least about 30%, at least about 40%, at least about 50%, at least about 60%, at least about 70%, at least about 80%, at least about 90%, or at least about 100% after the administration compared to a reference tumor weight. In some aspects, the reference tumor weight is the tumor weight in the subject prior to the administration of the cell composition of the disclosure. In further aspects, the reference tumor weight is the tumor weight in a corresponding subject that did not receive the administration.

In some aspects, administering the cell composition of the disclosure (e.g., an immune cell such as a T cell expressing a CAR or TCR prepared according to the methods disclosed herein) to a subject, e.g., suffering from a tumor, can increase the number and/or percentage of TILs (e.g., $CD4^+$ or $CD8^+$) in a tumor and/or a tumor microenvironment (TME) of the subject. In certain aspects, the number and/or percentage of TILs in a tumor and/or TME is increased by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, or at least about 300% or more compared to a reference (e.g., corresponding value in a subject that did not receive the cell composition of the present disclosure or the same subject prior to the administration of the cell composition of the present disclosure).

In some aspects, administering the cell composition of the disclosure (e.g., an immune cell such as a T cell expressing a CAR or TCR prepared according to the methods disclosed herein) to a subject, e.g., suffering from a tumor, can increase the duration of an immune response in a subject relative to the duration of an immune response in a subject administered a similar cell therapy comprising cells prepared according to conventional methods, e.g., cultured in a medium not comprising a potassium ion concentration of at least 50 mM. In certain aspects, the duration of the immune response is increased by at least about 10%, at least about 20%, at least about 30%, at least about 40%, at least about 50%, at least about 75%, at least about 100%, at least about 150%, at least about 200%, at least about 300%, at least about 400%, at least about 500%, or at least about 1000% or more compared to a reference (e.g., a subject administered a similar cell therapy comprising cells prepared according to conventional methods, e.g., cultured in a medium not comprising a potassium ion concentration of at least 50 mM). In certain aspects, the duration of the immune response is increased by at least about 2-fold, at least about 3-fold, at least about 4-fold, at least about 5-fold, at least about 6-fold, at least about 7-fold, at least about 8-fold, at least about 9-fold, or at least about 10-fold or more compared to a reference (e.g., a subject administered a similar cell therapy comprising cells prepared according to conventional methods, e.g., cultured in a medium not comprising a potassium ion concentration of at least 50 mM).

In addition to the above, administering the cell composition of the disclosure (e.g., an immune cell such as a T cell expressing a CAR or TCR prepared according to the methods disclosed herein) can have other effects which are conducive for the treatment of a tumor.

As described herein, the cell composition of the disclosure (e.g., an immune cell such as a T cell expressing a CAR or TCR prepared according to the methods disclosed herein) can be used to treat variety of cancer types, e.g., a tumor derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, carcinoma, sarcoma, leukemia, lymphoma, myeloma, or a combination thereof.

In some aspects, the cell composition of the disclosure (e.g., an immune cell such as a T cell expressing a CAR or TCR prepared according to the methods disclosed herein) can be used in combination with other therapeutic agents (e.g., anti-cancer agents and/or immunomodulating agents). Accordingly, in certain aspects, a method of treating a tumor disclosed herein comprises administering the cell composition of the disclosure in combination with one or more additional therapeutic agents.

In some aspects, the cell composition of the disclosure (e.g., an immune cell such as a T cell expressing a CAR or TCR prepared according to the methods disclosed herein) can be used in combination with one or more anti-cancer agents, such that multiple elements of the immune pathway can be targeted. In some aspects, an anti-cancer agent comprises an immune checkpoint inhibitor (i.e., blocks signaling through the particular immune checkpoint pathway).

Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. In some aspects, the checkpoint inhibitor is a PD-1 antagonist. In some aspects, the checkpoint inhibitor is an anti-PD-1 antibody. In some aspects, the checkpoint inhibitor is an anti-PD-L1 antibody. A comprehensive and non-limiting list of combination treatment is disclosed in detail elsewhere in this application.

In some aspects, the cell composition of the disclosure (e.g., an immune cell such as a T cell expressing a CAR or TCR prepared according to the methods disclosed herein) is administered to the subject prior to or after the administration of the additional therapeutic agent. In other aspects, the cell composition of the disclosure (e.g., an immune cell such as a T cell expressing a CAR or TCR prepared according to the methods disclosed herein) is administered to the subject concurrently with the additional therapeutic agent. In certain aspects, the cell composition of the disclosure (e.g., an immune cell such as a T cell expressing a CAR or TCR prepared according to the methods disclosed herein) and the additional therapeutic agent can be administered concurrently as a single composition in a pharmaceutically acceptable carrier. In other aspects, the cell composition of the disclosure (e.g., an immune cell such as a T cell expressing a CAR or TCR prepared according to the methods disclosed herein) and the additional therapeutic agent are administered concurrently as separate compositions.

In some aspects, the subject is a nonhuman animal such as a rat or a mouse. In some aspects, the subject is a human.

In some aspects, a cell composition disclosed herein (e.g., an immune cell such as a T cell expressing a CAR or TCR prepared according to the methods disclosed herein) can be used in combination with other therapeutic agents (e.g., anti-cancer agents and/or immunomodulating agents). Accordingly, in certain aspects, a method of treating a tumor disclosed herein comprises administering a cell composition of the present disclosure (e.g., an immune cell such as a T cell expressing a CAR or TCR prepared according to the methods disclosed herein) in combination with one or more additional therapeutic agents to a subject. Such agents can include, for example, chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof.

In some aspects, a cell composition disclosed herein (e.g., an immune cell such as a T cell expressing a CAR or TCR prepared according to the methods disclosed herein) can be used in combination with a standard of care treatment (e.g., surgery, radiation, and chemotherapy). Methods described herein can also be used as a maintenance therapy, e.g., a therapy that is intended to prevent the occurrence or recurrence of tumors.

In some aspects, a cell composition of the present disclosure (e.g., an immune cell such as a T cell expressing a CAR or TCR prepared according to the methods disclosed herein) can be used in combination with one or more anti-cancer agents, such that multiple elements of the immune pathway can be targeted. Non-limiting of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD-1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically engineered cells, e.g., cells engineered to express a chimeric antigen receptor (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; blocking of immuno repressive cytokines; or any combination thereof.

In some aspects, an anti-cancer agent comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. Non-limiting examples of such immune checkpoint inhibitors include the following: anti-PD1 antibody (e.g., nivolumab (OPDIVO®), pembrolizumab (KEYTRUDA®; MK-3475), pidilizumab (CT-011), PDR001, MEDI0680 (AMP-514), TSR-042, REGN2810, JS001, AMP-224 (GSK-2661380), PF-06801591, BGB-A317, BI 754091, SHR-1210, and combinations thereof); anti-PD-L1 antibody (e.g., atezolizumab (TECENTRIQ®; RG7446; MPDL3280A; R05541267), durvalumab (MEDI4736, IMFINZI®), BMS-936559, avelumab (BAVENCIO®), LY3300054, CX-072 (Proclaim-CX-072), FAZ053, KN035, MDX-1105, and combinations thereof); and anti-CTLA-4 antibody (e.g., ipilimumab (YERVOY®), tremelimumab (ticilimumab; CP-675,206), AGEN-1884, ATOR-1015, and combinations thereof).

In some aspects, an anti-cancer agent comprises an immune checkpoint activator (i.e., promotes signaling through the particular immune checkpoint pathway). In certain aspects, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), TIM3 agonist (e.g., anti-TIM3 antibody), or combinations thereof.

In some aspects, a cell composition disclosed herein (e.g., an immune cell such as a T cell expressing a CAR or TCR prepared according to the methods disclosed herein) is administered to the subject prior to or after the administration of the additional therapeutic agent. In other aspects, cell composition disclosed herein (e.g., an immune cell such as a T cell expressing a CAR or TCR prepared according to the methods disclosed herein) is administered to the subject concurrently with the additional therapeutic agent. In certain aspects, the cell composition disclosed herein (e.g., an immune cell such as a T cell expressing a CAR or TCR prepared according to the methods disclosed herein) and the additional therapeutic agent can be administered concurrently as a single composition in a pharmaceutically acceptable carrier. In other aspects, the cell composition disclosed herein (e.g., an immune cell such as a T cell expressing a CAR or TCR prepared according to the methods disclosed herein) and the additional therapeutic agent are administered concurrently as separate compositions. In some aspects, the additional therapeutic agent and the cell composition disclosed herein (e.g., an immune cell such as a T cell expressing a CAR or TCR prepared according to the methods disclosed herein) are administered sequentially.

Certain aspects of the present disclosure are directed to methods of treating an autoimmune disease, comprising administering a cell, e.g., a Treg cell, cultured according to any of the methods disclosed herein. Other aspects of the present disclosure are directed to methods of treating an inflammatory pathology, comprising administering a cell, e.g., a Treg cell, cultured according to any of the methods disclosed herein. In some aspects, the inflammatory pathology comprises cytokine release syndrome. In some aspects, the inflammatory pathology comprises sepsis. In some aspects, the inflammatory pathology comprises graft-versus host disease. In some aspects, the cell, e.g., the Treg cell, is engineered.

EXAMPLES

Example 1. Methods

Media preparation: T cell conditioned media ($T_{CM}$) was supplemented with immune Cell Serum Replacement (Thermo Fisher), 2 mM L-glutamine (Gibco), 2 mM Glutamax (Gibco), MEM Non-Essential Amino Acids Solution (Gibco), Sodium pyruvate (Gibco), IL-2, 200 IU/mL; IL-7, 120 IU/ml; IL-15, 20 IU/ml.

For hypotonic conditioning medium, TCM media with varying concentrations of sodium, potassium, glucose and calcium were adjusted by adding NaCl, glucose, and calcium free RPMI. After adding defined NaCl free RPMI to TCM, the final concentrations were in the range of: NaCl (40-80 mM), KCl (40-80 mM), Calcium (0.5-2.8 mM), Glucose (10-24 mM) and osmolality (~250-260 mOsmol). See Table. 1.

TABLE 1

Hypotonic conditioning medium with varying concentrations of potassium, sodium, glucose, and calcium

| Media | K (mM) | NaCl (mM) | Glucose (mM) | Ca (mM) | Osmolality (mOsmol) | Tonicity* (mOsmol) |
|---|---|---|---|---|---|---|
| Basal Media | 4 | 118.47 | ~24 mM | ~2.8 mM | 245 | 245 |
| Hyper K | 80 mM | 55.6 mM | 15 mM | 1.2 mM | ~262.26 | 271.2 |
| Hyper K | 75 | 59.3 | 15.4 | 1.3 | ~260 | 268.6 |
| Hyper K | 70 | 63.9 | 15.9 | 1.4 | ~259.7 | 267.8 |
| Hyper K | 65 | 67.6 | 16.3 | 1.5 | ~257.5 | 265.2 |
| Hyper K | 60 | 72.2 | 16.8 | 1.6 | ~257.2 | 264.4 |
| Hyper K | 55 | 76 | 17.2 | 1.7 | ~255.2 | 262 |
| Hyper K | 50 | 80.5 | 17.7 | 1.8 | ~254.7 | 261 |
| RPMI Gibco + ICSR | 5.34 | 103 | 11.1 | 0.4 | | 216.7 |
| RPMI 1640 + 50 mM K+ | 55.34 | 103 | | | | 316.7 |

*Tonicity is calculated based on the following formula: 2 × (concentration of K + concentration of NaCl)

We also tested the effect of tonicity on T cells by maintaining constant tonicity conditions (250 mOsmol—hypotonic, 280 mOsmol—isotonic, 320 mOsmol—hypertonic) with varying potassium concentrations. Final concentrations in hypotonic conditions, NaCl (35-75 mM), KCl (50-90 mM), final concentrations in isotonic conditions NaCl (50-90 mM), KCl (50-90 mM), final concentrations in hypertonic conditions NaCl (70-110 mM), KCl (50-90 mM). See Table. 2.

TABLE 2

Hypotonic, isotonic, hypertonic solutions with varying concentrations of potassium and NaCl

| Tonicity * | mOsmol | K (mM) | NaCl (mM) |
|---|---|---|---|
| Hypotonic | 250 | 50 | 75 |
| | | 60 | 65 |
| | | 70 | 55 |
| | | 80 | 45 |
| | | 90 | 35 |
| Isotonic | 280 | 50 | 90 |
| | | 60 | 80 |
| | | 70 | 70 |
| | | 80 | 60 |
| | | 90 | 50 |
| Hypertonic | 320 | 50 | 110 |
| | | 60 | 100 |
| | | 70 | 90 |
| | | 80 | 80 |
| | | 90 | 70 |

* Tonicity is calculated according to the formula: Tonicity = ([K] + [NaCl]) × 2 wherein "[K]" is the potassium concentration and "[NaCl]" is the sodium chloride concentration of the media.

Cell culture and Transduction: Healthy donor cryopreserved human CD4 and CD8 cells were activated with TransAct (Miltenyi) in T cell conditioned media-TCM, basal media, or hypotonic conditioning medium. After 24 hours of activation in the TCM or hypotonic conditioning medium, T cells were transduced with lentiviral particles to introduce chimeric antigen receptor (anti-CD19 CAR) in Grex plates (Wilson Wolf). The following day after transduction, T cells were supplemented with fresh media to dilute the TransAct and end T-cell activation. Depending on the cell growth and density, T cells were fed with warm 2× cytokine media by aspirating half of the media in the Grex plate. On day 7, cells were harvested, counted and analyzed for the expression of stemness markers by flow cytometry.

Intracellular Cytokine assays: On day 7, T cells were washed and placed in control media and subjected to a 5-hour re-stimulation with phorbol myrystate acetate (PMA) and ionomycin in the presence of brefeldin A to measure intracellular cytokines, IL-2, IFNγ, and TNFα. T cells were stained with surface antibody staining in FACS buffer containing fixable live/dead solution. Cells were stained with respective antibodies for intracellular cytokines following fixation and permeabilization. Quantification of intracellular cytokine expression was assessed using flow cytometry.

Stemness phenotype CAR expression measurement via flow cytometry: On day 7, live T cells from the respective treatments were assessed via flow cytometry. Cells were first washed with cell staining buffer and stained with anti-CCR7 for 15 minutes at 37° C. Following this, a 2× master mix of the antibodies against several other antigens (as detailed below) was added to cells and incubated for 20 minutes at 4° C. Cells were washed with cell staining buffer and permeabilized with the foxp3 staining kit (ebioscience) as per manufacturers' protocol. After fixing, the cells were stained for TCF7 for twenty minutes at 4° C. following which, cells were analyzed by flow cytometry on aurora (cytek). The following are the list of antibodies used for assessing the stemness markers: CD8 (BD-#563795), CD4 (BD-#612936), CD27 (BD-#612829), CD3 (Thermo-#612893), CD28 (Biolegend-#302936), CD62L, CAR-EGFR (Thermo-#352911), CD45RO (BD #564290), CD39 (Biolegend-#328236), TCF7 (Cell signaling-#14456), CCR7 (BD-#562381), CD127 (Bio legend-#351324), CD45RA (BD-#560673)

Example 2. Results

Figure 1A:
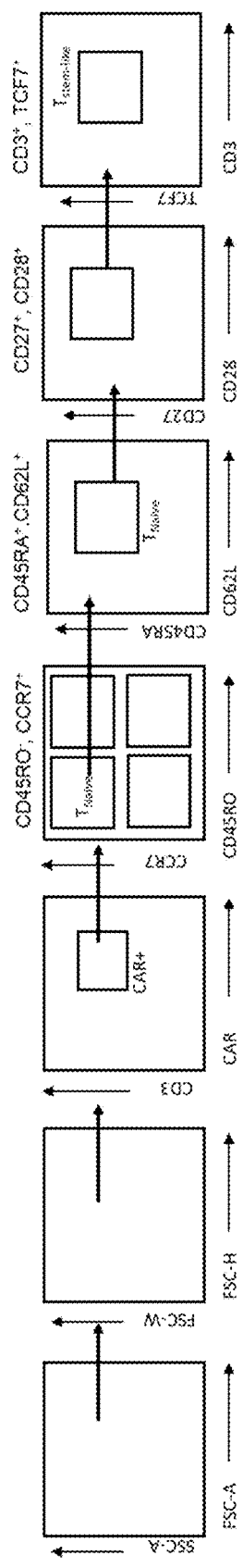
Figure 1B:
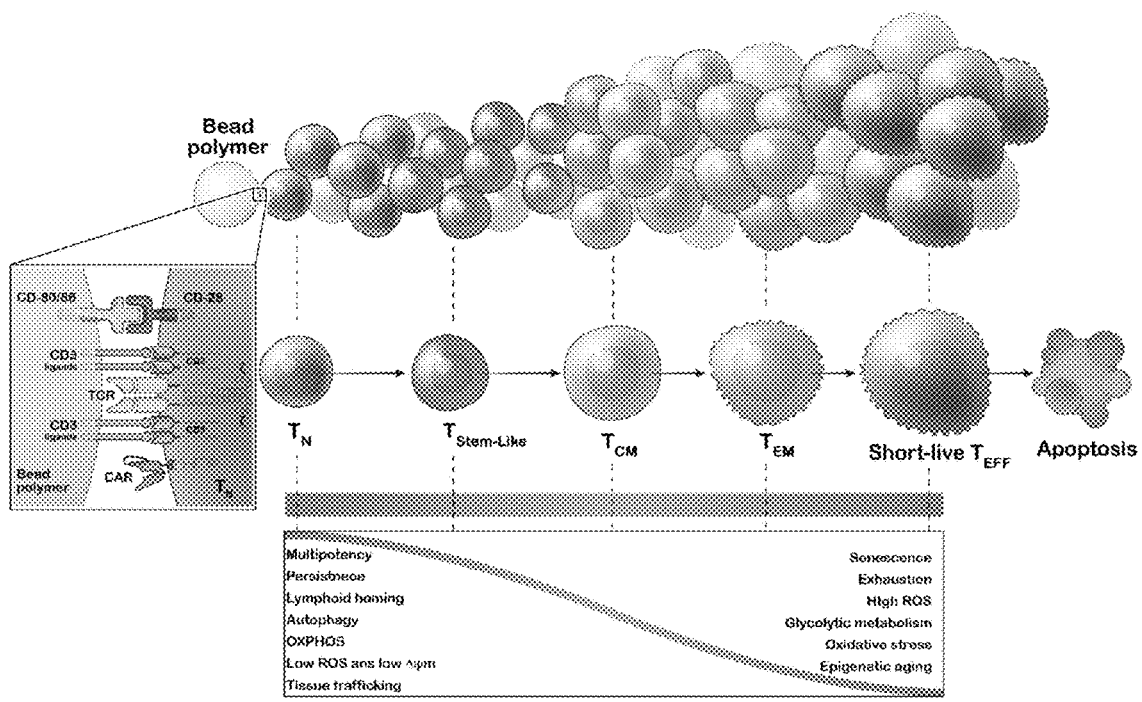

Multiple avenues of manipulation of media components can result in profound alterations to the generated T cell product. In sum, we manipulated one or more of the following: tonicity, inorganic salts, nutrients (glucose), and/or cytokine content both in sequence and parallel. We started with manipulation of the diluent tonicity to assess its role in affecting the final T cell stemness, as assessed by multiple surface markers. To summarize the stemness of the final T cell population we depicted the flow cytometry gating schema to quantify the relative population of the desired subpopulation of T cells with the highest amount of relative stemness (FIG. 1A). The depicted flow cytometry schema is a well-accepted surrogate for the anticipated stemness, metabolic function, and in vivo behavior of the resulting T cells (FIG. 1B).

We quantified the effect of these interventions by the relative number of T cells that were CD3$^+$, CD45RO$^-$, CCR7$^+$, CD45RA$^+$, CD62L$^+$, CD27$^+$, CD28$^+$, and TCF7$^+$ as assessed by cell enumeration and polychromatic flow cytometry (FIGS. 2A-2F). In tandem with tonicity we concurrently altered Na$^+$, K$^+$, and Ca$^{2+}$ as these have all reported roles in controlling T cell fate and function (Trebak & Kinet, *Nature reviews* (2019), Verkhratsky et al, *Exp. Physio* (2019)). Chloride was additionally altered in concert with alterations to the described cationic ions. We found that a relatively "hypotonic" solution with an elevated concentration of potassium, lower concentration of Na, and lowered concentration of Ca resulted in the largest number of stem-like cells (FIG. 2A-2F). In particular, culture of T cells in hypotonic media (<280 mOsm/L) having 50 mM, 55 mM, or 60 mM potassium had at least a 1-fold increase and up to 2.5-fold increase (typically closer to the higher end of the range) in the relative number of stem-like cells, as compared to T cells cultured in control media. Further, culture of T cells in hypotonic media having 65 mM, 70 mM, 75 mM, 80 mM, 85 mM, or 90 mM potassium had at least a 2.5-fold increase and up to a 15-fold increase (typically at least 4-5-fold increase) in the relative number of stem-like cells, as compared to T cells cultured in control media. Similarly, T cells cultured in isotonic media (~270-300 mOsm/L) having 50 mM, 55 mM, 60 mM, 65 mM, or 70 mM potassium had at least a 1-fold increase and up to 2.5-fold increase (typically closer to the higher end of the range) in the relative number of stem-like cells, as compared to T cells cultured in control media.

Increased potassium levels generally correlated with acceptable or even improved cell yields, to a certain degree. In particular, T cells cultured in hypotonic media or isotonic media having 50 mM, 55 mM, 60 mM, 65 mM, 70 mM, or 75 mM potassium had therapeutically acceptable cell yields, as compared to T cells cultured in control media. Conversely, an increase of K+ concentration beyond 70-75 mM was reproducibly harmful to cell yield across multiple donors (FIG. 2D-2F).

Glucose concentration was additionally manipulated across these titrations. Nutrient restriction has been reported to promote T cell stemness and longevity, with inhibition of glycolysis promoting stemness. Conversely, higher glucose concentrations promote effector function and coincident loss of stemness. Consistent with this, the media formulation that demonstrated the most desirable T cell profile had a lower glucose concentration. Thus, we conclude that the reformulated media with the most desirable cell product, consisting of the highest number of stem-like T cells is hypotonic, moderately hyperkalemic, hyponatremic, hypocalcemic, and hypoglycemic relative to control media conditions.

Figure 3A:
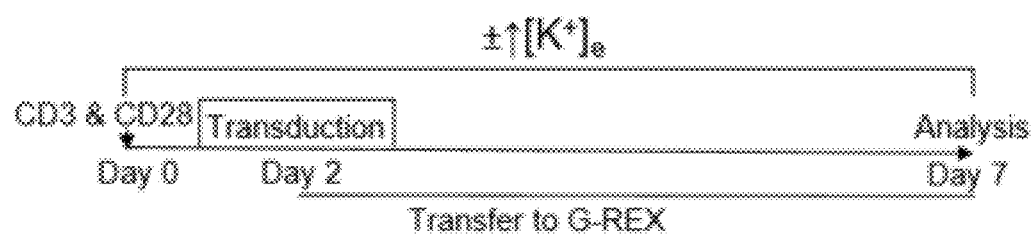
Figure 3B:
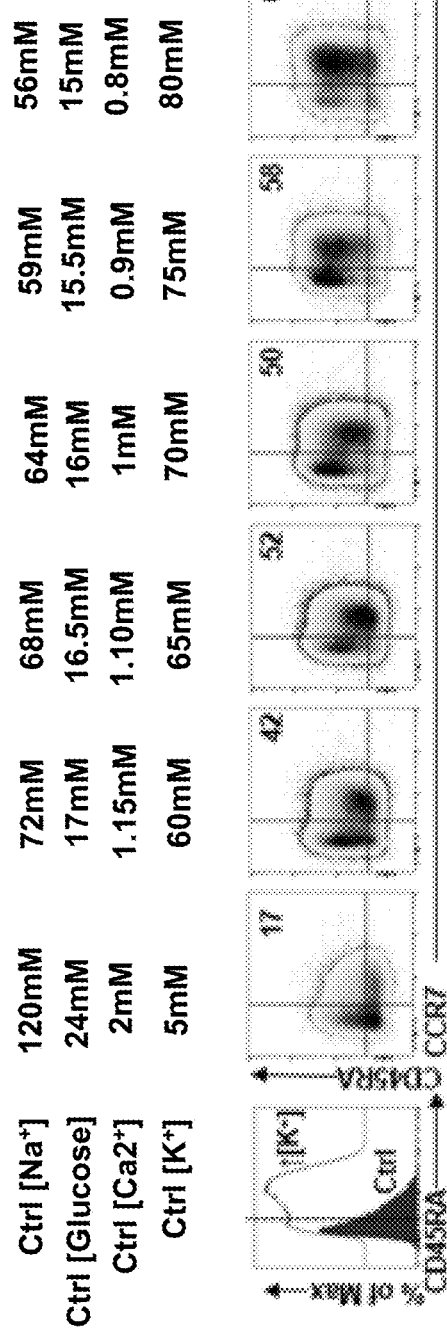
Figure 3C:
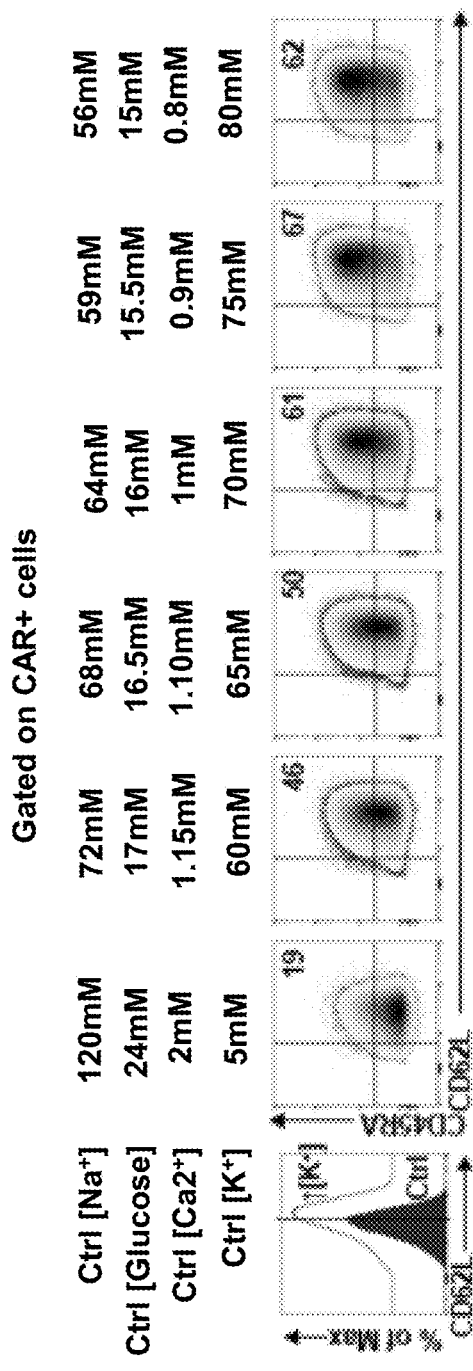
Figure 3D:
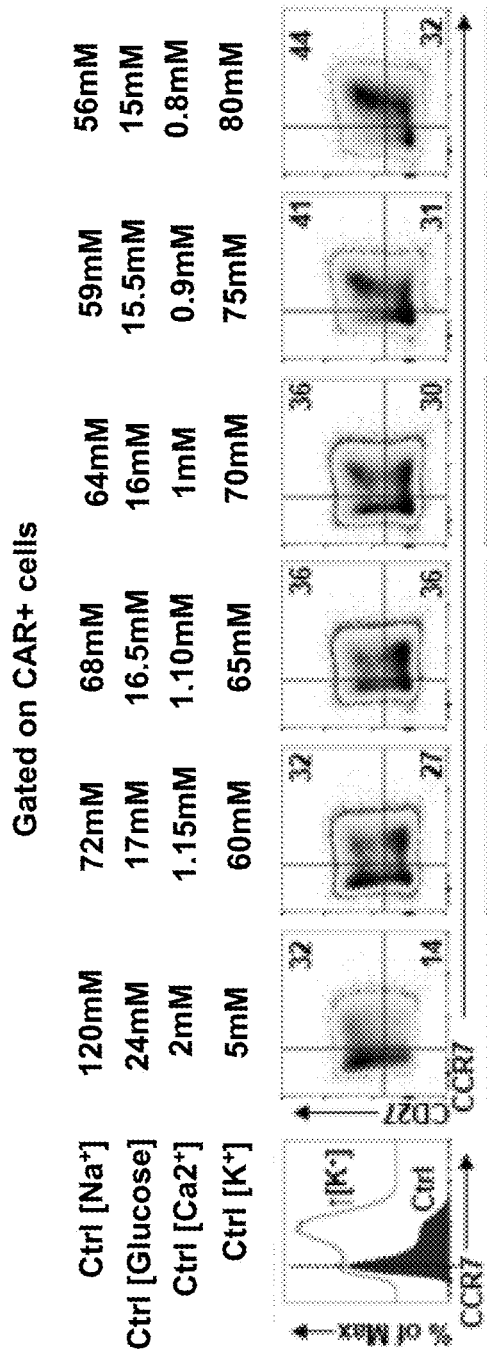
Figure 3E:
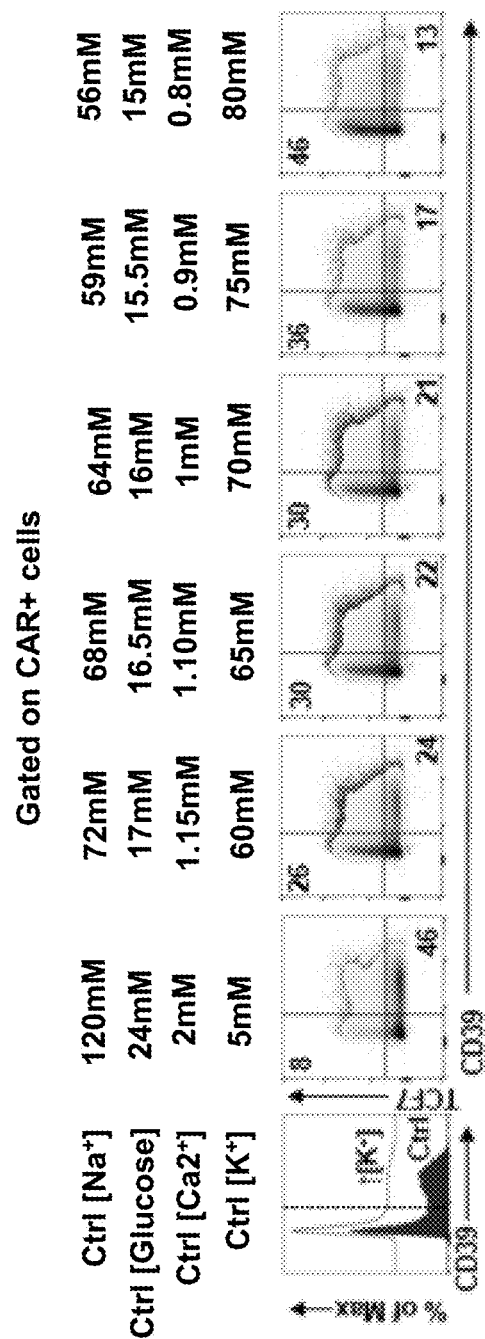
Figure 3F:
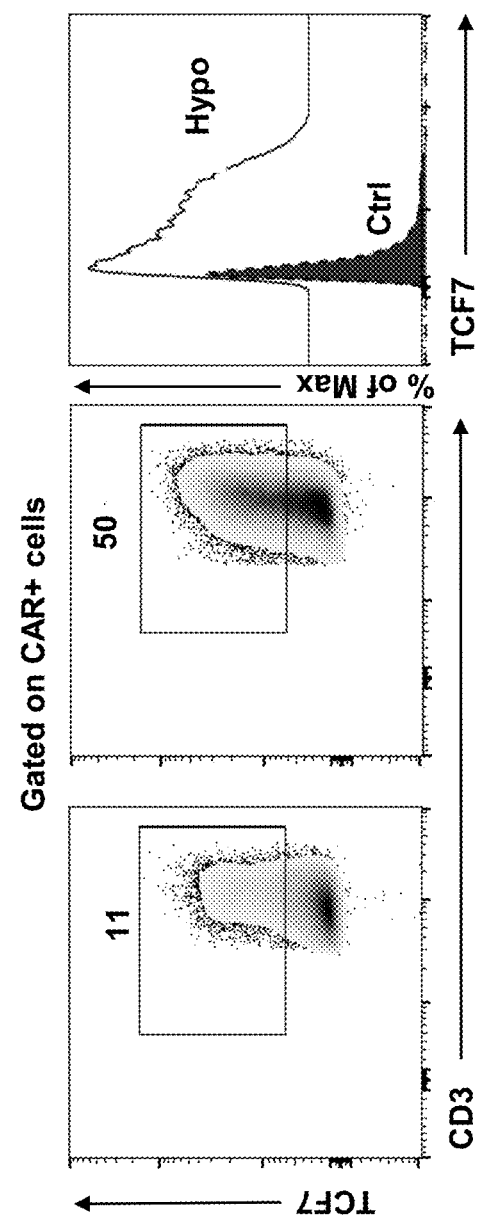
Figure 3G:
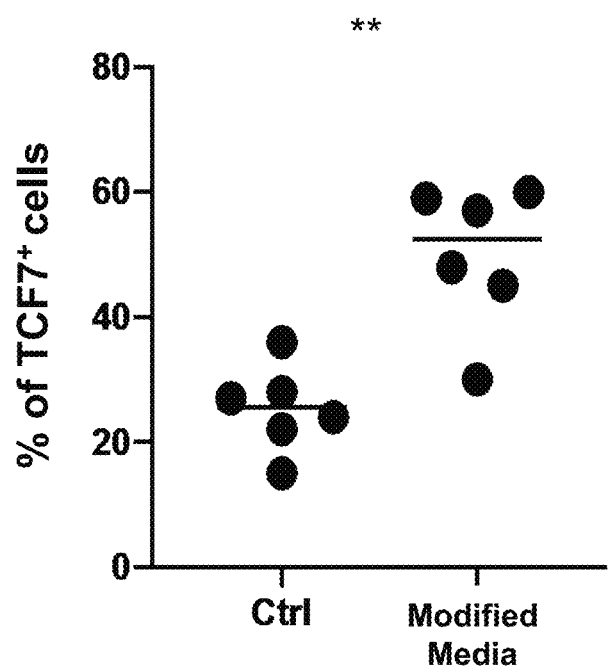

Across, titrations of ionic salts in hypotonic culture conditions (FIG. 3A) we found increased expression of CD45RA$^+$ along with the lymph node homing molecules CCR7$^+$, CD62L$^+$, and T cell persistence associated marker CD27 (FIGS. 3B-3D). Table 1 shows each medium with potassium (50-90 mM), sodium chloride (50-90 mM), glucose (15-20 mM), calcium (1.2-2.0 mM), osmolality, and tonicity. Table 1 also includes control media, i.e., a hypertonic medium with elevated potassium (55.3 mM) in an RPMI basal medium, which contains about 103 mM NaCl (data for this experiment is not shown). Compared to control conditions, hypotonic media with elevated potassium resulted in ~30-50% increase in CD45RA$^+$, CCR7$^+$ expression, ~30-50% increase in CD45RA$^+$, CD62L$^+$ expression and ~10-20% increase in CCR7$^+$CD27$^+$ cells (FIGS. 3B-3D). CD39 is an ecto-ATP/ADPase expressed on activated T cells and is involved in T cell effector differentiation, exhaustion and apoptosis. Increased expression of CD39 is a measure of accelerated aging and coincidental loss of stem cell-like phenotype. Compared to control conditions, hypotonic conditioned media resulted in ~20-30% decrease in CD39$^+$ expression (FIG. 3E). These results indicate that elevated potassium enriches less differentiated cells while preventing exhaustion in T cells. The results also indicate that hypotonic conditioning increased TCF7 and decreased CD39 expression in CAR$^+$ T cells (FIG. 3E). Transcription factor TCF7 plays a major role in maintenance of T stem cell-like phenotype and ability to self-renew and produce more effector T cells. Compared to control conditions, media with elevated potassium ranging from 60 mM-80 mM resulted in ~20-40% increase in TCF7$^+$ expression (FIGS. 3F-3G). These results indicate that hypotonic conditioning to CAR-T or T-cell products is associated with the ability to survive and persist following adoptive transfer.

Figure 4A:
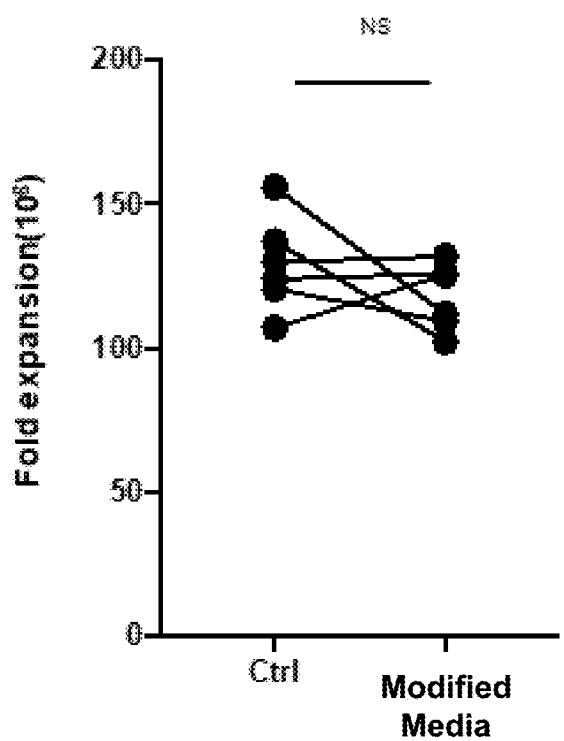
Figure 4B:
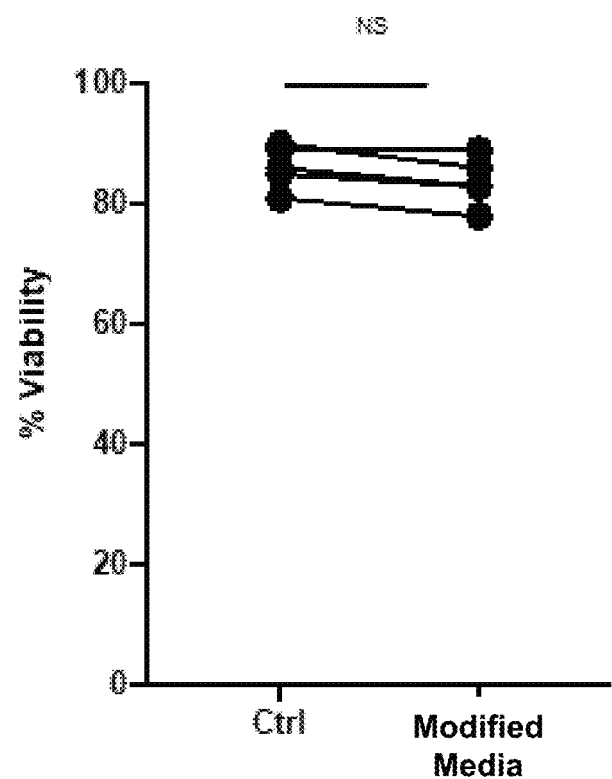

Culturing in hypotonic conditioning did not affect the yield or viability of the T cells during in vitro expansion (FIGS. 4A-4B). T cell yields and viability were consistent across multiple donors demonstrating that hypotonic media can be effectively used to produce cellular products containing less differentiated cells using clinical grade reagents.

Figure 5A:
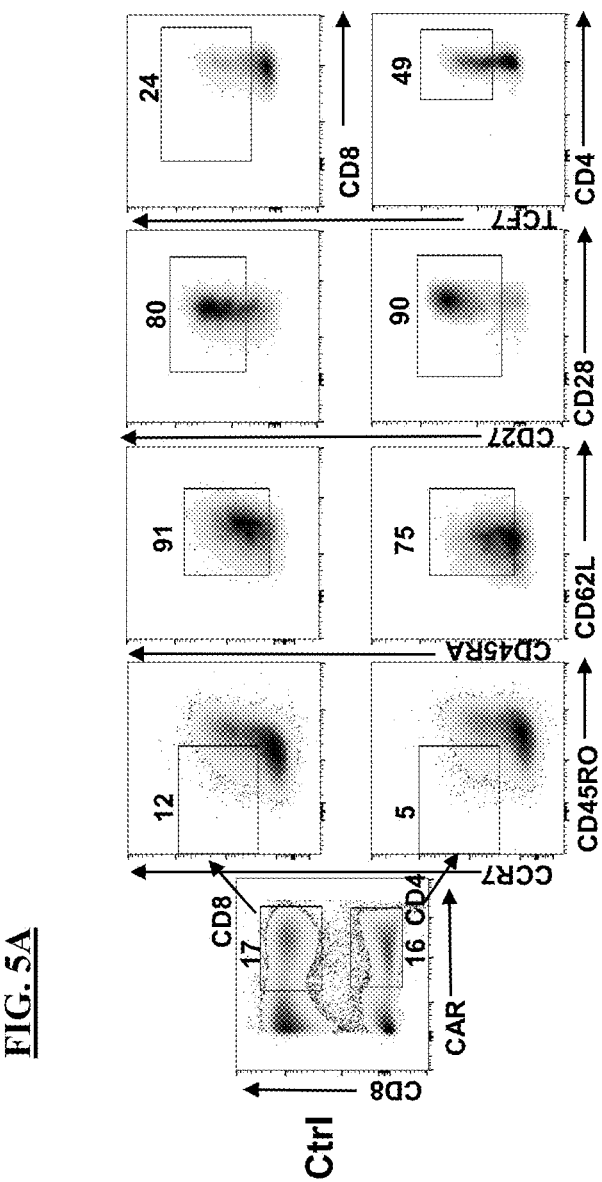
Figure 5B:
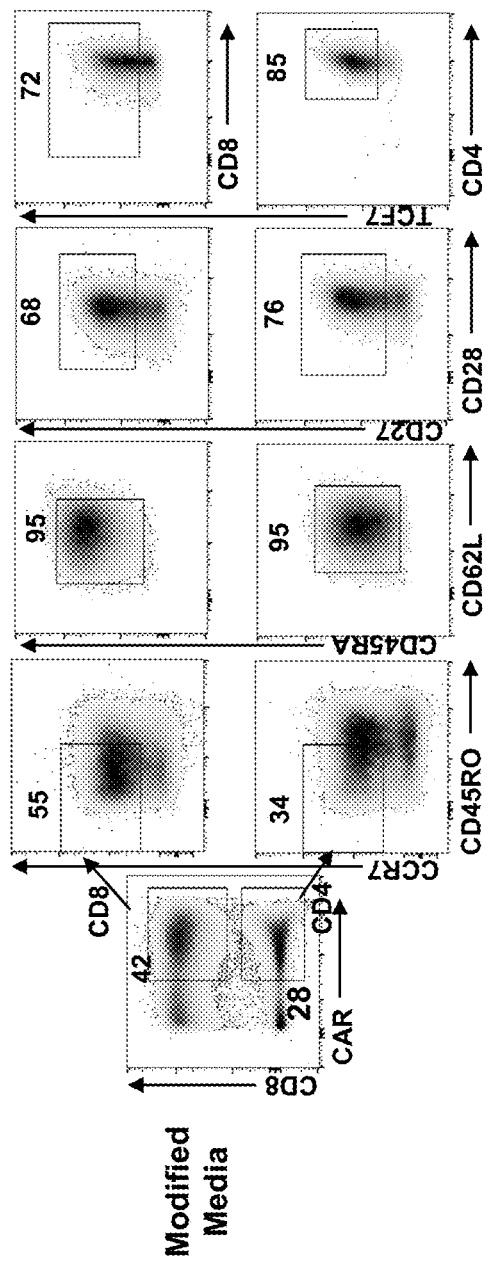
Figure 6:
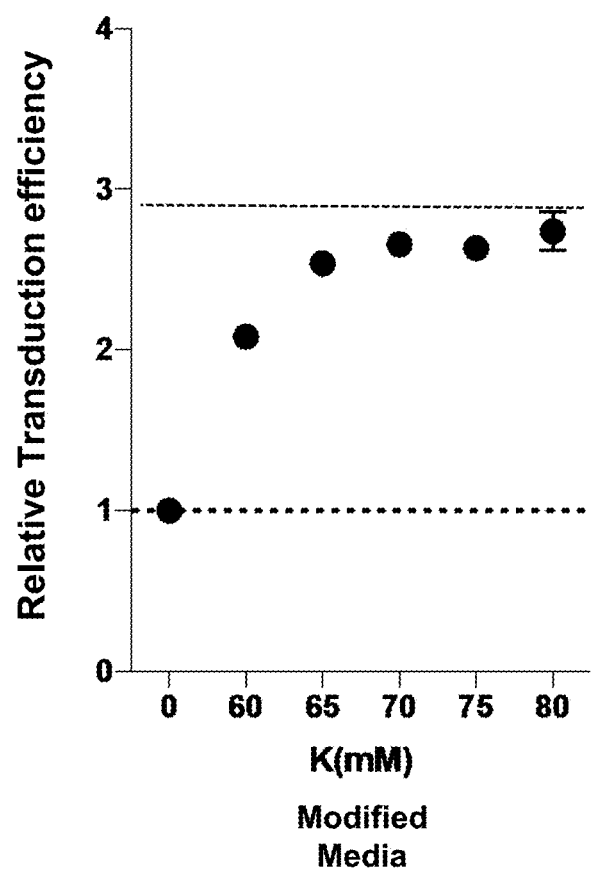
FIG. 6 shows the effect of modified media on transduction efficiency. The modified (hypotonic) media have elevated potassium and NaCl such that the combination of the potassium ion and NaCl is less than 140 mM.
Figure 7:
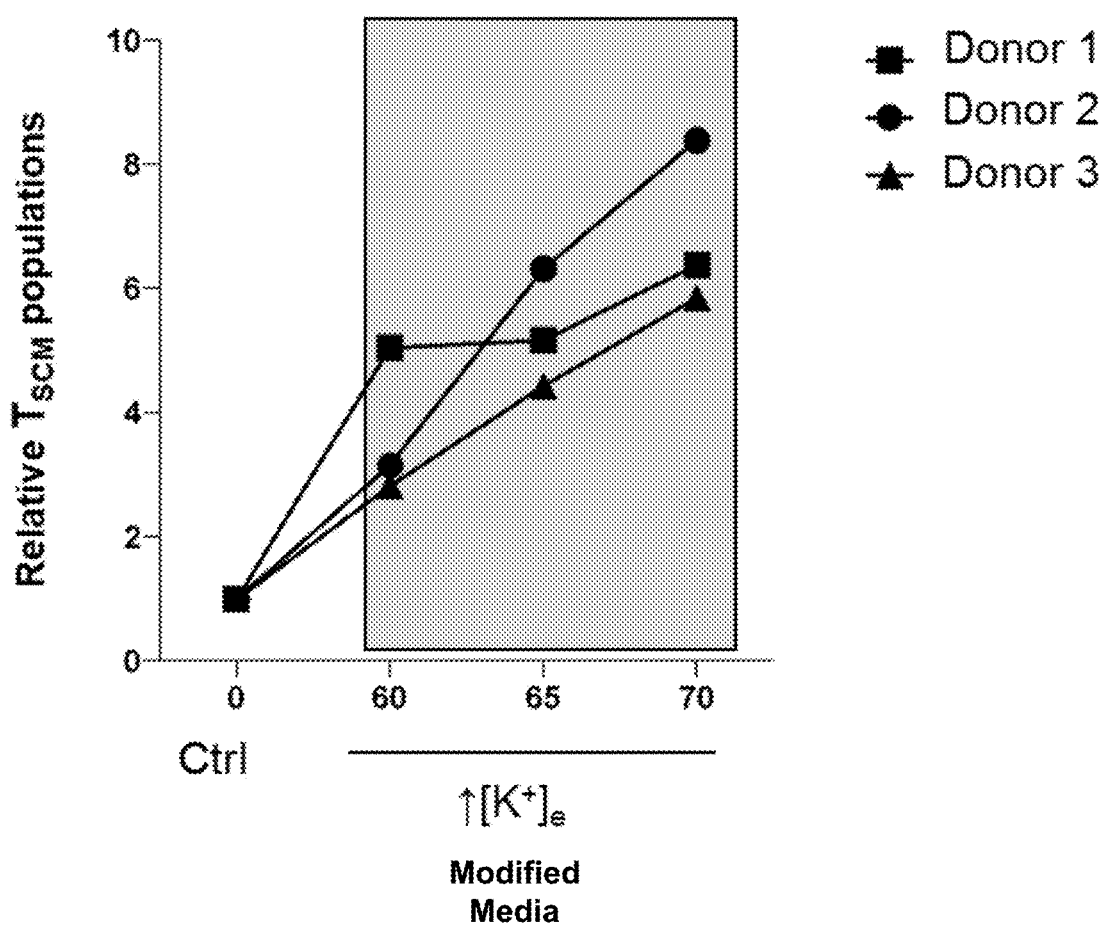
FIG. 7 shows the effect of elevated potassium in the modified media on $T_{SCM}$ populations.

Since elevated potassium conditioning enriched less differentiated cells, we next sought to check $T_{SCM}$ populations using stringent surface marker and transcription factors that accurately define "stem-like" T cells (FIG. 1A) (See, e.g., Gattinoni et al, Nature Medicine 2011). Our results indicated that hypotonic conditioning enriched CD45RO$^-$CCR7$^+$ CD45RA$^+$CD62L$^+$CD27$^+$CD28$^+$TCF7$^+$ in both CD4 and CD8 CAR$^+$ T cells (FIGS. 5A-5B). Compared to control conditions, hypotonic conditioned media increased the transduction efficiency by ~2-3 fold (FIG. 6). Using these stringent criteria, we found that elevated potassium increases stem-like populations by 3- to 8-fold compared to control conditions (FIG. 7).

Previous reports indicate that in vitro acquisition of full effector functions impairs the efficacy of adoptively transferred T cells, with per cell production of IFNγ being a reliable surrogate for this acquisition of effector function (Gattinoni et al, *JCI* 2005). Conversely, those T cells with retained capacity for IL-2 production represent a population with retained capacity for stemness (Gattinoni et al., *JCI* (2005); Wang et al., *STM* (2012)). We therefore assessed the fate of effector functions of T cell populations generated using hypotonic conditioned media. Compared to control conditions, hypotonic conditioned media preserved lymphoid homing receptors with enhanced IL-2 expression by 3-fold and reduced IGNγ expression by 3-fold (FIGS. 8A-8C). The opposing effects of IGNγ and IL-2 are crucial to maintain less differentiated state during in vitro expansion of T-cells. This phenomenon is observed in both CD4 and CD8 subsets without the loss of CCR7 expression (FIGS. 8A-8B).

Previous reports indicate that while IL-2 is of great utility for the production of large numbers of activated T cells, a concurrent rapid differentiation and coincident loss of stemness is also observed following in vitro exposure to IL-2 differentiation and proliferation of T cells (Waldmann et al, *Nat Rev Immunol,* 2006). Conversely, prior reports (Hinrichs et al, *Blood,* 2008) have indicated that utilization of alternative common gamma chain cytokines can result in similar cell yield with a comparative preservation of T cell stemness. To this end, we tested whether titrated amounts of different combinations of these cytokines could provide an added benefit to our otherwise reformulated media with respect to T cell stemness and total cell yield. Our results indicated that combination of IL-7 and IL-21 was sufficient to enrich less differentiated products (FIGS. 9A-9B). Combinations of these cytokines had very minimal effects in enriching naïve-like cells compared to standard culture conditions. However, using stringent markers including CD45RO$^-$CCR7$^+$CD45RA$^+$CD62L$^+$CD27$^+$CD28$^+$TCF7$^+$, our results indicate that compared to standard culture conditions IL-7, IL-21 with elevated potassium and hypotonic culture conditions resulted in relatively higher number (~20 fold more) of stem-like cells in CAR engineered products (FIGS. 10A-10B).

The effects of culturing CAR engineered T cells in hypotonic media comprising elevated potassium were also observed in recombinant TCR-modified immune cells. T cells were transfected with an NY-ESO-1 TCR, and cultured in hypotonic media with elevated potassium, as described above. Culture of such TCR-modified immune cells in hypotonic media with elevated potassium resulted in similar cell yield (~150 million cells), viability (greater than or equal to 90%), and a stem-like phenotype (~50% of CD3$^+$ cells expressed CCR7 and CD45RA) as CAR-T cells cultured under similar hypotonic conditions with elevated potassium (data not show).

Example 3. Characterization of CAR T Cells Cultured in Hypotonic Media

CD4+ and CD8+ donor matched T cells were cultured in control media or hypotonic media with elevated potassium as described above, both of which were supplemented with 200 IU/ml IL-2, 1200 IU/ml IL-7, and 200 IU/ml IL-15 (R&D systems) and activated using Transact (Miltenyi Biotec). 24 or 48 hours post activation, cells were transduced with lentivirus encoding a ROR1 chimeric antigen receptor (CAR). T cells were resuspended at 2.5e6 live T cells/ml in either control media or hypotonic media with elevated potassium, supplemented with 200 IU/ml IL-2, 1200 IU/ml IL-7, and 200 IU/ml IL-15. After overnight incubation, cells were transferred to G-REX® plates (Wilson Wolf) for expansion for 7 days post-activation before cryopreservation for subsequent use in the assays described below.

Culture in hypotonic media with elevated potassium substantially improves retention of a less differentiated T cells during production. Such stem-like T cells also have higher capacity for proliferation upon target stimulation and tumor cell killing capacity (data not shown).

At day 7 post expansion, 1×10$^6$ CAR T cells per group were stimulated with a PMA and ionomycin cocktail followed by golgi-inhibitors (Biolegend, per manufacturer's instructions). Cytokine production was assessed via intracellular staining and flow cytometry measured by live/CD3+/CAR+ and then comparing IL-2+, IFNγ+, IL-2+/IFNγ+ double positive, and double negative subsets.

CAR T cells expanded in hypotonic media with elevated potassium show enrichment for IL-2+ and IL-2+/IFNγ+ double positive T cells compared to CAR T cells expanded in control media (FIG. 11; average of three unique donors). This cytokine profile is consistent with the surface marker analysis, in which culturing of cells in hypotonic media with elevated potassium produces a CAR T cell population that has more T cells that are less differentiated and stem-like. IL-2 production in T cells is indicative of a less differentiated T cell in comparison to solely IFNγ production or no cytokine production. Moreover, increased IL-2 production would support persistence of the CAR T cells and thus a better therapeutic.

To assess T cell cytotoxicity, ROR1 CART cells generated as described above were seeded at a 1:5 (E:T) ratio with Nuclight Red labeled (NLR) H1975-ROR1+ target tumor cells in a 24 well plate with 3× technical replicates per CAR T condition. Tumor cell killing was determined via Incucyte fluorescent measurement over time of mean NLR intensity compared to tumor cells alone. After 3 days of culture one-third of T cells were removed from target cell wells, seeded on fresh target cells, and replaced in the Incucyte. This was repeated for up to 3-4 more times at either 3 or 4-day intervals.

CART cells cultured in hypotonic media with elevated potassium showed enhanced cytotoxicity as compared to CAR T cells cultured in control media (FIG. 12; y-axis represents target cell density). CAR T cells cultured in control media lose the ability to control target tumor cell growth over time. This increased cytotoxicity indicates that CAR T cells cultured in hypotonic media with elevated potassium have a greater and more persistent anti-tumor effect.

Cytokine secretion of the CAR T cells from the sequential killing assays above was assessed. Briefly, after each stimulation (e.g., on days 3, 7, and 10), media supernatant was collected after 24 hours of coculture with target tumor cells. Cytokine secretion was measured using a V-PLEX Proinflammatory Panel 1 Human Kit (MSD).

ROR1 CAR T cells cultured in hypotonic media with elevated potassium produced significantly more IL-2 (FIG. 13A) and IFNγ (FIG. 13B) in co-culture with H1975 target tumor cells as compared to CAR T cells cultured in control media. Similar to the data obtained with PMA/ionomycin stimulated T cells shown in FIG. 11, CAR T cells cultured in hypotonic media with elevated potassium show increased IL-2 (~4×) and IFNγ (~4×) secretion when co-cultured with target tumor cells, as assessed via ELISA. Upon repeat stimulation, IL-2 secretion is lost in all samples; however, CAR T cells cultured in hypotonic media with elevated potassium showed substantially higher IFNγ throughout three target cell stimulations. The increased magnitude and duration of cytokine secretion with CAR T cells cultured in hypotonic media with elevated potassium indicates a stronger anti-tumor response with delayed terminal differentiation of the CART cells.

CAR T cells cultured in hypotonic media with elevated potassium also show enhanced proliferation in co-culture with H1975 target tumor cells in the sequential killing assay (FIG. 14). The greater proliferation indicates that hypotonic media with elevated potassium produced cells are more stem-like with high proliferative capacity. The increased expansion also supports that CAR T cells produced by culturing in hypotonic media with elevated potassium have a superior anti-tumor response.

Example 4. Methods of Preparing Media and Culturing TILs

Commercially available T cell media (e.g., CTS™ OPTI-MIZER™, IMMUNOCULT™ or TEXMACS™) was prepared. Hypotonic conditioning medium with elevated potassium was also prepared: The inorganic salt ion concentrations of T cell media were adjusted using NaCl free T cell media. The final concentrations of the hypotonic conditioning medium were the following: NaCl (40-80 mM), KCl (40-90 mM), Calcium (0.5-2.8 mM), and Glucose (10-24 mM).

TILs were cultured in either control media or hypotonic conditioning medium with elevated potassium that was supplemented with 2.5% serum supplement (CTS™ Immune Cell SR, Thermo Fisher), 2 mM L-glutamine (Gibco), 2 mM L-glutamax (Gibco), MEM Non-Essential Amino Acids Solution (Gibco), Pen-strep (Gibco), 20 μg/ml FUNGIN™ (InvivoGen), Sodium pyruvate (Gibco), and 1 mM of O-Acetyl-L-carnitine hydrochloride (Sigma).

TILs were isolated from multiple tumors surgically resected from various tumor types (colon, lung, hepatocellular carcinoma, renal, pancreas, breast, melanoma, and prostate) were seeded and cultured in either the control media or hypotnic media with elevated potassium. TILs were then moved to fresh control media for final expansion.

TILs cultured in hypotonic media with elevated potassium show TILs with a less-differentiated, stem-like phenotype (data not shown).

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

The contents of all cited references (including literature references, U.S. or foreign patents or patent applications, and websites) that are cited throughout this application are hereby expressly incorporated by reference as if written herein in their entireties for any purpose, as are the references cited therein. Where any inconsistencies arise, material literally disclosed herein controls.

What is claimed is:

1. A method of expanding CD45RA and CCR7 expressing immune cells by at least about 5.0 fold, comprising culturing an immune cell population comprising CD45RA and CCR7 expressing immune cells obtained from a human patient in a medium comprising potassium ion at a concentration from about 65 mM to about 80 mM and NaCl at a concentration from about 35 mM to about 75 mM, wherein the total concentration of potassium ion and NaCl in the medium is between about 110 mM and about 140 mM; whereby the immune cells expanded during the culturing to produce a number of immune cells that express CD45RA and CCR7 greater by at least about 5.0 fold relative to the number of immune cells that expressed CD45RA and CCR7 at the start of the culturing.

2. The method of claim 1, wherein the medium further comprises:
   (i) one or more cytokines;
   (ii) calcium ion;
   (iii) glucose;
   (iv) a cell expansion agent; or
   (v) any combination of (i)-(iv).

3. The method of claim 2, wherein the one or more cytokines comprise Interleukin-2 (IL-2), Interleukin-7 (IL-7), Interleukin-21 (IL-21), Interleukin-15 (IL-15), or any combination thereof.

4. The method of claim 1, wherein the immune cells comprise T cells, TILs, NK cells, Tregs, or any combination thereof.

5. The method of claim 1, wherein the immune cells express a chimeric antigen receptor (CAR), an engineered T cell receptor (TCR), or a combination thereof.

6. The method of claim 2, wherein the cell expansion agent comprises a GSK3B inhibitor, an ACLY inhibitor, a PI3K inhibitor, an AKT inhibitor, or any combination thereof.

7. The method of claim 6, wherein:
   (i) the PI3K inhibitor comprises LY294002, pictilisib, CAL101, IC87114, or any combination thereof;
   (ii) the AKT inhibitor comprises MK2206, A443654, AKTi-VIII, or any combination thereof; or
   (iii) both (i) and (ii).

8. The method of claim 2, wherein:
   (i) the concentration of glucose is from about 10 mM to about 25 mM;
   (ii) the concentration of calcium ion is from about 0.4 mM to about 2.5 mM; or
   iii) both (i) and (ii).

9. The method of claim 1, wherein the immune cells expressing CD45RA and CCR7, after the culturing, further express: CD3, CD62L, CD27, CD28, or TCF7, or any combination thereof.

10. The method of claim 1, wherein the medium comprises:
    (i) IL-2 at a concentration from about 0.1 ng/mL to about 20 ng/ml;
    (ii) IL-21 at a concentration from about 0.1 ng/mL to about 20 ng/ml;
    (iii) IL-7 at a concentration from about 0.1 ng/ml to about 20 ng/ml;
    (iv) IL-15 at a concentration from about 0.1 ng/ml to about 20 ng/ml; or
    (v) any combination of (i)-(iv).

11. The method of claim 10, wherein:
    (i) the concentration of IL-2 is from about 1.0 ng/ml to about 10 ng/mL;
    (ii) the concentration of IL-21 is from about 1.0 ng/ml to about 10 ng/ml;
    (iii) the concentration of IL-7 is from about 1.0 ng/ml to about 10 ng/mL;
    (iv) the concentration of IL-15 is from about 1.0 ng/ml to about 10 ng/ml; or
    (v) any combination of (i)-(iv).

12. The method of claim 1, wherein the CD45RA and CCR7 expressing immune cells produced are administered to the human patient following the culturing.

13. The method of claim 1, further comprising transducing the CD45RA and CCR7 expressing immune cells with a vector comprising a nucleic acid encoding a chimeric antigen receptor (CAR), a T cell receptor (TCR), or a TCR mimic.

14. The method of claim 13, wherein:
(i) the CAR targets CD19, TRAC, TCRβ, BCMA, CLL-1, CSI, CD38, TSHR, CD123, CD22, CD30, CD70, CD171, CD33, EGFRVIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WTI, NY-ESO-1, LAGE-la, MAGE-Al, legumain, HPV E6, E7, MAGE AI, ETV6-AML, sperm protein 17, XAGE1, Tie 2, MAD-CT-1, MAD-CT-2, Fos-related antigen 1, p53, p53 mutant, prostein, survivin, telomerase, PCTA-1/Galectin 8, MelanA/MARTI, Ras mutant, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, or any combinations thereof;
(ii) the TCR targets AFP, CD19, TRAC, TCRβ, BCMA, CLL-1, CSI, CD38, TSHR, CD123, CD22, CD30, CD171, CD33, EGFRVIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCRI, ADRB3, PANX3, GPR20, LY6K, OR51E2, TARP, WTI, NY-ESO-1, LAGE-la, MAGE-Al, legumain, HPV E6, E7, MAGE AI, ETV6-AML, sperm protein 17, XAGE1, Tie 2, MAD-CT-1, MAD-CT-2, Fos-related antigen 1, p53, p53 mutant, prostein, survivin, telomerase, PCTA-1/Galectin 8, MelanA/MARTI, Ras mutant, hTERT, sarcoma translocation breakpoints, ML-IAP, ERG (TMPRSS2 ETS fusion gene), NA17, PAX3, androgen receptor, cyclin BI, MYCN, RhoC, TRP-2, CYP1B1, BORIS, SART3, PAX5, OY-TES1, LCK, AKAP-4, SSX2, RAGE-1, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD38, CD4, CD5, CD7, the extracellular portion of the APRIL protein, or any combinations thereof; or
(iii) any combination of (i) and (ii).

15. The method of claim 1, wherein the concentration of potassium ion is from about 65 mM to about 70 mM.

16. The method of claim 1, wherein the concentration of potassium ion is from about 70 mM to about 75 mM.

17. The method of claim 1, wherein the concentration of potassium ion is from about 75 mM to about 80 mM.

18. The method of claim 1, wherein the concentration of potassium ion is about 65 mM, and the concentration of NaCl is about 70 mM, about 69 mM, about 68 mM, about 67 mM, about 66 mM, about 65 mM, about 60 mM, about 55 mM, or about 50 mM.

19. The method of claim 1, wherein the concentration of potassium ion is about 70 mM, and the concentration of NaCl is about 65 mM, about 64 mM, about 63 mM, about 62 mM, about 61 mM, about 60 mM, about 55 mM, or about 50 mM.

20. The method of claim 1, wherein the concentration of potassium ion is about 75 mM, and the concentration of NaCl is about 60 mM, about 59 mM, about 58 mM, about 57 mM, about 56 mM, about 55 mM, about 50 mM, about 45 mM, or about 40 mM.

21. The method of claim 1, wherein the concentration of potassium ion is about 80 mM, and the concentration of NaCl is about 55 mM, about 54 mM, about 53 mM, about 52 mM, about 51 mM, about 50 mM, about 45 mM, about 40 mM, or about 35 mM.

22. The method of claim 13, wherein the concentration of potassium ion is from about 65 mM to about 70 mM.

23. The method of claim 13, wherein the concentration of potassium ion is from about 70 mM to about 75 mM.

24. The method of claim 13, wherein the concentration of potassium ion is from about 75 mM to about 80 mM.

25. The method of claim 13, wherein the concentration of potassium ion is about 65 mM, and the concentration of NaCl is about 70 mM, about 69 mM, about 68 mM, about 67 mM, about 66 mM, about 65 mM, about 60 mM, about 55 mM, or about 50 mM.

26. The method of claim 13, wherein the concentration of potassium ion is about 70 mM, and the concentration of NaCl is about 65 mM, about 64 mM, about 63 mM, about 62 mM, about 61 mM, about 60 mM, about 55 mM, or about 50 mM.

27. The method of claim 13, wherein the concentration of potassium ion is about 75 mM, and the concentration of NaCl is about 60 mM, about 59 mM, about 58 mM, about 57 mM, about 56 mM, about 55 mM, about 50 mM, about 45 mM, or about 40 mM.

28. The method of claim 13, wherein the concentration of potassium ion is about 80 mM, and the concentration of NaCl is about 55 mM, about 54 mM, about 53 mM, about 52 mM, about 51 mM, about 50 mM, about 45 mM, about 40 mM, or about 35 mM.

29. The method of claim 1, wherein the immune cells are cultured in the medium until the total number of viable cells is at least about $10^4$ total cells.

30. The method of claim 1, wherein the number of immune cells that express CD45RA and CCR7 after the culturing is increased by at least about 9.0 fold relative to the number of immune cells that express CD45RA and CCR7 prior to the culturing.

31. The method of claim 1, wherein the number of immune cells that express CD45RA and CCR7 after the culturing is increased by at least about 20 fold relative to the number of immune cells that express CD45RA and CCR7 prior to the culturing.

32. The method of claim 1, wherein after the culturing, at least 15% of the total number of CD8+ cells express CD45RA and CCR7, and at least 15% of the total number of CD4+ cells express CD45RA and CCR7.

\* \* \* \* \*